United States Patent
Zhou et al.

(10) Patent No.: US 11,485,713 B2
(45) Date of Patent: Nov. 1, 2022

(54) ANDROGEN RECEPTOR MODULATORS AND METHODS FOR THEIR USE

(71) Applicants: ESSA Pharma, Inc., Vancouver (CA); The University of British Columbia, Vancouver (CA); Provincial Health Services Authority, Vancouver (CA)

(72) Inventors: Han-Jie Zhou, Foster City, CA (US); Peter Virsik, Portola Valley, CA (US); Raymond John Andersen, Vancouver (CA); Marianne Dorothy Sadar, West Vancouver (CA); Kunzhong Jian, Surrey (CA); Daniel Andrew Golec, Vancouver (CA)

(73) Assignees: ESSA Pharma, Inc., Vancouver (CA); The University of British Columbia, Vancouver (CA); Provincial Health Services Authority, Vancouver (CA)

( * ) Notice: Subject to any disclaimer, the term of this patent is extended or adjusted under 35 U.S.C. 154(b) by 55 days.

(21) Appl. No.: 17/058,481

(22) PCT Filed: May 24, 2019

(86) PCT No.: PCT/US2019/033921
§ 371 (c)(1),
(2) Date: Nov. 24, 2020

(87) PCT Pub. No.: WO2019/226991
PCT Pub. Date: Nov. 28, 2019

(65) Prior Publication Data
US 2021/0198213 A1  Jul. 1, 2021

Related U.S. Application Data

(60) Provisional application No. 62/803,514, filed on Feb. 10, 2019, provisional application No. 62/747,206, filed on Oct. 18, 2018, provisional application No. 62/676,802, filed on May 25, 2018.

(51) Int. Cl.
| | | |
|---|---|---|
| C07D 239/34 | (2006.01) | |
| A61K 45/06 | (2006.01) | |
| C07C 69/712 | (2006.01) | |
| C07C 235/74 | (2006.01) | |
| C07C 317/24 | (2006.01) | |
| C07C 317/28 | (2006.01) | |
| C07D 207/24 | (2006.01) | |
| C07D 263/56 | (2006.01) | |
| C07D 295/26 | (2006.01) | |
| C07D 305/06 | (2006.01) | |

(52) U.S. Cl.
CPC ........... *C07D 239/34* (2013.01); *A61K 45/06* (2013.01); *C07C 69/712* (2013.01); *C07C 235/74* (2013.01); *C07C 317/24* (2013.01); *C07C 317/28* (2013.01); *C07D 207/24* (2013.01); *C07D 263/56* (2013.01); *C07D 295/26* (2013.01); *C07D 305/06* (2013.01)

(58) Field of Classification Search
CPC .................................................. C07D 239/34
See application file for complete search history.

(56) References Cited

U.S. PATENT DOCUMENTS

| | | |
|---|---|---|
| 2,571,217 A | 10/1951 | Davis et al. |
| 2,890,189 A | 6/1959 | Greenlee |
| 3,074,974 A | 1/1963 | Gebura |
| 3,162,615 A | 12/1964 | Bremmer |
| 4,284,574 A | 8/1981 | Bagga |
| 4,369,298 A | 1/1983 | Kida et al. |
| 4,855,184 A | 8/1989 | Klun et al. |
| 4,904,760 A | 2/1990 | Gaku et al. |
| 5,043,375 A | 8/1991 | Henning et al. |
| 5,155,196 A | 10/1992 | Kolb et al. |
| 5,362,615 A | 11/1994 | Hagemann et al. |
| 5,403,697 A | 4/1995 | Doessel et al. |
| 5,753,730 A | 5/1998 | Nagata et al. |
| 5,807,899 A | 9/1998 | Rolf et al. |
| 5,998,674 A | 12/1999 | Taketani et al. |
| 6,218,430 B1 | 4/2001 | Allegretto et al. |
| 6,245,117 B1 | 6/2001 | Nishikawa et al. |
| 7,183,323 B2 | 2/2007 | Chinn et al. |
| 7,273,867 B2 | 9/2007 | Dorsch et al. |
| 7,595,345 B2 | 9/2009 | Bunel et al. |
| 7,666,868 B2 | 2/2010 | Maier et al. |

(Continued)

FOREIGN PATENT DOCUMENTS

| | | |
|---|---|---|
| CA | 2206422 A1 | 6/1996 |
| CA | 2226469 A1 | 1/1997 |

(Continued)

OTHER PUBLICATIONS

Alabi, A. et al., "Quick and simple sample treatment for multiresidue analysis of bisphenols, bisphenol diglycidyl ethers and their derivatives in canned food prior to liquid chromatography and fluorescence detection," J. of Chromatography A, 2014, 1336, 23-33.

(Continued)

*Primary Examiner* — Golam M Shameem
(74) *Attorney, Agent, or Firm* — Cooley LLP

(57) ABSTRACT

Compounds having a structure of formula (I), (I-A), (Ia)-(Ie), (A)-(E), and (II) or a pharmaceutically acceptable salt, tautomer or stereoisomer thereof are provided. Uses of such compounds for modulating androgen receptor activity, imaging diagnostics in cancer and therapeutics, and methods for treatment of disorders including prostate cancer are also provided.

28 Claims, No Drawings

(56) References Cited

U.S. PATENT DOCUMENTS

| | | |
|---|---|---|
| 7,674,795 B2 | 3/2010 | Mailliet et al. |
| 8,048,888 B2 | 11/2011 | Wosikowski-Buters et al. |
| 8,445,507 B2 | 5/2013 | Jung |
| 8,455,477 B2 | 6/2013 | Katz |
| 8,686,050 B2 | 4/2014 | Sadar et al. |
| 9,173,939 B2 | 11/2015 | Andersen et al. |
| 9,365,510 B2 | 6/2016 | Andersen et al. |
| 9,375,496 B2 | 6/2016 | Andersen et al. |
| 9,388,112 B2 | 7/2016 | Sadar et al. |
| 9,862,667 B2 | 1/2018 | Sadar et al. |
| 10,654,811 B2 | 5/2020 | Andersen et al. |
| 11,059,795 B2 | 7/2021 | Zhou et al. |
| 11,242,324 B2 | 2/2022 | Zhou et al. |
| 2003/0092724 A1 | 5/2003 | Kao et al. |
| 2003/0105268 A1 | 6/2003 | Boriack et al. |
| 2004/0049004 A1 | 3/2004 | Boriack et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2009/0246158 A1 | 10/2009 | Rudolph et al. |
| 2011/0230556 A1 | 9/2011 | Sadar et al. |
| 2013/0045204 A1 | 2/2013 | Sadar et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1 | 1/2015 | Andersen et al. |
| 2015/0125389 A1 | 5/2015 | Andersen et al. |
| 2015/0210681 A1 | 7/2015 | Bourque et al. |
| 2016/0068466 A1 | 3/2016 | Andersen et al. |
| 2016/0367707 A1 | 12/2016 | Andersen et al. |
| 2017/0056336 A1 | 3/2017 | Sadar et al. |
| 2017/0121261 A1 | 5/2017 | Sadar et al. |
| 2017/0298033 A1 | 10/2017 | Andersen et al. |
| 2017/0368036 A1 | 12/2017 | Hattersley et al. |
| 2018/0064657 A1 | 3/2018 | Andersen et al. |
| 2018/0235925 A1 | 8/2018 | Andersen et al. |
| 2018/0327368 A1 | 11/2018 | Andersen et al. |
| 2019/0022093 A1 | 1/2019 | Wipf et al. |
| 2020/0123117 A1 | 4/2020 | Zhou et al. |
| 2020/0247763 A1 | 8/2020 | Zhou et al. |
| 2020/0325106 A1 | 10/2020 | Andersen et al. |
| 2021/0198213 A1 | 7/2021 | Zhou et al. |
| 2021/0323931 A1 | 10/2021 | Zhou et al. |
| 2021/0332016 A1 | 10/2021 | Zhou et al. |
| 2021/0387957 A1 | 12/2021 | Andersen et al. |
| 2022/0105093 A1 | 4/2022 | Virsik et al. |

FOREIGN PATENT DOCUMENTS

| | | |
|---|---|---|
| CA | 2339775 A1 | 3/2000 |
| CA | 2606262 A1 | 11/2006 |
| CA | 2728219 A1 | 1/2010 |
| CA | 2786319 A1 | 7/2011 |
| CN | 102083780 A | 6/2011 |
| CN | 103342892 A | 10/2013 |
| EP | 0056175 A1 | 7/1982 |
| EP | 0155238 A2 | 9/1985 |
| EP | 0293768 A1 | 12/1988 |
| EP | 0515128 A1 | 11/1992 |
| FR | 1389005 | 2/1965 |
| JP | B-S45-008432 | 3/1970 |
| JP | S56-5472 A | 1/1981 |
| JP | 63-196675 | 8/1988 |
| JP | 63-317539 A | 12/1988 |
| JP | H01-503541 | 11/1989 |
| JP | H02-4815 | 1/1990 |
| JP | 6-049473 A2 | 2/1994 |
| JP | 7-117349 A | 5/1995 |
| JP | 09-176240 A | 7/1997 |
| JP | H10133427 A | 5/1998 |
| JP | A-H10-316803 | 12/1998 |
| JP | 11-166087 A2 | 6/1999 |
| JP | 2000-072705 A2 | 3/2000 |
| JP | 2001-511170 A | 8/2001 |
| JP | 2005-325301 A | 11/2005 |
| JP | 2006-208607 A | 8/2006 |
| JP | 2006-265351 A2 | 10/2006 |
| JP | 2007-513089 A | 5/2007 |
| JP | 2007-290980 | 11/2007 |
| KR | 10-2011-0044216 A | 4/2011 |
| PL | 141793 B1 | 8/1987 |
| RU | 2454394 C2 | 6/2012 |
| SU | 638596 | 12/1978 |
| SU | 929630 | 5/1982 |
| WO | WO 1988/009782 A1 | 12/1988 |
| WO | WO 1996/16646 A1 | 6/1996 |
| WO | WO 1998/034930 A1 | 8/1998 |
| WO | WO 2000/001813 A2 | 1/2000 |
| WO | WO 2000/010958 A1 | 3/2000 |
| WO | WO 2001/088013 A2 | 11/2001 |
| WO | WO 2002/005813 A2 | 1/2002 |
| WO | WO 2003/004481 A1 | 1/2003 |
| WO | WO 2005/042464 A1 | 5/2005 |
| WO | WO 2005/077967 A1 | 8/2005 |
| WO | WO 2008/101806 A2 | 8/2008 |
| WO | WO 2010/000066 A1 | 1/2010 |
| WO | WO 2011/082487 A1 | 7/2011 |
| WO | WO 2011/082488 A1 | 7/2011 |
| WO | WO 2012/139039 A2 | 10/2012 |
| WO | WO 2012/145328 A1 | 10/2012 |
| WO | WO 2012/145330 A1 | 10/2012 |
| WO | WO 2013/028572 A1 | 2/2013 |
| WO | WO 2013/028791 A1 | 2/2013 |
| WO | WO 2014/011220 A2 | 1/2014 |
| WO | WO 2014/179867 A1 | 11/2014 |
| WO | WO 2015/031984 A1 | 3/2015 |
| WO | WO 2016/058080 A1 | 4/2016 |
| WO | WO 2016/058082 A1 | 4/2016 |
| WO | WO 2016/112455 A1 | 7/2016 |
| WO | WO 2016/141458 A1 | 9/2016 |
| WO | WO 2017/177307 A1 | 10/2017 |
| WO | WO 2017/210771 A1 | 12/2017 |
| WO | WO 2018/045450 A1 | 3/2018 |
| WO | WO 2018/157232 A1 | 9/2018 |
| WO | WO 2019/226991 A1 | 11/2019 |
| WO | WO 2020/081999 A1 | 4/2020 |
| WO | WO 2020/198710 A1 | 10/2020 |
| WO | WO 2020/198711 A1 | 10/2020 |
| WO | WO 2020/198712 A1 | 10/2020 |

OTHER PUBLICATIONS

Alvarez, C. et al., "Conformational and Experimental Studies on the Dipole Moments of Models of Comblike Polymers", Macromolecules, 30(20): 6369-6375 (1997).

Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).

Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), Ref. No. 13510 and 39700 (EFSA-Q-2003-178), The EFSA Journal, 86:1-40 (2004).

Antonarakis et al., "Androgen receptor variant-driven prostate cancer: clinical implications and therapeutic targeting," Prostate Cancer and Prostatic Diseases (2016), 1-11.

Antonarakis et al., "Targeting the N-Terminal Domain of the Androgen Receptor: A New Approach for the Treatment of Advanced Prostate Cancer," The Oncologist 2016;21:1-9.

Auzou et al., European Journal of Medicinal Chemistry, 9(5):548-554 (1974) (with English Abstract).

Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).

(56) References Cited

OTHER PUBLICATIONS

Banker (ed.) et al., Modern Pharmaceutics, Third Edition, Revised and Expanded, Marcel Dekker, Inc., 1997, pp. 451 and 596.
Banuelos et al., "Sintckamide A is a novel antagonist of androgen receptor that uniquely binds activation function-1 in its amino-terminal domain," The Journal of Biological Chemistry, vol. 291, No. 42, pp. 22231-22243, Oct. 14, 2016.
Bao, B. et al., "Androgen signaling is required for the vitamin D-mediated growth inhibition in human prostate cancer cells", Oncogene, 23:3350-3360 (2004).
Berge, S.M. et al., "Pharmaceutical Salts", Pharmaceutical Sciences, 66(1):1-19 (1977).
Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6):1367-1376 (2000).
Biles, J.E. et al., "Determination of the Diglycidyl Ether of Bisphenol A and its Derivatives in Canned Foods", J. Agric. Food Chem., 47:1965-1969 (1999).
Bisson, W.H. et al., "Discovery of antiandrogen activity of nonsteroidal scaffolds of marketed drugs", PNAS, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).
Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Brzozowski, Z. et al., "Precursors for bisphenolic resins", CAPLUS Database Accession No. 1990:36690, Document No. 112:33690, (1987), 1 page (Abstract).
Bruckheimer, E.M et al., "Apoptosis in prostate carcinogenesis A growth regulator and a therapeutic target", Cell Tissue Res, 301:153-162 (2000).
Cascini, et al., "$^{124}$Iodine: A Longer-Life Positron Emitter Isotope—New Opportunities in Molecular Imaging." Hindawi Publishing Corp.Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M. et al., "Estrogen action in human ovarian cancer", Critical Reviews in Oncology/Hematology, 25:1-9 (1997).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", Journal of Macromolecular Science, Pure and Applied Chemistry, A31(9):1105-1119 (1994).
Cook, W. D., "Fracture and Structure of Highly Crosslinked Polymer Composites", Journal of Applied Polymer Science, 42:1259-1269 (1991).

Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debasish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11,9, 2499-2505.
Dehm, S. et al., "Ligand-independent Androgen Receptor Activity is Activation Function-2-independent and Resistant to Antiandrogens in Androgen Refractory Prostate Cancer Cells", The Journal of Biological Chemistry, 281 (38):27882-27893 (2006).
Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).
Estebanez-Perpiñá, E. et al., "A surface on the androgen receptor that allosterically regulates coactivator binding," PNAS, 104(41):16074-16079 (2007).
Estebanez-Perpiñá, E. et al., "The Molecular Mechanisms of Coactivator Utilization in Ligand-dependent Transactivation by the Androgen Receptor," The Journal of Biological Chemistry, 280(9):8060-8068 (2005).
Fehlberg S. et al., "Bisphenol A diglycidyl ether induces apoptosis in tumor cells independently of peroxisome proliferator-activated receptor-γ, in caspase-dependent and -independent manners," Biochem. J., 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garuti, L., et al., "Irreversible Protein Kinase Inhibitors", Current Medicinal Chemistry, 18:2981-2994 (2011).
Garcia et al., "Determination of compounds from epoxy resins in food simulants by HPLC-fluorescence." Chromatographia, 58(5-6): 337-342 (2003).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion-Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the $NH_2$-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Henke, H., "Selektive präparative gelchromatographische Trennung niedermolekularer Verbindungen an Sephadex LH-20", Journal of Chromatography, 254: 296-308 (1983).

(56) References Cited

OTHER PUBLICATIONS

Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived from Splicing of Cryptic Exons Signify Hormone-Refractory Prostate Cancer", Cancer Research, 69:16-22 (2009).
Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274):1303-1312 (2004).
Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.
Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Isaacs, J.T., "Antagonistic Effect of Androgen on Prostatic Cell Death", The Prostate, 5:545-557 (1984).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection dated Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270.13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kato, M. et al., "Cotargeting androgen receptor splice variants and mTOR signaling pathway for the treatment of castration-resistant prostate cancer," Clin Cancer Res, Jun. 2016, vol. 22, pp. 2744-2754.
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454 (1999).
Kim, D. et al., "Androgen Receptor Expression and Cellular Proliferation During Transition from Androgen-Dependent to Recurrent Growth after Castration in the CWR22 Prostate Cancer Xenograft", American Journal of Pathology, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", J. Am. Chem. Soc., 123:6809-6818 (2001).
Kumar, S. et al., "Synthesis of new crown analogs derived from bisphenol," Indian Journal Chemistry, 36B:656-661 (1997).
L'Heureux, A. et al., "Aminodifluorosulfinium Salts: Selective Fluorination Reagents with Enhanced Thermal Stability and Ease of Handling", J. Org. Chem, 75:3401-3411 (2010).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al., "N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and Levoin et al., "Supporting Information—Determination of the binding mode and interacting amino-acids for dibasic H3 receptor agonists", Bioorganic & Medicinal Chemistry, vol. 21, Jan. 2013, pages SI-S3.
Loren, J.C. et al., "Synthesis of achiral and racemic catenanes based on terpyridine and a directionalized terpyridine mimic, pyridyl-phenanthroline", Org. Biomol. Chem., 3(17):3105-3116 (2005).
Louie, M.C. et al., "Androgen-induced recruitment of RNA polymerase II to a nuclear receptor-p160 coactivator complex", PNAS, 100(5):2226-2230 (2003).
Makary, P., "Principles of salt formation." UK Journal of Pharmaceutical and Biosciences (2014); 2(4): 01-04.
Marriott et al., "Pharmaceutical Compounding and Dispensing," Second Edition, Pharmaceutical Press, 305 pages (2005).
Martin, S.J. et al., "A new precursor for the radiosynthesis of [$^{18}$F]FLT", Nuclear Medicine and Biology, 29:263-273 (2002).
Martin, S.K. et al., "N-terminal targeting of androgen receptor variant enhances response of castration resistant prostate cancer to taxane chemotherapy," Molecular Oncology, 2015, vol. 9, pp. 628-639.
Masiello, D. et al., "Bicalutamide Functions as an Androgen Receptor Antagonist by Assembly of a Transcriptionally Inactive Receptor", The Journal of Biological Chemistry, 277(29):26321-26326 (2002).
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).
Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).
Miller, J.I. et al., "The Clinical Usefulness of Serum Prostate Specific Antigen After Hormonal Therapy of Metastatic Prostate Cancer", The Journal of Urology, 147:956-961 (1992).
Mitsiades, C.S. et al., "Molecular biology and cellular physiology of refractoriness to androgen ablation therapy in advanced prostate cancer", Expert Opin. Investig. Drugs, 10(6):1099-1115 (2001).
Lima, Lidia M., and Barreiro, Eliezer J. "Bioisosterism: a useful strategy for molecular modification and drug design." Current Medicinal Chemistry (2005); 12.1: 23-49.
Myung, J-K et al., "An androgen receptor N-terminal domain antagonist for treating prostate cancer", The Journal of Clinical Investigation, 123(7):2948-2960 (2013).
Nakazawa, H. et al., "In vitro assay of hydrolysis and chlorohydroxy derivatives of bisphenol A diglycidyl ether for estrogenic activity", Food and Chemical Toxicology, 40:1827-1832 (2002).
Nazareth, L.V. et al., "Activation of the Human Androgen Receptor through a Protein Kinase A Signaling Pathway", The Journal of Biological Chemistry, 271(33): 19900-19907 (1996).
Nedolya, N. A. et al., Zhurnal Organicheskoi Khimii, 30(8):1163-1166 (1994) (non English document).
Nishikawa et al., "Epichlorohydrin derivative-based modifier of cellulose fibers and modification method of cellulose fibers," Accession No. 2000:98153 CAPLUS (2009).
Noble, R. L., "The development of prostatic adenocarcinoma in Nb Rats following prolonged sex hormone administration", Cancer Research, 37:1929-1933 (1977).

(56) References Cited

OTHER PUBLICATIONS

Noble, R. L., "Sex steroids as a cause of adenocarcinoma of the dorsal prostate in Nb Rats, and their influence on the growth of transplants", Oncology, 34:138-141 (1977).
Ogawa, Y. et al., "Estrogenic activities of chemicals related to food contact plastics and rubbers tested by the yeast two-hybrid assay," Food Additives and Contaminants, 23:4, 422-430 (2006).
Paris, F. et al., "Phenylphenols, biphenols, bisphenol-A and 4-tert-octyphenol exhibit α and β estrogen activities and antiandrogen activity in reporter cell lines," Molecular and Cellular Endocrinology, 193:43-49 (2002).
Patani and LaVoie, "Bioisosterism: A Rational Approach in Drug Design", Chem. Rev., 96: 3147-3176 (1996).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-277 (1995).
Petersen, H. et al., "Determination of bisphenol A diglycidyl ether (BADGE) and its derivatives in food: identification and quantification by internal Standard", Eur. Food Res. Technol., 216:355-364 (2003).
Poouthree, K. et al., "Comparison of resolution in microemulsion EKC and MEKC employing suppressed electroosmosis: Application to bisphenol-A-diglycidyl ether and its derivatives", Electrophoresis, 28(20):3705-3711 (2007).
Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221-229 (2006).
Poustková et al., "Stability of bisphenol A diglycidyl ether and bisphenol F diglycidyl ether in water-based food simulants." European Food Research and Technology, 219(5): 534-539 (2004).
PubChem Compound Summary for CID 15305867, '4-Acetyl-4'-ethylbiphenyl', U.S. National Library of Medicine, Feb. 9, 2007, pp. 1-17; retrieved from https://pubchem.ncbi.nlm.nih.gov/compound/15305867.
PubChem Compound Summary for CID 18533308, '2-[4-[[4-(Aminomethoxy)phenyl]methyl]-2-methylphenoxy]acetic acid', U.S. National Library of Medicine, Dec. 4, 2007, pp. 1-15 retrieved from https://pubchem.ncbi.nlm.nih.gov/compound/18533308.
Quayle, S. et al., "Androgen receptor decoy molecules block the growth of prostate cancer", PNAS, 104(4): 1331-1336 (2007).
Rao, B.R. et al., "Endocrine Factors in Common Epithelial Ovarian Cancer", Endocrine Reviews, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", Journal of the National Cancer Institute, 90(23):1774-1786 (1998).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Roberts, J. T. et al., "Adenocarcinoma of Prostate in 40-Year-Old Body-Builder", Lancet, 2:742 (1986).
Roberts et al., "Emerging drugs for hepatocellular carcinoma," Expert Opin Emerg Drugs, 11(3):469-487 (2006).
Rokicki, G. et al., "Reactions of 4-chloromethyl-1,3-dioxolan-2-one with phenols as a new route to polyols and cyclic carbonates", Journal f. prakt. Chemie., 327:718-722 (1985).
Ross, R.K. et al., "Androgen Metabolism and Prostate Cancer: Establishing a Model of Genetic Susceptibility", European Urology, 35:355-361 (1999).

Roulin et al., "Targeting renal cell carcinoma with NVP-BEZ235, a dual PI3K/mTOR inhibitor, in combination with sorafenib," Mol Cancer, 10:90 (2011), 12 pages.
Rusu, E. et al.: "Photosensitive compounds with chloromethyl groups", Revue Roumaine de Chimie, 45(5):451-456 (2000).
Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).
Sadar, M. et al., "Prostate cancer: molecular biology of early progression to androgen independence", Endocrine-Related Cancer, 6:487-502 (1999).
Sadar, M.D. et al., "Characterization of a New in Vivo Hollow Fiber Model for the Study of Progression of Prostate Cancer to Androgen Independence", Molecular Cancer Therapeutics, 1:629-637 (2002).
Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).
Sato, N. et al., "A Metastatic and Androgen-sensitive Human Prostate Cancer Model Using Intraprostatic Inoculation of LNCaP Cells in SCID Mice", Cancer Research, 57:1584-1589 (1997).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", Food and Chemical Toxicology, 42:983-993 (2004).
Schaefer, A. et al., "Migration from can coatings: Part 3. Synthesis, identification and quantification of migrating epoxy-based substances below 1000 Da", Food Additives and Contaminants, 21(4):390-405 (2004).
Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016;22(17):4280-4282.
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
Strub and McKim, "Dimethyl Sulfoxide USP, PhEur in Approved Pharmaceutical Products and Medical Devices", PharmaTech.com, 6 pages (2008). http://www.pharmtech.com/print/224268 ?page=full&rel=canonical.
Sun, S. et al., "Castration resistance in human prostate cancer is conferred by a frequently occurring androgen receptor splice variant", The Journal of Clinical Investigation, 120(8):2715-30 (2010).
Tanji, N. et al., "Growth Factors: Roles in Andrology", Archives of Andrology, 47:1-7 (2001).
Taplin, M.E. et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by Interleukin-6 via MAPK and STAT3 Signal Transduction Pathways", The Journal of Biological Chemistry, 277(9):7076-7085 (2002).

(56) References Cited

OTHER PUBLICATIONS

Ueda, T. et al., "Ligand-independent Activation of the Androgen Receptor by Interleukin-6 and the Role of Steroid Receptor Coactivator-1 in Prostate cancer Cells", The Journal of Biological Chemistry, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese market", Food Additives and Contaminants, 18(2):177-185 (2001).
Van der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and Lipper, Robert A. "Role of the development scientist in compound lead selection and optimization." Journal of Pharmaceutical Sciences (2000); 89.2: 145-154.
Vippagunta et al., "Crystalline solids," Advanced Drug Delivery Reviews (2001) 48: 3-26.
Walfried et al., "Bisphenol F-Diglycidylether (BFDGE) und Folgeprodukte in Konservenfüllgütern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).
Wilson, J.D. et al., "Long-Term Consequences of Castration in Men: Lessons from the Skoptzy and the Eunuchs of the Chinese and Ottoman Courts", The Journal of Clinical Endocrinology & Metabolism, 84:4324-4331 (1999).
Wolff (ed.) et al., Burger's Medicinal Chemistry and Drug Discovery, Fifth Edition, vol. I: Principles and Practice, 1995, pp. 975-977.
Wong, C. et al., "Steroid Requirement for Androgen Receptor Dimerization and DNA Binding", J. Bioi. Chem., 268(25):19004-19012 (1993).
Xu, X. et al., "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.
Yong, Eu Leong, et al. "Molecular basis of androgen receptor diseases." Annals of Medicine (2000); 32.1: 15-22.
Zuhayra, M. et al., "New approach for the synthesis of [$^{18}$F]fluoroethyltyrosine for cancer imaging: Simple, fast, and high yielding automated synthesis", Bioorganic & Medicinal Chemistry, 17:7441-7448 (2009).
Extended European Search Report in Application No. EP 12768410.8 dated Sep. 22, 2014, 10 pages.
Extended European Search Report in Application No. EP 14793978.9 dated Sep. 1, 2016, 8 pages.
Supplementary European Search Report in EP Application No. 09771876.1 dated Jun. 20, 2011, 5 pages.
Supplementary European Search Report in EP Application No. 11731645.5 dated mailed Jun. 20, 2013, 11 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Extended European Search Report in Application No. 16736999.0 dated May 24, 2018, 14 pages.
Extended European Search Report for European Application No. 17781660.0 dated Oct. 31, 2019, 8 pages.
Decision of Refusal for Japanese Application No. 2011-515039, dated Dec. 2, 2014, 18 pages (English translation).
International Search Report for International Application No. PCT/CA2009/000902 dated Sep. 1, 2009, 4 pages.
Written Opinion for International Application No. PCT/CA2009/000902 dated Sep. 1, 2009, 6 pages.
International Preliminary Report on Patentability for International Application No. PCT/CA2009/000902 dated Jan. 5, 2011, 7 pages.
International Search Report for International Application No. PCT/US2012/032584 dated Jul. 31, 2012, 3 pages.
Written Opinion for International Application No. PCT/US2012/032584 dated Jul. 31, 2012, 5 pages.
International Preliminary Report on Patentability for PCT/US2012/032584 dated Oct. 8, 2013, 6 pages.
International Search Report for International Application No. PCT/US2012/033959 dated Jul. 18, 2012, 3 pages.
Written Opinion for International Application No. PCT/US2012/033959 dated Jul. 18, 2012, 7 pages.
International Preliminary Report on Patentability for International Application No. PCT/US2012/033959 dated Oct. 22, 2013, 8 pages.
International Search Report for International Application No. PCT/US2012/033957 dated Jul. 18, 2012, 3 pages.
Written Opinion for International Application No. PCT/US2012/033957 dated Jul. 18, 2012, 5 pages.
International Preliminary Report on Patentability for International Application No. PCT/US2012/033957 dated Oct. 22, 2013, 6 pages.
International Search Report for International Application No. PCT/CA2011/000019 dated Mar. 21, 2011, 7 pages.
Written Opinion for International Application No. PCT/CA2011/000019 dated Mar. 21, 2011, 7 pages.
International Preliminary Report on Patentability for International Application No. PCT/CA2011/000019 dated Jul. 10, 2012, 8 pages.
International Search Report for International Application No. PCT/CA2011/000021 dated Apr. 18, 2011, 8 pages.
Written Opinion for International Application No. PCT/CA2011/000021 dated Apr. 18, 2011, 7 pages.
International Preliminary Report on Patentability for International Application No. PCT/CA2011/000021 dated Jul. 10, 2012, 8 pages.
International Search Report for International Application No. PCT/US2012/051481 dated Nov. 26, 2012, 4 pages.
Written Opinion for International Application No. PCT/US2012/051481 dated Nov. 26, 2012, 7 pages.
International Preliminary Report on Patentability for International Application No. PCT/US2012/051481 dated Feb. 25, 2014, 8 pages.
International Search Report for International Application No. PCT/US2012/051923 dated Jan. 28, 2013, 4 pages.
Written Opinion for International Application No. PCT/US2012/051923 dated Jan. 28, 2013, 8 pages.
International Preliminary Report on Patentability for International Application No. PCT/US2012/051923 dated Feb. 25, 2014, 9 pages.
International Search Report and Written Opinion for International Application No. PCT/CA2014/000414 dated Aug. 5, 2014, 6 pages.
International Preliminary Report on Patentability for International Application No. PCT/CA2014/000414 dated Nov. 10, 2015, 7 pages.
International Search Report and Written Opinion for International Application No. PCT/CA2014/000685 dated Dec. 4, 2014, 13 pages.

(56) References Cited

OTHER PUBLICATIONS

International Preliminary Report on Patentability for International Application No. PCT/CA2014/000685 dated Mar. 15, 2016, 7 pages.
International Search Report and Written Opinion for International Application No. PCT/CA2015/000533 dated Dec. 18, 2015, 11 pages.
International Preliminary Report on Patentability for International Application No. PCT/CA2015/000533 dated Apr. 18, 2017, 7 pages.
International Search Report and Written Opinion for International Application No. PCT/CA2015/000535 dated Dec. 23, 2015, 9 pages.
International Preliminary Report on Patentability for International Application No. PCT/CA2015/000535 dated Apr. 18, 2017, 6 pages.
International Search Report and Written Opinion for International Application No. PCT/CA2016/000008 dated Mar. 15, 2016, 13 pages.
International Preliminary Report on Patentability for International Application No. PCT/CA2016/000008 dated Jul. 18, 2017, 7 pages.
International Search Report and Written Opinion for International Application No. PCT/CA2016/000070 dated Jun. 2, 2016, 10 pages.
International Search Report and Written Opinion for International Application No. PCT/CA2017/000083 dated Aug. 3, 2017, 14 pages.
International Preliminary Report on Patentability for International Application No. PCT/CA2016/000070 dated Sep. 12, 2017, 6 pages.
International Search Report and Written Opinion for International Application No. PCT/CA2017/000141 dated Sep. 1, 2017, 11 pages.
International Search Report and Written Opinion for International Application No. PCT/CA2017/000201 dated Dec. 8, 2017, 9 pages.
International Search Report and Written Opinion for International Application No. PCT/US2019/057034 dated Feb. 6, 2020, 10 pages.
De Santis, M et al., "Practical Guidance on the Role of Corticosteroids in the Treatment of Metastatic Castration-resistant Prostate Cancer," Urology, 2016, vol. 96, pp. 156-164.
Mathur, A et al., "Subverting ER-Stress towards Apoptosis by Nelfinavir and Curcumin Coexposure Augments Docetaxel Efficacy in Castration Resistant Prostate Cancer Cells," PLoS ONE (2014) 9(8): e103109, 14 pages.
McClurg, UL et al., "The novel anti-androgen candidate galeterone targets deubiguitinating enzymes, USP12 and USP46, to control prostate cancer growth and survival," Oncotarget, 2018, vol. 9, No. 38, pp. 24992-25007.
Qin et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression," J Med Chem. 2018. vol. 61(15), pp. 6665-6704.
Raina et al., "PROTAC-induced BET protein degradation as a therapy for castration-resistant prostate cancer," PNAS, Jun. 28, 2016, vol. 113, No. 26, pp. 7124-7129.
Zurth, "Drug-Drug Interaction Potential of Darolutamide: In Vitro and Clinical Studies," European Journal of Drug Metabolism and Pharmacokinetics (2019) 44:747-759.
Extended European Search Report in Application No. 21212648.6 dated Feb. 21, 2022, 8 pages.
International Search Report and Written Opinion for International Application No. PCT/US2020/025545 dated Jul. 9, 2020, 11 pages.
International Search Report and Written Opinion for International Application No. PCT/US2020/025542 dated Aug. 14, 2020, 10 pages.
International Search Report and Written Opinion for International Application No. PCT/US2020/025539 dated Aug. 18, 2020, 11 pages.
International Search Report and Written Opinion for International Application No. PCT/US2021/027771 dated Jul. 9, 2021, 8 pages.
International Search Report and Written Opinion for International Application No. PCT/US2021/050644 dated Feb. 3, 2022, 8 pages.

ANDROGEN RECEPTOR MODULATORS AND METHODS FOR THEIR USE

CROSS-REFERENCE TO RELATED APPLICATIONS

This application is a U.S. National Stage application under 35 U.S.C. § 371 of International Application No. PCT/US2019/033921, filed May 24, 2019, which claims priority to U.S. Provisional Application No. 62/676,802, filed May 25, 2018, U.S. Provisional Application No. 62/747,206, filed Oct. 18, 2018, and U.S. Provisional Application No. 62/803,514, filed Feb. 10, 2019, each of which are hereby incorporated by reference in their entireties for all purposes.

FIELD OF DISCLOSURE

This disclosure generally relates to bisphenol-related compounds and their use for treatment of various indications. In particular the disclosure relates to bisphenol-related compounds and their use for treatment of various cancers, for example prostate cancer, including but not limited to, primary/localized prostate cancer (newly diagnosed), locally advanced prostate cancer, recurrent prostate cancer, metastatic prostate cancer, metastatic castration-resistant prostate cancer (CRPC), and hormone-sensitive prostate cancer. This disclosure also relates to bisphenol-related compounds and their use for modulating androgen receptor (AR) activity-including truncated AR.

BACKGROUND

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross et al. Eur Urol 35, 355-361 (1999); A. A. Thomson, Reproduction 121, 187-195 (2001); N. Tanji, K. Aoki & M. Yokoyama, Arch Androl 47, 1-7 (2001)). Several lines of evidence show that androgens are associated with the development of prostate carcinogenesis. Firstly, androgens induce prostatic carcinogenesis in rodent models (R. L. Noble, Cancer Res 37, 1929-1933 (1977); R. L. Noble, Oncology 34, 138-141 (1977)) and men receiving androgens in the form of anabolic steroids have a higher incidence of prostate cancer (J. T. Roberts & D. M. Essenhigh, Lancet 2, 742 (1986); J. A. Jackson et al. Arch Intern Med 149, 2365-2366 (1989); P. D. Guinan et al. Am J Surg 131, 599-600 (1976)). Secondly, prostate cancer does not develop if humans or dogs are castrated before puberty (J Clin Endocrinol Metab 84, 4324-4331 (1999); G. Wilding, Cancer Surv 14, 113-130 (1992)). Castration of adult males causes involution of the prostate and apoptosis of prostatic epithelium while eliciting no effect on other male external genitalia (E. M. Bruckheimer & N. Kyprianou, Cell Tissue Res 301, 153-162 (2000); J. T. Isaacs, Prostate 5, 545-557 (1984)). This dependency on androgens provides the underlying rationale for treating prostate cancer with chemical or surgical castration (androgen ablation).

Androgens also play a role in female diseases such as polycystic ovary syndrome as well as cancers. One example is ovarian cancer where elevated levels of androgens are associated with an increased risk of developing ovarian cancer (K. J. Helzlsouer et al. JAMA 274, 1926-1930 (1995); R. J. Edmondson et al. Br J Cancer 86, 879-885 (2002)). The AR has been detected in a majority of ovarian cancers (H. A. Risch, J Natl Cancer Inst 90, 1774-1786 (1998); B. R. Rao & B. J. Slotman, Endocr Rev 12, 14-26 (1991); G. M. Clinton & W. Hua, Crit Rev Oncol Hematol 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate luminal cells. Androgen ablation therapy causes a temporary reduction in tumor burden concomitant with a decrease in serum prostate-specific antigen (PSA). Unfortunately, prostate cancer can eventually grow again in the absence of testicular androgens (castration-resistant disease) (Huber et al. 1987 Scand J. Urol Nephrol. 104, 33-39). Castration-resistant prostate cancer that is still driven by AR is biochemically characterized by a rising titre of serum PSA (Miller et al. 1992 J. Urol. 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains two transcriptional activation units (tau1 and tau5) within activation function-1 (AF-1). Binding of androgen (ligand) to the LBD of the AR results in its activation such that the receptor can effectively bind to its specific DNA consensus site, termed the androgen response element (ARE), on the promoter and enhancer regions of androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al. 1994 Cancer Res. 54, 5474-5478; Nazareth et al 1996 J. Biol. Chem. 271, 19900-19907; Sadar 1999 J. Biol. Chem. 21 A, 7777-7783; Ueda et al 2002 A J. Biol. Chem. 211, 7076-7085; and Ueda et al 2002 B J. Biol. Chem. 277, 38087-38094).

Clinically available inhibitors of the AR include non-steroidal antiandrogens such as bicalutamide (Casodex™), nilutamide, flutamide, and enzalutamide. There is also a class of steroidal antiandrogens, such as cyproterone acetate and spironolactone. Both steroidal and non-steroidal antiandrogens target the LBD of the AR and predominantly fail presumably due to poor affinity, mutations that lead to activation of the AR by these same antiandrogens (Taplin, M. E. et al. Cancer Res., 59, 2511-2515 (1999)), and constitutively active AR splice variants lacking the AR ligand-binding domain. Abiraterone and antiandrogens have no effect on constitutively active AR splice variants that lack the ligand-binding domain (LBD), which are associated with castration-recurrent prostate cancer (Dehm S M et al. Cancer Res 68, 5469-77, 2008; Guo Z et al. Cancer Res. 69, 2305-13, 2009; Hu et al. 2009 Cancer Res. 69, 16-22; Sun et al. 2010 J Clin Invest. 2010 120, 2715-30; Antonarakis et al. N Engl J Med. 2014, 371, 1028-38; Scher et al. JAMA Oncol. 2016).

AR antagonists other than the bisphenol ether derivatives previously reported (see, WO 2010/000066, WO 2011/082487; WO 2011/082488; WO 2012/145330; WO 2015/031984; WO 2016/058080; and WO 2016/058082) that bind to full-length AR and/or truncated AR splice variants that are currently being developed include: AR degraders such as niclosamide (Liu C et al. 2014), galeterone (Njar et al. 2015; Yu Z at al 2014), and ARV-330/Androgen receptor PROTAC (Neklesa et al. 2016 J Clin Oncol 34 suppl 2S; abstr 267); AR DBD inhibitor VPC-14449 (Dalai K et al. 2014 J Biol Chem. 289(38):26417-29; Li H et al. 2014 J Med Chem. 57(15):6458-67); antiandrogens apalutamide (Clegg N J et al. 2012), ODM-201 (Moilanen A M et al. 2015), ODM-204 (Kallio et al. J Clin Oncol 2016 vol. 34 no. 2_suppl 230), TAS3681 (Minamiguchi et al. 2015 J Clin Oncol 33, suppl 7; abstr 266); and AR NTD inhibitors 3E10-AR441bsAb (Goicochea N L et al 2015), and sintokamide (Sadar et al 2008; Banuelos et al 2016).

The AR-NTD is also a target for drug development (e.g. WO 2000/001813), since the NTD contains Activation-Function-1 (AF-1) which is the essential region required for AR transcriptional activity (Jenster et al. 1991. Mol Endocrinol. 5, 1396-404). The AR-NTD importantly plays a role in activation of the AR in the absence of androgens (Sadar, M. D. 1999 J. Biol. Chem. 21 A, 7777-7783; Sadar M D et al. 1999 Endocr Relat Cancer. 6, 487-502; Ueda et al. 2002 J. Biol. Chem. 277, 7076-7085; Ueda 2002 J. Biol. Chem. 277, 38087-38094; Blaszczyk et al. 2004 Clin Cancer Res. 10, 1860-69; Dehm et al. 2006 J Biol Chem. 28, 27882-93; Gregory et al. 2004 J Biol Chem. 219, 7119-30). The AR-NTD is important in hormonal progression of prostate cancer as shown by application of decoy molecules (Quayle et al. 2007, Proc Natl Acad Sci USA. 104, 1331-1336).

While the crystal structure has been resolved for the AR C-terminal LBD, this has not been the case for the NTD due to its high flexibility and intrinsic disorder in solution (Reid et al. 2002 J. Biol. Chem. 277, 20079-20086) thereby hampering virtual docking drug discovery approaches. Compounds that modulate AR, potentially through interaction with NTD domain, include the bisphenol compounds disclosed in published PCT Nos: WO 2010/000066, WO 2011/082487; WO 2011/082488; WO 2012/145330; WO 2012/139039; WO 2012/145328; WO 2013/028572; WO 2013/028791; WO 2014/179867; WO 2015/031984; WO 2016/058080; WO 2016/058082; WO 2016/112455; WO 2016/141458; WO 2017/177307; WO 2017/210771; and WO 2018/045450, and which are hereby incorporated by reference in their entireties.

Significant advances have been made in this field. However, there remains a need for improved treatment for AR-mediated disorders including prostate cancer, especially metastatic castration-resistant prostate cancer.

SUMMARY OF THE INVENTION

The compounds of the present disclosure are androgen receptor modulators which may be useful in treating various diseases and conditions as disclosed herein. In one embodiment, the present disclosure provides compounds comprising the structure of formula (I-A)

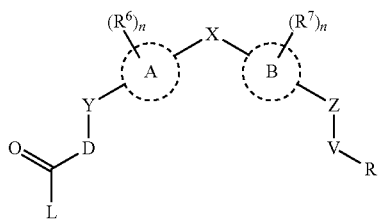

(I-A)

or a pharmaceutically acceptable salt, tautomer, stereoisomer or prodrug thereof, wherein:

A and B are each independently aryl or heteroaryl;

X is a bond, $-(CR^8R^9)_t-$, $-O-$, $-C(=O)-$, $-S(O)_p-$, $-NR^{10}-$, $-CONR^{10}-$, $-NR^{10}CO-$, $-SO_2NR^{10}-$, or $-NR^{10}SO_2-$;

Y and Z are each independently a bond, $-(CR^8R^9)_t-$, $-O-$, $-S(O)_p-$, $-NR^{10}-$, $-CONR^1-$, $-NR^{10}CO-$, $-SO_2NR^{10}-$, or $-NR^{10}SO_2-$;

V is a bond, optionally substituted $-(CR^{11}R^{12})_m-$, $-C(=O)-$, $-N(R^{10})CO-$, $-CONR^{10}-$, or $-NSO_2R^{10}-$;

R is $-(CR^{4a}R^{4b})-(CR^{5a}R^{5b})-W$ or W;

W is hydrogen, halogen, $-CF_3$, $-CF_2R^{10}$, $-CN$, $-OR^{13}$, $-NR^{13}R^{14}$, optionally substituted $-CONR^{13}R^{14}$, optionally substituted carbocyclyl, optionally substituted heterocyclyl, optionally substituted aryl, or optionally substituted heteroaryl;

D is $-(CR^{1a}R^{1b})_q-$, $-O-$, or $-NR^{10}-$;

L is $-(CR^{2a}R^{2b})-R^3$ or $-E-R^3$;

E is $-(CR^{2a}R^{2b})_g-$, $-O-$, $-NR^{10}-$, or $-NR^{10}-(CR^{2a}R^{2b})_g-$;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{1a}$ and $R^{1b}$ taken together form an optionally substituted carbocyclyl, optionally substituted heterocyclyl, optionally substituted aryl, or optionally substituted heteroaryl;

or alternatively, $R^{2a}$ and $R^{2b}$ taken together are CO, optionally substituted carbocyclyl, optionally substituted heterocyclyl, optionally substituted aryl, or optionally substituted heteroaryl;

or alternatively, $R^{1a}$, $R^{1b}$, $R^{2a}$ and $R^{2b}$ taken together form an optionally substituted carbocyclyl, optionally substituted heterocyclyl, optionally substituted aryl, or optionally substituted heteroaryl;

$R^{4a}$, $R^{4b}$, $R^{5a}$, and $R^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{4a}$ and $R^{4b}$ taken together form CO, optionally substituted carbocyclyl, optionally substituted heterocyclyl, optionally substituted aryl, or optionally substituted heteroaryl;

or alternatively, $R^{4a}$, $R^{4b}$, $R^{5a}$ and $R^{5b}$ taken together form an optionally substituted carbocyclyl, optionally substituted heterocyclyl, optionally substituted aryl, or optionally substituted heteroaryl;

$R^3$ is absent, hydrogen, $-CN$, $-CF_3$, $-OH$, optionally substituted $C_1$-$C_6$ alkyl, optionally substituted $C_2$-$C_6$ alkenyl, optionally substituted $C_2$-$C_6$ alkynyl, optionally substituted $-OR^{15}$, optionally substituted $C_1$-$C_6$ alkoxy, $-NH_2$, $-NR^{16}R^{17}$, $-NR^{16}COR^{18}$, $-NR^{16}S(O)_pR^{18}$, $-CONR^{14}R^{15}$, $-SONR^{14}R^{15}$, $-SO_2NR^{14}R^{15}$, optionally substituted —S(O)$_p$R$^{18}$, —N$_3$, optionally substituted carbocyclyl, optionally substituted heterocyclyl, optionally substituted aryl, or optionally substituted heteroaryl;

or alternatively, R$^{2a}$, R$^{2b}$ and R$^3$ taken together form an optionally substituted carbocyclyl, optionally substituted heterocyclyl, optionally substituted aryl, or optionally substituted heteroaryl;

or alternatively, R$^{2a}$ and R$^{10}$ taken together form an optionally substituted heterocyclyl;

R$^6$ and R$^7$ are each independently H, methyl, methoxy, —CN, halogen, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^8$, R$^9$, R$^{11}$ and R$^{12}$ are each independently hydrogen, —OH, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted C$_1$-C$_6$ alkylamino, optionally substituted —OCO (C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl;

or alternatively, R$^8$ and R$^9$ taken together form an optionally substituted carbocyclyl or optionally substituted heterocyclyl;

or alternatively, R$^{11}$ and R$^{12}$, on a same carbon atom or a different carbon atom, taken together form an optionally substituted carbocyclyl, optionally substituted heterocyclyl, optionally substituted aryl, or optionally substituted heteroaryl;

R$^{10}$ is hydrogen, halogen, optionally substituted C$_1$-C$_6$ alkyl, optionally substituted C$_1$-C$_6$ alkoxy, —CO(C$_1$-C$_6$ alkyl), optionally substituted C$_1$-C$_6$ alkylamino, optionally substituted carbocyclyl, optionally substituted heterocyclyl, optionally substituted aryl, or optionally substituted heteroaryl;

R$^{13}$, R$^{14}$, R$^{15}$, R$^{16}$, R$^{17}$ and R$^{18}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl;

or alternatively, R$^{14}$ and R$^{15}$ are taken together to form an optionally substituted heterocyclyl, or optionally substituted heteroaryl;

or alternatively, R$^{16}$ and R$^{17}$ are taken together to form an optionally substituted heterocyclyl, or optionally substituted heteroaryl;

m is 0, 1, 2, 3, or 4;
each n is independently 0, 1 or 2;
each p is independently 0, 1 or 2;
q is 0, 1 or 2;
each g is independently 0, 1, 2, 3, or 4; and
each t is independently 1 or 2.

In one embodiment of the compounds of formula (I-A), R is W.

In one embodiment of the compounds of formula (I-A), W is hydrogen, halogen, —CF$_3$, or —NR$^{13}$R$^{14}$.

In one embodiment of the compounds of formula (I-A), L is -E-R$^3$.

In one embodiment of the compounds of formula (I-A), R$^3$ is selected from hydrogen, optionally substituted C$_1$-C$_6$ alkyl, optionally substituted —OR$^{15}$, optionally substituted —SR$^{18}$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, or optionally substituted —SO$_2$R$^{18}$. In one embodiment of the compounds of formula (I-A), R$^3$ is selected from hydrogen, —C$_1$-C$_3$ alkyl, —NR$^{16}$SO(C$_1$-C$_3$ alkyl), —NR$^{16}$SO$_2$(C$_1$-C$_3$ alkyl), —SONR$^{14}$R$^{15}$, —SO$_2$NR$^{14}$R$^{15}$, —SOR$^{18}$, or —SO$_2$R$^{18}$.

In one aspect, the present disclosure provides a compound having the structure (I):

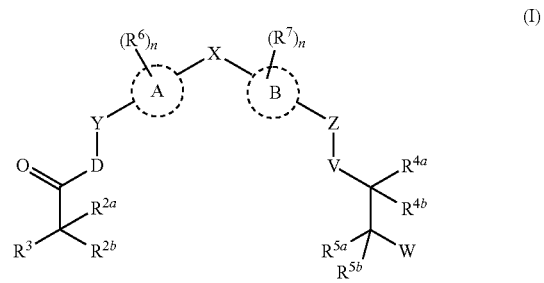

or a pharmaceutically acceptable salt, tautomer, stereoisomer or prodrug thereof, wherein:

A and B are each independently aryl or heteroaryl;

X, Y, Z are each independently a bond, (C(R$^8$R$^9$))$_t$, O, S(O)$_p$, NR, CONR$^{10}$, NR$^{10}$CO, SO$_2$NR$^{10}$, or NR$^{10}$SO$_2$;

V is a bond or optionally substituted (C(R$^{11}$R$^{12}$))$_m$;

W is hydrogen, halogen, CF$_3$, CN, OR$^{13}$ or optionally substituted CON(R$^{13}$R$^{14}$);

D is (C(R$^{1a}$R$^{1b}$))$_m$;

R$^{1a}$, R$^{1b}$, R$^{2a}$, R$^{2b}$, R$^{4a}$, 4$^{4b}$, R$^{5a}$, R$^{5b}$ are each independently hydrogen, halogen, hydroxy, optionally substituted C$_{1-6}$ alkyl, or optionally substituted C$_{1-6}$ alkoxy; or R$^{1a}$ and R$^{1b}$ taken together are optionally substituted carbocyclyl, optionally substituted heterocyclyl, optionally substituted aryl, or optionally substituted heteroaryl; or R$^{2a}$ and R$^{2b}$ taken together are CO, optionally substituted carbocyclyl, optionally substituted heterocyclyl, optionally substituted aryl, or optionally substituted heteroaryl; or R$^{1a}$, R$^{1b}$, R$^{2a}$ and R$^{2b}$ taken together are optionally substituted carbocyclyl, optionally substituted heterocyclyl, optionally substituted aryl, or optionally substituted heteroaryl; or R$^{4a}$ and R$^{4b}$ taken together are CO, optionally substituted carbocyclyl, optionally substituted heterocyclyl, optionally substituted aryl, or optionally substituted heteroaryl; or R$^{4a}$, R$^{4b}$, R$^{5a}$ and R$^{5b}$ taken together are optionally substituted carbocyclyl, optionally substituted heterocyclyl, optionally substituted aryl, or optionally substituted heteroaryl;

R$^3$ is absent, hydrogen, OH, OR$^{15}$, NH$_2$, NR$^{16}$R$^{17}$, NR$^{16}$COR$^{18}$, NR$^{16}$S(O)$_p$R$^{18}$, S(O)$_p$R$^{18}$, N$_3$, optionally substituted carbocyclyl, optionally substituted heterocyclyl, optionally substituted aryl, or optionally substituted heteroaryl; or $R^{2a}$, $R^{2b}$ and $R^3$ taken together are optionally substituted carbocyclyl, optionally substituted heterocyclyl, optionally substituted aryl, or optionally substituted heteroaryl;

each $R^6$ and $R^7$ is independently H, methyl, methoxy, CN, F, Cl, Br, I, $^{123}$I or $CF_3$;

$R^8$, $R^9$, $R^{10}$, $R^{11}$ and $R^{12}$ are each independently hydrogen, halogen, optionally substituted $C_1$-$C_6$ alkyl, optionally substituted $C_1$-$C_6$ alkoxy, or optionally substituted $C_1$-$C_6$ alkylamino; or $R^8$ and $R^9$ are optionally substituted carbocyclyl or optionally substituted heterocyclyl; or $R^{11}$ and $R^{12}$ taken together form an optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted carbocyclyl, optionally substituted heterocyclyl, optionally substituted aryl, or optionally substituted heteroaryl; or $R^{16}$ and $R^{17}$ are taken together to form an optionally substituted heterocyclyl, or optionally substituted heteroaryl; and each m is independently 0, 1 or 2;
each n is independently 0, 1 or 2;
each p is independently 0, 1 or 2; and
each t is independently 1 or 2.

In one embodiment of the compounds of formula (I-A) or (I), the compound has the structure of formula (Ia):

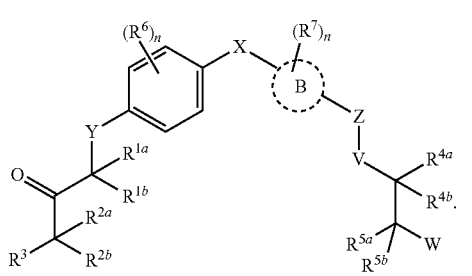

(Ia)

In one embodiment of the compounds of formula (I-A), (I) or (Ia), B is phenyl, pyridinyl, pyrimidinyl, or thiophene.

In one embodiment of the compounds of formula (I-A) or (I), the compound has the structure of formula (Ib):

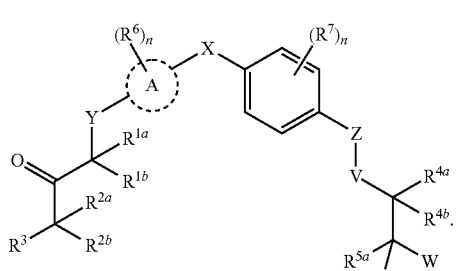

(Ib)

In one embodiment of the compounds of formula (I-A), (I) or (Ib), A is phenyl, pyridinyl, pyrimidinyl, or thiophene.

In one embodiment of the compounds of formula (I-A) or (I), the compound has the structure of formula (Ic):

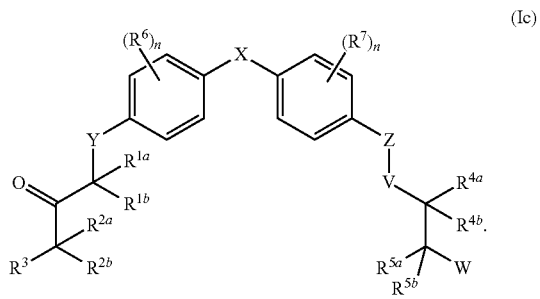

(Ic)

In one embodiment of the compounds of formula (I-A), (I) or (Ia)-(Ic), X is a bond. In other embodiments, X is —$(CR^8R^9)_t$— or —$NR^{10}$—. In another embodiment, X is —$NR^{10}$—. In some embodiments, X is —$NR^{10}$—, wherein $R^{10}$ is hydrogen or optionally substituted $C_1$-$C_6$ alkyl. In another embodiment, $R^{10}$ is hydrogen. In some embodiments, X is —$NR^{10}$—, wherein $R^1$ is methyl.

In one embodiment of the compounds of formula (I-A), (I) or (Ia)-(Ic), X is —$(CR^8R^9)_t$—. In some embodiments, X is —$(CR^8R^9)_t$—, wherein each $R^8$ and $R^9$ are independently hydrogen or optionally substituted $C_1$-$C_6$ alkyl. In some embodiments, X is —$(CR^8R^9)_t$—, wherein each R and $R^9$ are hydrogen. In some embodiments, X is —$(CR^8R^9)_t$—, wherein each $R^8$ and $R^9$ are methyl.

In one embodiment of the compounds of formula (I-A), (I) or (Ia)-(Ic), the instance of t when X is —$(CR^8R^9)_t$— is 1. In other embodiments, the instance of t when X is —$(CR^8R^9)_t$— is 2.

In one embodiment of the compounds of formula (I-A), (I) or (Ia)-(Ic), Y is —$(CR^8R^9)_t$—, —O—, or —$NR^{10}$—. In other embodiments, Y is —O—. In another embodiment, Y is —$(CR^8R^9)_t$—. In another embodiment, Y is —$(CR^8R^9)_t$—, wherein each $R^8$ and $R^9$ are hydrogen.

In one embodiment of the compounds of formula (I-A), (I) or (Ia)-(Ic), the instance of t when Y is —$(CR^8R^9)_t$— is 1.

In one embodiment of the compounds of formula (I-A), (I) or (Ia)-(Ic), Y is —$NR^{10}$—. In another embodiment, Y is —$NR^{10}$—, wherein $R^1$ is hydrogen or optionally substituted $C_1$-$C_6$ alkyl. In another embodiment, Y is —$NR^1$—, $R^1$ is hydrogen. In another embodiment, Y is —$NR^1$—, $R^1$ is methyl.

In one embodiment of the compounds of formula (I-A), (I) or (Ia)-(Ic), Z is —$(CR^8R^9)_t$—, O, or $NR^{10}$. In one embodiment, Z is O. In some embodiments, Z is —$(CR^8R^9)_t$—. In another embodiment, Z is —$(CR^8R^9)_t$—, wherein each $R^8$ and $R^9$ are hydrogen.

In one embodiment of the compounds of formula (I-A), (I) or (Ia)-(Ic), the instance of t when Z is —$(CR^8R^9)_t$— is 1.

In one embodiment of the compounds of formula (I-A), (I) or (Ia)-(Ic), Z is —$NR^{10}$—. In some embodiments, Z is —$NR^{10}$—, wherein $R^1$ is hydrogen or optionally substituted $C_1$-$C_6$ alkyl. In some embodiments, Z is —$NR^{10}$—, wherein $R^1$ is hydrogen. In some embodiments, Z is —$NR^{10}$—, wherein $R^{10}$ is methyl.

In one embodiment of the compounds of formula (I-A), (I) or (Ia)-(Ic), V is a bond. In other embodiments, V is optionally substituted —$C(R^{11}R^{12})_m$—. In one embodiment, is optionally substituted —$C(R^{11}R^{12})_m$—, wherein each $R^{11}$ and $R^{12}$ are hydrogen.

In one embodiment of the compounds of formula (I-A), (I) or (Ia)-(Ic), m is 1.

In one embodiment of the compounds of formula (I-A) or (I), the compound has the structure of formula (Id):

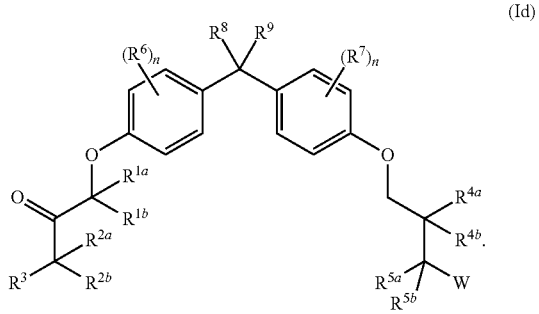

In one embodiment of the compounds of formula (I-A), (I) or (Ia)-(Id), each R and $R^9$ are independently hydrogen or optionally substituted $C_1$-$C_6$ alkyl.

In one embodiment of the compounds of formula (I-A) or (I), the compound has the structure of formula (Ie):

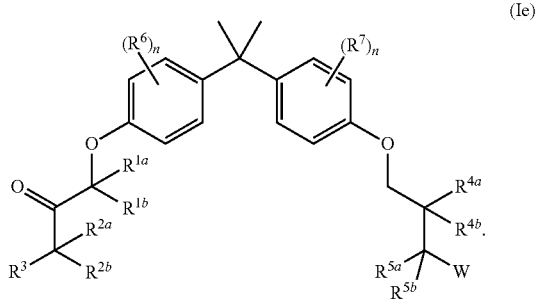

In one embodiment of the compounds of formula (I-A), (I) or (Ia)-(Ie), $R^{1a}$ and $R^{1b}$ are each hydrogen or optionally substituted $C_{1-6}$ alkyl. In other embodiments, $R^{1a}$ and $R^{1b}$ are each hydrogen.

In one embodiment of the compounds of formula (I-A), (I) or (Ia)-(Ie), $R^{2a}$ and $R^{2b}$ are each hydrogen or optionally substituted $C_{1-6}$ alkyl. In other embodiments, $R^{2a}$ and $R^{2b}$ are each hydrogen.

In one embodiment of the compounds of formula (I-A), (I) or (Ia)-(Ie), $R^3$ is —$NR^{16}R^{17}$, —$NR^{16}COR^{18}$, —$NR^{16}S(O)_pR^{18}$, —$S(O)_pR^8$, optionally substituted carbocyclyl, optionally substituted heterocyclyl, optionally substituted aryl, or optionally substituted heteroaryl. In other embodiments, $R^3$ is —$NR^{16}R^{17}$.

In one embodiment of the compounds of formula (I-A), (I) or (Ia)-(Ie), $R^{16}$ and $R^{17}$ are taken together with the intervening atom to form an optionally substituted heterocyclyl or optionally substituted heteroaryl.

In one embodiment of the compounds of formula (I-A), (I) or (Ia)-(Ie), $R^3$ is —$NR^{16}S(O)_pR^{18}$ or —$S(O)_pR^{18}$.

In one embodiment of the compounds of formula (I-A), (I) or (Ia)-(Ie), $R^{18}$ is $C_1$-$C_6$ alkyl; and p is 2.

In one embodiment of the compounds of formula (I-A), (I) or (Ia)-(Ie), $R^{2a}$, $R^{2b}$ and $R^3$ taken together with the intervening atom are optionally substituted carbocyclyl, optionally substituted heterocyclyl, optionally substituted aryl, or optionally substituted heteroaryl. In other embodiments, $R^{2a}$, $R^{2b}$ and $R^3$ taken together with the intervening atom are optionally substituted heteroaryl. In some embodiments, $R^{2a}$, $R^{2b}$ and $R^3$ taken together with the intervening atom are optionally substituted tetrazolyl, imidazolyl, 1,2,3-triazolyl, oxazole, pyrazinyl, pyrimidinyl, or 1,3,5-triazinyl.

In one embodiment of the compounds of formula (I-A), (I) or (Ia)-(Ie), R is hydrogen, halogen, optionally substituted $C_{1-6}$ alkyl, or optionally substituted $C_{1-6}$ alkoxy. In some embodiments, $R^{4a}$ is optionally substituted $C_{1-6}$ alkyl or hydrogen. In other embodiments, $R^{4a}$ is hydroxy.

In one embodiment of the compounds of formula (I-A), (I) or (Ia)-(Ie), $R^{4b}$ is hydrogen, halogen, optionally substituted $C_{1-6}$ alkyl, or optionally substituted $C_{1-6}$ alkoxy. In some embodiments, $R^{4b}$ is hydrogen.

In one embodiment of the compounds of formula (I-A), (I) or (Ia)-(Ie), $R^{5a}$ is hydrogen, halogen, optionally substituted $C_{1-6}$ alkyl, or optionally substituted $C_{1-6}$ alkoxy. In one embodiment, $R^{5a}$ is hydrogen.

In one embodiment of the compounds of formula (I-A), (I) or (Ia)-(Ie), $R^{5b}$ is hydrogen, halogen, optionally substituted $C_{1-6}$ alkyl, or optionally substituted $C_{1-6}$ alkoxy. In one embodiment, $R^{5b}$ is hydrogen.

In one embodiment of the compounds of formula (I-A), (I) or (Ia)-(Ie), W is a halogen. In other embodiments, W is Cl.

In one embodiment of the compounds of formula (I-A), (I) or (Ia)-(Ie), n is 1. In other embodiments, n is 2.

In one embodiment of the compounds of formula (I-A), (I) or (Ia)-(Ie), each occurrence of $R^6$ and $R^7$ is independently H, methyl, methoxy, CN, F, Cl, Br, or I. In other embodiments, each occurrence of $R^6$ and $R^7$ is F, Cl, Br, or I. In one embodiment, each occurrence of R and $R^7$ is Cl.

In one embodiment of the compounds of formula (I-A), (I) or (Ia)-(Ie), D is —$(CH_2)_2$—.

In one embodiment of the compounds of formula (I-A), the compound has the structure of formula (A):

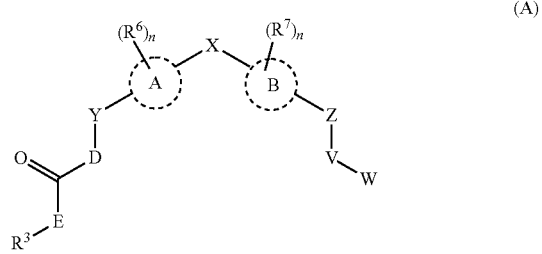

or a pharmaceutically acceptable salt, tautomer, stereoisomer or prodrug thereof, wherein:

A and B are each independently aryl or heteroaryl;

X is a bond, —$(CR^{8a}R^{9a})_t$—, —O—, —C(=O)—, —S—, —S(=O)—, —$SO_2$—, —$NR^{10}$—, —$N(R^{10})CO$—, —$CON(R^{10})$—, —$NR^{10}SO_2$—, or —$SO_2NR^{10}$—;

Y and Z are each independently a bond, —$(CR^{8b}R^{9b})_t$—, —O—, —S—, —S(=O)—, —$SO_2$—, —$NR^{10}$—, —$N(R^{10})CO$—, —$CON(R^{10})$—, —$NR^{10}SO_2$—, or —$SO_2NR^{10}$—;

V is a bond, optionally substituted —$(CR^{11}R^{12})_m$—, —C(=O)—, —$N(R^{10})CO$—, —$CONR^{10}$—, or —$NSO_2R^{10}$—;

W is hydrogen, halogen, —$CF_3$, —$CF_2R^{10}$, —CN, —$OR^{13}$—$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —O— or —NR$^{10}$— and E is —(CR$^{2a}$R$^{2b}$)$_g$—, —O—, —NR$^{10}$—, or —NR$^{10}$—(CR$^{2a}$R$^{2b}$)$_g$—;

or alternatively, E is —O—, —NR$^{10}$— or —NR$^{10}$—(CR$^{2a}$R$^{2b}$)$_g$—, and D is —(CR$^{1a}$R$^{1b}$)$_q$—, —O—, or —NR$^{10}$—;

R$^{1a}$, R$^{1b}$, R$^{2a}$, and R$^{2b}$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or (R$^{1a}$ and R$^{1b}$) or (R$^{2a}$ and R$^{2b}$) taken together form an oxo (═O), an optionally substituted carbocyclyl, optionally substituted heterocyclyl, an optionally substituted aryl, or an optionally substituted heteroaryl; or R$^{2a}$ and R$^1$ taken together form an optionally substituted heterocyclyl;

R$^{11}$ and R$^{12}$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^{11}$ and R$^{12}$, on a same carbon atom or a different carbon atom, taken together form an optionally substituted carbocyclyl, optionally substituted heterocyclyl, an optionally substituted aryl, or an optionally substituted heteroaryl;

R$^3$ is hydrogen, halogen, —CN, —CF$_3$, —OH, —NH$_2$, —N$_3$, optionally substituted C$_1$-C$_6$ alkyl, optionally substituted C$_2$-C$_6$ alkenyl, optionally substituted C$_2$-C$_6$ alkynyl, optionally substituted —OR$^{15}$, optionally substituted —SR$^8$, optionally substituted C$_1$-C$_6$ alkoxy, —NR$^{16}$R$^{17}$, —NR$^{16}$SR$^8$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, optionally substituted —SO$_2$R$^{18}$, optionally substituted carbocyclyl, optionally substituted heterocyclyl, optionally substituted aryl, or optionally substituted heteroaryl;

R$^6$ and R$^7$ are each independently H, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^{8a}$ and R$^{9a}$ are each independently hydrogen, halogen, —OH, or C$_1$-C$_3$ alkyl; or R$^{8a}$ and R$^{9a}$ taken together form an optionally substituted carbocyclyl or optionally substituted heterocyclyl;

R$^{8b}$, and R$^{9b}$ are each independently hydrogen, —OH, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or R$^{8b}$ and R$^{9b}$ taken together form an optionally substituted carbocyclyl or optionally substituted heterocyclyl;

R$^{10}$ is hydrogen, optionally substituted C$_1$-C$_6$ alkyl, optionally substituted C$_2$-C$_6$ alkenyl, optionally substituted C$_2$-C$_6$ alkynyl, —CO(C$_1$-C$_6$ alkyl), optionally substituted carbocyclyl, optionally substituted heterocyclyl, optionally substituted aryl, or optionally substituted heteroaryl;

or alternatively, R$^{2a}$ and R$^{10}$ taken together form an optionally substituted heterocyclyl;

R$^{13}$, R$^{14}$, R$^1$, R$^{16}$, R$^{17}$ and R$^{18}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl; or R$^{14}$ and R$^{15}$ taken together form an optionally substituted heterocyclyl;

m is 0, 1, 2, 3, or 4;

each n is independently 0, 1 or 2;

q is 0, 1 or 2;

each g is independently 0, 1, 2, 3, or 4; and each t is independently 1 or 2.

In one embodiment of the compounds of formula (I-A) or (A), A and B are each independently 5- or 6-membered aryl or heteroaryl. In other embodiments, A and B are each independently selected from phenyl, pyridyl, pyrimidyl, or thiophene.

In one embodiment of the compounds of formula (I-A) or (A), A has a meta or para connectivity with X and Y.

In one embodiment of the compounds of formula (I-A) or (A), B has a meta or para connectivity with X and Z.

In one embodiment of the compounds of formula (I-A) or (A), D is —(CR$^{1a}$R$^{1b}$)$_q$—; E is —O—, —NR$^{10}$—, or —NR$^{10}$—(CR$^{2a}$R$^{2b}$)$_g$—; and q is 1 or 2.

In one embodiment of the compounds of formula (I-A) or (A), D is —O— or —NR$^{10}$—; E is —(CR$^{2a}$R$^{2b}$)$_g$—; and g is 1, 2, 3, or 4.

In one embodiment of the compounds of formula (I-A) or (A), D is —O— or —NR$^{10}$—; and E is —O—, —NR$^{10}$— or —NR$^{10}$—(CR$^{2a}$R$^{2b}$)$_g$—.

In one embodiment of the compounds of formula (I-A) or (A), R$^3$ is selected from hydrogen, optionally substituted C$_1$-C$_6$ alkyl, optionally substituted —OR$^{15}$, optionally substituted —SR$^{18}$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, or optionally substituted —SO$_2$R$^{18}$. In one embodiment, R$^3$ is selected from hydrogen, —C$_1$-C$_3$ alkyl, —NR$^{16}$SO(C$_1$-C$_3$ alkyl), —NR$^{16}$SO$_2$(C$_1$-C$_3$ alkyl), —SONR$^{14}$R$^{15}$, —SO$_2$NR$^{14}$R$^{15}$, —SOR$^{18}$, or —SO$_2$R$^{18}$. In other embodiments, R$^3$ is selected from —NHSO$_2$(C$_1$-C$_3$ alkyl), —NCH$_3$SO$_2$(C$_1$-C$_3$ alkyl), or —SO$_2$(C$_1$-C$_3$ alkyl).

In one embodiment of the compounds of formula (I-A) or (A), Z is a bond, —CH$_2$—, —C(CH$_3$)H—, —O—, —S—, —NH—, —NCH$_3$—, or —N(COCH$_3$)—; and V is —(CR$^{11}$R$^{12}$)$_m$—.

In one embodiment of the compounds of formula (I-A) or (A), Z is a bond, —CH$_2$—, —C(CH$_3$)H—, —O—, —S—, —NH—, —NCH$_3$—, or —N(COCH$_3$)—; V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—; and W is halogen, —NH$_2$, or —CF$_3$.

In one embodiment of the compounds of formula (I-A) or (A), X is a bond, —NR$^{10}$—, or —(CR$^{8a}$R$^{9a}$)$_t$—. In other embodiments, X is a bond, —NH—, —CH$_2$—, —C(CH$_3$)$_2$—, or —CH$_2$CH$_2$—.

In one embodiment of the compounds of formula (I-A) or (A), Y is a bond, —CH$_2$—, —C(CH$_3$)H—, —O—, —S—, —NH—, —NCH$_3$—, or —N(COCH$_3$)—.

In one embodiment of the compounds of formula (I-A) or (A), W is hydrogen, halogen, —CF$_3$, or —NH$_2$. In some embodiments, W is aryl, optionally substituted with halogen, C$_1$-C$_3$ alkyl, —CN, —CF$_3$, —OH, C$_1$-C$_3$ alkoxy, —NR$^{13}$R$^{14}$, or —SO$_2$R$^{16}$. In another embodiment, W is a phenyl, optionally substituted with halogen, C$_1$-C$_3$ alkyl, —CN, —CF$_3$, —OH, or C$_1$-C$_3$ alkoxy.

In one embodiment of the compounds of formula (I-A) or (A), R$^6$ and R$^7$ is each independently halogen, —CN, —CF$_3$, —OH, methyl, or methoxy. In another embodiment, R and R$^7$ is each independently Cl, —CN, —CF$_3$, —OH, methyl, or methoxy.

In one embodiment of the compounds of formula (I-A) or (A), R$^{8b}$ and R$^{9b}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl. In one embodiment, R$^{11}$ and R$^{12}$ are not —OH.

In one embodiment of the compounds of formula (I-A) or (A), R$^{11}$ and R$^{12}$ are each independently hydrogen, halogen, —OH, or C$_1$-C$_3$ alkyl.

In one embodiment of the compounds of formula (I-A) or (A), g is independently 0, 1, 2, or 3.

In one embodiment of the compounds of formula (I-A) or (A), the compound has the structure of formula (B):

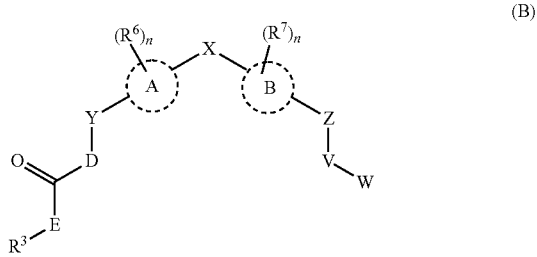

(B)

or a pharmaceutically acceptable salt, tautomer, stereoisomer or prodrug thereof, wherein:

A and B are each independently selected from phenyl, pyridyl, pyrimidyl, or thiophene;

X is a bond, —NR$^1$—, or —(CR$^{8a}$R$^{9a}$)$_t$—;

Y is a bond, —(CR$^{8b}$R$^{9b}$)$_t$—, —O—, —S—, —S(=O)—, —SO$_2$—, or —NR$^{10}$—;

Z is a bond, —CH$_2$—, —C(CH$_3$)H—, —O—, —S—, —NH—, —NCH$_3$—, or —N(COCH$_3$)—;

V is —(CR$^{11}$R$^{12}$)$_m$—;

W is halogen, —NH$_2$, or —CF$_3$;

D is —O— or —NR$^{10}$— and E is —(CR$^{2a}$R$^{2b}$)$_g$—, —O—, —NR$^{10}$—, or —NR$^{10}$—(CR$^{2a}$R$^{2b}$)$_g$—;

or alternatively, E is —O—, —NR$^{10}$— or —NR$^{10}$—(CR$^{2a}$R$^{2b}$)$_g$—, and D is —(CR$^{1a}$R$^{1b}$)$_q$—, —O—, or —NR$^{10}$—;

R$^{1a}$, R$^{1b}$, R$^{2a}$, and R$^{2b}$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or (R$^{1a}$ and R$^{1b}$) or (R$^{2a}$ and R$^{2b}$) taken together form an oxo (=O), an optionally substituted carbocyclyl, optionally substituted heterocyclyl, an optionally substituted aryl, or an optionally substituted heteroaryl;

R$^3$ is hydrogen, halogen, —CN, —CF$_3$, —OH, —NH$_2$, —N$_3$, optionally substituted —OR$^1$, optionally substituted —SR$^{18}$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, optionally substituted —SO$_2$R$^{18}$, optionally substituted carbocyclyl, optionally substituted heterocyclyl, optionally substituted aryl, or optionally substituted heteroaryl;

R$^{11}$ and R$^{12}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, or —OCO(C$_1$-C$_3$ alkyl);

R$^6$ and R$^7$ is each independently halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^{8a}$ and R$^{9a}$ are each independently hydrogen, halogen, —OH, or C$_1$-C$_3$ alkyl; or R$^{8a}$ and R$^{9a}$ taken together form an optionally substituted carbocyclyl or optionally substituted heterocyclyl;

R$^{8b}$ and R$^{9b}$ are each independently hydrogen, —OH, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or $R^{8b}$ and $R^{9b}$ taken together form an optionally substituted carbocyclyl or optionally substituted heterocyclyl;

$R^{10}$ is each independently hydrogen, optionally substituted $C_1$-$C_6$ alkyl, optionally substituted $C_2$-$C_6$ alkenyl, optionally substituted $C_2$-$C_6$ alkynyl, —CO($C_1$-$C_6$ alkyl), optionally substituted carbocyclyl, optionally substituted heterocyclyl, optionally substituted aryl, or optionally substituted heteroaryl;

$R^{13}$, $R^{14}$, $R^1$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl; or $R^{14}$ and $R^{15}$ taken together form an optionally substituted heterocyclyl;

m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (B), $R^{1a}$, $R^1$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (═O), an optionally substituted carbocyclyl, or an optionally substituted heterocyclyl.

In one embodiment of the compounds of formula (I-A) or (B), $R^3$ is selected from hydrogen, optionally substituted $C_1$-$C_6$ alkyl, optionally substituted —$OR^{15}$, optionally substituted —$SR^{18}$, optionally substituted $C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, optionally substituted —$SOR^{18}$, or optionally substituted —$SO_2R^{18}$. In one embodiment, $R^3$ is selected from hydrogen, —$C_1$-$C_3$ alkyl, —$NR^{16}SO(C_1$-$C_3$ alkyl), —$NR^{16}SO_2(C_1$-$C_3$ alkyl), —$SONR^{14}R^{15}$, —$SO_2NR^{14}R^{15}$, —$SOR^{18}$, or —$SO_2R^{18}$. In another embodiment, $R^3$ is selected from —$NHSO_2(C_1$-$C_3$ alkyl), —$NCH_3SO_2(C_1$-$C_3$ alkyl), or —$SO_2(C_1$-$C_3$ alkyl).

In one embodiment of the compounds of formula (I-A) or (B), Z is a bond, —$CH_2$—, —$C(CH_3)H$—, —O—, —S—, —NH—, —$NCH_3$—, or —$N(COCH_3)$—; V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—; and W is halogen, —$NH_2$, or —$CF_3$.

In one embodiment of the compounds of formula (I-A) or (A), the compound has the structure of formula (C):

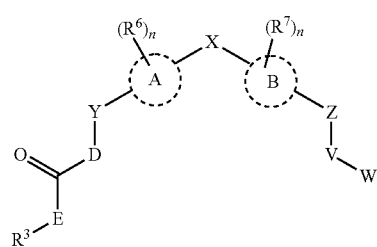

(C)

or a pharmaceutically acceptable salt, tautomer, stereoisomer or prodrug thereof, wherein:

A and B are each independently selected from phenyl, pyridyl, pyrimidyl, or thiophene;

X is a bond, —$NR^{10}$—, or —($CR^{8a}R^{9a}$)$_t$;

Y and Z are each independently a bond, —($CR^8R^9$)$_t$—, —O—, —S—, —S(═O)—, —$SO_2$—, or —$NR^{10}$—;

V is a bond, optionally substituted —($CR^{11}R^{12}$)$_m$—, —C(═O)—, —N(R')CO—, —$CONR^{10}$—, or —$NSO_2R^{10}$—;

W is hydrogen, halogen, —$CF_3$, —$CF_2R^{10}$, —CN, —$OR^{13}$ —$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —($CR^{1a}R^{1b}$)$_q$— and E is —O—, —$NR^{10}$—, or —$NR^{10}$—($CR^{2a}R^{2b}$)$_g$—.

or alternatively, D is —O— or —$NR^{10}$— and E is —($CR^{2a}R^{2b}$)$_g$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (═O), an optionally substituted carbocyclyl, or an optionally substituted heterocyclyl;

$R^{11}$ and $R^{12}$ are each independently hydrogen, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{11}$ and $R^{12}$, on a same carbon atom or a different carbon atom, taken together form an optionally substituted carbocyclyl, optionally substituted heterocyclyl, an optionally substituted aryl, or an optionally substituted heteroaryl;

$R^3$ is selected from hydrogen, optionally substituted $C_1$-$C_6$ alkyl, optionally substituted —$OR^{15}$, optionally substituted —$SR^8$, optionally substituted $C_1$-$C_6$ alkoxy, —$NR^{16}R^{17}$, —$NR^{16}SR^{18}$, —$NR^6SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, optionally substituted —$SOR^{18}$, or optionally substituted —$SO_2R^{18}$;

$R^6$ and $R^7$ are each independently H, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, or optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^{8a}$ and $R^{9a}$ are each independently hydrogen, halogen, —OH, or $C_1$-$C_3$ alkyl; or $R^{8a}$ and $R^{9a}$ taken together form an optionally substituted carbocyclyl or optionally substituted heterocyclyl;

$R^{8b}$ and $R^{9b}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8b}$ and $R^{9b}$ taken together form an optionally substituted carbocyclyl or optionally substituted heterocyclyl;

$R^{10}$ is each independently hydrogen, optionally substituted $C_1$-$C_6$ alkyl, optionally substituted $C_2$-$C_6$ alkenyl, optionally substituted $C_2$-$C_6$ alkynyl, —CO($C_1$-$C_6$ alkyl), optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl; or $R^{14}$ and $R^{15}$ taken together form an optionally substituted heterocyclyl;

m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (C), Z is a bond, —$CH_2$—, —C($CH_3$)H—, —O—, —S—, —NH—, —$NCH_3$—, or —N($COCH_3$)—; V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—; and W is halogen, —$NH_2$, or —$CF_3$.

In one embodiment of the compounds of formula (I-A) or (A)-(C), A has a meta or para connectivity with X and Y.

In one embodiment of the compounds of formula (I-A) or (A)-(C), B has a meta or para connectivity with X and Z.

In one embodiment of the compounds of formula (I-A) or (A)-(C), A and B are each phenyl.

In one embodiment of the compounds of formula (I-A) or (A)-(C), $R^3$ is selected from —$NHSO_2$($C_1$-$C_3$ alkyl), —$NCH_3SO_2$($C_1$-$C_3$ alkyl), or —$SO_2$($C_1$-$C_3$ alkyl).

In one embodiment of the compounds of formula (I-A) or (A), the compound has the structure of formula (D):

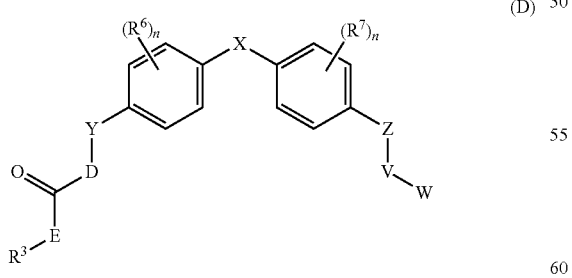

(D)

or a pharmaceutically acceptable salt, tautomer, stereoisomer or prodrug thereof, wherein:
X is a bond, —$NR^{10}$—, or —$(CR^{8a}R^{9a})_t$—;
Y and Z are each independently a bond, —$CH_2$—, —C($CH_3$)H—, —O—, —S—, —NH—, —$NCH_3$—, or —N($COCH_3$)—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;
W is halogen, —$NH_2$, or —$CF_3$.
D is —O— or —$NR^{10}$— and E is —$(CR^{2a}R^{2b})_g$—, —O—, —$NR^{10}$—, or —$NR^{10}$—$(CR^{2a}R^{2b})_g$—;
or alternatively, E is —O—, —$NR^{10}$— or —$NR^{10}$—$(CR^{2a}R^{2b})_g$—, and D is —$(CR^{1a}R^{1b})_q$—, —O—, or —$NR^{10}$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^8$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;

$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;

$R^{10}$ is each independently hydrogen, $C_1$-$C_3$ alkyl, $C_2$-$C_3$ alkenyl, $C_2$-$C_3$ alkynyl, —CO($C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and R taken together form an optionally substituted 5- or 6-membered heterocyclyl;

m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (A), the compound has the structure of formula (E):

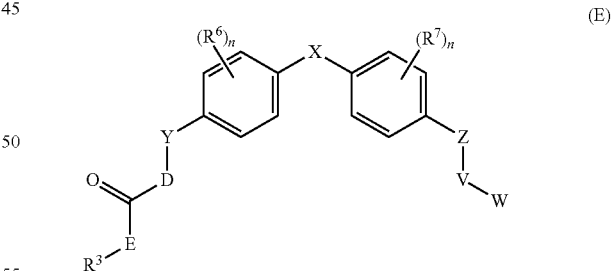

(E)

or a pharmaceutically acceptable salt, tautomer, stereoisomer or prodrug thereof, wherein:
X is a bond, —$NR^{10}$—, or —$(CR^{8a}R^{9a})_t$—;
Y and Z are each independently a bond, —$CH_2$—, —C($CH_3$)H—, —O—, —S—, —NH—, —$NCH_3$—, or —N($COCH_3$)—;
V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;
W is halogen, —$NH_2$ or —$CF_3$;

D is —O— or —NR$^{10}$— and E is —(CR$^{2a}$R$^{2b}$)$_{gg}$—;
or alternatively, E is —O—, —NR$^{10}$— or —NR$^{10}$—(CR$^{2a}$R$^{2b}$)$_g$—, and D is —(CR$^{1a}$R$^{1b}$)$_q$—;

R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —C$_1$-C$_6$ alkyl, —OR$^{15}$, —SR$^8$, —C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, —SOR$^{18}$ or —SO$_2$R$^{18}$;

R$^6$ and R$^7$ are each independently H, halogen, —CN, —CF$_3$, —OH, or C$_1$-C$_3$ alkyl;

R$^{8a}$ and R$^{9a}$ are each independently hydrogen, halogen, —OH, or C$_1$-C$_3$ alkyl; or R$^{8a}$ and R$^{9a}$ taken together form an 3- to 6-membered carbocyclyl or heterocyclyl;

R$^{10}$ is each independently hydrogen, C$_1$-C$_3$ alkyl, C$_2$-C$_3$ alkenyl, C$_2$-C$_3$ alkynyl, or —CO(C$_1$-C$_3$ alkyl);

R$^{13}$, R$^{14}$, R$^{15}$, R$^{16}$R$^{17}$ and R$^{18}$ are each independently hydrogen, C$_1$-C$_3$ alkyl, C$_2$-C$_3$ alkenyl, or C$_2$-C$_3$ alkynyl; or R$^{14}$ and R$^{15}$ taken together form an optionally substituted 5- or 6-membered heterocyclyl;

m is 0, 1, 2, 3, or 4;
each n is independently 0, 1 or 2;
q is 1 or 2;
g is 0, 1, 2, 3, or 4;
gg is 1, 2, 3, or 4; and
t is 1 or 2.

In one embodiment of the compounds of formula (I-A), (D), or (E), W is Cl, Br, I, or F.

In one embodiment of the compounds of formula (I-A), (D), or (E), D is —CH$_2$—, —CH(CH$_3$)—, —C(CH$_3$)$_2$—, or —CH$_2$CH$_2$—.

In one embodiment of the compounds of formula (I-A), (D), or (E), q is 0.

In one embodiment of the compounds of formula (I-A), (D), or (E), E is —CH$_2$—, —CH(CH$_3$)—, —C(CH$_3$)$_2$—, —CH$_2$CH$_2$—, or —CH$_2$CH$_2$CH$_2$—.

In one embodiment of the compounds of formula (I-A), (D), or (E), g is 0.

In one embodiment of the compounds of formula (I-A), (D), or (E), R$^3$ is selected from —NHSO$_2$(C$_1$-C$_3$ alkyl), —NCH$_3$SO$_2$(C$_1$-C$_3$ alkyl), or —SO$_2$(C$_1$-C$_3$ alkyl).

In one embodiment of the compounds of formula (I-A), (D), or (E), R$^3$ is C$_1$-C$_6$ alkyl.

In one embodiment of the compounds of formula (I-A), (D), or (E), R$^6$ and R$^7$ are each independently H, halogen, —CN, or methyl.

In one embodiment of the compounds of formula (I-A), (D), or (E), X is a bond, —CH$_2$—, —C(CH$_3$)$_2$—, —CH$_2$CH$_2$—, —NH—, —N(CH$_3$)—, —N(iPr)-, or —N(COCH$_3$)—.

In one embodiment of the compounds of formula (I-A), (D), or (E), Z is —CH$_2$—, —O—, —NH—, —NCH$_3$—, or —N(COCH$_3$)—.

In one embodiment of the compounds of formula (I-A), (D), or (E), Y is —CH$_2$—, —O—, —NH—, or —NCH$_3$—.

In one embodiment of the compounds of formula (I-A), (D), or (E), at least one of Z and Y is —O—.

In one embodiment of the compounds of formula (I-A), the compound has the structure of formula (II):

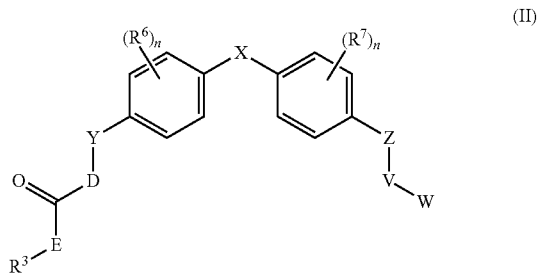

(II)

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is —CF$_2$R$^{10}$, —NR$^{13}$R$^{14}$, optionally substituted carbocyclyl, optionally substituted heterocyclyl, optionally substituted aryl, or optionally substituted heteroaryl;

D is —(CR$^{1a}$R$^{1b}$)$_q$;
E is —(CR$^{2a}$R$^{2b}$)$_g$;

R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —C$_1$-C$_6$ alkyl, —OR$^{15}$, —SR$^8$, —C$_1$-C$_6$ alkoxy, —NR$^{16}$R$^{17}$, —NR$^{16}$SR$^{18}$, —NR$^6$SOR$^{18}$, —NR$^{16}$SO$_2$R$^8$, —NR$^6$COR$^{18}$, —CONR$^{14}$R$^{15}$, —SONR$^{14}$R$^{15}$, —SO$_2$NR$^{14}$R$^{15}$, —SOR$^{18}$, or —SO$_2$R$^{18}$;

R$^6$ and R$^7$ are each independently H, halogen, —CN, —CF$_3$, —OH, or C$_1$-C$_3$ alkyl;

R$^{8a}$ and R$^{9a}$ are each independently hydrogen, halogen, —OH, or C$_1$-C$_3$ alkyl; or R$^{8a}$ and R$^{9a}$ taken together form an optionally substituted carbocyclyl or optionally substituted heterocyclyl;

R$^{10}$ is each independently hydrogen, C$_1$-C$_3$ alkyl, C$_2$-C$_3$ alkenyl, C$_2$-C$_3$ alkynyl, or —CO(C$_1$-C$_3$ alkyl);

R$^{13}$, R$^{14}$, R$^{15}$, R$^{16}$R$^{17}$ and R$^{18}$ are each independently hydrogen, C$_1$-C$_3$ alkyl, C$_2$-C$_3$ alkenyl, or C$_2$-C$_3$ alkynyl; or R$^{14}$ and R$^{15}$ taken together form an optionally substituted 5- or 6-membered heterocyclyl;

m is 0, 1, 2, 3, or 4;
each n is independently 0, 1 or 2;
q is 0, 1 or 2;
g is 0, 1, 2, 3, or 4; and
t is 1 or 2.

In one embodiment of the compounds of formula (II), X is —(CR$^{8a}$R$^{9a}$)— and R$^{8a}$ and R$^{9a}$ taken together form 3- to 6-membered carbocyclyl or 3- to 6-membered heterocyclyl containing one heteroatom selected from O, S, or N.

In one embodiment, the present disclosure provides compounds as disclosed in Table A1 or a pharmaceutically acceptable salt, tautomer, stereoisomer or prodrug thereof.

In one embodiment, the present disclosure provides compounds as disclosed in Table A2 or a pharmaceutically acceptable salt, tautomer, stereoisomer or prodrug thereof.

In one embodiment, the present disclosure provides compounds as disclosed in Table A3 or a pharmaceutically acceptable salt, tautomer, stereoisomer or prodrug thereof. In one embodiment, the present disclosure provides compounds as disclosed in Table B or a pharmaceutically acceptable salt, tautomer, stereoisomer or prodrug thereof.

In certain aspects, the present disclosure provides a pharmaceutical composition comprising any one of the compound as disclosed herein (e.g., a compound of formula (I), (I-A), (Ia)-(Ie), (A)-(E), and (II) and compounds of Tables A1, A2, A3 and B) and a pharmaceutically acceptable carrier.

In one embodiment, the pharmaceutical composition of the present disclosure, further comprising one or more additional therapeutic agents. In some embodiments, the one or more additional therapeutic agents is for treating prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

In one embodiment, the present disclosure provides a method for modulating androgen receptor activity, comprising administering any one of the compound as disclosed herein (e.g., compounds of formula (I), (I-A), (Ia)-(Ie), (A)-(E), and (II) and compounds of Tables A1, A2, A3 and B) to a subject in need thereof. In one embodiment, the modulating androgen receptor activity is for treating a condition or disease selected from prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

In some aspects, the present disclosure provides a method for modulating androgen receptor activity, comprising administering a pharmaceutical composition comprising a compound of any one of the compound as disclosed herein (e.g., compounds of formula (I), (I-A), (Ia)-(Ie), (A)-(E), and (II) and compounds of Tables A1, A2, A3 and B), to a subject in need thereof.

In one embodiment, the present disclosure provides a method of treating cancer comprising administering any one of the compound as disclosed herein e.g., compounds of formula (I), (I-A), (Ia)-(Ie), (A)-(E), and (II) and compounds of Tables A1, A2, A3 and B) to a subject in need thereof. In some embodiments, the cancer is selected from prostate cancer, breast cancer, ovarian cancer, bladder cancer, pancreatic cancer, hepatocellular cancer, endometrial cancer, or salivary gland carcinoma. In one embodiment, the cancer is prostate cancer.

In one embodiment of any one of the methods of treatment of prostate cancer as disclosed herein, the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer. In one embodiment, the prostate cancer is metastatic castration-resistant prostate cancer. In other embodiments, the prostate cancer expresses full-length androgen receptor or truncated androgen receptor splice variant.

These, and other embodiments, are further described herein.

DETAILED DESCRIPTION

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, ±2%, ±1%, less than 1%, or any other value or range of values therein or therebelow. Furthermore, the phrases "less than about [a value]" or "greater than about [a value]" should be understood in view of the definition of the term "about" provided herein. The terms "about" and "approximately" can be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range can be an endpoint for the range encompassed thereby (e.g., the range 50-80 includes the ranges with endpoints such as 55-80, 50-70, etc.).

The term "a" or "an" refers to one or more of that entity; for example, "a androgen receptor modulator" refers to one or more androgen receptor modulators or at least one androgen receptor modulator. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors. Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

In the following description, certain specific details are set forth in order to provide a thorough understanding of various embodiments. However, one skilled in the art will understand that the disclosure can be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-Naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the disclosure with one or more molecules of solvent. The solvent can be water, in which case the solvate can be a hydrate. Alternatively, the solvent can be an organic solvent. Thus, the compounds of the present disclosure can exist as a hydrate, including a monohydrate, dihydrate, hemihydrate, sesquihydrate, trihydrate, tetrahydrate and the like, as well as the corresponding solvated forms. The compound of the disclosure can be true solvates, while in other cases, the compound of the disclosure can merely retain adventitious water or be a mixture of water plus some adventitious solvent.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents or excipients therefor.

An "effective amount" can refer to a therapeutically effective amount or a prophylactically effective amount.

A "therapeutically effective amount" refers to an amount effective, at dosages and for periods of time necessary, to achieve the desired therapeutic result, such as reduced tumor size, increased life span or increased life expectancy. A therapeutically effective amount of a compound can vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to a castration-resistant form. Typically, a prophylactic dose is used in subjects prior to or at an earlier stage of disease, so that a prophylactically effective amount can be less than a therapeutically effective amount.

In some embodiments, "Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" can be used interchangeably or can be different in that the particular malady or condition cannot have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present disclosure includes tautomers of any said compounds.

A "prodrug" refers to a derivative of a compound of the present disclosure that will be converted to the compound in vivo. In one embodiment of the present disclosure, a prodrug includes a compounds of formula (I), (I-A), (Ia)-(Ie), (A)-(E), or (II) having a free hydroxyl group (—OH) that is acetylated (—OCOMe) at one or more positions.

As used herein, a "subject" can be a human, non-human primate, mammal, rat, mouse, cow, horse, pig, sheep, goat, dog, cat and the like. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals and household pets (e.g., cats, dogs, swine, cattle, sheep, goats, horses, rabbits), and non-domestic animals such as wildlife and the like.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof.

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

The terms below, as used herein, have the following meanings, unless indicated otherwise:

"Amino" refers to the —NH$_2$ group.

"Cyano" refers to the —CN group.

"Halo" or "halogen" refers to bromo, chloro, fluoro or iodo.

"Hydroxy" or "hydroxyl" refers to the —OH group.

"Imino" refers to the =NH group.

"Nitro" refers to the —NO$_2$ group.

"Oxo" refers to the =O group.

"Thioxo" refers to the =S group.

"Acetyl" or "Ac" refers to —C(=O)CH$_3$ group.

"Alkyl" or "alkyl group" refers to a fully saturated, straight or branched hydrocarbon chain group having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-Nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain group, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the group through a single bond. The points of attachment of the alkylene chain to the rest of the molecule and to the group can be through one carbon or any two carbons within the chain. Unless stated otherwise specifically in the specification, an alkylene chain can be optionally substituted.

"Alkenyl" or "alkenyl group" refers to a straight or branched hydrocarbon chain group having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-Nonenyl, 2-Nonenyl, 3-Nonenyl, 4-Nonenyl, 5-Nonenyl, 6-Nonenyl, 7-Nonenyl, 8-Nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Examples of $C_1$-$C_3$ alkyl includes methyl, ethyl, n-propyl, and i-propyl. Examples of $C_1$-$C_4$ alkyl includes methyl, ethyl, n-propyl, i-propyl, n-butyl, i-butyl, and sec-butyl. Unless stated otherwise specifically in the specification, an alkyl group can be optionally substituted.

"Alkenylene" or "alkenylene chain" refers to a straight or branched divalent hydrocarbon chain group, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the group through a single bond. The points of attachment of the alkenylene chain to the rest of the molecule and to the group can be through one carbon or any two carbons within the chain. Unless stated otherwise specifically in the specification, an alkenylene chain can be optionally substituted.

"Alkynyl" or "alkynyl group" refers to a straight or branched hydrocarbon chain group having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain group, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the group through a single bond. The points of attachment of the alkynylene chain to the rest of the molecule and to the group can be through one carbon or any two carbons within the chain. Unless stated otherwise specifically in the specification, an alkynylene chain can be optionally substituted.

"Alkoxy" refers to a group of the formula —OR$_a$ where R$_a$ is an alkyl, alkenyl or alkenyl group as defined above containing one to twelve carbon atoms. Unless stated otherwise specifically in the specification, an alkoxy group can be optionally substituted.

"Alkylamino" refers to a group of the formula —NHR$_a$ or —NR$_a$R$_a$ where each R$_a$ is, independently, an alkyl, alkenyl or alkynyl group as defined above containing one to twelve carbon atoms. Unless stated otherwise specifically in the specification, an alkylamino group can be optionally substituted.

"Alkylcarbonyl" refers to the —C(=O)R$_a$ moiety, wherein R$_a$ is an alkyl, alkenyl or alkynyl group as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in R$_a$, as defined above. For example, "C$_1$-C$_{10}$ acyl" refers to alkylcarbonyl group as defined above, where R$_a$ is C$_1$-C$_{10}$ alkyl, C$_1$-C$_{10}$ alkenyl, or C$_1$-C$_{10}$ alkynyl group as defined above. Unless stated otherwise specifically in the specification, an alkyl carbonyl group can be optionally substituted.

"Aryl" refers to a hydrocarbon ring system group comprising hydrogen, 6 to 18 carbon atoms and at least one aromatic ring. For purposes of this invention, the aryl group can be a monocyclic, bicyclic, tricyclic or tetracyclic ring system, which can include fused or bridged ring systems. Aryl groups include, but are not limited to, aryl groups derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl groups that are optionally substituted.

"Aralkyl" refers to a group of the formula —R$_b$—R$_c$ where R$_b$ is an alkylene, alkenylene or alkynylene group as defined above and R$_c$ is one or more aryl groups as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon group consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl groups include, for example, cyclopropyl, cyclobutyl, cyclopentyl, cyclohexyl, cycloheptyl, and cyclooctyl. Polycyclic cycloalkyl groups include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon group consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl groups include, for example, cyclopentenyl, cyclohexenyl, cycloheptenyl, cyclooctenyl, and the like. Polycyclic cycloalkenyl groups include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon group consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl groups include, for example, cycloheptynyl, cyclooctynyl, and the like. Unless otherwise stated specifically in the specification, a cycloalkynyl group can be optionally substituted.

"Cycloalkylalkyl" refers to a group of the formula —R$_b$—R$_a$ where R$_b$ is an alkylene, alkenylene, or alkynylene group as defined above and Rd is a cycloalkyl, cycloalkenyl, cycloalkynyl group as defined above. Unless stated otherwise specifically in the specification, a cycloalkylalkyl group can be optionally substituted.

"Haloalkyl" refers to an alkyl group, as defined above, that is substituted by one or more halo groups, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl group, as defined above, that is substituted by one or more halo groups, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl group, as defined above, that is substituted by one or more halo groups, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring group which consists of two to twelve carbon atoms and from one to six heteroatoms selected from the group consisting of nitrogen, oxygen and sulfur. Heterocyclycl or heterocyclic rings include heteroaryls as defined below. Unless stated otherwise specifically in the specification, the heterocyclyl group can be a monocyclic, bicyclic, tricyclic or tetracyclic ring system, which can include fused or bridged ring systems; and the nitrogen, carbon or sulfur atoms in the heterocyclyl group can be optionally oxidized; the nitrogen atom can be optionally quaternized; and the heterocyclyl group can be partially or fully saturated. Examples of such heterocyclyl groups include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

"N-heterocyclyl" refers to a heterocyclyl group as defined above containing at least one nitrogen and where the point of attachment of the heterocyclyl group to the rest of the molecule is through a nitrogen atom in the heterocyclyl group. Unless stated otherwise specifically in the specification, a N-heterocyclyl group can be optionally substituted.

"Heterocyclylalkyl" refers to a group of the formula —$R_b$—$R_e$ where $R_b$ is an alkylene, alkenylene, or alkynylene chain as defined above and $R_e$ is a heterocyclyl group as defined above, and if the heterocyclyl is a nitrogen-containing heterocyclyl, the heterocyclyl can be attached to the alkyl, alkenyl, alkynyl group at the nitrogen atom. Unless stated otherwise specifically in the specification, a heterocyclylalkyl group can be optionally substituted.

"Heteroaryl" refers to a 5- to 20-membered ring system group comprising hydrogen atoms, one to thirteen carbon atoms, one to six heteroatoms selected from the group consisting of nitrogen, oxygen and sulfur, and at least one aromatic ring. For purposes of this invention, the heteroaryl group can be a monocyclic, bicyclic, tricyclic or tetracyclic ring system, which can include fused or bridged ring systems; and the nitrogen, carbon or sulfur atoms in the heteroaryl group can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl group as defined above containing at least one nitrogen and where the point of attachment of the heteroaryl group to the rest of the molecule is through a nitrogen atom in the heteroaryl group. Unless stated otherwise specifically in the specification, an N-heteroaryl group can be optionally substituted.

"Heteroarylalkyl" refers to a group of the formula —$R_b$—$R_f$ where $R_b$ is an alkylene, alkenylene, or alkynylene chain as defined above and $R_f$ is a heteroaryl group as defined above. Unless stated otherwise specifically in the specification, a heteroarylalkyl group can be optionally substituted.

"$^{123}$I" refers to the radioactive isotope of iodine having atomic mass 123. The compounds of Formula I can comprise at least one $^{123}$I moiety. Throughout the present application, where structures depict a $^{123}$I moiety at a certain position it is meant that the I moiety at this position is enriched for $^{123}$I. In other words, the compounds contain more than the natural abundance of $^{123}$I at the indicated position(s). It is not required that the compounds comprise 100% $^{123}$I at the indicated positions, provided $^{123}$I is present in more than the natural abundance. Typically the $^{123}$I isotope is enriched to greater than 50%, greater than 60%, greater than 70%, greater than, 80% or greater than 90%, relative to $^{127}$I.

"$^{18}$F" refers to the radioactive isotope of fluorine having atomic mass 18. "F" or "19F" refers to the abundant, non-radioactive fluorine isotope having atomic mass 19. The compounds of Formula I can comprise at least one $^{18}$F moiety. Throughout the present application, where structures depict a $^{18}$F moiety at a certain position it is meant that the F moiety at this position is enriched for $^{18}$F. In other words, the compounds contain more than the natural abundance of $^{18}$F at the indicated position(s). It is not required that the compounds comprise 100% $^{18}$F at the indicated positions, provided $^{18}$F is present in more than the natural abundance. Typically the $^{18}$F isotope is enriched to greater than 50%, greater than 60%, greater than 70%, greater than 80% or greater than 90%, relative to $^{19}$F.

"Thioalkyl" refers to a group of the formula —$SR_a$ where $R_a$ is an alkyl, alkenyl, or alkynyl group as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —OC(=O)$NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —C(=O)$R_g$, —C(=O)$OR_g$, —C(=O)$NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing groups can also be optionally substituted with one or more of the above groups.

As used herein, the symbol

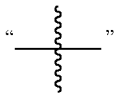

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

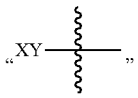

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

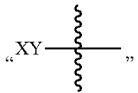

infers that when $R^3$ is "XY", the point of attachment bond is the same bond as the bond by which $R^3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

The disclosure herein is also meant to encompass the in vivo metabolic products of the disclosed compounds. Such products can result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabelled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances can or cannot occur, and that the description includes instances where said event or circumstance occurs and instances in which it does not. For example, "optionally substituted aryl" means that the aryl group can or cannot be substituted and that the description includes both substituted aryl groups and aryl groups having no substitution.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 and/or ChemDraw Professional 16.0.0.82 software naming program (CambridgeSoft), or the like. For complex chemical names employed herein, a group is named before the group to which it attaches. For example, cyclopropylethyl comprises an ethyl backbone with cyclopropyl group. Except as described below, all bonds are identified in the chemical structure diagrams herein, except for some carbon atoms, which are assumed to be bonded to sufficient hydrogen atoms to complete the valency.

Compounds of the Present Disclosure

The compound of the present disclosure can be useful for modulating androgen receptor (AR). Further, the compound of the present disclosure can be useful for treating various diseases and conditions including, but not limited to, cancer. In some embodiments, the cancer is prostate cancer or breast cancer.

In one embodiment, the present disclosure provides compounds comprising the structure of formula (I-A):

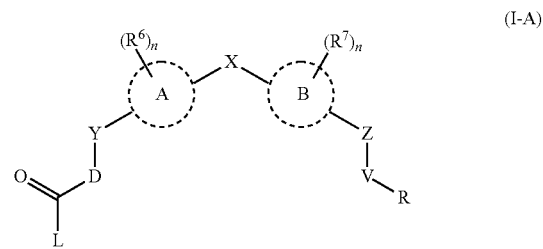

or a pharmaceutically acceptable salt, tautomer, stereoisomer or prodrug thereof, wherein:

A and B are each independently aryl or heteroaryl;

X is a bond, —$(CR^8R^9)_t$—, —O—, —C(=O)—, —$S(O)_p$—, —$NR^{10}$—, —$CONR^{10}$—, —$NR^{10}CO$—, —$SO_2NR^{10}$—, or —$NR^{10}SO_2$—;

Y and Z are each independently a bond, —$(CR^8R^9)_t$—, —O—, —$S(O)_p$—, —$NR^{10}$—, —$CONR^{10}$—, —$NR^{10}CO$—, —$SO_2NR^{10}$—, or —$NR^{10}SO_2$—;

V is a bond, optionally substituted —$(CR^{11}R^{12})_m$—, —C(=O)—, —$N(R^{10})CO$—, —$CONR^{10}$—, or —$NSO_2R^{10}$—;

R is —$(CR^{4a}R^{4b})$—$(CR^{5a}R^{5b})$—W or W;

W is hydrogen, halogen, —$CF_3$, —$CF_2R^{10}$, —CN, —$OR^{13}$, —$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —$(CR^{1a}R^{1b})_q$, —O—, or —$NR^{10}$—;

L is —$(CR^{2a}R^{2b})$—$R^3$ or -E-$R^3$;

E is —$(CR^{2a}R^{2b})_g$, —O—, —$NR^1$—, or —$NR^{10}$—$(CR^{2a}R^{2b})_g$—;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted —$OCO(C_1$-$C_6$ alkyl), —$NR^{13}R^{14}$, optionally substituted —$(C_1$-$C_6$ alkyl)-$NR^{13}R^{14}$, —$NR^{14}COR^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl;

or alternatively, R$^{1a}$ and R$^{1b}$ taken together form an optionally substituted carbocyclyl, optionally substituted heterocyclyl, optionally substituted aryl, or optionally substituted heteroaryl;

or alternatively, R$^{2a}$ and R$^{2b}$ taken together form a CO, optionally substituted carbocyclyl, optionally substituted heterocyclyl, optionally substituted aryl, or optionally substituted heteroaryl;

or alternatively, R$^{1a}$, R$^{1b}$, R$^{2a}$ and R$^{2b}$ taken together form an optionally substituted carbocyclyl, optionally substituted heterocyclyl, optionally substituted aryl, or optionally substituted heteroaryl;

R$^{4a}$, R$^{4b}$, R$^{5a}$, and R$^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted —OCO($C_1$-$C_6$ alkyl), —NR$^{13}$R$^{14}$, optionally substituted —($C_1$-$C_6$ alkyl)-NR$^{13}$R$^{14}$, NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl;

or alternatively, R$^{4a}$ and R$^{4b}$ taken together form a CO, optionally substituted carbocyclyl, optionally substituted heterocyclyl, optionally substituted aryl, or optionally substituted heteroaryl;

or alternatively, R$^{4a}$, R$^{4b}$, R$^{5a}$ and R$^{5b}$ taken together form an optionally substituted carbocyclyl, optionally substituted heterocyclyl, optionally substituted aryl, or optionally substituted heteroaryl;

R$^3$ is absent, hydrogen, —CN, —CF$_3$, —OH, optionally substituted $C_1$-$C_6$ alkyl, optionally substituted $C_2$-$C_6$ alkenyl, optionally substituted $C_2$-$C_6$ alkynyl, optionally substituted —OR$^{15}$, optionally substituted $C_1$-$C_6$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted carbocyclyl, optionally substituted heterocyclyl, optionally substituted aryl, or optionally substituted heteroaryl;

R$^{2a}$, R$^{2b}$ and R$^3$ taken together form an optionally substituted carbocyclyl, optionally substituted heterocyclyl, optionally substituted aryl, or optionally substituted heteroaryl;

R$^6$ and R$^7$ are each independently H, halogen, —CN, —CF$_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —NR$^{13}$R$^{14}$, optionally substituted —($C_1$-$C_6$ alkyl)-NR$^{13}$R$^{14}$, —NR$^{14}$SO$_2$R$^{16}$, optionally substituted —($C_1$-$C_6$ alkyl)NR$^{14}$SO$_2$R$^{16}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, —SO$_2$NR$^{14}$R$^{15}$, optionally substituted —($C_1$-$C_6$ alkyl)-SO$_2$NR$^{14}$R$^{15}$, optionally substituted —SO$_2$R$^{16}$, optionally substituted —($C_1$-$C_6$ alkyl)-SO$_2$R$^{16}$, optionally substituted carbocyclyl, optionally substituted heterocyclyl, optionally substituted aryl, or optionally substituted heteroaryl;

R$^8$, R$^9$, R$^{11}$ and R$^{12}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkylamino, optionally substituted —OCO($C_1$-$C_6$ alkyl), —NR$^{13}$R$^{14}$, optionally substituted —($C_1$-$C_6$ alkyl)-NR$^{13}$R$^{14}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl;

or alternatively, R$^8$ and R$^9$ taken together form an optionally substituted carbocyclyl or optionally substituted heterocyclyl;

or alternatively, R$^{11}$ and R$^{12}$, on a same carbon atom or a different carbon atom, taken together form an optionally substituted carbocyclyl, optionally substituted heterocyclyl, optionally substituted aryl, or optionally substituted heteroaryl;

R$^{10}$ is hydrogen, halogen, optionally substituted $C_1$-$C_6$ alkyl, optionally substituted $C_1$-$C_6$ alkoxy, —CO($C_1$-$C_6$ alkyl), optionally substituted $C_1$-$C_6$ alkylamino, optionally substituted carbocyclyl, optionally substituted heterocyclyl, optionally substituted aryl, or optionally substituted heteroaryl;

or alternatively, R$^{2a}$ and R$^{10}$ taken together form an optionally substituted heterocyclyl;

R$^{13}$, R$^{14}$, R$^{15}$, R$^{16}$, R$^{17}$ and R$^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl;

or alternatively, R$^{14}$ and R$^{15}$ are taken together to form an optionally substituted heterocyclyl, or optionally substituted heteroaryl;

or alternatively, R$^{16}$ and R$^{17}$ are taken together to form an optionally substituted heterocyclyl, or optionally substituted heteroaryl;

m is 0, 1, 2, 3, or 4;

each n is independently 0, 1 or 2;

each p is independently 0, 1 or 2;

q is 0, 1 or 2;

each g is independently 0, 1, 2, 3, or 4; and each t is independently 1 or 2.

In one embodiment of the compounds of formula (I-A), R is W.

In one embodiment of the compounds of formula (I-A), W is hydrogen, halogen, —CF$_3$, or —NR$^{13}$R$^{14}$.

In one embodiment of the compounds of formula (I-A), L is -E-R$^3$.

In one embodiment of the compounds of formula (I-A), R$^3$ is selected from hydrogen, optionally substituted $C_1$-$C_6$ alkyl, optionally substituted —OR$^{15}$, optionally substituted —SR$^{18}$, optionally substituted $C_1$-$C_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, or optionally substituted —SO$_2$R$^{18}$. In one embodiment of the compounds of formula (I-A), R$^3$ is selected from hydrogen, —$C_1$-$C_3$ alkyl, —NR$^{16}$SO($C_1$-$C_3$ alkyl), —NR$^{16}$SO$_2$($C_1$-$C_3$ alkyl), —SONR$^{14}$R$^{15}$, —SO$_2$NR$^{14}$R$^{15}$, —SOR$^{18}$, or —SO$_2$R$^{18}$.

In one aspect, the present disclosure provides a compound having the structure (I):

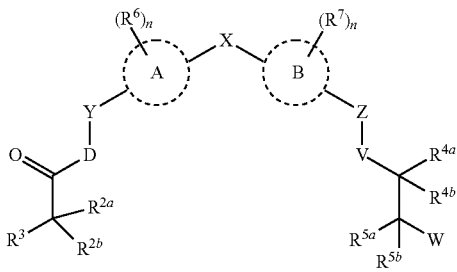

or a pharmaceutically acceptable salt, tautomer or stereoisomer thereof, wherein:

A and B are each independently aryl or heteroaryl;

X, Y, Z are each independently a bond, $(C(R^8R^9))_t$, O, $S(O)_p$, $NR^1$, $CONR^{10}$, $NR^{10}CO$, $SO_2NR^{10}$, or $NR^{10}SO_2$;

V is a bond or optionally substituted $(C(R^{11}R^{12}))_m$;

W is hydrogen, halogen, $CF_3$, CN, $OR^{13}$ or optionally substituted $CON(R^{13}R^{14})$;

D is $(C(R^{1a}R^{1b}))_m$;

$R^{1a}$, $R^{1b}$, $R^{2a}$, $R^{2b}$, $R^{4a}$, $4^{4b}$, $R^{5a}$, $R^{5b}$ are each independently hydrogen, halogen, hydroxy, optionally substituted $C_{1-6}$ alkyl, or optionally substituted $C_{1-6}$ alkoxy; or $R^{1a}$ and $R^{1b}$ taken together are optionally substituted carbocyclyl, optionally substituted heterocyclyl, optionally substituted aryl, or optionally substituted heteroaryl; or $R^{2a}$ and $R^{2b}$ taken together are CO, optionally substituted carbocyclyl, optionally substituted heterocyclyl, optionally substituted aryl, or optionally substituted heteroaryl; or $R^{1a}$, $R^{1b}$, $R^{2a}$ and $R^{2b}$ taken together are optionally substituted carbocyclyl, optionally substituted heterocyclyl, optionally substituted aryl, or optionally substituted heteroaryl; or $R^{4a}$ and $R^{4b}$ taken together are CO, optionally substituted carbocyclyl, optionally substituted heterocyclyl, optionally substituted aryl, or optionally substituted heteroaryl; or $R^{4a}$, $R^{4b}$, $R^{5a}$ and $R^{5b}$ taken together are optionally substituted carbocyclyl, optionally substituted heterocyclyl, optionally substituted aryl, or optionally substituted heteroaryl;

$R^3$ is absent, hydrogen, OH, $OR^{15}$, $NH_2$, $NR^{16}R^{17}$, $NR^{16}COR^{18}$, $NR^{16}S(O)_pR^{18}$, $S(O)_pR^{18}$, $N_3$, optionally substituted carbocyclyl, optionally substituted heterocyclyl, optionally substituted aryl, or optionally substituted heteroaryl; or $R^{2a}$, $R^{2b}$ and $R^3$ taken together are optionally substituted carbocyclyl, optionally substituted heterocyclyl, optionally substituted aryl, or optionally substituted heteroaryl;

each $R^6$ and $R^7$ is independently H, methyl, methoxy, CN, F, Cl, Br, I, $^{123}$I or $CF_3$;

$R^8$, $R^9$, $R^{10}$, $R^{11}$ and $R^{12}$ are each independently hydrogen, halogen, optionally substituted $C_1$-$C_6$ alkyl, optionally substituted $C_1$-$C_6$ alkoxy, or optionally substituted $C_1$-$C_6$ alkylamino; or $R^8$ and $R^9$ are optionally substituted carbocyclyl or optionally substituted heterocyclyl; or $R^1$ and $R^{12}$ taken together form an optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted carbocyclyl, optionally substituted heterocyclyl, optionally substituted aryl, or optionally substituted heteroaryl; or $R^{16}$ and $R^{17}$ are taken together to form an optionally substituted heterocyclyl, or optionally substituted heteroaryl; and each m is independently 0, 1 or 2;

each n is independently 0, 1 or 2;

each p is independently 0, 1 or 2; and each t is independently 1 or 2.

In some embodiments, the compound of formula (I) has the structure (Ia):

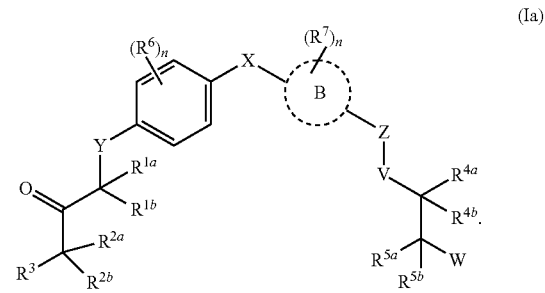

In some embodiments, the compound of formula (I) has the structure (Ib):

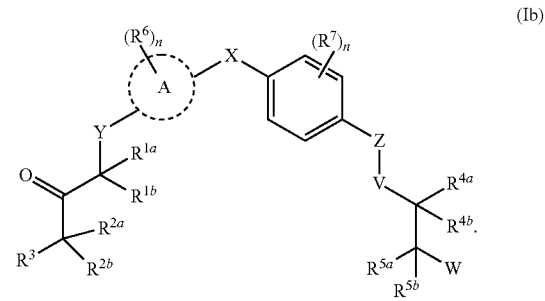

In some embodiments, the compound of formula (I) has the structure (Ic):

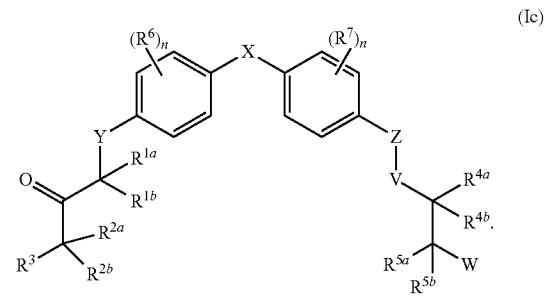

In some embodiments, the compound of formula (I) has the structure (Id):

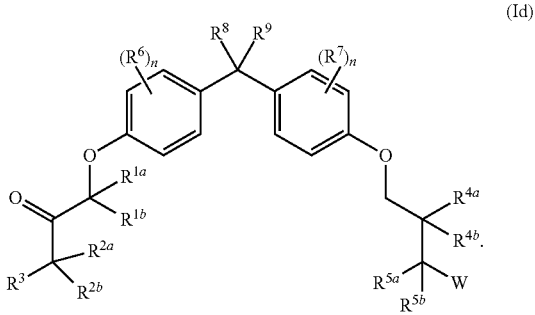

(Id)

In some embodiments, the compound of formula (I) has the structure (e):

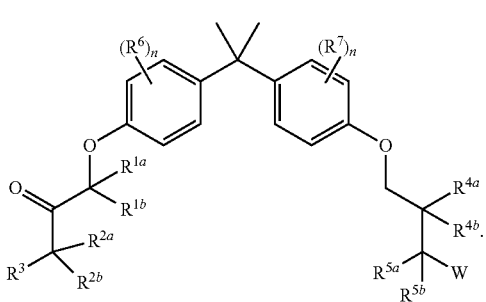

(Ie)

In some embodiments, A is phenyl, pyridinyl, pyrimidinyl, or thiophenyl. In some embodiments, B is phenyl, pyridinyl, pyrimidinyl, or thiophenyl (thiophene).

In some embodiments, X is a bond. In some embodiments, X is $(C(R^8R^9))_t$ or $NR^{10}$. In some embodiments, X is $NR^{10}$. In some embodiments, $R^{10}$ is hydrogen or optionally substituted $C_1$-$C_6$ alkyl. In some embodiments, $R^{10}$ is hydrogen. In some embodiments, $R^{10}$ is methyl. In some embodiments, X is $(C(R^8R^9))_n$. In some embodiments, $R^8$ and $R^9$ are independently hydrogen or optionally substituted $C_1$-$C_6$ alkyl. In some embodiments, $R^8$ and $R^9$ are hydrogen. In some embodiments, each $R^8$ and $R^9$ are methyl. In some embodiments, t is 1. In some embodiments, t is 2.

In some embodiments, Y is $(C(R^8R^9))_t$, O, or $NR^{10}$. In some embodiments, Y is O. In some embodiments, Y is $(C(R^8R^9))_t$. In some embodiments, $R^8$ and $R^9$ are hydrogen. In some embodiments, Y is $NR^1$.

In some embodiments, Z is $(C(R^8R^9))_t$, O, or $NR^1$. In some embodiments, Z is O. In some embodiments, Z is $(C(R^8R^9))_n$. In some embodiments, $R^8$ and $R^9$ are hydrogen. In some embodiments, $R^{10}$ is hydrogen or optionally substituted $C_1$-$C_6$ alkyl. In some embodiments, V is a bond. In some embodiments, V is optionally substituted $C(R^{11}R^{12})_m$. In some embodiments, $R^{11}$ and $R^{12}$ are hydrogen. In some embodiments, m is 0. In some embodiments, m is 1. In some embodiments, m is 2.

In some embodiments, $R^8$ and $R^9$ are independently hydrogen or optionally substituted $C_1$-$C_6$ alkyl. In some embodiments, $R^{1a}$ and $R^{1b}$ are each hydrogen or optionally substituted $C_{1-6}$ alkyl. In some embodiments, $R^{1a}$ and $R^{1b}$ are each hydrogen. In some embodiments, $R^{2a}$ and $R^{2b}$ are each hydrogen or optionally substituted $C_{1-6}$ alkyl. In some embodiments, $R^{2a}$ and $R^{2b}$ are each hydrogen.

In some embodiments, $R^3$ is $NR^{16}R^{17}$, $NR^{16}COR^{18}$, $NR^{16}S(O)_pR^{18}$, $S(O)_pR^{18}$, optionally substituted carbocyclyl, optionally substituted heterocyclyl, optionally substituted aryl, or optionally substituted heteroaryl. In some embodiments, $R^3$ is $NR^{16}R^{17}$.

In some embodiments, $R^{16}$ and $R^{17}$ are taken together with the intervening atom to form an optionally substituted heterocyclyl or optionally substituted heteroaryl. In some embodiments, $R^3$ is $NR^{16}S(O)_pR^{18}$ or $S(O)_pR^{18}$. In some embodiments, $R^{16}$ is hydrogen; $R^{18}$ is $C_1$-$C_6$ alkyl; and p is 2.

In some embodiments, $R^{2a}$, $R^{2b}$ and $R^3$ taken together with the intervening atom are optionally substituted carbocyclyl, optionally substituted heterocyclyl, optionally substituted aryl, or optionally substituted heteroaryl. In some embodiments, $R^{2a}$, $R^{2b}$ and $R^3$ taken together with the intervening atom are optionally substituted heteroaryl. In some embodiments, $R^{2a}$, $R^{2b}$ and $R^3$ taken together with the intervening atom are optionally substituted tetrazolyl, imidazolyl, 1,2,3-triazolyl, oxazole, pyrazinyl, pyrimidinyl, or 1,3,5-triazinyl.

In some embodiments, $R^{4a}$ is hydrogen, halogen, optionally substituted $C_{1-6}$ alkyl, or optionally substituted $C_{1-6}$ alkoxy. In some embodiments, $R^{4a}$ is optionally substituted $C_{1-6}$ alkyl or hydrogen. In some embodiments, $R^{4a}$ is hydroxy.

In some embodiments, $R^{4b}$ is hydrogen, halogen, optionally substituted $C_{1-6}$ alkyl, or optionally substituted $C_{1-6}$ alkoxy. In some embodiments, $R^{4b}$ is hydrogen.

In some embodiments, $R^{5a}$ is hydrogen, halogen, optionally substituted $C_{1-6}$ alkyl, or optionally substituted $C_{1-6}$ alkoxy. In some embodiments, $R^{5a}$ is hydrogen.

In some embodiments, $R^{5b}$ is hydrogen, halogen, optionally substituted $C_{1-6}$ alkyl, or optionally substituted $C_{1-6}$ alkoxy.

In some embodiments, W is a halogen. In some embodiments, W is Cl.

In some embodiments, n is 0. In some embodiments, n is 1. In some embodiments, n is 2.

In some embodiments, each occurrence of $R^6$ and $R^7$ is independently H, methyl, methoxy, CN, F, Cl, Br, or I. In some embodiments, each occurrence of $R^6$ and $R^7$ is F, Cl, Br, or I. In some embodiments, each occurrence of $R^6$ and $R^7$ is Cl.

In some embodiments, D is $(CH_2)_2$.

In one embodiment of the compounds of formula (I-A) or (I), the compound has the structure of formula (Ia):

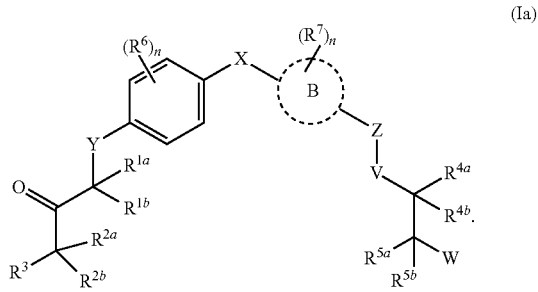

(Ia)

In one embodiment of the compounds of formula (I-A), (I) or (Ia), B is phenyl, pyridinyl, pyrimidinyl, or thiophene.

In one embodiment of the compounds of formula (I-A) or (I), the compound has the structure of formula (Ib):

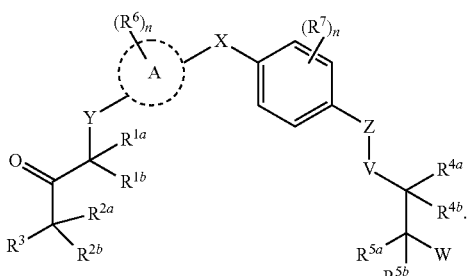

(Ib)

In one embodiment of the compounds of formula (I-A), (I) or (Ib), A is phenyl, pyridinyl, pyrimidinyl, or thiophene.

In one embodiment of the compounds of formula (I-A) or (I), the compound has the structure of formula (Ic):

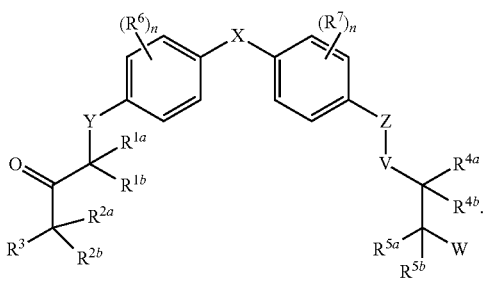

(Ic)

In one embodiment of the compounds of formula (I-A), (I) or (Ia)-(Ic), X is a bond. In other embodiments, X is —(CR$^8$R$^9$)$_t$— or —NR$^{10}$—. In another embodiment, X is —NR$^{10}$—. In some embodiments, X is —NR$^{10}$—, wherein R$^{10}$ is hydrogen or optionally substituted C$_1$-C$_6$ alkyl. In another embodiment, R$^{10}$ is hydrogen. In some embodiments, X is —NR$^{10}$—, wherein R$^{10}$ is methyl.

In one embodiment of the compounds of formula (I-A), (I) or (Ia)-(Ic), X is —(CR$^8$R$^9$)$_t$—. In some embodiments, X is —(CR$^8$R$^9$)$_t$—, wherein each R$^8$ and R$^9$ are independently hydrogen or optionally substituted C$_1$-C$_6$ alkyl. In some embodiments, X is —(CR$^8$R$^9$)$_t$—, wherein each R$^8$ and R$^9$ are hydrogen. In some embodiments, X is —(CR$^8$R$^9$)$_t$—, wherein each R$^8$ and R$^9$ are methyl.

In one embodiment of the compounds of formula (I-A), (I) or (Ia)-(Ic), the instance of t when X is —(CR$^8$R$^9$)$_t$— is 1. In other embodiments, the instance of t when X is —(CR$^8$R$^9$)$_t$— is 2.

In one embodiment of the compounds of formula (I-A), X is —(CR$^8$R$^9$)$_t$—, wherein R$^8$ and R$^9$ taken together form an optionally substituted carbocyclyl or optionally substituted heterocyclyl. In some embodiments, X is —(CR$^8$R$^9$)$_t$—, wherein R$^8$ and R$^9$ taken together form an optionally 3- to 6-membered carbocyclyl or heterocyclyl. In some embodiments, X is —(CR$^8$R$^9$)—, wherein R$^8$ and R$^9$ taken together form a 3- to 6-membered heterocyclyl containing one heteroatom selected from O, S, or N. In one embodiment, X is —(CR$^8$R$^9$)—, wherein R$^8$ and R$^9$ taken together form a 4-membered heterocyclyl containing one O.

In one embodiment of the compounds of formula (I-A), (I) or (Ia)-(Ic), Y is —(CR$^8$R$^9$)$_t$—, —O—, or —NR$^{10}$—. In other embodiments, Y is —O—. In another embodiment, Y is —(CR$^8$R$^9$)$_t$—. In another embodiment, Y is —(CR$^8$R$^9$)$_t$—, wherein each R$^8$ and R$^9$ are hydrogen.

In one embodiment of the compounds of formula (I-A), (I) or (Ia)-(Ic), the instance of t when Y is —(CR$^8$R$^9$)$_t$— is 1.

In one embodiment of the compounds of formula (I-A), (I) or (Ia)-(Ic), Y is —NR$^{10}$—. In another embodiment, Y is —NR$^{10}$—, wherein R$^{10}$ is hydrogen or optionally substituted C$_1$-C$_6$ alkyl. In another embodiment, Y is —NR$^{10}$—, R$^{10}$ is hydrogen. In another embodiment, Y is —NR$^{10}$—, R$^1$ is methyl.

In one embodiment of the compounds of formula (I-A), (I) or (Ia)-(Ic), Z is —(CR$^8$R$^9$)$_t$—, O, or NR$^{10}$. In one embodiment, Z is O. In some embodiments, Z is —(CR$^8$R$^9$)$_t$—. In another embodiment, Z is —(CR$^8$R$^9$)$_t$—, wherein each R$^8$ and R$^9$ are hydrogen.

In one embodiment of the compounds of formula (I-A), (I) or (Ia)-(Ic), the instance of t when Z is —(CR$^8$R$^9$)$_t$— is 1.

In one embodiment of the compounds of formula (I-A), (I) or (Ia)-(Ic), Z is —NR$^{10}$—. In some embodiments, Z is —NR$^{10}$—, wherein R$^{10}$ is hydrogen or optionally substituted C$_1$-C$_6$ alkyl. In some embodiments, Z is —NR$^{10}$—, wherein R$^{10}$ is hydrogen. In some embodiments, Z is —NR$^{10}$—, wherein R$^{10}$ is methyl.

In one embodiment of the compounds of formula (I-A), (I) or (Ia)-(Ic), V is a bond. In other embodiments, V is optionally substituted —C(R$^{11}$R$^{12}$)$_m$—. In one embodiment, is optionally substituted —C(R$^{11}$R$^{12}$)$_m$—, wherein each R$^{11}$ and R$^{12}$ are hydrogen.

In one embodiment of the compounds of formula (I-A), (I) or (Ia)-(Ic), m is 1.

In one embodiment of the compounds of formula (I-A) or (I), the compound has the structure of formula (Id):

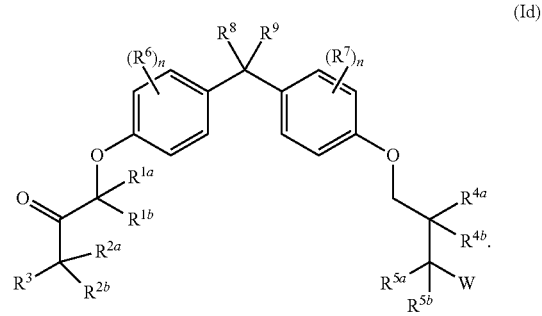

(Id)

In one embodiment of the compounds of formula (I-A), (I) or (Ia)-(Id), each R$^8$ and R$^9$ are independently hydrogen or optionally substituted C$_1$-C$_6$ alkyl.

In one embodiment of the compounds of formula (I-A) or (I), the compound has the structure of formula (Ie):

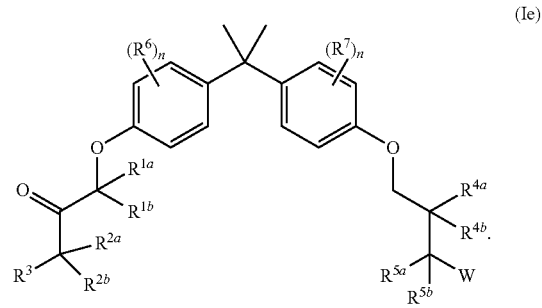

(Ie)

In one embodiment of the compounds of formula (I-A), (I) or (Ia)-(Ie), $R^{1a}$ and $R^{1b}$ are each hydrogen or optionally substituted $C_{1-6}$ alkyl. In other embodiments, $R^{1a}$ and $R^{1b}$ are each hydrogen.

In one embodiment of the compounds of formula (I-A), (I) or (Ia)-(Ie), $R^{2a}$ and $R^{2b}$ are each hydrogen or optionally substituted $C_{1-6}$ alkyl. In other embodiments, $R^{2a}$ and $R^{2b}$ are each hydrogen.

In one embodiment of the compounds of formula (I-A), (I) or (Ia)-(Ie), $R^3$ is —$NR^{16}R^{17}$, —$NR^{16}COR^{18}$, —$NR^{16}S(O)_pR^{18}$, —$S(O)_pR^{18}$, optionally substituted carbocyclyl, optionally substituted heterocyclyl, optionally substituted aryl, or optionally substituted heteroaryl. In other embodiments, $R^3$ is —$NR^{16}R^{17}$.

In one embodiment of the compounds of formula (I-A), (I) or (Ia)-(Ie), $R^{16}$ and $R^{17}$ are taken together with the intervening atom to form an optionally substituted heterocyclyl or optionally substituted heteroaryl.

In one embodiment of the compounds of formula (I-A), (I) or (Ia)-(Ie), $R^3$ is —$NR^{16}S(O)_pR^{18}$ or —$S(O)_pR^{18}$.

In one embodiment of the compounds of formula (I-A), (I) or (Ia)-(Ie), $R^{18}$ is $C_1$-$C_6$ alkyl; and p is 2.

In one embodiment of the compounds of formula (I-A), (I) or (Ia)-(Ie), $R^{2a}$, $R^{2b}$ and $R^3$ taken together with the intervening atom are optionally substituted carbocyclyl, optionally substituted heterocyclyl, optionally substituted aryl, or optionally substituted heteroaryl. In other embodiments, $R^{2a}$, $R^{2b}$ and $R^3$ taken together with the intervening atom are optionally substituted heteroaryl. In some embodiments, $R^{2a}$, $R^{2b}$ and $R^3$ taken together with the intervening atom are optionally substituted tetrazolyl, imidazolyl, 1,2,3-triazolyl, oxazole, pyrazinyl, pyrimidinyl, or 1,3,5-triazinyl.

In one embodiment of the compounds of formula (I-A), (I) or (Ia)-(Ie), $R^{4a}$ is hydrogen, halogen, optionally substituted $C_{1-6}$ alkyl, or optionally substituted $C_{1-6}$ alkoxy. In some embodiments, $R^{4a}$ is optionally substituted $C_{1-6}$ alkyl or hydrogen. In other embodiments, $R^{4a}$ is hydroxy.

In one embodiment of the compounds of formula (I-A), (I) or (Ia)-(Ie), $R^{4b}$ is hydrogen, halogen, optionally substituted $C_{1-6}$ alkyl, or optionally substituted $C_{1-6}$ alkoxy. In some embodiments, $R^{4b}$ is hydrogen.

In one embodiment of the compounds of formula (I-A), (I) or (Ia)-(Ie), $R^{5a}$ is hydrogen, halogen, optionally substituted $C_{1-6}$ alkyl, or optionally substituted $C_{1-6}$ alkoxy. In one embodiment, $R^{5a}$ is hydrogen.

In one embodiment of the compounds of formula (I-A), (I) or (Ia)-(Ie), $R^{5b}$ is hydrogen, halogen, optionally substituted $C_{1-6}$ alkyl, or optionally substituted $C_{1-6}$ alkoxy. In one embodiment, $R^{5b}$ is hydrogen.

In one embodiment of the compounds of formula (I-A), (I) or (Ia)-(Ie), W is a halogen. In other embodiments, W is Cl.

In one embodiment of the compounds of formula (I-A), (I) or (Ia)-(Ie), n is 1. In other embodiments, n is 2.

In one embodiment of the compounds of formula (I-A), (I) or (Ia)-(Ie), each occurrence of $R^6$ and $R^7$ is independently H, methyl, methoxy, CN, F, Cl, Br, or I. In other embodiments, each occurrence of $R^6$ and $R^7$ is F, Cl, Br, or I. In one embodiment, each occurrence of $R^6$ and $R^7$ is Cl.

In one embodiment of the compounds of formula (I-A), (I) or (Ia)-(Ie), D is —$(CH_2)_2$—.

In one embodiment of the compounds of formula (I-A), the compound has the structure of formula (A):

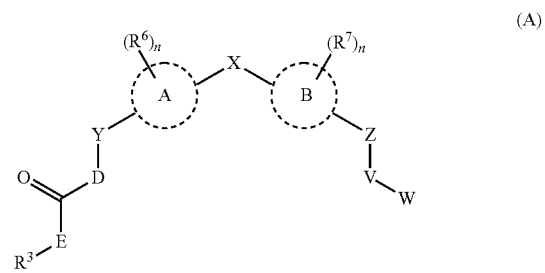

or a pharmaceutically acceptable salt, tautomer, stereoisomer or prodrug thereof, wherein:

A and B are each independently aryl or heteroaryl;

X is a bond, —$(CR^{8a}R^{9a})_t$—, —O—, —C(=O)—, —S—, —S(=O)—, —$SO_2$—, —$NR^{10}$—, —$N(R^{10})CO$—, —$CON(R^{10})$—, —$NR^{10}SO_2$—, or —$SO_2NR^{10}$—;

Y and Z are each independently a bond, —$(CR^{8a}R^{8b})_t$—, —O—, —S—, —S(=O)—, —$SO_2$—, —$NR^{10}$—, —$N(R^{10})CO$—, —$CON(R^{10})$—, —$NR^{10}SO_2$—, or —$SO_2NR^{10}$—;

V is a bond, optionally substituted —$(CR^{11}R^{12})_m$—, —C(=O)—, —$N(R^1)CO$—, —$CONR^1$—, or —$NSO_2R^{10}$—;

W is hydrogen, halogen, —$CF_3$, —$CF_2R^{10}$, —CN, —$OR^{13}$—$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —O— or —$NR^1$— and E is —$(CR^{2a}R^{2b})_g$—, —O—, —$NR^{10}$—, or —$NR^{10}$—$(CR^{2a}R^{2b})_g$—;

or alternatively, E is —O—, —$NR^{10}$— or —$NR^{10}$—$(CR^{2a}R^{2b})_g$—, and D is —$(CR^{1a}R^{1b})_q$—, —O—, or —$NR^{10}$—;

$R^{1a}$, $R^{1b}$, $R^{2a}$, and $R^{2b}$ are each independently hydrogen, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —$OCO(C_1$-$C_6$ alkyl), —$NR^{13}R^{14}$, optionally substituted —$(C_1$-$C_6$ alkyl)-$NR^{13}R^{14}$, —$NR^{14}COR^{16}$, optionally substituted —$(C_1$-$C_6$ alkyl)-$NR^{14}COR^{16}$, —$CONR^{14}R^{15}$, optionally substituted —$(C_1$-$C_6$ alkyl)-$CONR^{14}R^{15}$, optionally substituted carbocyclyl, optionally substituted heterocyclyl, optionally substituted aryl, or optionally substituted heteroaryl; or ($R^{1a}$ and $R^{1b}$) or ($R^{2a}$ and $R^{2b}$) taken together form an oxo (=O), an optionally substituted carbocyclyl, optionally substituted heterocyclyl, an optionally substituted aryl, or an optionally substituted heteroaryl; or $R^{2a}$ and $R^{10}$ taken together form an optionally substituted heterocyclyl;

$R^{11}$ and $R^{12}$ are each independently hydrogen, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —$OCO(C_1$-$C_6$ alkyl), —$NR^{13}R^{14}$, optionally substituted —$(C_1$-$C_6$ alkyl)-$NR^{13}R^{14}$, —$NR^{14}COR^{16}$, optionally substituted —$(C_1$-$C_6$ alkyl)-$NR^{14}COR^{16}$, —$CONR^{14}R^{15}$, optionally substituted —$(C_1$-$C_6$ alkyl)-$CONR^{14}R^{15}$, optionally substituted carbocyclyl, optionally substituted heterocyclyl, optionally substituted aryl, or optionally substituted heteroaryl; or $R^{11}$ and $R^{12}$, on a same carbon atom or a different carbon atom, taken together form an optionally substituted carbocyclyl, optionally substituted heterocyclyl, an optionally substituted aryl, or an optionally substituted heteroaryl;

$R^3$ is hydrogen, halogen, —CN, —CF$_3$, —OH, —NH$_2$, —N$_3$, optionally substituted C$_1$-C$_6$ alkyl, optionally substituted C$_2$-C$_6$ alkenyl, optionally substituted C$_2$-C$_6$ alkynyl, optionally substituted —OR$^{15}$, optionally substituted —SR$^{18}$, optionally substituted C$_1$-C$_6$ alkoxy, —NR$^{16}$R$^{17}$, —NR$^{16}$SR$^{18}$, —NR$^6$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, optionally substituted —SO$_2$R$^{18}$, optionally substituted carbocyclyl, optionally substituted heterocyclyl, optionally substituted aryl, or optionally substituted heteroaryl;

$R^6$ and $R^7$ are each independently H, halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

$R^{8a}$ and $R^{9a}$ are each independently hydrogen, halogen, —OH, or C$_1$-C$_3$ alkyl; or $R^{8a}$ and $R^{9a}$ taken together form an optionally substituted carbocyclyl or optionally substituted heterocyclyl;

$R^{8b}$, and $R^{9b}$ are each independently hydrogen, —OH, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or $R^{8b}$ and $R^{9b}$ taken together form an optionally substituted carbocyclyl or optionally substituted heterocyclyl;

$R^{10}$ is hydrogen, optionally substituted C$_1$-C$_6$ alkyl, optionally substituted C$_2$-C$_6$ alkenyl, optionally substituted C$_2$-C$_6$ alkynyl, —CO(C$_1$-C$_6$ alkyl), optionally substituted carbocyclyl, optionally substituted heterocyclyl, optionally substituted aryl, or optionally substituted heteroaryl;

or alternatively, $R^{2a}$ and $R^{10}$ taken together form an optionally substituted heterocyclyl;

$R^{13}$, $R^{14}$, $R^{15}$, $R^{16}$, $R^{17}$ and $R^{18}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl; or $R^{14}$ and $R^{15}$ taken together form an optionally substituted heterocyclyl;

m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (A), the compound has the structure of formula (B):

(B)

or a pharmaceutically acceptable salt, tautomer, stereoisomer or prodrug thereof, wherein:

A and B are each independently selected from phenyl, pyridyl, pyrimidyl, or thiophene;

X is a bond, —NR$^{10}$—, or —(CR$^{8a}$R$^{9a}$)$_t$—;

Y is a bond, —(CR$^{8b}$R$^{9b}$)$_t$, —O—, —S—, —S(=O)—, —SO$_2$—, or —NR$^{10}$—;

Z is a bond, —CH$_2$—, —C(CH$_3$)H—, —O—, —S—, —NH—, —NCH$_3$—, or —N(COCH$_3$)—;

V is —(CR$^{11}$R$^{12}$)$_m$—;

W is halogen, —NH$_2$, or —CF$_3$;

D is —O— or —NR$^{10}$— and E is —(CR$^{2a}$R$^{2b}$)$_g$—, —O—, —NR$^{10}$—, or —NR$^{10}$—(CR$^{2a}$R$^{2b}$)$_g$;

or alternatively, E is —O—, —NR$^{10}$— or —NR$^{10}$—(CR$^{2a}$R$^{2b}$)$_g$—, and D is —(CR$^{1a}$R$^{1b}$)$_q$—, —O—, or —NR$^{10}$—;

$R^{1a}$, $R^{1b}$, $R^{2a}$, and $R^{2b}$ are each independently hydrogen, halogen, —OH, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl; or ($R^{1a}$ and $R^{1b}$) or ($R^{2a}$ and $R^{2b}$) taken together form an oxo (=O), an optionally substituted carbocyclyl, optionally substituted heterocyclyl, an optionally substituted aryl, or an optionally substituted heteroaryl;

$R^3$ is hydrogen, halogen, —CN, —CF$_3$, —OH, —NH$_2$, —N$_3$, optionally substituted —OR$^5$, optionally substituted —SR$^8$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, optionally substituted —SO$_2$R$^{18}$, optionally substituted carbocyclyl, optionally substituted heterocyclyl, optionally substituted aryl, or optionally substituted heteroaryl;

$R^{11}$ and $R^{12}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, or —OCO(C$_1$-C$_3$ alkyl);

$R^6$ and $R^7$ is each independently halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-

$C_6$ alkyl)-$SO_2R^{16}$, optionally substituted carbocyclyl, optionally substituted heterocyclyl, optionally substituted aryl, or optionally substituted heteroaryl;

$R^{8a}$ and $R^{9a}$ are each independently hydrogen, halogen, —OH, or $C_1$-$C_3$ alkyl; or $R^{8a}$ and $R^{9a}$ taken together form an optionally substituted carbocyclyl or optionally substituted heterocyclyl;

$R^{8b}$ and $R^{9b}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8b}$ and $R^{9b}$ taken together form an optionally substituted carbocyclyl or optionally substituted heterocyclyl;

$R^{10}$ is each independently hydrogen, optionally substituted $C_1$-$C_6$ alkyl, optionally substituted $C_2$-$C_6$ alkenyl, optionally substituted $C_2$-$C_6$ alkynyl, —CO($C_1$-$C_6$ alkyl), optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl; or $R^{14}$ and $R^{15}$ taken together form an optionally substituted heterocyclyl;

m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (A), the compound has the structure of formula (C):

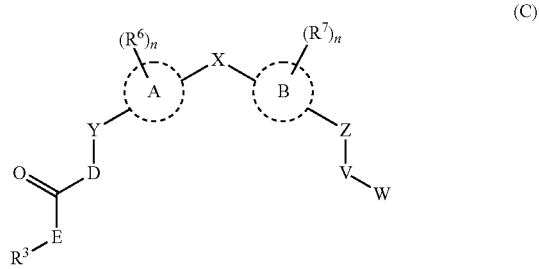

or a pharmaceutically acceptable salt, tautomer, stereoisomer or prodrug thereof, wherein:

A and B are each independently selected from phenyl, pyridyl, pyrimidyl, or thiophene;

X is a bond, —$NR^{10}$—, or —($CR^{8a}R^{9a}$)$_t$—;

Y and Z are each independently a bond, —($CR^{8b}R^{9b}$)$_t$—, —O—, —S—, —S(=O)—, —$SO_2$—, or —$NR^{10}$—;

V is a bond, optionally substituted —($CR^{11}R^{12}$)$_m$—, —C(=O)—, —N(R')CO—, —$CONR^{10}$—, or —$NSO_2R^{10}$—;

W is hydrogen, halogen, —$CF_3$, —$CF_2R^{10}$, —CN, —$OR^{13}$—$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —($CR^{1a}R^{1b}$)$_q$— and E is —O—, —$NR^{10}$—, or —$NR^{10}$—($CR^{2a}R^{2b}$)$_g$—;

or alternatively, D is —O— or —$NR^{10}$— and E is —($CR^{2a}R^{2b}$)$_g$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^{11}$ and $R^{12}$ are each independently hydrogen, halogen, —OH, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{11}$ and $R^{12}$, on a same carbon atom or a different carbon atom, taken together form an optionally substituted carbocyclyl, optionally substituted heterocyclyl, an optionally substituted aryl, or an optionally substituted heteroaryl;

$R^3$ is selected from hydrogen, optionally substituted $C_1$-$C_6$ alkyl, optionally substituted —$OR^{15}$, optionally substituted —$SR^{18}$, optionally substituted $C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, optionally substituted —$SOR^{18}$, or optionally substituted —$SO_2R^{18}$;

$R^6$ and $R^7$ are each independently H, halogen, —CN, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{15}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, or optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^{8a}$ and $R^{9a}$ are each independently hydrogen, halogen, —OH, or $C_1$-$C_3$ alkyl; or $R^{8a}$ and $R^{9a}$ taken together form an optionally substituted carbocyclyl or optionally substituted heterocyclyl;

$R^{8b}$ and $R^{9b}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl; or $R^{8b}$ and $R^{9b}$ taken together form an optionally substituted carbocyclyl or optionally substituted heterocyclyl;

$R^{10}$ is each independently hydrogen, optionally substituted $C_1$-$C_6$ alkyl, optionally substituted $C_2$-$C_6$ alkenyl, optionally substituted $C_2$-$C_6$ alkynyl, —CO($C_1$-$C_6$ alkyl), optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl; or $R^{14}$ and $R^{15}$ taken together form an optionally substituted heterocyclyl;

m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (A), the compound has the structure of formula (D):

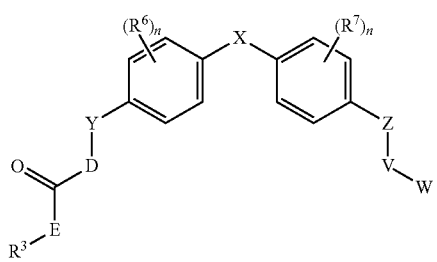

(D)

or a pharmaceutically acceptable salt, tautomer, stereoisomer or prodrug thereof, wherein:

X is a bond, —$NR^{10}$—, or —($CR^{8a}R^{9a}$)$_t$—;
Y and Z are each independently a bond, —$CH_2$—, —$C(CH_3)H$—, —O—, —S—, —NH—, —$NCH_3$—, or —$N(COCH_3)$—;
V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;
W is halogen, —$NH_2$, or —$CF_3$.
D is —O— or —$NR^{10}$— and E is —($CR^{2a}R^{2b}$)$_g$—, —O—, —$NR^{10}$—, or —$NR^{10}$—($CR^{2a}R^{2b}$)$_g$—;
or alternatively, E is —O—, —$NR^{10}$— or —$NR^{10}$—($CR^{2a}R^{2b}$)$_g$—, and D is —($CR^{1a}R^{1b}$)$_q$—, —O—, or —$NR^{10}$—;
$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;
$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;
$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;
$R^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);
$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;
m is 0, 1, 2, 3, or 4;
each n is independently 0, 1 or 2;
q is 0, 1 or 2;
each g is independently 0, 1, 2, 3, or 4; and
each t is independently 1 or 2.

In one embodiment of the compounds of formula (I-A) or (A), the compound has the structure of formula (E):

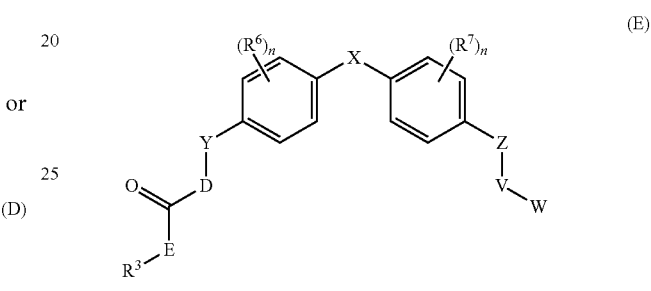

(E)

or a pharmaceutically acceptable salt, tautomer, stereoisomer or prodrug thereof, wherein:

X is a bond, —$NR^{10}$—, or —($CR^{8a}R^{9a}$)$_t$—;
Y and Z are each independently a bond, —$CH_2$—, —$C(CH_3)H$—, —O—, —S—, —NH—, —$NCH_3$—, or —$N(COCH_3)$—;
V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;
W is halogen, —$NH_2$ or —$CF_3$;
D is —O— or —$NR^{10}$— and E is —($CR^{2a}R^{2b}$)$_{gg}$—;
or alternatively, E is —O—, —$NR^{10}$— or —$NR^{10}$—($CR^{2a}R^{2b}$)$_g$—, and D is —($CR^{1a}R^{1b}$)$_q$—;
$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;
$R^3$ is selected from hydrogen, —$C_1$-$C_6$ alkyl, —$OR^{15}$, —$SR^8$, —$C_1$-$C_6$ alkoxy, —$NR^{16}R^{17}$, —$NR^{16}SR^{18}$, —$NR^6SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;
$R^6$ and $R^7$ are each independently H, halogen, —CN, —$CF_3$, —OH, or $C_1$-$C_3$ alkyl;
$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;
$R^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);
$R^{13}$, $R^{14}$, $R^{15}$, $R^{16}R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

m is 0, 1, 2, 3, or 4;
each n is independently 0, 1 or 2;
q is 1 or 2;
g is 0, 1, 2, 3, or 4;
gg is 1, 2, 3, or 4; and
t is 1 or 2.

In one embodiment of the compounds of formula (I-A), the compound has the structure of formula (II):

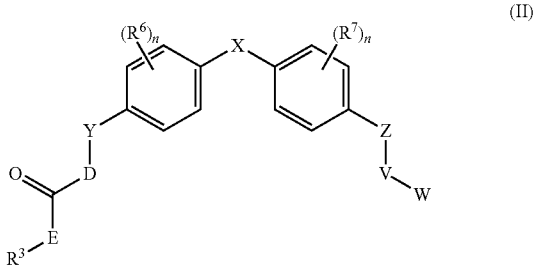

(II)

or a pharmaceutically acceptable salt, tautomer, stereoisomer or prodrug thereof, wherein:

X is a bond, —$NR^{10}$—, or —$(CR^{8a}R^{9a})_t$—;

Y and Z are each independently a bond, —$CH_2$—, —$C(CH_3)H$—, —O—, —S—, —NH—, —$NCH_3$—, or —$N(COCH_3)$—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;

W is —$CF_2R^{10}$, —$NR^{13}R^{14}$, optionally substituted carbocyclyl, optionally substituted heterocyclyl, optionally substituted aryl, or optionally substituted heteroaryl;

D is —$(CR^{1a}R^{1b})_q$—;

E is —$(CR^{2a}R^{2b})_g$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —$OCO(C_1$-$C_3$ alkyl), —$NR^{13}R^{14}$, —$(C_1$-$C_3$ alkyl)-$NR^{13}R^{14}$, —$NR^{14}COR^{16}$, —$(C_1$-$C_3$ alkyl)-$NR^{14}COR^{16}$, —$CONR^{14}R^{15}$, or —$(C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^8$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$ or —$SO_2R^{18}$;

$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an optionally substituted carbocyclyl or optionally substituted heterocyclyl;

$R^{10}$ is each independently hydrogen, $C_1$-$C_3$ alkyl, $C_2$-$C_3$ alkenyl, $C_2$-$C_3$ alkynyl, or —$CO(C_1$-$C_3$ alkyl);

$R^{13}$, $R^{14}$, $R^{15}$, $R^{16}R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

m is 0, 1, 2, 3, or 4;
each n is independently 0, 1 or 2;
q is 0, 1 or 2;
g is 0, 1, 2, 3, or 4; and
t is 1 or 2.

In one embodiment of the compounds of formula (I-A), (I), or (A)-(C), A and B are each independently 5- or 6-membered aryl or heteroaryl. In one embodiment, A and B are each independently selected from phenyl, pyridyl, pyrimidyl, benzooxazole, or thiophene. In one embodiment, A and B are each independently selected from phenyl, pyridyl, pyrimidyl, or thiophene. In one embodiment, A and B are each phenyl.

In one embodiment of the compounds of formula (I-A), (I), (Ib) or (A)-(C), A has a meta or para connectivity with X and Y.

In one embodiment of the compounds of formula (I-A), (I), (Ia) or (A)-(C), B has a meta or para connectivity with X and Z.

In one embodiment of the compounds of formula (I-A), (I), (Ia) or (A)-(C), A has para connectivity with X and Y and B has a para connectivity with X and Z. In one embodiment, A has a meta connectivity with X and Y and B has a meta connectivity with X and Z. In one embodiment, A has a para connectivity with X and Y and B has a meta connectivity with X and Z. In one embodiment, A has a meta connectivity with X and Y and B has a para connectivity with X and Z.

In one embodiment of the compounds of formula (I-A), (I), or (A)-(C), A and B are phenyl and has one of the connectivity as shown:

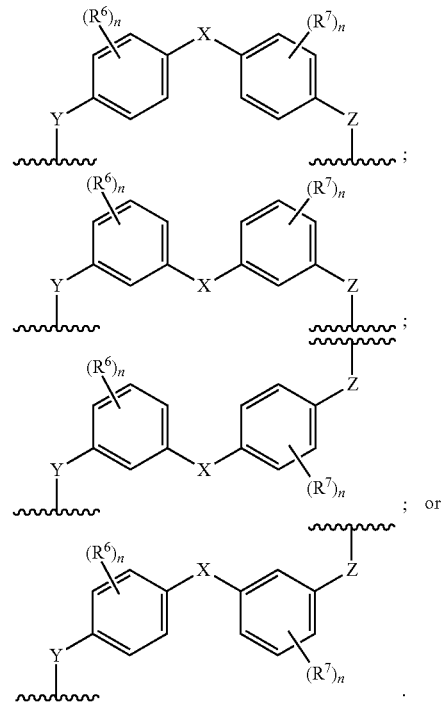

In one embodiment of the compounds of formula (I-A), (I), or (A)-(E), D is —$(CR^{1a}R^{1b})_q$—. In one embodiment, D is —$(CR^{1a}R^{1b})_q$—, wherein q is 0, 1, or 2. In one embodiment, D is —$(CR^{1a}R^{1b})_q$—, wherein q is 0 (i.e., D is absent). In one embodiment, D is —$CH_2$—, —$CH(CH_3)$—, —$C(CH_3)_2$—, or —$CH_2CH_2$—. In one embodiment, D is —$CH_2$— or —$CH_2CH_2$—.

In one embodiment of the compounds of formula (I-A), (I), or (A)-(E), D is —O— or —$NR^{10}$—.

In one embodiment of the compounds of formula (I-A), (I), or (A)-(E), D is —$NR^{10}$—. In one embodiment, D is —NH— or —$NCH_3$—.

In one embodiment of the compounds of formula (I-A), (I), or (A)-(E), D is —O—. In one embodiment, D is —O— and Y is a bond or —(CR$^8$R$^9$)$_t$—.

In one embodiment of the compounds of formula (I-A), (I), or (A)-(E), E is —(CR$^{2a}$R$^{2b}$)$_g$—. In one embodiment, E is —(CR$^{2a}$R$^{2b}$)$_g$—, wherein g is 0, 1, 2, or 3. In some embodiments, E is —(CR$^{2a}$R$^{2b}$)$_g$—, wherein g is 0 (i.e., E is absent). In one embodiment, E is —CH$_2$—, —CH(CH$_3$)—, —C(CH$_3$)$_2$—, —CH$_2$CH$_2$—, or —CH$_2$CH$_2$CH$_2$—. In other embodiments, E is —CH$_2$—, —CH$_2$CH$_2$—, or —CH$_2$CH$_2$CH$_2$—.

In one embodiment of the compounds of formula (I-A), (I), or (A)-(E), E is —O—, —NR$^{10}$— or —NR$^{10}$—(CR$^{2a}$R$^{2b}$)$_g$—. In one embodiment, E is —O—, —NH— or —NCH$_3$—.

In one embodiment of the compounds of formula (I-A), (I), or (A)-(E), E is —NR$^{10}$— or —NR$^{10}$—(CR$^{2a}$R$^{2b}$)$_g$—. In one embodiment, E is —NH— or —NCH$_3$—. In other embodiments, E is —NH—(CR$^{2a}$R$^{2b}$)$_g$— or —NCH$_3$—(CR$^{2a}$R$^{2b}$)$_g$—. In some embodiments, E is —NR$^{10}$—(CR$^{2a}$R$^{2b}$)$_g$, wherein g is 1, 2, or 3. In other embodiments, E is —NH—CH$_2$—, —NH—CH$_2$CH$_2$—, —NH—CH$_2$CH$_2$CH$_2$—, —NCH$_3$—CH$_2$—, —NCH$_3$—CH$_2$CH$_2$—, or —NCH$_3$—CH$_2$CH$_2$CH$_2$—.

In one embodiment of the compounds of formula (I-A), (I), or (A)-(E), E is —O—. In one embodiment, D is —O— and R$^3$ is hydrogen, —CF$_3$, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In one embodiment, D is —O— and R$^3$ is hydrogen, optionally substituted C$_1$-C$_6$ alkyl, optionally substituted C$_2$-C$_6$ alkenyl, or optionally substituted C$_2$-C$_6$ alkynyl.

In one embodiment of the compounds of formula (I-A), D is —NR$^1$— and E is —(CR$^{2a}$R$^{2b}$)$_g$—, —NR$^{10}$—, or —NR$^{10}$—(CR$^{2a}$R$^{2b}$)$_g$—. In some embodiments, E is —NR$^1$— or —NR$^{10}$—(CR$^{2a}$R$^{2b}$)$_g$—, and D is —(CR$^{1a}$R$^{1b}$)$_q$— or —NR$^{10}$—. In other embodiments, D is —NR$^{10}$— and E is —(CR$^{2a}$R$^{2b}$)$_g$—. In another embodiment, E is —NR$^{10}$— or —NR$^{10}$—(CR$^{2a}$R$^{2b}$)$_g$—, and D is —(CR$^{1a}$R$^{1b}$)$_q$.

In one embodiment of the compounds of formula (I-A), D is —O— or —NR$^{10}$— and E is —(CR$^{2a}$R$^{2b}$)$_g$—, —O—, —NR$^{10}$—, or —NR$^{10}$—(CR$^{2a}$R$^{2b}$)$_g$—. In some embodiments, E is —O—, —NR$^{10}$— or —NR$^{10}$—(CR$^{2a}$R$^{2b}$)$_g$—, and D is —(CR$^{1a}$R$^{1b}$)$_q$—, —O—, or —NR$^1$—. In other embodiments, D is —O— or —NR$^{10}$— and E is —(CR$^{2a}$R$^{2b}$)$_g$—. In another embodiment, E is —O—, —NR$^{10}$— or —NR$^{10}$—(CR$^{2a}$R$^{2b}$)$_g$—, and D is —(CR$^{1a}$R$^{1b}$)$_q$.

In one embodiment of the compounds of formula (I-A), (I), or (A)-(E), D is —(CR$^{1a}$R$^{1b}$)$_q$—; E is —O—, —NR$^{10}$—, or —NR$^{10}$—(CR$^{2a}$R$^{2b}$)$_g$—; and q is 1 or 2. In one embodiment, D is —O— or —NR$^{10}$—; E is —(CR$^{2a}$R$^{2b}$)$_g$—; and g is 1, 2, 3, or 4. In some embodiments, D is —O— or —NR$^{10}$—; and E is —O—, —NR$^{10}$— or —NR$^{10}$—(CR$^{2a}$R$^{2b}$)$_g$—.

In one embodiment of the compounds of formula (I-A), (I), or (A)-(E), D is —(CR$^{1a}$R$^{1b}$)$_q$—; E is —NR$^1$—, or —NR$^{10}$—(CR$^{2a}$R$^{2b}$)$_g$—; and q is 1 or 2. In one embodiment, D is —NR$^1$—; E is —(CR$^{2a}$R$^{2b}$)$_g$—; and g is 1, 2, 3, or 4. In some embodiments, D is —NR$^{10}$—; and E is —NR$^{10}$— or —NR$^{10}$—(CR$^{2a}$R$^{2b}$)$_g$—.

In one embodiment of the compounds of formula (I-A), (I), or (A)-(E), D is —(CR$^{1a}$R$^{1b}$)$_q$—; E is —O—. In one embodiment, D is —O—; E is —(CR$^{2a}$R$^{2b}$)$_g$—; and g is 1, 2, 3, or 4. In some embodiments, D is —O—; and E is —NR$^{10}$— or —NR$^{10}$—(CR$^{2a}$R$^{2b}$)$_g$—. In some embodiments, D is —NR$^{10}$—; and E is —O—.

In one embodiment of the compounds of formula (I-A), (I), or (A)-(E), D and Y are not both —O—.

In one embodiment of the compounds of formula (I-A) or (II), Y is —O—, D is —(CR$^{1a}$R$^{1b}$)$_q$—, L is —(CR$^{2a}$R$^{2b}$)—R$^3$, and R$^3$ is —NR$^{16}$S(O)$_p$R$^{18}$. In one embodiment, Y is —O—, D is —(CR$^{1a}$R$^{1b}$)—, L is —(CR$^{2a}$R$^{2b}$)—R$^3$, and R$^3$ is —NR$^{16}$S(O)$_2$(C$_1$-C$_3$ alkyl). In one embodiment, Y is —O—, D is —CH$_2$—, —CH(CH$_3$)—, or —C(CH$_3$)$_2$—, L is —CH$_2$—R$^3$, and R$^3$ is —NHS(O)$_2$CH$_3$.

In one embodiment of the compounds of formula (I), Y is —O—, D is —(CR$^{1a}$R$^b$)$_q$—, and R$^3$ is —NR$^{16}$S(O)$_p$R$^{18}$. In one embodiment, Y is —O—, D is —(CR$^{1a}$R$^{1b}$)—, and R$^3$ is —NR$^{16}$S(O)$_2$(C$_1$-C$_3$ alkyl). In one embodiment, Y is —O—, D is —CH$_2$—, —CH(CH$_3$)—, or —C(CH$_3$)$_2$—, R$^{2a}$ and R$^{2b}$ are each H, and R$^3$ is —NHS(O)$_2$CH$_3$.

In one embodiment of the compounds of formula (I-A), (I), or (A)-(E), when E is —O—, R$^3$ is hydrogen, —CF$_3$, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In other embodiments, when E is —O—, R$^3$ is hydrogen, —CF$_3$, C$_1$-C$_3$ alkyl, C$_2$-C$_3$ alkenyl, C$_2$-C$_3$ alkynyl, carbocyclyl, heterocyclyl, aryl, or heteroaryl.

In one embodiment of the compounds of formula (I-A), (I), (Ia)-(Ie), (II), or (A)-(E), R$^3$ is selected from hydrogen, optionally substituted C$_1$-C$_6$ alkyl, optionally substituted —OR$^{15}$, optionally substituted —SR$^{18}$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, or optionally substituted —SO$_2$R$^{18}$. In one embodiment, R$^3$ is selected from hydrogen, —C$_1$-C$_3$ alkyl, —NR$^{16}$SO(C$_1$-C$_3$ alkyl), —NR$^{16}$SO$_2$(C$_1$-C$_3$ alkyl), —SONR$^{14}$R$^{15}$, —SO$_2$NR$^{14}$R$^{15}$, —SOR$^{18}$, or —SO$_2$R$^{18}$.

In one embodiment of the compounds of formula (I-A), (I), (Ia)-(Ie), (II), or (A)-(E), R$^3$ is hydrogen, —CN, —CF$_3$, —OH, optionally substituted C$_1$-C$_6$ alkyl, optionally substituted C$_2$-C$_6$ alkenyl, optionally substituted C$_2$-C$_6$ alkynyl, optionally substituted —OR$^{15}$, optionally substituted C$_1$-C$_6$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted carbocyclyl, optionally substituted heterocyclyl, optionally substituted aryl, or optionally substituted heteroaryl. In some embodiments, R$^3$ is hydrogen, —CN, —CF$_3$, —OH, optionally substituted C$_1$-C$_3$ alkyl, optionally substituted C$_2$-C$_3$ alkenyl, optionally substituted C$_2$-C$_3$ alkynyl, optionally substituted —OR$^{15}$, optionally substituted C$_1$-C$_3$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted 3- to 7-membered carbocyclyl, optionally substituted 3- to 7-membered heterocyclyl, optionally substituted 6- to 12-membered aryl, or optionally substituted 5- to 12-membered heteroaryl. In other embodiments, R$^3$ is hydrogen, —CN, —CF$_3$, —OH, optionally substituted C$_1$-C$_3$ alkyl, optionally substituted C$_2$-C$_3$ alkenyl, optionally substituted C$_2$-C$_3$ alkynyl, optionally substituted —OR$^{15}$, optionally substituted C$_1$-C$_3$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, or —N$_3$. In one embodiment, R$^3$ is optionally substituted 3- to 7-membered carbocyclyl, optionally substituted 3- to 7-membered heterocyclyl, optionally substituted 6-membered aryl, or optionally substituted 5- to 6-membered heteroaryl.

In one embodiment of the compounds of formula (I-A), (I), (Ia)-(Ie), (II), or (A)-(E), $R^3$ is selected from hydrogen, $C_1$-$C_6$ alkyl, $C_1$-$C_6$ alkoxy, —NHSO$_2$($C_1$-$C_6$ alkyl), —NCH$_3$SO$_2$($C_1$-$C_6$ alkyl), —SO$_2$($C_1$-$C_6$ alkyl), —NHCO($C_1$-$C_6$ alkyl), or —N($C_1$-$C_6$ alkyl)CO($C_1$-$C_6$ alkyl). In another embodiment, $R^3$ is hydrogen, $C_1$-$C_3$ alkyl, $C_1$-$C_3$ alkoxy, —NHS$_2$($C_1$-$C_3$ alkyl), —NCH$_3$SO$_2$($C_1$-$C_3$ alkyl), —SO$_2$($C_1$-$C_3$ alkyl), —NHCO($C_1$-$C_3$ alkyl), or —N($C_1$-$C_3$ alkyl)CO($C_1$-$C_3$ alkyl). In other embodiments, $R^3$ is selected from —NHSO$_2$($C_1$-$C_3$ alkyl), —NCH$_3$SO$_2$($C_1$-$C_3$ alkyl), or —SO$_2$($C_1$-$C_3$ alkyl). In one embodiment, $R^3$ is selected from hydrogen, $C_1$-$C_3$ alkyl, $C_2$-$C_3$ alkenyl, $C_2$-$C_3$ alkynyl, $C_1$-$C_3$ alkoxy, —S($C_1$-$C_3$ alkyl), —SO($C_1$-$C_3$ alkyl), —SO$_2$($C_1$-$C_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON($C_1$-$C_3$ alkyl)$_2$, —CONH($C_1$-$C_3$ alkyl), —NHCO($C_1$-$C_3$ alkyl), or —N(CH$_3$)CO($C_1$-$C_3$ alkyl). In one embodiment, $R^3$ is selected from hydrogen, methyl, ethyl, propyl, isopropyl, methoxy, —SO$_2$CH$_3$, —NHSO$_2$CH$_3$, or —N(CH$_3$)SO$_2$CH$_3$. In one embodiment, $R^3$ is selected from —SO$_2$CH$_3$, —NHSO$_2$CH$_3$, or —N(CH$_3$)SO$_2$CH$_3$.

In one embodiment of the compounds of formula (I-A), (I), (Ia)-(Ie), (II), or (A)-(E), $R^3$ is $C_1$-$C_6$ alkyl.

In one embodiment of the compounds of formula (A)-(E) or (II), X is a bond, —NR$^{10}$—, or —(CR$^{8a}$R$^{9a}$)$_t$—. In one embodiment, X is —NR$^{10}$—, wherein R$^{10}$ is H, $C_1$-$C_6$ alkyl, or —CO($C_1$-$C_6$ alkyl). In one embodiment, X is —NR$^{10}$—, wherein R$^{10}$ is H, $C_1$-$C_3$ alkyl, or —CO($C_1$-$C_3$ alkyl). In one embodiment, X is a bond or —(CR$^{8a}$R$^{9a}$)$_t$—, wherein t is 1, or 2. In one embodiment, X is a bond or —(CR$^{8a}$R$^{9a}$)$_t$, wherein R$^{8a}$ and R$^{9a}$ are each selected from H, halogen, —OH, or $C_1$-$C_6$ alkyl and t is 1, or 2. In other embodiments, X is a bond, —NH—, —N(COCH$_3$)—, —N($C_1$-$C_3$ alkyl)-, —CH$_2$—, —CH(CH$_3$)—, —C(CH$_3$)$_2$—, —CH$_2$CH$_2$—, —CH(OH)—, —CHF—, or —CHF$_2$—. In other embodiments, X is a bond, —CH$_2$—, —C(CH$_3$)$_2$—, —CH$_2$CH$_2$—, —NH—, —N(CH$_3$)—, —N(iPr)-, or —N(COCH$_3$)—.

In one embodiment of the compounds of formula (I-A), (I), or (Ia)-(Ic), X is a bond, —(CR$^8$R$^9$)$_t$— or —NR$^1$—. In one embodiment, X is —NR$^{10}$—, wherein R$^1$ is H, $C_1$-$C_6$ alkyl, or —CO($C_1$-$C_6$ alkyl). In one embodiment, X is —NR$^{10}$—, wherein R$^{10}$ is H, $C_1$-$C_3$ alkyl, or —CO($C_1$-$C_3$ alkyl). In another embodiment, X is a bond or —(CR$^8$R$^9$)$_t$—, wherein t is 1, or 2. In one embodiment, X is a bond or —(CR$^8$R$^9$)$_t$—, wherein R$^8$ and R$^9$ are each selected from H, halogen, —OH, or $C_1$-$C_6$ alkyl and t is 1, or 2. In other embodiments, X is a bond, —NH—, —N(COCH$_3$)—, —N($C_1$-$C_3$ alkyl)-, —CH$_2$—, —CH(CH$_3$)—, —C(CH$_3$)$_2$—, —CH$_2$CH$_2$—, —CH(OH)—, —CHF—, or —CHF$_2$—.

In one embodiment of the compounds of formula (I-A), (I), or (Ia)-(Ic), X is —(CR$^8$R$^9$)— wherein R$^8$ and R$^9$ are each selected from H, halogen, —OH, or $C_1$-$C_6$ alkyl.

In one embodiment of the compounds of formula (I-A), (A)-(C) or (II), X—(CR$^{8a}$R$^{9a}$)$_t$—, wherein R$^{8a}$ and R$^{9a}$ taken together form an optionally substituted carbocyclyl or optionally substituted heterocyclyl. In one embodiment of the compounds of formula (I-A), (A)-(E) or (II), X—(CR$^{8a}$R$^{9a}$)$_t$—, wherein R$^{8a}$ and R$^{9a}$ taken together form an optionally substituted 3- to 6-membered carbocyclyl or an optionally substituted 3- to 6-membered heterocyclyl containing one heteroatom selected from O, S, or N. In one embodiment of the compounds of formula (I-A), (A)-(E) or (II), X—(CR$^{8a}$R$^{9a}$)$_t$—, wherein R$^{8a}$ and R$^{9a}$ taken together form a 3- to 6-membered carbocyclyl or a 3- to 6-membered heterocyclyl containing one heteroatom selected from O, S, or N. In one embodiment of the compounds of formula (I-A), (A)-(E) or (II), X—(CR$^{8a}$R$^{9a}$)$_t$, wherein R$^{8a}$ and R$^{9a}$ taken together form a 4-membered heterocyclyl containing one O.

In one embodiment of the compounds of formula (I-A), (I), (Ia)-(Ic), (II), or (A)-(E), Z is a bond, —CH$_2$—, —C(CH$_3$)H—, —O—, —S—, —NH—, —NCH$_3$—, or —N(COCH$_3$)—. In one embodiment, Z is —CH$_2$—, —C(CH$_3$)H—, —O—, —S—, —NH—, —NCH$_3$—, or —N(COCH$_3$)—. In some embodiments, Z is a bond, —CH$_2$—, —O—, or —NCH$_3$—. In some embodiments, Z is a bond, —CH$_2$—, —O—, or —NH—. In some embodiments, Z is —O—.

In one embodiment of the compounds of formula (A) or (C), Z is —(CR$^{8b}$R$^{9b}$)$_t$—, wherein R$^{8b}$ and R$^{9b}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —NR$^{13}$R$^{14}$, optionally substituted —($C_1$-$C_6$ alkyl)-NR$^{13}$R$^{14}$, NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl.

In one embodiment of the compounds of formula (I-A), (I), (Ia)-(Ic), (II), or (A)-(E), Y is a bond, —CH$_2$—, —C(CH$_3$)H—, —O—, —S—, —NH—, —NCH$_3$—, or —N(COCH$_3$)—. In one embodiment, Y is a —CH$_2$—, —C(CH$_3$)H—, —O—, —S—, —NH—, —NCH$_3$—, or —N(COCH$_3$)—. In some embodiments, Y is —CH$_2$—, —O—, —NH—, or —NCH$_3$—. In some embodiments, Y is a bond, —CH$_2$—, —O—, or —NCH$_3$—. In some embodiments, Y is a bond, —CH$_2$—, —O—, or —NH—. In some embodiments, Y is —O—.

In one embodiment of the compounds of formula (I-A), (I), (Ia)-(Ic), (II), or (A)-(E), at least one of Z and Y is —O—.

In one embodiment of the compounds of formula (I-A), (II), or (A)-(E), -D-C(O)-E-R$^3$ is

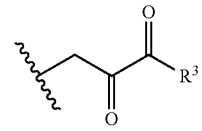

or its tautomeric form

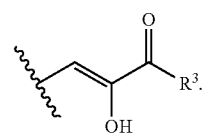

In one embodiment of the compounds of formula (I-A), (II), or (A)-(E), —Y-D-C(O)-E-R$^3$ is

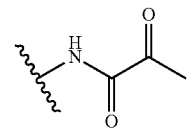 [SMILES: *NC(=O)C(C)=O]

or its tautomeric form

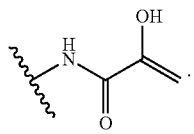

In one embodiment of the compounds of formula (I-A) or (A), -D-C(O)-E-R$^3$ is

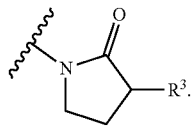

In one embodiment of the compounds of formula (A)-(C), Y is —(CR$^{8b}$R$^{9b}$)$_t$—, wherein R$^{8b}$ and R$^{9b}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl.

In one embodiment of the compounds of formula (I-A), (I), (Ia)-(Ic), (II), or (A)-(E), V is a bond, —(CR$^{11}$R$^{12}$)$_m$—, —C(=O)—, —N(R$^{10}$)CO—, —CONR$^{10}$—, or —NSO$_2$R$^{10}$—. In some embodiments, V is —(CR$^{11}$R$^{12}$)$_m$—. In some embodiments, V is —(CR$^{11}$R$^{12}$)$_m$—, wherein m is 1, 2, or 3. In some embodiments, V is —(CR$^{11}$R$^{12}$)$_m$—, wherein R$^{11}$ and R$^{12}$ are each selected from H, halogen, —OH, or C$_1$-C$_6$ alkyl. In some embodiments, V is —(CR$^{11}$R$^{12}$)$_m$—, wherein m is 1, 2, or 3. In some embodiments, V is —(CR$^{11}$R$^{12}$)$_m$—, wherein R$^{11}$ and R$^{12}$ are each selected from H, halogen, —OH, or C$_1$-C$_3$ alkyl.

In one embodiment of the compounds of formula (I-A), (I), (Ia)-(Ic), (II), or (A)-(E), V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—.

In one embodiment of the compounds of formula (I-A), (I), (Ia)-(Ie), (II), or (A)-(E), W is hydrogen, halogen, —CF$_3$, or —NH$_2$. In some embodiments, W is aryl, optionally substituted with halogen, C$_1$-C$_3$ alkyl, —CN, —CF$_3$, —OH, C$_1$-C$_3$ alkoxy, —NR$^{13}$R$^{14}$, or —SO$_2$R$^{16}$. In another embodiment, W is a phenyl, optionally substituted with halogen, C$_1$-C$_3$ alkyl, —CN, —CF$_3$, —OH, or C$_1$-C$_3$ alkoxy. In some embodiments, W is Cl, Br, I, or F. In some embodiments, W is C$_1$.

In one embodiment of the compounds of formula (I-A), (I), (Ia)-(Ic), (II), or (A)-(E), Z is a bond, —CH$_2$—, —C(CH$_3$)H—, —O—, —S—, —NH—, —NCH$_3$—, or —N(COCH$_3$)—; and V is —(CR$^{11}$R$^{12}$)$_m$—.

In one embodiment of the compounds of formula (I-A), (I), (Ia)-(Ic), (II), or (A)-(E), Z is a bond, —CH$_2$—, —C(CH$_3$)H—, —O—, —S—, —NH—, —NCH$_3$—, or —N(COCH$_3$)—; V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—; and W is halogen, —NH$_2$, or —CF$_3$.

In one embodiment of the compounds of formula (I-A), (I) or (A)-(E), R$^6$ and R$^7$ are each independently halogen, —CN, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl)-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$. In one embodiment, R$^6$ and R$^7$ are each independently halogen, —CN, —CF$_3$, —OH, optionally substituted C$_1$-C$_3$ alkyl, C$_1$-C$_3$ alkoxy, optionally substituted —(C$_1$-C$_3$ alkyl)-(C$_1$-C$_3$ alkoxy), optionally substituted —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, optionally substituted —(C$_1$-C$_3$ alkyl)NR$^{14}$SO$_2$R$^{16}$, —NR$^{14}$COR$^{16}$, optionally substituted —(C$_1$-C$_3$ alkyl)-NR$^{14}$COR$^{16}$, —CONR$^{14}$R$^{15}$, optionally substituted —(C$_1$-C$_3$ alkyl)-CONR$^{14}$R$^{15}$, —SO$_2$NR$^{14}$R$^{15}$, optionally substituted —(C$_1$-C$_3$ alkyl)-SO$_2$NR$^{14}$R$^{15}$, —SO$_2$R$^{16}$, or optionally substituted —(C$_1$-C$_3$ alkyl)-SO$_2$R$^{16}$. In one embodiment, R$^6$ and R$^7$ are each independently halogen, —CN, —CF$_3$, —OH, C$_1$-C$_3$ alkyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^4$SO$_2$R$^{16}$, —NR$^4$COR$^{16}$, —(C$_1$-C$_3$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$R$^{16}$, or —(C$_1$-C$_3$ alkyl)-SO$_2$R$^{16}$.

In one embodiment of the compounds of formula (I-A), (I) or (A)-(E), R$^6$ and R$^7$ are each independently halogen, —CN, —CF$_3$, —OH, C$_1$-C$_3$ alkyl, or —CONR$^{14}$R. In some embodiments, R$^6$ and R$^7$ are each independently halogen, —CN, —CF$_3$, —OH, methyl, methoxy, or —CONH$_2$. In one embodiment, R$^6$ and R$^7$ are each independently C$_1$, —CN, —CF$_3$, —OH, methyl, methoxy, or —CONH$_2$. In one embodiment, R$^6$ and R$^7$ are each independently halogen, —CN, —CF$_3$, —OH, or methyl. In one embodiment, R$^6$ and R$^7$ is each independently halogen, —CN, —CF$_3$, —OH, methyl, or methoxy. In another embodiment, R$^6$ and R$^7$ is each independently C$_1$, —CN, —CF$_3$, —OH, methyl, or methoxy. In one embodiment, R$^6$ and R$^7$ are each independently H, halogen, —CN, or methyl.

In one embodiment of the compounds of formula (I-A), (I) or (A)-(E), R$^6$ and R$^7$ are each independently optionally substituted carbocyclyl, optionally substituted heterocyclyl, optionally substituted aryl, or optionally substituted heteroaryl. In one embodiment, R$^6$ and R$^7$ are each independently 3- to 7-membered carbocyclyl, 3- to 7-membered heterocyclyl, phenyl, or 5- to 6-membered heteroaryl.

In one embodiment of the compounds of formula (I-A), (I), (Ia)-(Ic), (II), or (A)-(E), R$^6$ and R$^7$ is independently H, methyl, methoxy, CN, F, Cl, Br, I, $^{123}$I or CF$_3$.

In one embodiment of the compounds of formula (I-A), (I), (Ia)-(Ie), (II), or (A)-(E), R$^6$ have one of the connectivity as shown below with respect to X and Y:

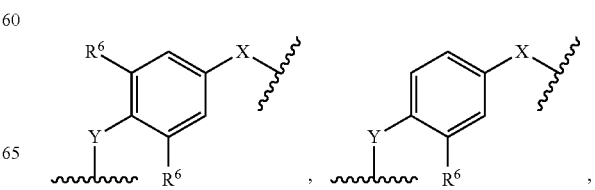

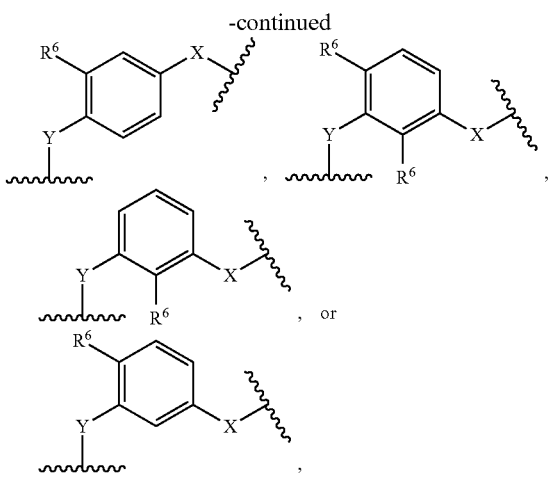

In one embodiment of the compounds of formula (I-A), (I), (Ia)-(Ie), (II), or (A)-(E), $R^7$ have one of the connectivity as shown below with respect to X and Z:

In one embodiment of the compounds of formula (I-A), (I), (Ia)-(Ie), (II), or (A)-(E), n

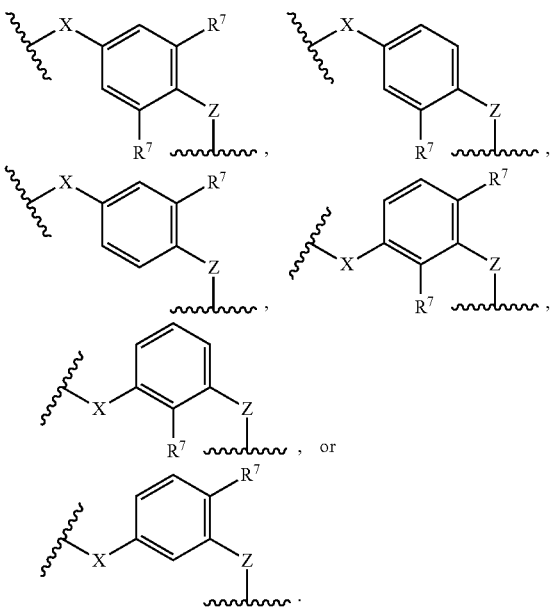

In one embodiment of the compounds of formula (I-A), (I), (Ia)-(Ic), (II), or (A)-(E), n in —$(R^6)_n$ is 0, 1, or 2. In some embodiments, n is 0 or 1. In other embodiments, n is 0. In some embodiments, n is 1.

In one embodiment of the compounds of formula (I-A), (I), (Ia)-(Ie), (II), or (A)-(E), n in —$(R^7)_n$ is 0, 1, or 2. In some embodiments, n is 0 or 1. In other embodiments, n is 0. In some embodiments, n is 1.

In one embodiment of the compounds of formula (I-A), (I), (Ia)-(Ie), (II), or (A)-(E), the sum of n in —$(R^6)_n$ and —$(R^7)_n$ is 0, 1, 2, 3, or 4. In some embodiments, the sum of n in —$(R^6)_n$ and —$(R^7)_n$ is v1, 2, 3, or 4. In some embodiments, the sum of n in —$(R^6)_n$ and —$(R^7)_n$ is 2 or 4. In some embodiments, the sum of n in —$(R^6)_n$ and —$(R^7)_n$ is 2.

In one embodiment of the compounds of formula (I-A), (I), (Ia)-(Ie), (II), or (A)-(E), $R^{1a}$, and $R^{1b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, —($C_1$-$C_6$ alkyl)-$CONR^{14}R^{15}$; or $R^{1a}$ and $R^{1b}$ taken together form an oxo (=O), an optionally substituted carbocyclyl, or an optionally substituted heterocyclyl. In some embodiments, $R^{1a}$ and $R^{1b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$. In one embodiment, $R^{1a}$ and $R^{1b}$ are each hydrogen or $R^{1a}$ and $R^{1b}$ taken together form an oxo (=O).

In one embodiment of the compounds of formula (I-A), (I), (Ia)-(Ie), (II), or (A)-(E), $R^{2a}$ and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or $R^{2a}$ and $R^{2b}$ taken together form an oxo (=O), an optionally substituted carbocyclyl, or an optionally substituted heterocyclyl. In some embodiments, $R^{2a}$ and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$. In one embodiment, $R^{2a}$ and $R^{2b}$ are each hydrogen or $R^{2a}$ and $R^{2b}$ taken together form an oxo (=O).

In one embodiment of the compounds of formula (I-A) or (I), $R^{4a}$ and $R^{4b}$ are hydrogen, halogen, optionally substituted $C_{1-6}$ alkyl, or optionally substituted $C_{1-6}$ alkoxy. In some embodiments, $R^{4a}$ and $R^{4b}$ are hydrogen, hydroxyl, halogen, $C_{1-6}$ alkyl, or $C_{1-6}$ alkoxy. In some embodiments, $R^{4a}$ and $R^{4b}$ are hydrogen, halogen, $C_{1-6}$ alkyl, or $C_{1-6}$ alkoxy. In some embodiments, $R^{4a}$ and $R^{4b}$ are hydrogen, hydroxyl, halogen, $C_{1-6}$ alkyl, or $C_{1-6}$ alkoxy. In some embodiments, $R^{4a}$ and $R^{4b}$ are hydrogen, hydroxyl, halogen, $C_{1-3}$ alkyl, or $C_{1-3}$ alkoxy. In one embodiment, $R^{4a}$ and $R^{4b}$ are hydrogen, hydroxyl, halogen, methyl, or methoxy.

In one embodiment of the compounds of formula (I-A) or (I), $R^{5a}$ and $R^{5b}$ are hydrogen, halogen, optionally substituted $C_{1-6}$ alkyl, or optionally substituted $C_{1-6}$ alkoxy. In some embodiments, $R^{5a}$ and $R^{5b}$ are hydrogen, hydroxyl, halogen, $C_{1-6}$ alkyl, or $C_{1-6}$ alkoxy. In some embodiments, $R^{5a}$ and $R^{5b}$ are hydrogen, halogen, $C_{1-6}$ alkyl, or $C_{1-6}$ alkoxy. In some embodiments, $R^{5a}$ and $R^{5b}$ are hydrogen, hydroxyl, halogen, $C_{1-6}$ alkyl, or $C_{1-6}$ alkoxy. In some embodiments, $R^{5a}$ and $R^{5b}$ are hydrogen, hydroxyl, halogen, $C_{1-3}$ alkyl, or $C_{1-3}$ alkoxy. In some embodiments, $R^{5a}$ and $R^{5b}$ are hydrogen, halogen, $C_{1-3}$ alkyl, or $C_{1-3}$ alkoxy. In one embodiment, $R^{5a}$ and $R^{5b}$ are hydrogen, hydroxyl, halogen, methyl, or methoxy.

In one embodiment of the compounds of formula (I-A) or (I), $R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl. In one embodiment, $R^8$ and $R^9$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, or optionally substituted —($C_1$-$C_6$ alkyl)-$CONR^{14}R$. In one embodiment, $R^8$ and $R^9$ hydrogen, halogen, —OH, or $C_1$-$C_3$ alkyl. In one embodiment, $R^8$ and $R^9$ hydrogen, halogen, —OH, or methyl. In one embodiment, $R^8$ and $R^9$ hydrogen, F, —OH, or methyl.

In one embodiment of the compounds of formula (A)-(E) $R^{8a}$ and $R^{9a}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl. In one embodiment, $R^{8a}$ and $R^{9a}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, or optionally substituted —($C_1$-$C_6$ alkyl)-$CONR^{14}R^{15}$. In one embodiment, $R^{8a}$ and $R^{9a}$ hydrogen, halogen, —OH, or $C_1$-$C_3$ alkyl. In one embodiment, $R^{8a}$ and $R^{9a}$ hydrogen, halogen, —OH, or methyl. In one embodiment, $R^{8a}$ and $R^{9a}$ hydrogen, F, —OH, or methyl.

In one embodiment of the compounds of formula (I-A), (I), (Ia)-(Ie), (II), or (A)-(E), $R^{10}$ is hydrogen, halogen, optionally substituted $C_1$-$C_6$ alkyl, or optionally substituted $C_1$-$C_6$ alkoxy. In some embodiments, $R^{10}$ is hydrogen, $C_1$-$C_6$ alkyl, or $C_1$-$C_6$ alkoxy. In some embodiments, $R^{10}$ is hydrogen, $C_1$-$C_3$ alkyl, or $C_1$-$C_3$ alkoxy.

In one embodiment of the compounds of formula (I-A) or (A), $R^{2a}$ and $R^{10}$ taken together form an optionally substituted heterocyclyl. In one embodiment, $^{2a}$ and $R^{10}$ taken together form an optionally substituted 5- or 6-membered heterocyclyl.

In one embodiment of the compounds of formula (I-A), (I), (Ia)-(Ie), (II), or (A)-(E), $R^{13}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, $R^{13}$ is hydrogen or optionally substituted $C_1$-$C_6$ alkyl. In some embodiments, $R^{13}$ is hydrogen or $C_1$-$C_6$ alkyl. In some embodiments, $R^{13}$ is hydrogen or $C_1$-$C_3$ alkyl.

In one embodiment of the compounds of formula (I-A), (I), (Ia)-(Ie), (II), or (A)-(E), $R^{14}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, $R^{14}$ is hydrogen or optionally substituted $C_1$-$C_6$ alkyl. In some embodiments, $R^{14}$ is hydrogen or $C_1$-$C_6$ alkyl. In some embodiments, $R^{14}$ is hydrogen or $C_1$-$C_3$ alkyl.

In one embodiment of the compounds of formula (I-A), (I), (Ia)-(Ie), (II), or (A)-(E), $R^{15}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, $R^{15}$ is hydrogen or optionally substituted $C_1$-$C_6$ alkyl. In some embodiments, $R^{15}$ is hydrogen or $C_1$-$C_6$ alkyl. In some embodiments, $R^{15}$ is hydrogen or $C_1$-$C_3$ alkyl.

In one embodiment of the compounds of formula (I-A), (I), (Ia)-(Ie), (II), or (A)-(E), $R^{14}$ and $R^{15}$ are taken together to form an optionally substituted heterocyclyl, or optionally substituted heteroaryl. In some embodiments, $R^{14}$ and $R^{15}$ are taken together to form an optionally substituted heterocyclyl. In some embodiments, $R^{14}$ and $R^{15}$ are taken together to form an 3- to 7-membered optionally substituted heterocyclyl. In some embodiments, $R^{14}$ and $R^{15}$ are taken together to form an 3- to 7-membered optionally substituted heterocyclyl, comprising one or more heteroatoms selected from N, O, or S.

In one embodiment of the compounds of formula (I-A), (I), (Ia)-(Ie), (II), or (A)-(E), $R^{16}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, $R^{16}$ is hydrogen or optionally substituted $C_1$-$C_6$ alkyl. In some embodiments, $R^{16}$ is hydrogen or $C_1$-$C_6$ alkyl. In some embodiments, $R^{16}$ is hydrogen or $C_1$-$C_3$ alkyl.

In one embodiment of the compounds of formula (I-A), (I), (Ia)-(Ie), (II), or (A)-(E), $R^{17}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, $R^{17}$ is hydrogen or optionally substituted $C_1$-$C_6$ alkyl. In some embodiments, $R^{17}$ is hydrogen or $C_1$-$C_6$ alkyl. In some embodiments, $R^{17}$ is hydrogen or $C_1$-$C_3$ alkyl.

In one embodiment of the compounds of formula (I-A), (I), (Ia)-(Ie), (II), or (A)-(E), $R^{18}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, $R^{18}$ is hydrogen or optionally substituted $C_1$-$C_6$ alkyl. In some embodiments, $R^{18}$ is hydrogen or $C_1$-$C_6$ alkyl. In some embodiments, $R^{18}$ is hydrogen or $C_1$-$C_3$ alkyl.

In one embodiment of the compounds of formula (I-A), (I), (Ia)-(Ie), (II), or (A)-(E), $R^{16}$ and $R^{17}$ are taken together to form an optionally substituted heterocyclyl, or optionally substituted heteroaryl. In some embodiments, $R^{16}$ and $R^{17}$ are taken together to form an optionally substituted heterocyclyl. In some embodiments, $R^{16}$ and $R^{17}$ are taken together to form an 3- to 7-membered optionally substituted heterocyclyl. In some embodiments, $R^{16}$ and $R^7$ are taken together to form an 3- to 7-membered optionally substituted heterocyclyl, comprising one or more heteroatoms selected from N, O, or S.

In one embodiment of the compounds of formula (I-A), (I), (Ia)-(Ie), (II), or (A)-(E), $R^3$ is —$NR^{16}R^{17}$, wherein $R^{16}$ and $R^{17}$ are taken together to form an 3- to 7-membered optionally substituted heterocyclyl. In one embodiment, $R^3$ is —$NR^{16}R^{17}$, wherein $R^{16}$ and $R^{17}$ are taken together to form a 6-membered optionally substituted heterocycle. In one embodiment, $R^3$ is —$NR^{16}R^{17}$, wherein $R^{16}$ and $R^{17}$ are taken together to form a 6-membered optionally substituted heterocycle. In one embodiment, $R^3$ is —$NR^{16}R^{17}$, wherein $R^{16}$ and $R^{17}$ are taken together to form an optionally substituted piperazine. In one embodiment, R³ is —NR¹⁶R¹⁷, wherein R¹⁶ and R¹⁷ are taken together to form a piperazine, optionally substituted with —SO₂CH₃, —NHSO₂CH₃, or —N(CH₃)SO₂CH₃. In one embodiment, R³ is

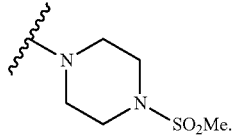

In one embodiment of the compounds of formula (I-A), (I), (Ia)-(Ie), (II), or (A)-(E), R¹¹ and R¹² are each independently hydrogen, halogen, —OH, or C₁-C₃ alkyl. In one embodiment, R¹¹ and R¹² are each independently hydrogen, halogen, or C₁-C₃ alkyl. In one embodiment, R¹¹ and R¹² are not —OH.

In one embodiment of the compounds of formula (I-A), (I), (Ia)-(Ie), (II), or (A)-(E), m is 1 or 2. In some embodiments, m is 1.

In one embodiment of the compounds of formula (I-A), (I), (Ia)-(Ie), (II), or (A)-(E), g is independently 0, 1, 2, or 3. In one embodiment, g is 0. In another embodiment, g is 1, 2, or 3. In some embodiments, g is 1 or 2.

In one embodiment of the compounds of formula (I-A) or (I), p in S(O)$_p$ is 2. In another embodiment, n is 1 or 2. In some embodiments, n is 0.

In one embodiment of the compounds of formula (I-A), (I), (Ia)-(Ie), (II), or (A)-(E), p is 2. In another embodiment, p is 1 or 2. In some embodiments, p is 0.

In one embodiment of the compounds of formula (I-A), (I), (Ia)-(Ie), (II), or (A)-(E), q is 0. In another embodiment, q is 1. In one embodiment, q is 2.

In one embodiment of the compounds of formula (I-A), (I), (Ia)-(Ie), (II), or (A)-(E), t is 1. In one embodiment, t is 2.

In one embodiment of the compounds of formula (E), gg is 1, 2, or 3. In some embodiments, gg is 1 or 2.

In one embodiment of the compounds of formula (I-A), (I), or (A)-(C), Z and V are not both a bond or absent (e.g., m is 0 in —(CR¹¹R¹²)$_m$—).

In one embodiment, the present disclosure provides compounds as disclosed in Table A1 or a pharmaceutically acceptable salt, tautomer, stereoisomer or prodrug thereof. In one embodiment, the present disclosure provides a compound selected from Compounds A1, A2, A4, A5, A6, A7, A9, A11, A12, A13, A14, A15, A21, A23, A24, A25, A27, A28, A30, A31, A32, A33, A34, A35, A36, A37, A38, A42, A43, A44, A45, A46, A47, A48, A49, A51, A52, A53, A55, A56, A61, A62, A63, A64, A65, A69, A70, A71, A73, A74, A75, A76, A77, A79, A80, A81, A84, A85, or A86, or a pharmaceutically acceptable salt, tautomer, stereoisomer or prodrug thereof. In one embodiment, the present disclosure provides a compound selected from Compounds A51(S), A51(R), A56(S) or A56(R), or a pharmaceutically acceptable salt, tautomer, or prodrug thereof. In one embodiment, the present disclosure provides compounds as disclosed in Table A1 or a pharmaceutically acceptable salt, tautomer, stereoisomer or prodrug thereof. In one embodiment, the present disclosure provides a compound selected from Compounds A3, A8, A10, A16, A17, A18, A19, A20, A22, A26, A29, A39, A40, A41, A50, A54, A57, A58, A59, A60, A66, A67, A68, A72, A78, A82, or A83, or a pharmaceutically acceptable salt, tautomer, stereoisomer or prodrug thereof. In one embodiment, the present disclosure provides compounds as disclosed in Table A2 or a pharmaceutically acceptable salt, tautomer, stereoisomer or prodrug thereof. In one embodiment, the present disclosure provides a compound selected from Compounds A99, A100, A101, A102, A103, or A104, or a pharmaceutically acceptable salt, tautomer, stereoisomer or prodrug thereof. In one embodiment, the present disclosure provides compounds as disclosed in Table A3 or a pharmaceutically acceptable salt, tautomer, stereoisomer or prodrug thereof.

TABLE A1

Compounds

| Compound ID | Structure |
|---|---|
| A1 | 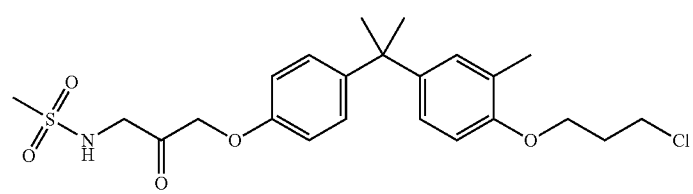 [SMILES: Cc1cc(C(C)(C)c2ccc(OCC(=O)CNS(C)(=O)=O)cc2)ccc1OCCCCl] |
| A2 | 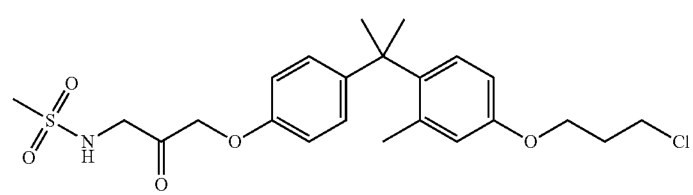 [SMILES: Cc1cc(OCCCCl)ccc1C(C)(C)c1ccc(OCC(=O)CNS(C)(=O)=O)cc1] |

TABLE A1-continued

Compounds

| Compound ID | Structure |
|---|---|
| A3 | 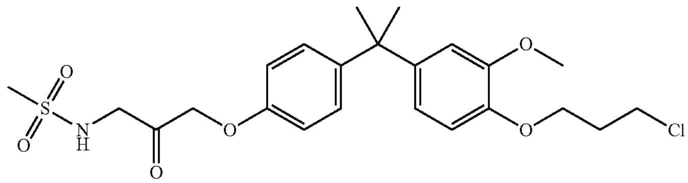 [SMILES: COc1cc(C(C)(C)c2ccc(OCC(=O)CNS(C)(=O)=O)cc2)ccc1OCCCCl] |
| A4 | 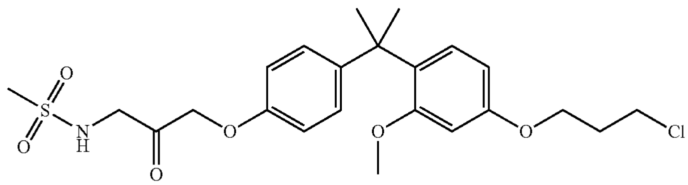 [SMILES: COc1cc(OCCCCl)ccc1C(C)(C)c1ccc(OCC(=O)CNS(C)(=O)=O)cc1] |
| A5 | 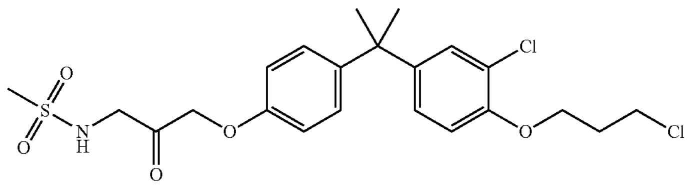 [SMILES: CC(C)(c1ccc(OCC(=O)CNS(C)(=O)=O)cc1)c1ccc(OCCCCl)c(Cl)c1] |
| A6 | 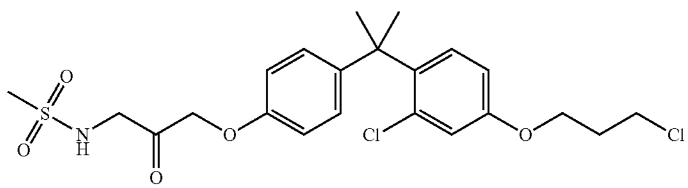 [SMILES: CC(C)(c1ccc(OCC(=O)CNS(C)(=O)=O)cc1)c1ccc(OCCCCl)cc1Cl] |
| A7 | 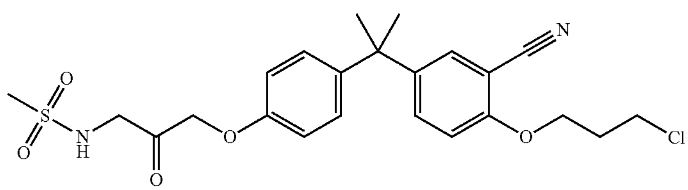 [SMILES: CC(C)(c1ccc(OCC(=O)CNS(C)(=O)=O)cc1)c1ccc(OCCCCl)c(C#N)c1] |
| A8 | 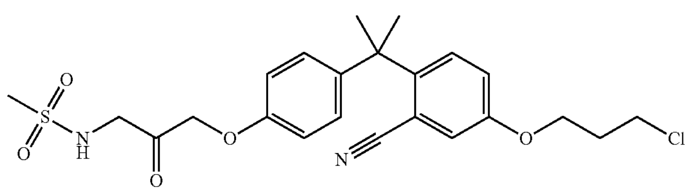 [SMILES: CC(C)(c1ccc(OCC(=O)CNS(C)(=O)=O)cc1)c1ccc(OCCCCl)cc1C#N] |
| A9 | 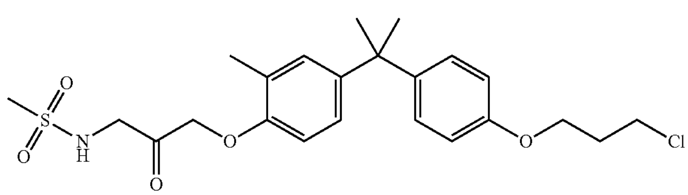 [SMILES: Cc1cc(C(C)(C)c2ccc(OCCCCl)cc2)ccc1OCC(=O)CNS(C)(=O)=O] |
| A10 | 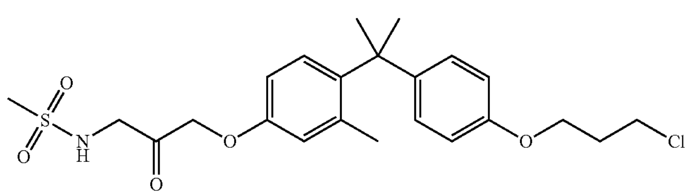 [SMILES: Cc1cc(OCC(=O)CNS(C)(=O)=O)ccc1C(C)(C)c1ccc(OCCCCl)cc1] |

TABLE A1-continued

Compounds

| Compound ID | Structure |
|---|---|
| A11 | 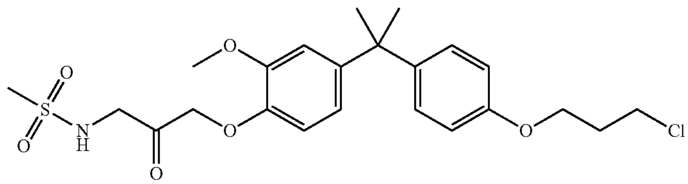 [SMILES: COc1cc(C(C)(C)c2ccc(OCCCCl)cc2)ccc1OCC(=O)CNS(C)(=O)=O] |
| A12 | 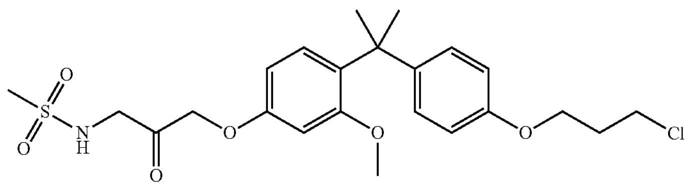 [SMILES: COc1cc(OCC(=O)CNS(C)(=O)=O)ccc1C(C)(C)c1ccc(OCCCCl)cc1] |
| A13 | 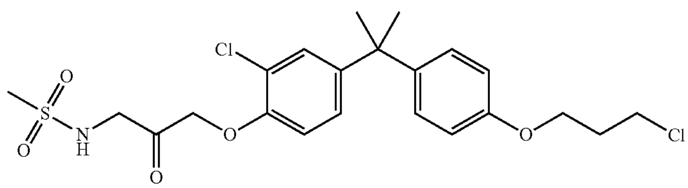 [SMILES: CC(C)(c1ccc(OCCCCl)cc1)c1ccc(OCC(=O)CNS(C)(=O)=O)c(Cl)c1] |
| A14 | 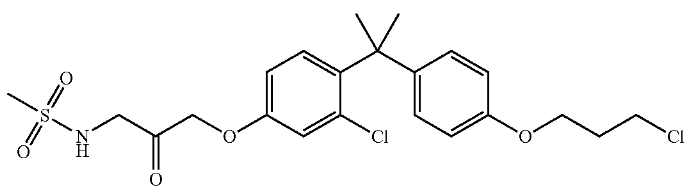 [SMILES: CC(C)(c1ccc(OCCCCl)cc1)c1ccc(OCC(=O)CNS(C)(=O)=O)cc1Cl] |
| A15 | 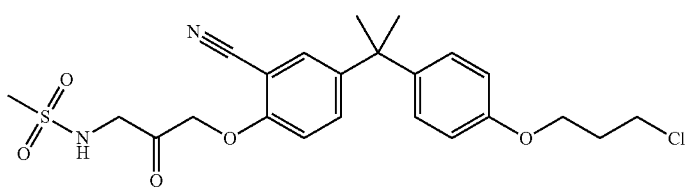 [SMILES: CC(C)(c1ccc(OCCCCl)cc1)c1ccc(OCC(=O)CNS(C)(=O)=O)c(C#N)c1] |
| A16 | 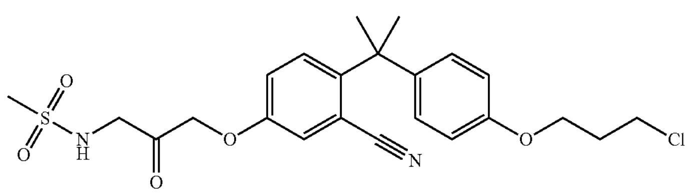 [SMILES: CC(C)(c1ccc(OCCCCl)cc1)c1ccc(OCC(=O)CNS(C)(=O)=O)cc1C#N] |
| A17 | 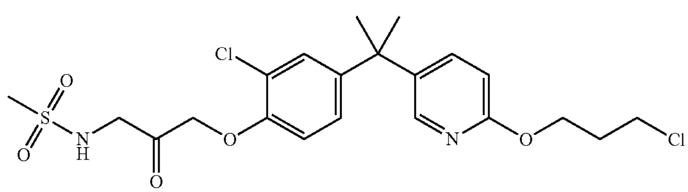 |
| A18 | 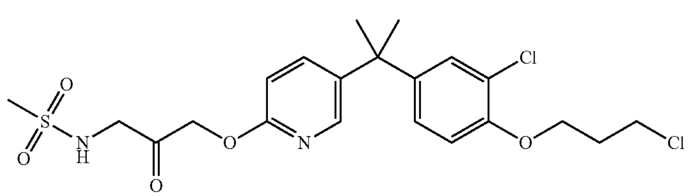 [SMILES: CC(C)(c1ccc(OCC(=O)CNS(C)(=O)=O)nc1)c1ccc(OCCCCl)c(Cl)c1] |

TABLE A1-continued
Compounds
| Compound ID | Structure |
|---|---|
| A19 | 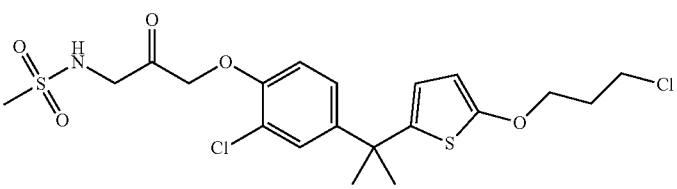 [SMILES: CC(C)(c1ccc(OCC(=O)CNS(C)(=O)=O)c(Cl)c1)c1ccc(OCCCCl)s1] |
| A20 | 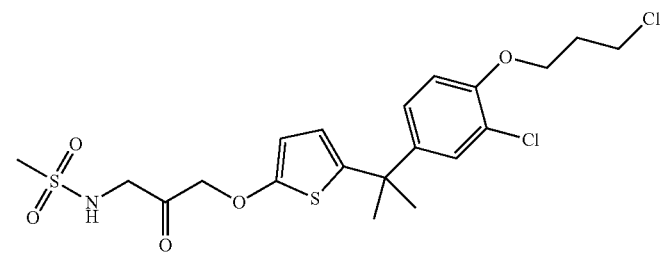 [SMILES: CC(C)(c1ccc(OCCCCl)c(Cl)c1)c1ccc(OCC(=O)CNS(C)(=O)=O)s1] |
| A21 | 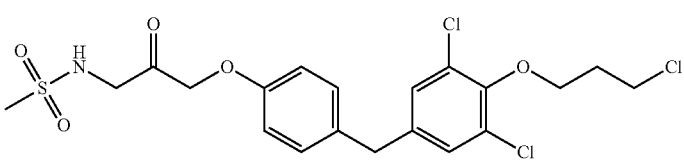 [SMILES: CS(=O)(=O)NCC(=O)COc1ccc(Cc2cc(Cl)c(OCCCCl)c(Cl)c2)cc1] |
| A22 | 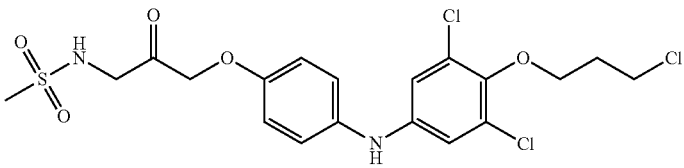 [SMILES: CS(=O)(=O)NCC(=O)COc1ccc(Nc2cc(Cl)c(OCCCCl)c(Cl)c2)cc1] |
| A23 | 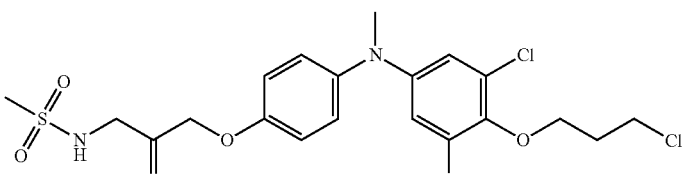 |
| A24 | 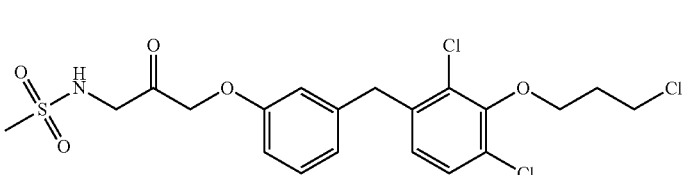 |
| A25 | 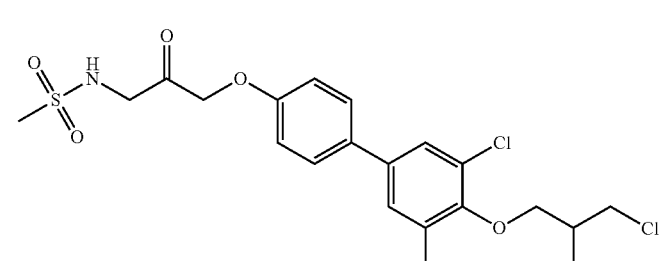 |

TABLE A1-continued

Compounds

| Compound ID | Structure |
|---|---|
| A26 | 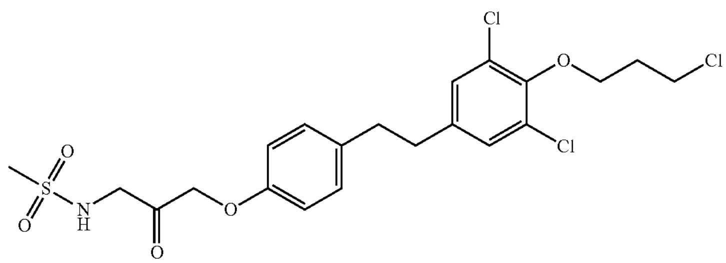 [SMILES: CS(=O)(=O)NCC(=O)COc1ccc(CCc2cc(Cl)c(OCCCCl)c(Cl)c2)cc1] |
| A27 | 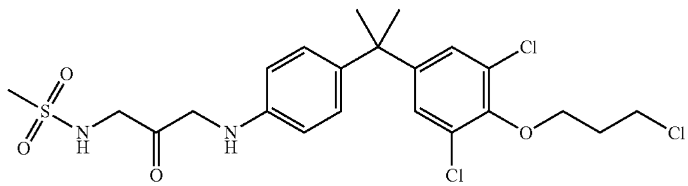 [SMILES: CC(C)(c1ccc(NCC(=O)CNS(C)(=O)=O)cc1)c1cc(Cl)c(OCCCCl)c(Cl)c1] |
| A28 | 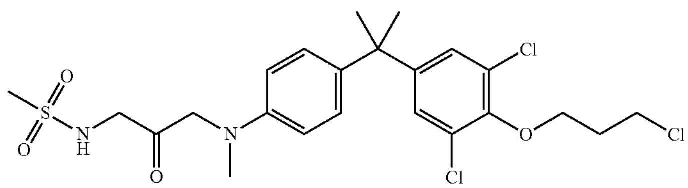 [SMILES: CN(CC(=O)CNS(C)(=O)=O)c1ccc(C(C)(C)c2cc(Cl)c(OCCCCl)c(Cl)c2)cc1] |
| A29 | 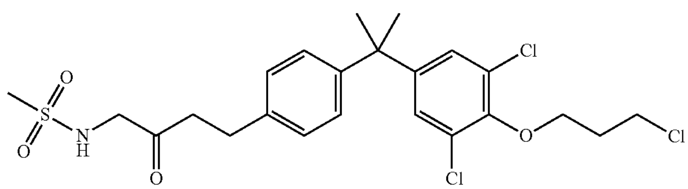 [SMILES: CC(C)(c1ccc(CCC(=O)CNS(C)(=O)=O)cc1)c1cc(Cl)c(OCCCCl)c(Cl)c1] |
| A30 | 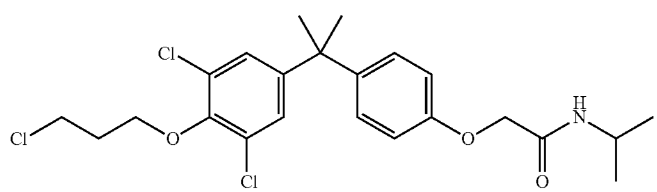 [SMILES: CC(C)NC(=O)COc1ccc(C(C)(C)c2cc(Cl)c(OCCCCl)c(Cl)c2)cc1] |
| A31 | 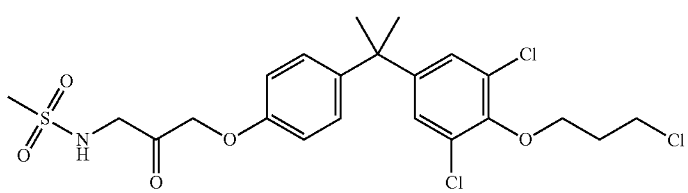 [SMILES: CC(C)(c1ccc(OCC(=O)CNS(C)(=O)=O)cc1)c1cc(Cl)c(OCCCCl)c(Cl)c1] |
| A32 | 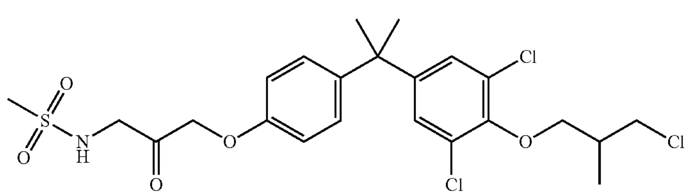 [SMILES: CC(CCl)COc1c(Cl)cc(C(C)(C)c2ccc(OCC(=O)CNS(C)(=O)=O)cc2)cc1Cl] |

TABLE A1-continued

Compounds

| Compound ID | Structure |
|---|---|
| A33 | *(chemical structure)* |
| A34 | *(chemical structure)* |
| A35 | *(chemical structure)* |
| A36 | *(chemical structure)* |
| A37 | *(chemical structure)* |
| A38 | *(chemical structure)* |
| A39 | *(chemical structure)* |

TABLE A1-continued
Compounds
| Compound ID | Structure |
|---|---|
| A40 | 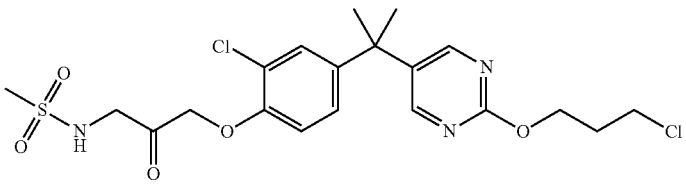 [SMILES: CC(C)(c1cnc(OCCCCl)nc1)c1ccc(OCC(=O)CNS(C)(=O)=O)c(Cl)c1] |
| A41 | 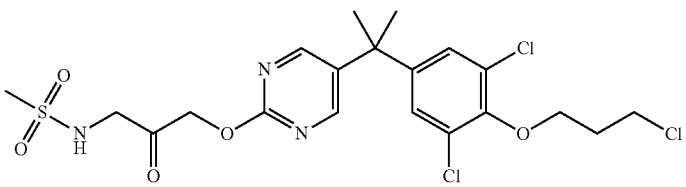 [SMILES: CC(C)(c1cnc(OCC(=O)CNS(C)(=O)=O)nc1)c1cc(Cl)c(OCCCCl)c(Cl)c1] |
| A42 | 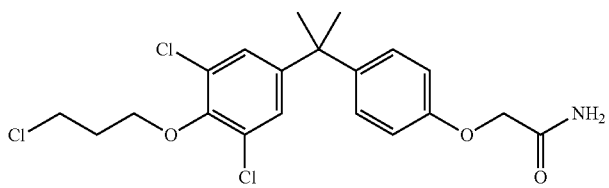 [SMILES: CC(C)(c1ccc(OCC(N)=O)cc1)c1cc(Cl)c(OCCCCl)c(Cl)c1] |
| A43 | 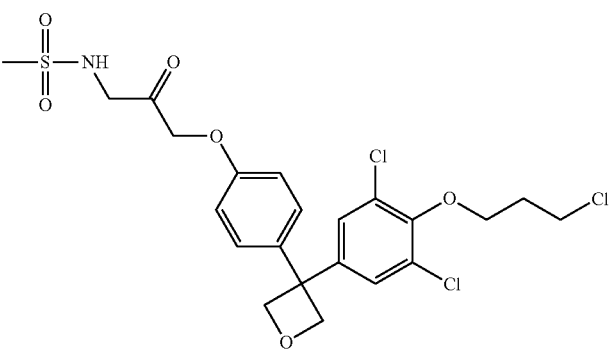 [SMILES: CS(=O)(=O)NCC(=O)COc1ccc(C2(c3cc(Cl)c(OCCCCl)c(Cl)c3)COC2)cc1] |
| A44 | 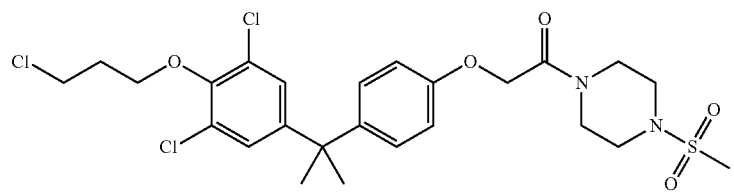 [SMILES: CC(C)(c1ccc(OCC(=O)N2CCN(S(C)(=O)=O)CC2)cc1)c1cc(Cl)c(OCCCCl)c(Cl)c1] |
| A45 | 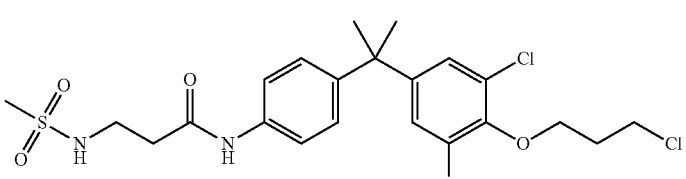 |
| A46 | 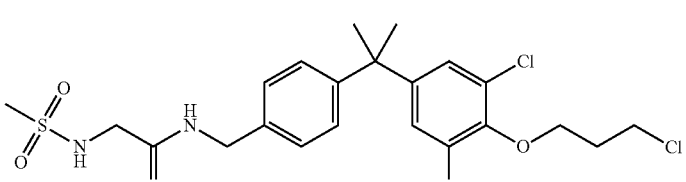 |

TABLE A1-continued

Compounds

| Compound ID | Structure |
|---|---|
| A47 | (structure) |
| A48 | (structure) |
| A49 | (structure) |
| A50 | (structure) |
| A51 | (structure) |
| A51(S) | (structure) |
| A51(R) | (structure) |

TABLE A1-continued
| Compound ID | Structure |
|---|---|
| A52 | 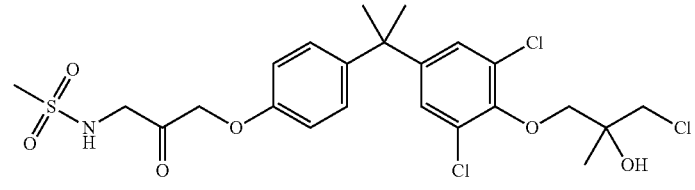 [SMILES: CC(O)(CCl)COc1c(Cl)cc(C(C)(C)c2ccc(OCC(=O)CNS(C)(=O)=O)cc2)cc1Cl] |
| A52(S) | 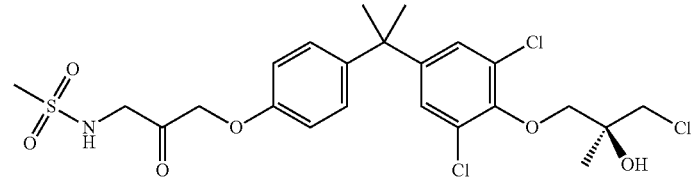 [SMILES: CC(C)(c1ccc(OCC(=O)CNS(C)(=O)=O)cc1)c1cc(Cl)c(OC[C@](C)(O)CCl)c(Cl)c1] |
| A52(R) | 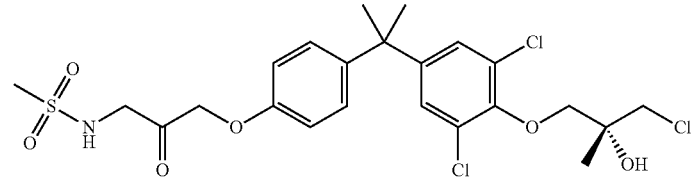 [SMILES: CC(C)(c1ccc(OCC(=O)CNS(C)(=O)=O)cc1)c1cc(Cl)c(OC[C@@](C)(O)CCl)c(Cl)c1] |
| A53 | 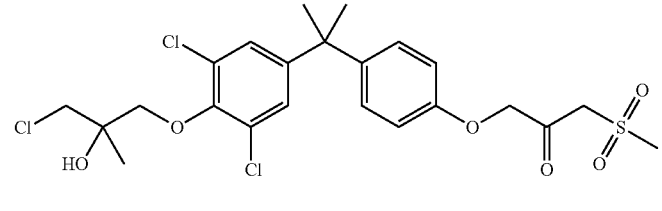 [SMILES: CC(O)(CCl)COc1c(Cl)cc(C(C)(C)c2ccc(OCC(=O)CS(C)(=O)=O)cc2)cc1Cl] |
| A53(S) | 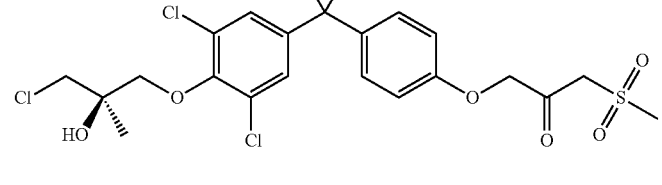 |
| A53(R) | 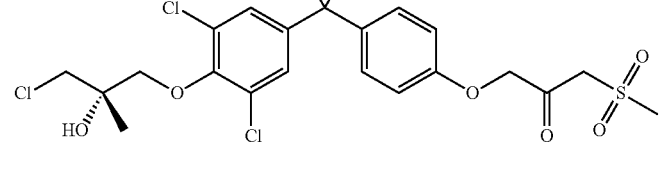 |
| A54 | 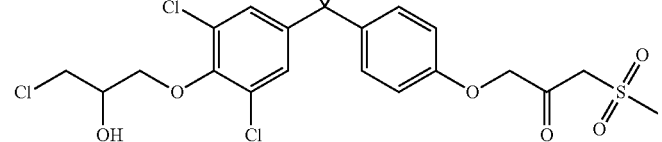 |

TABLE A1-continued

Compounds

| Compound ID | Structure |
|---|---|
| A54(S) | (structure) |
| A54(R) | (structure) |
| A55 | (structure) |
| A56 | (structure) |
| A56(S) | (structure) |
| A56(R) | (structure) |
| A57 | (structure) |
| A57(S) | (structure) |

TABLE A1-continued

Compounds

| Compound ID | Structure |
|---|---|
| A57(R) | 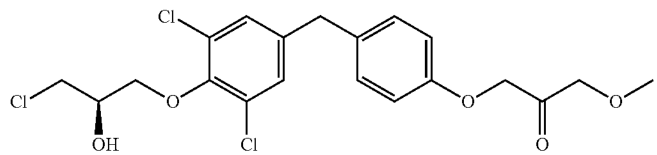 [SMILES: COCC(=O)COc1ccc(Cc2cc(Cl)c(OC[C@@H](O)CCl)c(Cl)c2)cc1] |
| A58 | 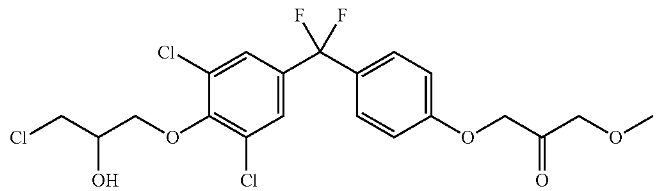 |
| A58(S) | 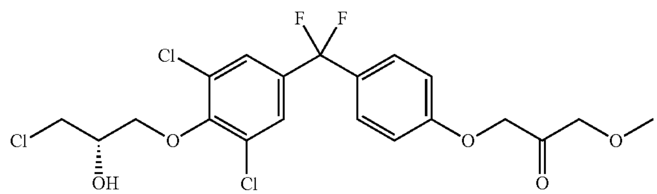 [SMILES: COCC(=O)COc1ccc(C(F)(F)c2cc(Cl)c(OC[C@H](O)CCl)c(Cl)c2)cc1] |
| A58(R) | 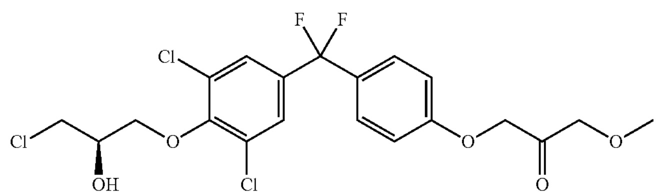 [SMILES: COCC(=O)COc1ccc(C(F)(F)c2cc(Cl)c(OC[C@@H](O)CCl)c(Cl)c2)cc1] |
| A59 | 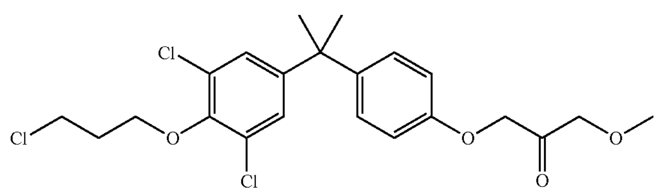 [SMILES: COCC(=O)COc1ccc(C(C)(C)c2cc(Cl)c(OCCCCl)c(Cl)c2)cc1] |
| A60 | 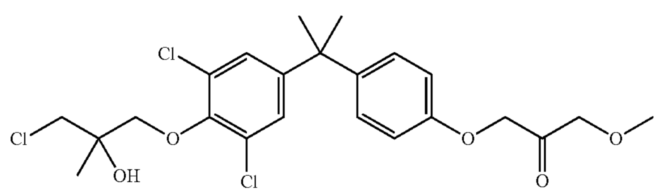 [SMILES: COCC(=O)COc1ccc(C(C)(C)c2cc(Cl)c(OCC(C)(O)CCl)c(Cl)c2)cc1] |
| A60(S) | 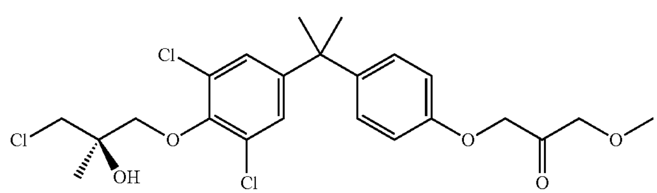 [SMILES: COCC(=O)COc1ccc(C(C)(C)c2cc(Cl)c(OC[C@@](C)(O)CCl)c(Cl)c2)cc1] |
| A60(R) | 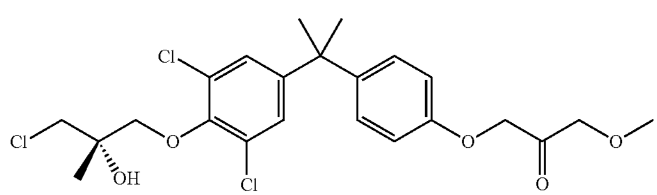 [SMILES: COCC(=O)COc1ccc(C(C)(C)c2cc(Cl)c(OC[C@](C)(O)CCl)c(Cl)c2)cc1] |

TABLE A1-continued

Compounds

| Compound ID | Structure |
|---|---|
| A61 | (structure) |
| A62 | (structure) |
| A63 | (structure) |
| A64 | (structure) |
| A65 | (structure) |
| A66 | (structure) |
| A67 | (structure) |
| A68 | (structure) |

TABLE A1-continued

Compounds

| Compound ID | Structure |
|---|---|
| A69 | 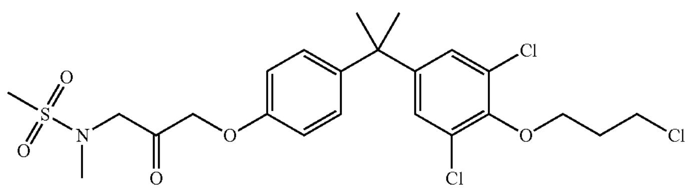 [SMILES: CN(CC(=O)COc1ccc(C(C)(C)c2cc(Cl)c(OCCCCl)c(Cl)c2)cc1)S(C)(=O)=O] |
| A70 | 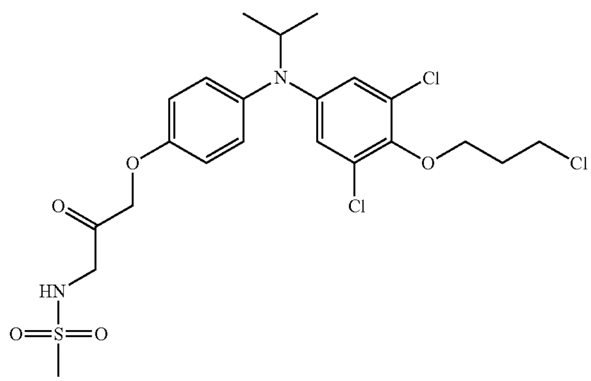 [SMILES: CC(C)N(c1ccc(OCC(=O)CNS(C)(=O)=O)cc1)c1cc(Cl)c(OCCCCl)c(Cl)c1] |
| A71 | 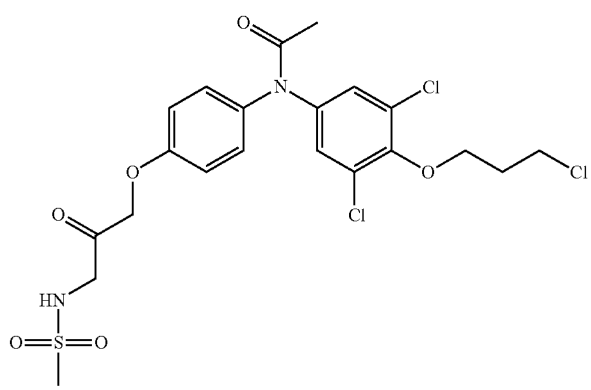 [SMILES: CC(=O)N(c1ccc(OCC(=O)CNS(C)(=O)=O)cc1)c1cc(Cl)c(OCCCCl)c(Cl)c1] |
| A72 | 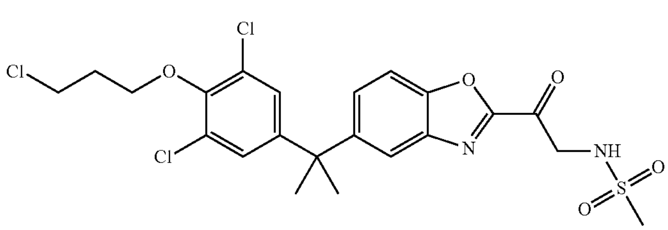 [SMILES: CC(C)(c1cc(Cl)c(OCCCCl)c(Cl)c1)c1ccc2oc(C(=O)CNS(C)(=O)=O)nc2c1] |
| A73 | 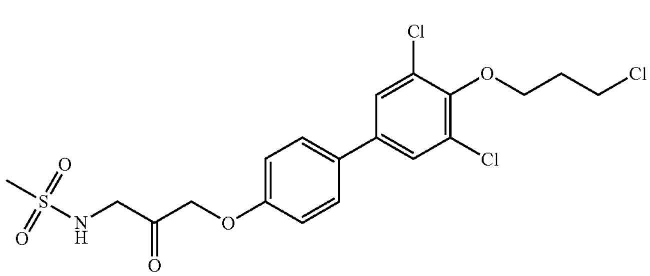 [SMILES: CS(=O)(=O)NCC(=O)COc1ccc(-c2cc(Cl)c(OCCCCl)c(Cl)c2)cc1] |

TABLE A1-continued

| Compound ID | Structure |
|---|---|
| A74 | 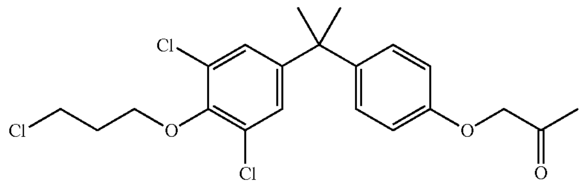 [SMILES: CC(=O)COc1ccc(C(C)(C)c2cc(Cl)c(OCCCCl)c(Cl)c2)cc1] |
| A75 | 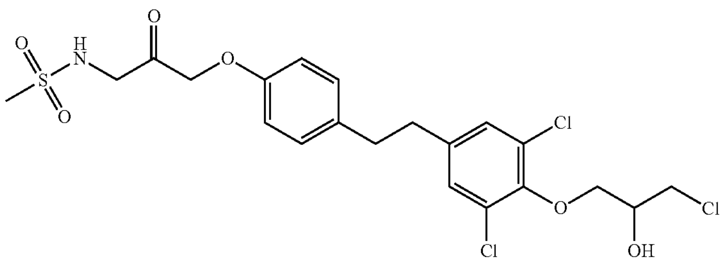 [SMILES: CS(=O)(=O)NCC(=O)COc1ccc(CCc2cc(Cl)c(OCC(O)CCl)c(Cl)c2)cc1] |
| A76 | 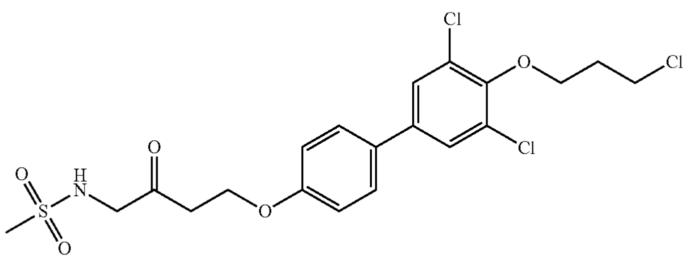 [SMILES: CS(=O)(=O)NCC(=O)CCOc1ccc(-c2cc(Cl)c(OCCCCl)c(Cl)c2)cc1] |
| A77 | 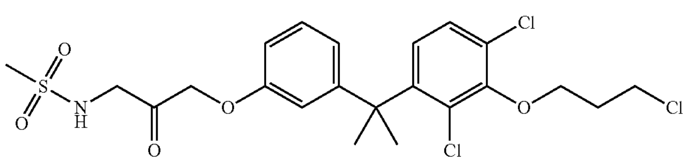 [SMILES: CC(C)(c1cccc(OCC(=O)CNS(C)(=O)=O)c1)c1ccc(Cl)c(OCCCCl)c1Cl] |
| A78 | 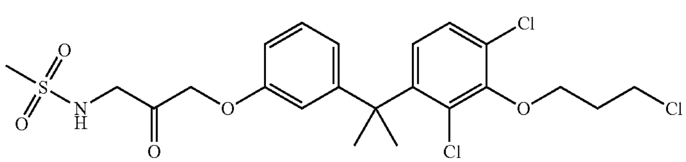 [SMILES: CC(C)(c1cccc(OCC(=O)CNS(C)(=O)=O)c1)c1ccc(Cl)c(OCCCCl)c1Cl] |
| A79 | 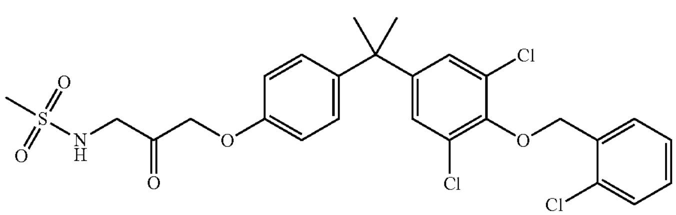 [SMILES: CC(C)(c1ccc(OCC(=O)CNS(C)(=O)=O)cc1)c1cc(Cl)c(OCc2ccccc2Cl)c(Cl)c1] |
| A80 | 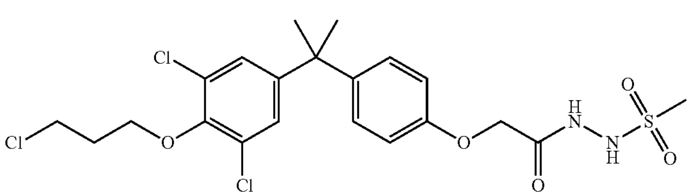 [SMILES: CC(C)(c1ccc(OCC(=O)NNS(C)(=O)=O)cc1)c1cc(Cl)c(OCCCCl)c(Cl)c1] |

TABLE A1-continued

| Compound ID | Structure |
|---|---|
| A81 | 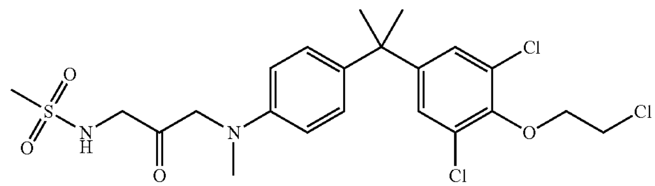 [SMILES: CN(CC(=O)CNS(C)(=O)=O)c1ccc(C(C)(C)c2cc(Cl)c(OCCCl)c(Cl)c2)cc1] |
| A82 | 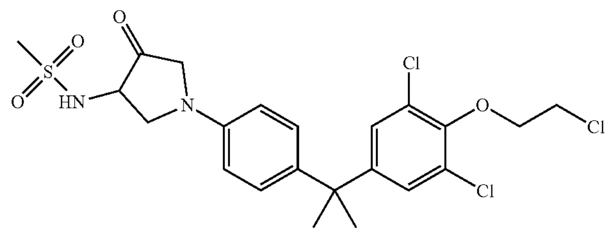 [SMILES: CC(C)(c1ccc(N2CC(=O)C(NS(C)(=O)=O)C2)cc1)c1cc(Cl)c(OCCCl)c(Cl)c1] |
| A83 | 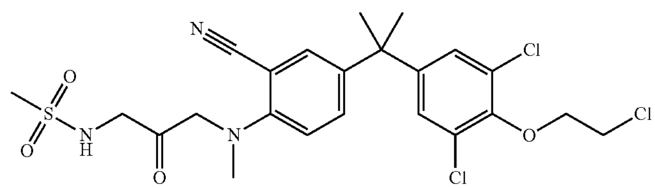 [SMILES: CN(CC(=O)CNS(C)(=O)=O)c1ccc(C(C)(C)c2cc(Cl)c(OCCCl)c(Cl)c2)cc1C#N] |
| A84 | 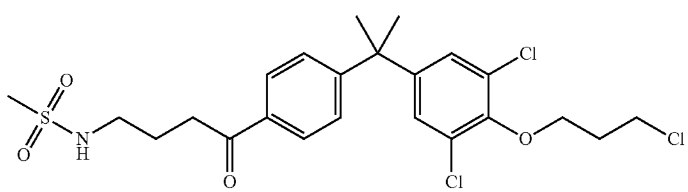 [SMILES: CC(C)(c1ccc(C(=O)CCCNS(C)(=O)=O)cc1)c1cc(Cl)c(OCCCCl)c(Cl)c1] |
| A85 | 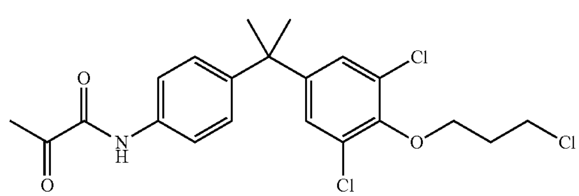 [SMILES: CC(=O)C(=O)Nc1ccc(C(C)(C)c2cc(Cl)c(OCCCCl)c(Cl)c2)cc1] |
| A86 | 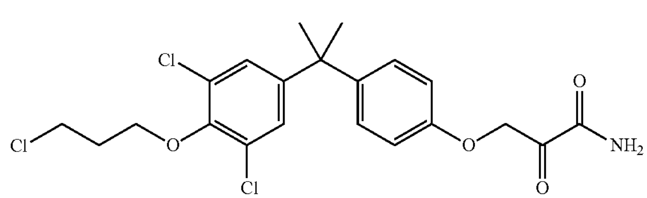 [SMILES: CC(C)(c1ccc(OCC(=O)C(N)=O)cc1)c1cc(Cl)c(OCCCCl)c(Cl)c1] |

TABLE A2

Compounds

| Compound ID | Structure |
|---|---|
| A87 | (structure) |
| A88 | (structure) |
| A89 | (structure) |
| A90 | (structure) |
| A91 | (structure) |
| A92 | (structure) |
| A93 | (structure) |
| A94 | (structure) |

TABLE A2-continued

Compounds

| Compound ID | Structure |
|---|---|
| A95 | (structure image) |
| A96 | (structure image) |
| A97 | (structure image) |
| A98 | (structure image) |

TABLE A3

Compounds

| Compound ID | Structure |
|---|---|
| A99 | (structure image) |
| A100 | (structure image) |

TABLE A3-continued
| Compound ID | Structure |
|---|---|
| A101 | 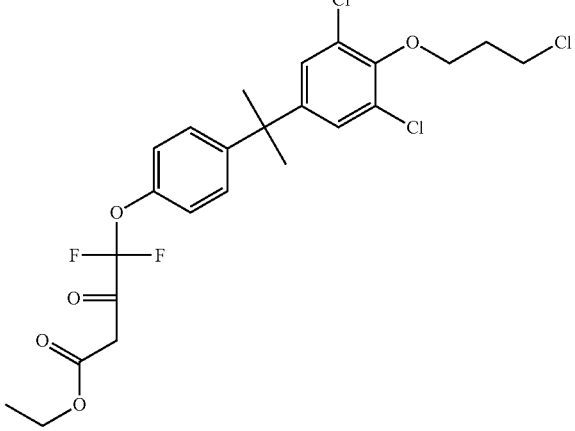 |
| A102 | 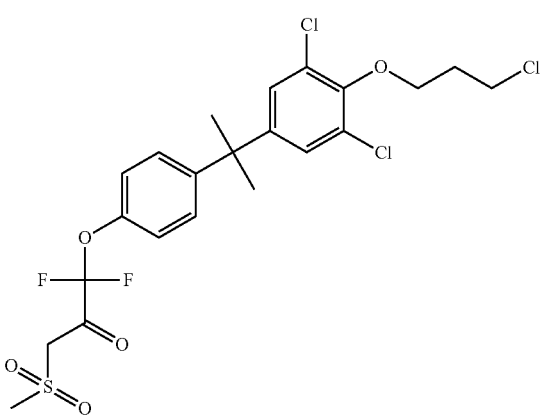 [SMILES: CC(C)(c1ccc(OC(F)(F)C(=O)CS(C)(=O)=O)cc1)c1cc(Cl)c(OCCCCl)c(Cl)c1] |
| A103 | 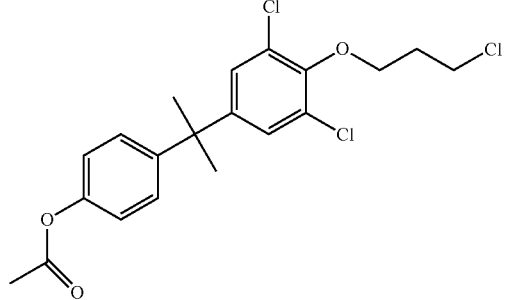 [SMILES: CC(=O)Oc1ccc(C(C)(C)c2cc(Cl)c(OCCCCl)c(Cl)c2)cc1] |

TABLE A3-continued

Compounds

| Compound ID | Structure |
|---|---|
| A104 | 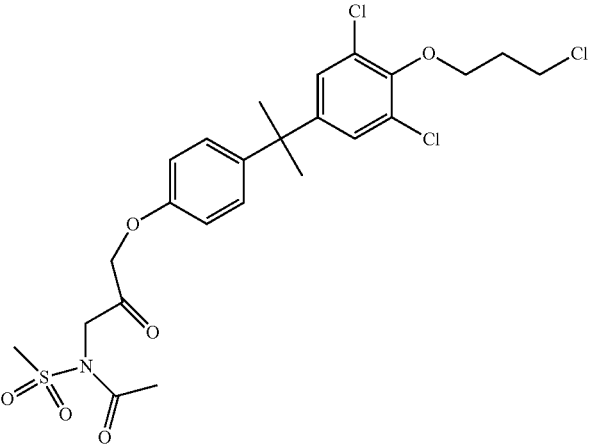 [SMILES: CC(=O)N(CC(=O)COc1ccc(C(C)(C)c2cc(Cl)c(OCCCCl)c(Cl)c2)cc1)S(C)(=O)=O] |

In some embodiments, the compound of formula (I) is selected from a compound in Table B, or a pharmaceutically acceptable salt, tautomer, stereoisomer or prodrug thereof.

TABLE B

Compounds

N-(3-(4-(2-(3,5-dichloro-4-(3-Chloro-2-hydroxypropoxy)phenyl)propan-2-yl)phenoxy)-2-oxopropyl)methanesulfonamide;
(S)-N-(3-(4-(2-(3,5-dichloro-4-(3-Chloro-2-hydroxypropoxy)phenyl)propan-2-yl)phenoxy)-2-oxopropyl)methanesulfonamide;
(R)-N-(3-(4-(2-(3,5-dichloro-4-(3-Chloro-2-hydroxypropoxy)phenyl)propan-2-yl)phenoxy)-2-oxopropyl)methanesulfonamide;
N-(3-(4-(2-(3,5-dichloro-4-(3-Chloro-2-hydroxy-2-methylpropoxy)phenyl)propan-2-yl)phenoxy)-2-oxopropyl)methanesulfonamide;
(R)-N-(3-(4-(2-(3,5-dichloro-4-(3-Chloro-2-hydroxy-2-methylpropoxy)phenyl)propan-2-yl)phenoxy)-2-oxopropyl)methanesulfonamide;
(S)-N-(3-(4-(2-(3,5-dichloro-4-(3-Chloro-2-hydroxy-2-methylpropoxy)phenyl)propan-2-yl)phenoxy)-2-oxopropyl)methanesulfonamide;
N-(3-(4-(2-(3,5-dichloro-4-(3-Chloro-2-hydroxy-2-methylpropoxy)phenyl)propan-2-yl)phenoxy)-2-oxopropyl)methanesulfonamide;
(S)-N-(3-(4-(2-(3,5-dichloro-4-(3-Chloro-2-hydroxy-2-methylpropoxy)phenyl)propan-2-yl)phenoxy)-2-oxopropyl)methanesulfonamide;
(R)-N-(3-(4-(2-(3,5-dichloro-4-(3-Chloro-2-hydroxy-2-methylpropoxy)phenyl)propan-2-yl)phenoxy)-2-oxopropyl)methanesulfonamide;
N-(3-(4-(2-(3,5-dichloro-4-(3-Chloropropoxy)phenyl)propan-2-yl)phenoxy)-2-oxopropyl)methanesulfonamide;
1-(4-(2-(3,5-dichloro-4-(3-Chloro-2-hydroxypropoxy)phenyl)propan-2-yl)phenoxy)-3-(methylsulfonyl)propan-2-one;
(S)-1-(4-(2-(3,5-dichloro-4-(3-Chloro-2-hydroxypropoxy)phenyl)propan-2-yl)phenoxy)-3-(methylsulfonyl)propan-2-one;
(R)-1-(4-(2-(3,5-dichloro-4-(3-Chloro-2-hydroxypropoxy)phenyl)propan-2-yl)phenoxy)-3-(methylsulfonyl)propan-2-one;
1-(4-(2-(3,5-dichloro-4-(3-Chloro-2-hydroxy-2-methylpropoxy)phenyl)propan-2-yl)phenoxy)-3-(methylsulfonyl)propan-2-one;
(R)-1-(4-(2-(3,5-dichloro-4-(3-Chloro-2-hydroxy-2-methylpropoxy)phenyl)propan-2-yl)phenoxy)-3-(methylsulfonyl)propan-2-one
(S)-1-(4-(2-(3,5-dichloro-4-(3-Chloro-2-hydroxy-2-methylpropoxy)phenyl)propan-2-yl)phenoxy)-3-(methylsulfonyl)propan-2-one;
1-(4-(2-(3,5-dichloro-4-(3-Chloropropoxy)phenyl)propan-2-yl)phenoxy)-3-(methylsulfonyl)propan-2-one;
1-(4-(2-(3,5-dichloro-4-(3-Chloro-2-hydroxypropoxy)phenyl)propan-2-yl)phenoxy)-3-methoxypropan-2-one;
(S)-1-(4-(2-(3,5-dichloro-4-(3-Chloro-2-hydroxypropoxy)phenyl)propan-2-yl)phenoxy)-3-methoxypropan-2-one;
(R)-1-(4-(2-(3,5-dichloro-4-(3-Chloro-2-hydroxypropoxy)phenyl)propan-2-yl)phenoxy)-3-methoxypropan-2-one;
1-(4-(3,5-dichloro-4-(3-Chloro-2-hydroxypropoxy)benzyl)phenoxy)-3-methoxy-propan-2-one;

TABLE B-continued

Compounds (S)-1-(4-(3,5-dichloro-4-(3-Chloro-2-hydroxypropoxy)benzyl)phenoxy)-3-methoxypropan-2-one;
(R)-1-(4-(3,5-dichloro-4-(3-Chloro-2-hydroxypropoxy)benzyl)phenoxy)-3-methoxypropan-2-one;
1-(4-((3,5-dichloro-4-(3-Chloro-2-hydroxypropoxy)phenyl)difluoromethyl)phenoxy)-3-methoxypropan-2-one;
(S)-1-(4-((3,5-dichloro-4-(3-Chloro-2-hydroxypropoxy)phenyl)difluoromethyl)phenoxy)-3-methoxypropan-2-one;
(R)-1-(4-((3,5-dichloro-4-(3-Chloro-2-hydroxypropoxy)phenyl)difluoromethyl)phenoxy)-3-methoxypropan-2-one;
1-(4-(2-(3,5-dichloro-4-(3-Chloro-2-hydroxy-2-methylpropoxy)phenyl)propan-2-yl)phenoxy)-3-methoxypropan-2-one;
(R)-1-(4-(2-(3,5-dichloro-4-(3-Chloro-2-hydroxy-2-methylpropoxy)phenyl)propan-2-yl)phenoxy)-3-methoxypropan-2-one;
(S)-1-(4-(2-(3,5-dichloro-4-(3-Chloro-2-hydroxy-2-methylpropoxy)phenyl)propan-2-yl)phenoxy)-3-methoxypropan-2-one;
N-(3-(4-(2-(4-(3-Chloropropoxy)-3-methylphenyl)propan-2-yl)phenoxy)-2-oxopropyl)methanesulfonamide;
N-(3-(4-(2-(4-(3-Chloropropoxy)-2-methylphenyl)propan-2-yl)phenoxy)-2-oxopropyl)methanesulfonamide;
N-(3-(4-(2-(4-(3-Chloropropoxy)-3-methoxyphenyl)propan-2-yl)phenoxy)-2-oxopropyl)methanesulfonamide;
N-(3-(4-(2-(4-(3-Chloropropoxy)-2-methoxyphenyl)propan-2-yl)phenoxy)-2-oxopropyl)methanesulfonamide;
N-(3-(4-(2-(3-Chloro-4-(3-Chloropropoxy)phenyl)propan-2-yl)phenoxy)-2-oxopropyl)methanesulfonamide;
N-(3-(4-(2-(2-Chloro-4-(3-Chloropropoxy)phenyl)propan-2-yl)phenoxy)-2-oxopropyl)methanesulfonamide;
N-(3-(4-(2-(4-(3-Chloropropoxy)-3-cyanophenyl)propan-2-yl)phenoxy)-2-oxopropyl)methanesulfonamide;
N-(3-(4-(2-(4-(3-Chloropropoxy)-2-cyanophenyl)propan-2-yl)phenoxy)-2-oxopropyl)methanesulfonamide;
N-(3-(4-(2-(4-(3-Chloropropoxy)phenyl)propan-2-yl)-2-methylphenoxy)-2-oxopropyl)methanesulfonamide;
N-(3-(4-(2-(4-(3-Chloropropoxy)phenyl)propan-2-yl)-3-methylphenoxy)-2-oxopropyl)methanesulfonamide;
N-(3-(4-(2-(4-(3-Chloropropoxy)phenyl)propan-2-yl)-2-methoxyphenoxy)-2-oxopropyl)methanesulfonamide;
N-(3-(4-(2-(4-(3-Chloropropoxy)phenyl)propan-2-yl)-3-methoxyphenoxy)-2-oxopropyl)methanesulfonamide;
N-(3-(2-Chloro-4-(2-(4-(3-Chloropropoxy)phenyl)propan-2-yl)phenoxy)-2-oxopropyl)methanesulfonamide;
N-(3-(3-Chloro-4-(2-(4-(3-Chloropropoxy)phenyl)propan-2-yl)phenoxy)-2-oxopropyl)methanesulfonamide;
N-(3-(4-(2-(4-(3-Chloropropoxy)phenyl)propan-2-yl)-2-cyanophenoxy)-2-oxopropyl)methanesulfonamide;
N-(3-(4-(2-(4-(3-Chloropropoxy)phenyl)propan-2-yl)-3-cyanophenoxy)-2-oxopropyl)methanesulfonamide;
N-(3-(2-Chloro-4-(2-(6-(3-Chloropropoxy)pyridin-3-yl)propan-2-yl)phenoxy)-2-oxopropyl)methanesulfonamide;
N-(3-45-(2-(3-Chloro-4-(3-Chloropropoxy)phenyl)propan-2-yl)pyridin-2-yl)oxy)-2-oxopropyl)methanesulfonamide;
N-(3-(2-Chloro-4-(2-(5-(3-Chloropropoxy)thiophen-2-yl)propan-2-yl)phenoxy)-2-oxopropyl)methanesulfonamide;
N-(3-((5-(2-(3-Chloro-4-(3-Chloropropoxy)phenyl)propan-2-yl)thiophen-2-yl)oxy)-2-oxopropyl)methanesulfonamide;
N-(3-(4-(3,5-dichloro-4-(3-Chloropropoxy)benzyl)phenoxy)-2-oxopropyl)methanesulfonamide;
N-(3-(4-((3,5-dichloro-4-(3-Chloropropoxy)phenyl)amino)phenoxy)-2-oxopropyl)methanesulfonamide;
N-(3-(4-((3,5-dichloro-4-(3-Chloropropoxy)phenyl)(methyDamino)phenoxy)-2-oxopropyl)methanesulfonamide;
N-(3-((3',5'-dichloro-4'-(3-Chloro-2-hydroxypropoxy)-[1,1'-biphenyl]-4-yl)oxy)-2-oxopropyl)methanesulfonamide;
N-(3-(4-(3,5-dichloro-4-(3-Chloropropoxy)phenethyl)phenoxy)-2-oxopropyl)methanesulfonamide;
N-(3-((4-(2-(3,5-dichloro-4-(3-Chloropropoxy)phenyl)propan-2-yl)phenyl)amino)-2-oxopropyl)methanesulfonamide;
N-(3-((4-(2-(3,5-dichloro-4-(3-Chloropropoxy)phenyl)propan-2-yl)phenyl)(methyl)amino)-2-oxopropyl)methanesulfonamide;
N-(4-(4-(2-(3,5-dichloro-4-(3-Chloropropoxy)phenyl)propan-2-yl)phenyl)-2-oxobutypmethanesulfonamide;
N-(3-(4-(2-(3,5-dichloro-4-(3-Chloro-2-methylpropoxy)phenyl)propan-2-yl)phenoxy)-2-oxopropyl)methanesulfonamide;
N-(3-(4-(2-(3,5-dichloro-4-(2-Chloroethoxy)phenyl)propan-2-yl)phenoxy)-2-oxopropyl)methanesulfonamide;
N-(3-(4-(2-(3,5-dichloro-4-(4-Chlorobutyl)phenyl)propan-2-yl)phenoxy)-2-oxopropyl)methanesulfonamide;

TABLE B-continued

Compounds

N-(3-(4-(2-(3,5-dichloro-4-((3-Chloropropyl)amino)phenyl)propan-2-yl)phenoxy)-2-oxopropyl)methanesulfonamide;
N-(3-(4-(2-(3,5-dichloro-4-((3-Chloropropyl)(methyl)amino)phenyl)propan-2-yl)phenoxy)-2-oxopropyl)methanesulfonamide;
N-(3-(4-(2-(3,5-dichloro-4-((3-Chlorobenzypoxy)phenyl)propan-2-yl)phenoxy)-2-oxopropyl)methanesulfonamide;
N-(3-(4-(2-(3,5-dichloro-4-((4-Chlorobenzypoxy)phenyl)propan-2-yl)phenoxy)-2-oxopropyl)methanesulfonamide;
N-(3-(2-Chloro-4-(2-(2-(3-Chloropropoxy)pyrimidin-5-yl)propan-2-yl)phenoxy)-2-oxopropyl)methanesulfonamide; or
N-(3-((5-(2-(3,5-dichloro-4-(3-Chloropropoxy)phenyl)propan-2-yl)pyrimidin-2-yl)oxy)-2-oxopropyl)methanesulfonamide.

Therapeutic Use

The present compounds find use in any number of methods. For example, in some embodiments the compounds are useful in methods for modulating androgen receptor (AR). Accordingly, in one embodiment, the present disclosure provides the use of any one of the foregoing compounds of formula (I), (I-A), (Ia)-(Ie), (A)-(E), and (II), or a pharmaceutically acceptable salt, tautomer, stereoisomer or prodrug thereof, for modulating androgen receptor (AR) activity. For example in some embodiments, modulating androgen receptor (AR) activity is in a mammalian cell. Modulating androgen receptor (AR) can be in a subject in need thereof (e.g., a mammalian subject) and for treatment of any of the described conditions or diseases. 10688 In another aspect, the present disclosure provides a method for modulating androgen receptor activity, comprising administering a pharmaceutical composition comprising a compound of formula (I), (I-A), (Ia)-(Ie), (A)-(E), and (II) to a subject in need thereof. In one embodiment, the modulating AR is binding to AR. In some aspects, modulating the androgen receptor (AR) is inhibiting androgen receptor. In one embodiment, the modulating AR is modulating AR N-terminal domain (NTD). In some embodiments, modulating the AR is inhibiting transactivation of androgen receptor N-terminal domain (NTD). In some embodiments, the subject is human.

In some embodiments, modulating the AR is for treating a condition or disease selected from prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration. In some embodiments, the condition or disease is prostate cancer. In some embodiments, the indication is prostate cancer. In other embodiments, the prostate cancer is primary/localized prostate cancer, locally advanced prostate cancer, recurrent prostate cancer, metastatic prostate cancer, advanced prostate cancer, or metastatic castration-resistant prostate cancer (CRPC), or hormone-sensitive prostate cancer. While in other embodiments, the prostate cancer is androgen dependent prostate cancer. In other embodiments, the spinal and bulbar muscular atrophy is Kennedy's disease.

In some embodiments, the prostate cancer is primary or localized prostate cancer, locally advanced prostate cancer, recurrent prostate cancer, advanced prostate cancer, metastatic prostate cancer, metastatic castration-resistant prostate cancer (CRPC), and hormone-sensitive prostate cancer. In some embodiments, the prostate cancer is CRPC. In some embodiments, the prostate cancer expresses full-length androgen receptor (AR) or truncated AR splice variant.

In one embodiment of the present disclosure, a method of treating a condition associated with cell proliferation in a patient in need thereof is provided, comprising administering a compounds of formula (I), (I-A), (Ia)-(Ie), (A)-(E), and (II), or a pharmaceutically acceptable salt, tautomer, stereoisomer or prodrug thereof, to a subject in need thereof. In one embodiment, the present invention provides a method of treating cancer or tumors. In another embodiment, the present invention provides a method of treating prostate cancer or breast cancer.

In one embodiment of the present disclosure, a method of reducing, inhibiting, or ameliorating proliferation, comprising administering a therapeutically effective amount of a compound of formula (I), (I-A), (Ia)-(Ie), (A)-(E), and (II), or a pharmaceutically acceptable salt, tautomer or stereoisomer thereof is provided. In one embodiment, the reducing, inhibiting, or ameliorating in the method disclosed herein, is in vivo. In another embodiment, the reducing, inhibiting, or ameliorating is in vitro.

In one embodiment, the cells in the method disclosed herein, are a cancer cells. In one embodiment, the cancer cells are a prostate cancer cells. In one embodiment, the prostate cancer cells are cells of primary/localized prostate cancer (newly diagnosed or early stage), locally advanced prostate cancer, recurrent prostate cancer (e.g., prostate cancer which was not responsive to primary therapy), metastatic prostate cancer, advanced prostate cancer (e.g., after castration for recurrent prostate cancer), metastatic castration-resistant prostate cancer (CRPC), or hormone-sensitive prostate cancer. In another embodiment, the prostate cancer cells are cells of a metastatic castration-resistant prostate cancer. In other embodiments, the prostate cancer cells are an androgen-dependent prostate cancer cells or an androgen-independent prostate cancer cells. In one embodiment, the cancer cells are breast cancer cells.

In one embodiment, the condition or disease associated with cell proliferation is cancer. In one embodiment of any one of the methods disclosed herein, the cancer is selected from the group consisting of prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In one embodiment, the condition or disease is prostate cancer. In one embodiment, prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In another embodiment, the prostate cancer is a metastatic castration-resistant prostate cancer. In some embodiments, the prostate cancer is an androgen-dependent prostate cancer cells or an androgen-independent prostate cancer. In one embodiment, the condition or disease is breast cancer.

In another embodiment of the present disclosure, a method for reducing or preventing tumor growth, comprising contacting tumor cells with a therapeutically effective amount of a compound of formula (I), (I-A), (Ia)-(Ie), (A)-(E), and (II), or a pharmaceutically acceptable salt, tautomer or stereoisomer thereof is provided.

In one embodiment, reducing or preventing tumor growth includes reduction in tumor volume. In one embodiment, reducing or preventing tumor growth includes complete elimination of tumors. In one embodiment, reducing or preventing tumor growth includes stopping or halting the existing tumor to grow. In one embodiment, reducing or preventing tumor growth includes reduction in the rate of tumor growth. In one embodiment, reducing or preventing tumor growth includes reduction in the rate of tumor growth such that the rate of tumor growth before treating a patient with the methods disclosed herein (r1) is faster than the rate of tumor growth after said treatment (r2) such that r1>r2.

In one embodiment, the reducing or preventing in the method disclosed herein is in vivo. In another embodiment, the treating is in vitro.

In one embodiment, the tumor cell in the method disclosed herein is selected from prostate cancer, breast cancer, ovarian cancer, endometrial cancer, or salivary gland carcinoma. In one embodiment, the tumor cells are prostate cancer tumor cells. In one embodiment, the prostate cancer tumor cells are tumor cells of primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the tumor cells are is breast cancer tumor cells.

In accordance with another embodiment, there is provided a use of the compounds of formula (I), (I-A), (Ia)-(Ie), (A)-(E), and (II), or a pharmaceutically acceptable salt, tautomer or stereoisomer thereof for preparation of a medicament for modulating androgen receptor (AR).

Pharmaceutical Compositions and Formulations

The present disclosure also includes pharmaceutical compositions for modulating androgen receptor (AR) in a subject. In one embodiment, a pharmaceutical composition comprises one or more compounds of formula (I), (I-A), (Ia)-(Ie), (A)-(E), and (II), or a pharmaceutically acceptable salt or solvate thereof.

In another aspect, the present disclosure provides pharmaceutical compositions comprising a compound of claim (I) and a pharmaceutically acceptable carrier.

In one embodiment of the present disclosure, a pharmaceutical composition comprises a therapeutically effective amounts of one or more compounds of formula (I), (I-A), (Ia)-(Ie), (A)-(E), and (II), or a pharmaceutically acceptable salt or solvate thereof.

In a specific embodiment, a pharmaceutical composition, as described herein, comprises one or more compounds selected from Table A1, or a pharmaceutically acceptable salt or solvate thereof. In one embodiment, a pharmaceutical composition comprises one or more compounds selected from Compounds A1, A2, A4, A5, A6, A7, A9, A11, A12, A13, A14, A15, A21, A23, A24, A25, A27, A28, A30, A31, A32, A33, A34, A35, A36, A37, A38, A42, A43, A44, A45, A46, A47, A48, A49, A51, A52, A53, A55, A56, A61, A62, A63, A64, A65, A69, A70, A71, A73, A74, A75, A76, A77, A79, A80, A81, A84, A85, or A86, or a pharmaceutically acceptable salt or solvate thereof. In one embodiment, a pharmaceutical composition comprises one or more compounds selected from Compounds A51(S), A51(R), A56(S) or A56(R), or a pharmaceutically acceptable salt, tautomer, or prodrug thereof. In one embodiment, a pharmaceutical composition comprises one or more compounds selected from Compounds A3, A8, A10, A16, A17, A18, A19, A20, A22, A26, A29, A39, A40, A41, A50, A54, A57, A58, A59, A60, A66, A67, A68, A72, A78, A82, or A83, or a pharmaceutically acceptable salt, tautomer, stereoisomer or prodrug thereof.

In one embodiment, a pharmaceutical composition as described herein comprise one or more compounds selected from Table A2, or a pharmaceutically acceptable salt or solvate thereof.

In one embodiment, a pharmaceutical composition as described herein comprise one or more compounds selected from Compounds A99, A100, A101, A102, A103, or A104, or a pharmaceutically acceptable salt, tautomer, stereoisomer or prodrug thereof. In one embodiment, a pharmaceutical composition as described herein comprise one or more compounds selected from Table A3, or a pharmaceutically acceptable salt or solvate thereof.

In one embodiment, a pharmaceutical composition as described herein comprise one or more compounds selected from Table B, or a pharmaceutically acceptable salt or solvate thereof.

In one embodiment, a pharmaceutical composition, as described herein, comprising one or more compounds of formula (I), (I-A), (Ia)-(Ie), (A)-(E), and (II), or a pharmaceutically acceptable salt or solvate thereof, further comprises one or more additional therapeutically active agents.

In some embodiments, the pharmaceutical composition comprises one or more additional therapeutic agents. In some embodiments, one or more additional therapeutic agents is/are for treating prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

In some embodiments, the one or more additional therapeutic agents is a poly (ADP-ribose) polymerase (PARP) inhibitor including but not limited to olaparib, niraparib, rucaparib, talazoparib; an androgen receptor ligand binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase inhibitor including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; a anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an androgen receptor N-terminal domain inhibitor including but not limited to a sintokamide; an alpha-particle emitting radioactive therapeutic agent including but not limited to radium 233 or a salt thereof; niclosamide; or related compounds thereof.

In some embodiments, the one or more additional therapeutic agents is a poly (ADP-ribose) polymerase (PARP) inhibitor including but not limited to olaparib, niraparib, rucaparib, talazoparib; an androgen receptor ligand binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase inhibitor including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an androgen receptor N-terminal domain inhibitor including but not limited to a sintokamide; an alpha-particle emitting radioactive therapeutic agent including but not limited to radium 233 or a salt thereof, niclosamide; or related compounds thereof, a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromitase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; CDK4/6 inhibitors including palbociclib, abemaciclib, ribociclib; HER2 receptor antagonist including but not limited to trastuzumab, neratinib; a mammalian target of rapamycin (mTOR) inhibitor including but not limited to everolimus, temsirolimus.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

In a further embodiment of the present disclosure, a pharmaceutical composition comprising one or more compounds of formula (I), (I-A), (Ia)-(Ie), (A)-(E), and (II), or a pharmaceutically acceptable salt or solvate thereof, and a pharmaceutically acceptable excipient or adjuvant is provided. The pharmaceutically acceptable excipients and adjuvants are added to the composition or formulation for a variety of purposes. In another embodiment, a pharmaceutical composition comprising one or more compounds of formula (I), (I-A), (Ia)-(Ie), (A)-(E), and (II), or a pharmaceutically acceptable salt or solvate thereof, further comprises a pharmaceutically acceptable carrier. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, Pa.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, the present disclosure provides a pharmaceutical composition comprising a compound of formula (I), (I-A), (Ia)-(Ie), (A)-(E), and (II), or a pharmaceutically acceptable salt or solvate thereof, as disclosed herein, combined with a pharmaceutically acceptable carrier. In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellent.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared using compounds of formula (I), (I-A), (Ia)-(Ie), (A)-(E), and (II), or a pharmaceutically acceptable salt or solvate thereof, and any other solid excipients where the components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location.

One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperitoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of formula (I), (I-A), (Ia)-(Ie), (A)-(E), and (II), or a pharmaceutically acceptable salt or solvate thereof are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the amount of the compound of formula (I), (I-A), (Ia)-(Ie), (A)-(E), and (II), or a pharmaceutically acceptable salt or solvate thereof, or compounds disclosed in Tables A1, A2, A3 and B, or a pharmaceutically acceptable salt or solvate thereof, can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-Nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the disclosure may be used alone or conjointly administered with another type of therapeutic agent.

The present disclosure includes the use of pharmaceutically acceptable salts of compounds of the disclosure in the compositions and methods of the present invention. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts. In certain embodiments, contemplated salts of the disclosure include, but are not limited to, 1-hydroxy-2-Naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, l-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, l-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-Chelating agents, such as citric acid, ethylenediamine tetraacetic acid (EDTA), sorbitol, tartaric acid, phosphoric acid, and the like.

Having now generally described the invention, the same will be more readily understood through reference to the following examples, which are provided by way of illustration and are not intended to be limiting of the present invention.

EXAMPLES

The disclosure now being generally described, it will be more readily understood by reference to the following examples which are included merely for purposes of illustration of certain aspects and embodiments of the present invention, and are not intended to limit the invention.

Example 1: Preparation of Exemplary Compounds of the Disclosure

The novel compounds of the present disclosure can be prepared in a variety of ways known to one skilled in the art of organic synthesis. The compounds of the present disclosure can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* 4th edition, John Wiley & Sons, publisher, New York, 1992 which are incorporated herein by reference in their entirety.

Compounds of the present disclosure can be prepared by the literature methods cited in the following text. The following schemes depict established, known syntheses of these scaffolds.

The groups and/or substituents of the compounds of the present disclosure can be synthesized and attached to these scaffolds by the literature methods cited in the following text. The following schemes depict the known techniques for accomplishing this joinder.

General Synthetic Schemes

Compounds of the present disclosure can be synthesized using the following methods. General reaction conditions are given, and reaction products can be purified by general known methods including crystallization, silica gel chromatography using various organic solvents such as hexane, cyclohexane, ethyl acetate, methanol and the like, preparative high pressure liquid chromatography or preparative reverse phase high pressure liquid chromatography.

General Synthetic Routes to Prepare Precursors (A)

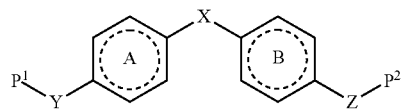

Wherein X is optionally substituted methenyl or ethenyl or a bond or amino group; A and B are each independently an optionally substituted 5- or 6-membered aromatic ring, and hydrogen of NH is protected by an appropriate protection group whenever there is NH within the aromatic ring; Y, Z are each independently O or amino and $P^1$, $P^2$ are either appropriate protections or moiety of the desired final product, alternatively, one or both of $YP^1$, $ZP^2$ are $SP^3$ carbon or hydrogen.

Multiple synthetic routes to prepare the key precursor A have been reported.

Scheme 01

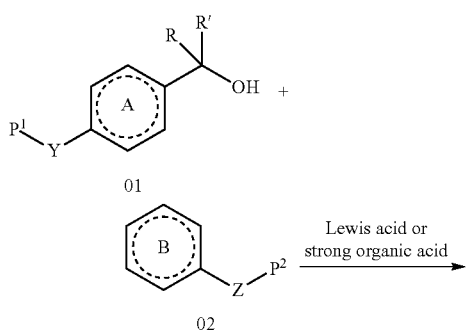

-continued

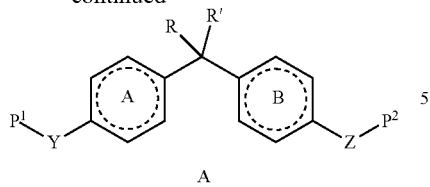

A

A common approach is to treat appropriately protected benzyl alcohol or other aromatic ring substituted methanol 01 with an appropriately protected benzene or other aromatic ring 02 in the presence of Lewis acid (i.e. AlCl$_3$, BF$_3$ etc.) or organic acid (i.e. TFA, TfOH, p-TSA, H$_2$SO$_4$, etc.) in common organic solvents (i.e. dioxane, toluene, DMF, THF, DCM, etc.) at the temperature of 0° C. to 100° C. to receive the desired product A in reasonable yield.

Scheme 02

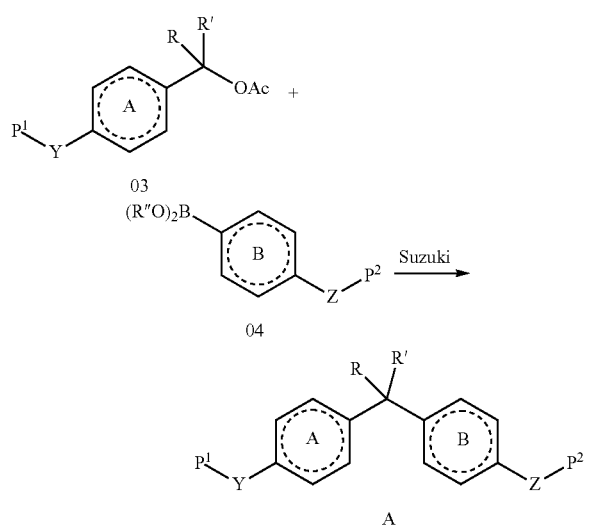

Another common approach is to treat appropriately protected benzyl acetate or other aromatic ring substituted methyl acetate 03 with an appropriately protected benzene or other aromatic ring-based boronic acid or ester 04 via Suzuki reaction in common organic solvents (i.e. dioxane, toluene, DMF, THF, DCM, etc.) at the temperature of 0° C. to 100° C. to receive the desired product A in reasonable yield.

Scheme 03

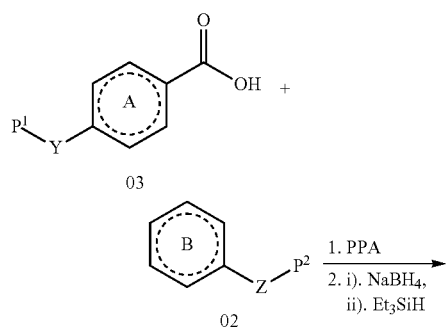

-continued

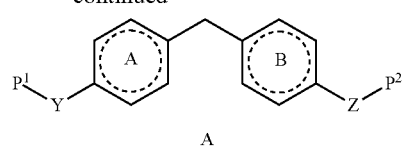

A

Alternative common approach, when X is unsubstituted methyl, is to treat appropriately protected benzoic acid or other aromatic ring substituted formic acid 03 with appropriately protected benzene or other aromatic ring-based intermediate 02 in the presence of reagents such as PPA in common organic solvents (i.e. dioxane, toluene, DMF, THF, DCM, etc.) at the temperature of 0° C. to 100° C. followed by reduction to receive the desired product A in reasonable yield.

Scheme 04

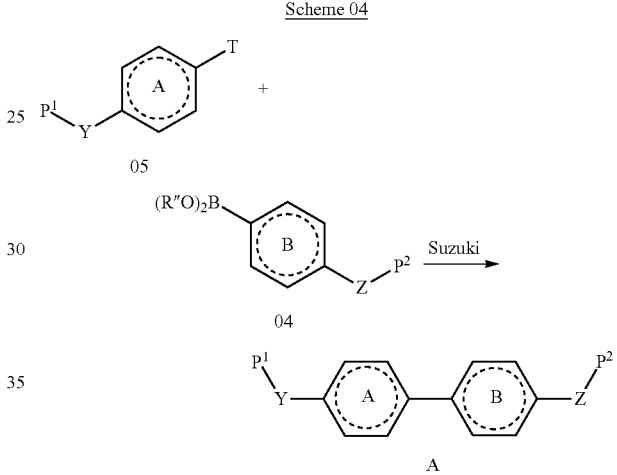

Alternative common approach, when X is a bond, is to treat appropriately protected benzene or other aromatic moiety 05 with T as halogen (i.e. Br, I) or tosylate or mesylate with an appropriately protected benzene or other aromatic ring-based boronic acid or ester 04 via Suzuki reaction in common organic solvents (i.e. dioxane, toluene, DMF, THF, DCM, etc.) at the temperature of 0° C. to 100° C. to receive the desired product A in reasonable yield.

Scheme 05

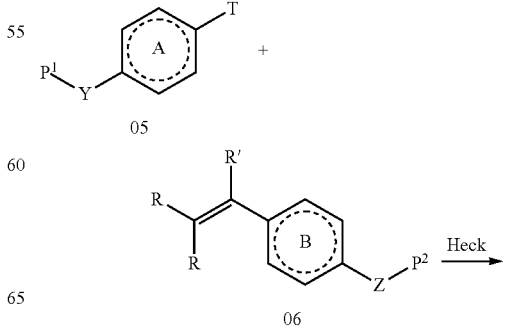

-continued

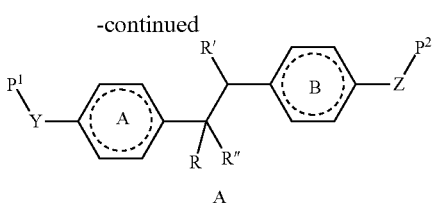

A

Alternative common approach, when X is an optionally substituted ethenyl, is to treat appropriately protected benzene or other aromatic moiety 05 with T as halogen (i.e. Br, I) or tosylate or mesylate with an appropriately protected styrene or other vinyl-substituted aromatic moiety 06 via Heck reaction in common organic solvents (i.e. dioxane, toluene, DMF, THF, DCM, etc.) at the temperature of 0° C. to 100° C. to receive the desired product A in reasonable yield.

Scheme 06

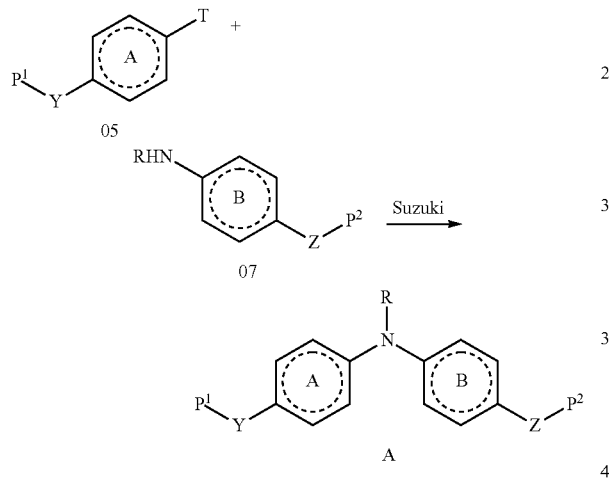

Alternative common approach, when X is amino, is to treat appropriately protected benzene or other aromatic moiety 05 with T as halogen (i.e. Br, I) or tosylate or mesylate with an appropriately protected aniline or other aromatic ring-based amine 07 via substitution reaction in common organic solvents (i.e. dioxane, toluene, DMF, THF, DCM, etc.) at the temperature of 0° C. to 100° C. to receive the desired product A in reasonable yield.

General Synthetic Routes to Install the Right-Side Chain into Precursors or the Desired Final Molecules (B)

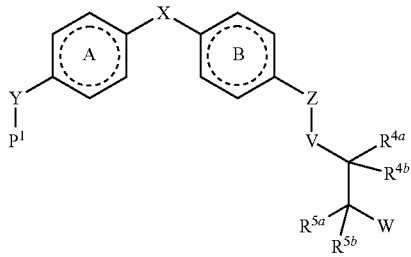

Wherein V is a bond or an optionally substituted alkenyl $(C(R^{11}R^{12})_m)$; W is selected from hydrogen, halogen, $CF_3$, CN, carboxamide $(CON(R^{13}R^{14}))$; $R^{4a}$, $4^{1b}$, $R^{5a}$, $R^{5b}$ are each independently selected from hydrogen, halogen, optionally substituted $C_{1-6}$ alkyl, optionally substituted $C_{1-6}$ alkoxy; Alternatively, $R^{4a}$ and $R^{4b}$ are taken together to form carbonyl (CO) or an optionally substituted 3-7 membered carbocyclyl, aryl, or heterocyclyl with optionally containing O, S, or N; Alternatively, $R^{4a}$, $4^{1b}$, $R^{5a}$ and $R^{5b}$ are all taken together to form an optionally substituted 3-7 membered carbocyclyl or heterocyclyl with optionally containing O, S, or N; or optionally substituted aryl when the carbons $R^{4a}$, $R^{4b}$, $R^{5a}$ and $R^{5b}$ linked with are $SP^2$ carbon.

Scheme 07

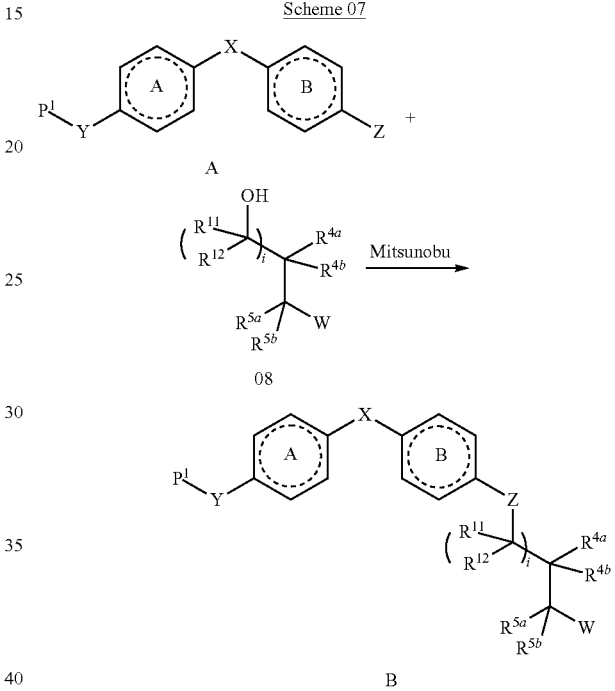

A common approach to prepare precursors or the desired final molecules (B), when Z is hydroxy or amino group, is to treat appropriate intermediate A with alkyl alcohol 08 via Mitsunobu reaction in common organic solvents (i.e. dioxane, toluene, DMF, THF, DCM, etc.) at the temperature of 0° C. to 100° C. to receive the desired product B in reasonable yield.

Scheme 08

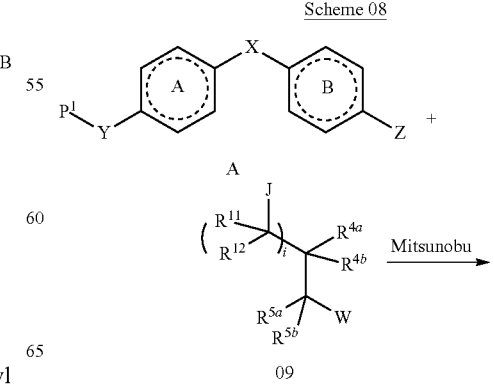

-continued

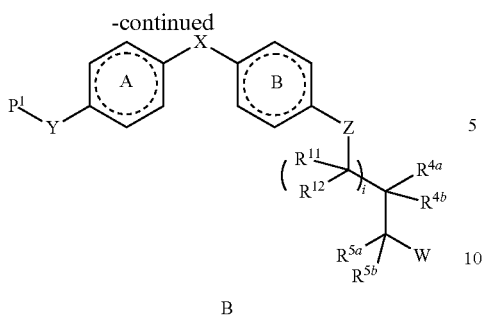

B

A common approach to prepare precursors or the desired final molecules (B), when Z is hydroxy or amino group, is to treat intermediate A with the reagent 09 with J as halogen (i.e. Cl, Br, I) or tosylate or mesylate via substitution reaction in common organic solvents (i.e. dioxane, toluene, DMF, THF, DCM, etc.) at the temperature of 0° C. to 100° C. to receive the desired product B in reasonable yield.

Scheme 09

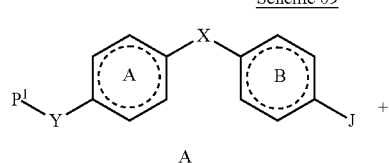

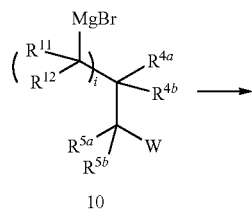

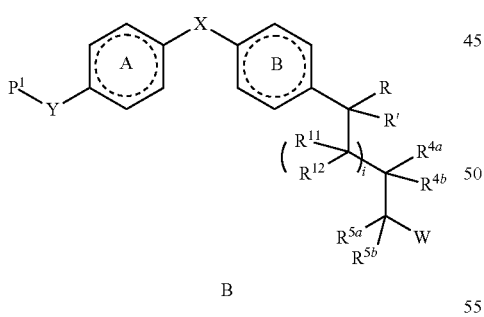

B

A common approach to prepare precursors or the desired final molecules (B), when Z is methenyl, is to treat appropriate intermediate A (J as halogen (i.e. Cl, Br, I) or tosylate or mesylate) with Grignard Reagents 10 in common organic solvents (i.e. dioxane, toluene, DMF, THF, DCM, etc.) at the temperature of 0° C. to 100° C. to receive the desired product B in reasonable yield.

General synthetic routes to install the left-side chain into precursors or the desired final molecules (C)

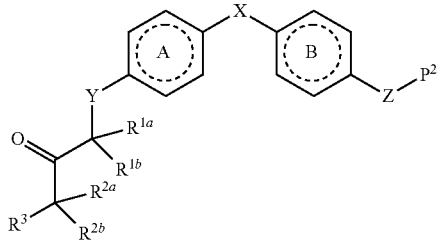

C

Wherein $R^{1a}$, $R^{1b}$, $R^{2a}$, $R^{2b}$ are each independently selected from hydrogen, halogen, optionally substituted $C_{1-6}$ alkyl, optionally substituted $C_{1-6}$ alkoxy; Alternatively, $R^{2a}$ and $R^{2b}$ are taken together to form carbonyl (CO) or an optionally substituted 3-7 membered carbocyclyl, aryl, or heterocyclyl with optionally containing O, S, or N; $R^3$ is nothing, hydrogen, halogen, hydroxy (OH), alkoxy ($OR^{15}$), amino ($NH_2$), alkylamino ($NR^{16}R^{17}$), aminocarbonyl ($NR^{16}COR^{18}$), aminosulfinyl or sulfonyl ($NR^{16}S(O)_rR^{18}$), sulfinyl or sulfonyl ($S(O)_rR^{18}$), $N_3$, optionally substituted 3-7 membered carbocyclyl or heterocyclyl or aryl with optionally containing O, S, or N.

Scheme 10

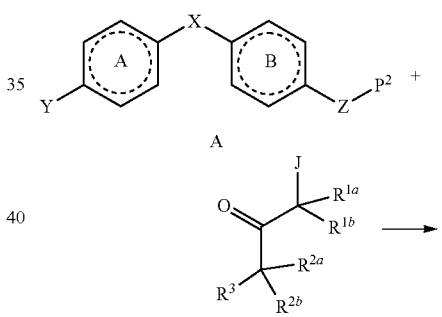

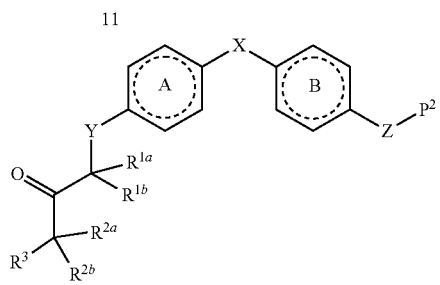

C

Another common approach to prepare precursors or the desired final molecules (C), when Y is hydroxy or amino group, is to treat the intermediate A with the reagent 11 with J as halogen (i.e. Cl, Br, I) or tosylate or mesylate via substitution reaction in common organic solvents (i.e. dioxane, toluene, DMF, THF, DCM, etc.) at the temperature of 0° C. to 100° C. to receive the desired product B in reasonable yield.

Scheme 11

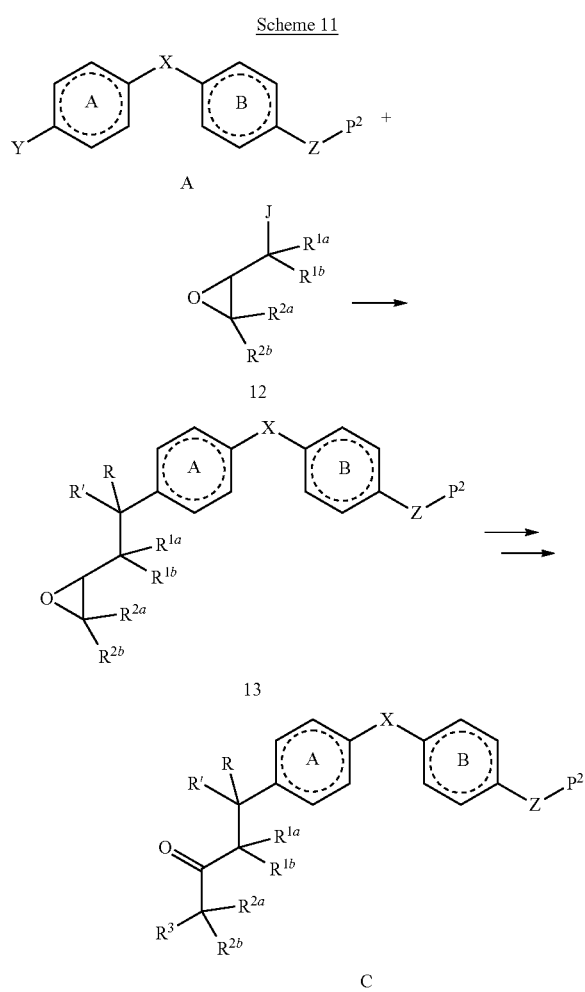

Another common approach to prepare precursors or the desired final molecules (C), when Y is hydroxy or amino group, is to treat the intermediate A with the reagent 12 with J as halogen (i.e. Cl, Br, I) or tosylate or mesylate via substitution reaction in common organic solvents (i.e. dioxane, toluene, DMF, THF, DCM, etc.) at the temperature of 0° C. to 100° C. to receive the intermediate 13, which was then converted into the desired product B in reasonable yield via opening the epoxide and oxidation.

Scheme 12

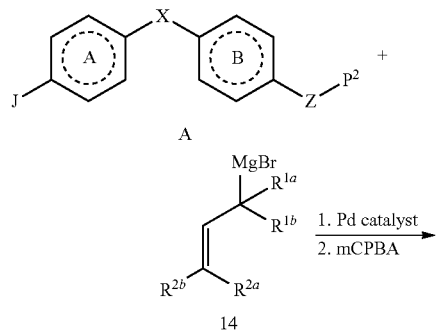

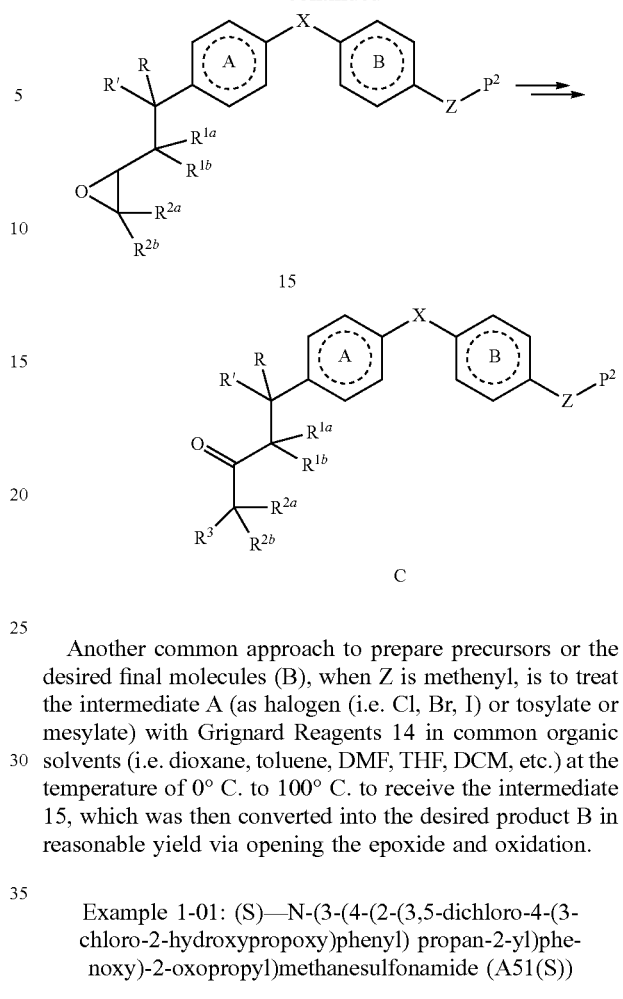

Another common approach to prepare precursors or the desired final molecules (B), when Z is methenyl, is to treat the intermediate A (as halogen (i.e. Cl, Br, I) or tosylate or mesylate) with Grignard Reagents 14 in common organic solvents (i.e. dioxane, toluene, DMF, THF, DCM, etc.) at the temperature of 0° C. to 100° C. to receive the intermediate 15, which was then converted into the desired product B in reasonable yield via opening the epoxide and oxidation.

Example 1-01: (S)—N-(3-(4-(2-(3,5-dichloro-4-(3-chloro-2-hydroxypropoxy)phenyl) propan-2-yl)phenoxy)-2-oxopropyl)methanesulfonamide (A51(S))

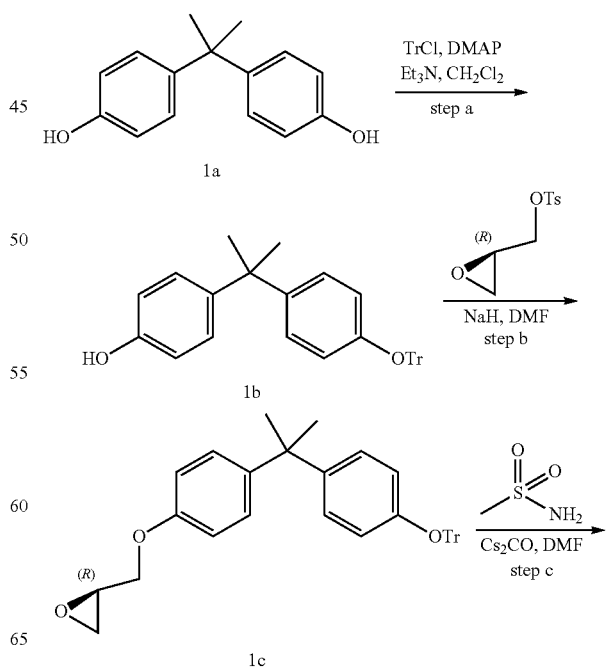

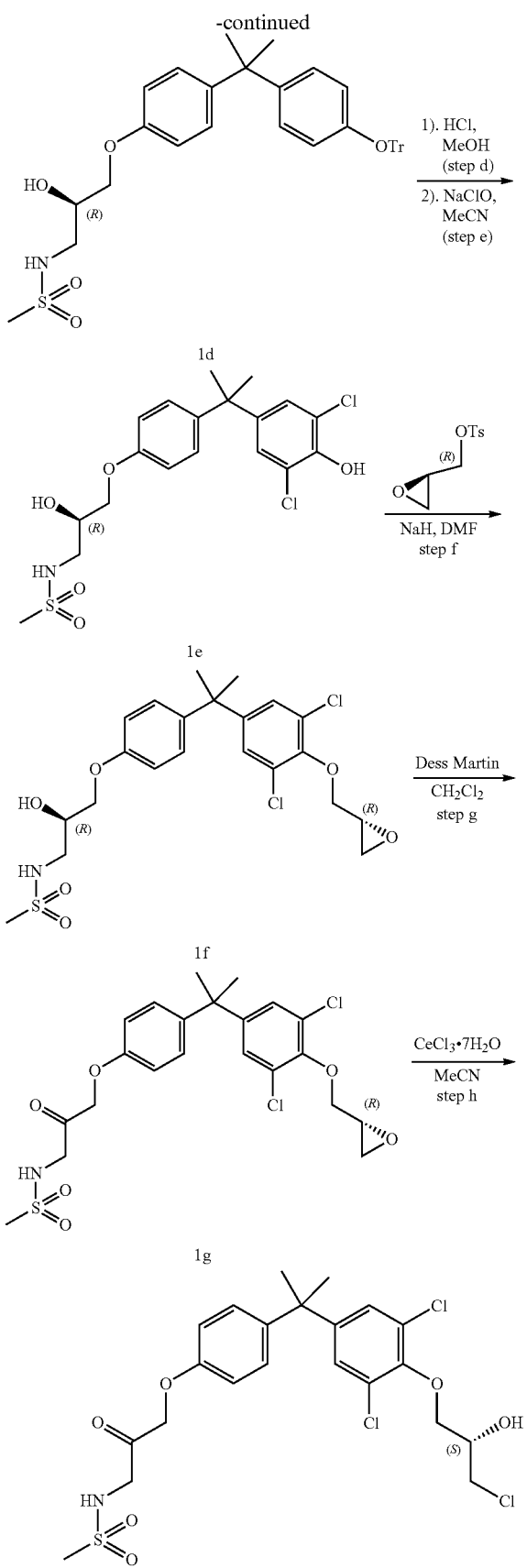

Steps a: Synthesis of 4-(2-(4-(trityloxy)phenyl)propan-2-yl)phenol. 4,4'-(Propane-2,2-diyl)diphenol (1a) (5.0 g, 1.0 eq) and DMAP (0.027 g, 0.01 eq) were dissolved in DCM (60 mL, 12 vol). Triethylamine (3.05 mL, 1.0 eq) was added and the reaction was cooled to 0-5° C. A solution of trityl chloride (4.89 g, 0.8 eq) in DCM (10 mL, 2 vol) was added dropwise. The reaction was continued at 0-5° C. for 80 min and the room temperature for 16 hours. The slurry was diluted with DCM and water. The organic layer was separated and diluted with equal volume of heptane. The solid was filtered off. The filtrate was concentrated to dryness and purified by flash chromatography using EtOAc/heptane to give 4-(2-(4-(trityloxy)phenyl)propan-2-yl)phenol (1b) (6.1 g, 59% yield) as colorless thick syrup. HPLC purity (96%). LRMS (M+H$^+$) m/z: calcd 229.12. found 229.

Steps b: Synthesis of (R)-2-((4-(2-(4-(trityloxy)phenyl)propan-2-yl)phenoxy)methyl) oxirane. The aforementioned intermediate (1b) (1.0 g) was dissolved in DMF (15 mL) and treated with 60% NaH in mineral oil (1.2 eq) at 0-5° C. for 15 min. Glycidyl tosylate (1.2 eq) was added. The reaction was stirred at the room temperature for 17 hours. HPLC showed no starting material remained. The reaction was quenched with water and extracted with EtOAc. The extract was washed with water, concentrated to dryness and dried under high vacuum to afford (R)-2-((4-(2-(4-(trityloxy)phenyl)propan-2-yl)phenoxy)methyl)oxirane (1c) as a white foam (97% yield). HPLC purity (92.9%). LRMS (M+H$^+$) m/z: calcd 527.68. found 527.7.

Step c: Synthesis of (R)—N-(2-hydroxy-3-(4-(2-(4-(trityloxy)phenyl)propan-2-yl)phenoxy)propyl)methanesulfonamide. To a solution of (R)-2-((4-(2-(4-(trityloxy)phenyl)propan-2-yl)phenoxy)methyl)oxirane (1c) (100 mg, 0.19 mmol, 1.0 eq.) and methanesulfonamide (27.1 mg, 0.29 mmol, 1.5 eq.) in anhydrous DMF (30 mL) was added Cs$_2$CO$_3$ (95 mg, 0.29 mmol, 1.5 eq.). The solution was heated to 100° C. for 16 hours. The reaction was quenched by the H$_2$O (20 mL) and the solution was extracted with ethyl acetate (3×30 mL). The combined organic layers were washed with deionized water (2×50 mL), dried over anhydrous magnesium sulfate, filtered, and concentrated under reduced pressure. The resulting residue was purified by gradient flash Si gel column chromatography (elution: ethyl acetate in hexane) to provide (R)—N-(2-hydroxy-3-(4-(2-(4-(trityloxy)phenyl)propan-2-yl)phenoxy)propyl)methanesulfonamide (1d) (85 mg, 72.0%) as a white foam. LRMS (M+Na$^+$) m/z: calcd 644.24. found 644.2.

Step d: Synthesis of (R)—N-(2-hydroxy-3-(4-(2-(4-hydroxyphenyl)propan-2-yl)phenoxy)propyl)methanesulfonamide. To a solution of (R)—N-(2-hydroxy-3-(4-(2-(4-(trityloxy)phenyl)propan-2-yl)phenoxy)propyl)methanesulfonamide (1d) (450 mg, 0.72 mmol, 1.0 eq.) in MeOH (6 mL) was added 6M HCl (0.6 mL, 3.6 mmol, 5.0 eq.) and the solution was stirred at the room temperature for 5 hours. The solution was extracted with ethyl acetate (3×50 mL). The combined organic layers were washed with sodium bicarbonate solution (100 mL) and deionized water (2×100 mL), dried over anhydrous magnesium sulfate, filtered, and concentrated under reduced pressure. The resulting residue was purified by gradient flash silica gel column chromatography (elution: methanol in DCM) to provide (R)—N-(2-hydroxy-3-(4-(2-(4-hydroxyphenyl)propan-2-yl)phenoxy)propyl)methanesulfonamide (271 mg) as a sticky oil.

Step e: Synthesis of (R)—N-(3-(4-(2-(3,5-dichloro-4-hydroxyphenyl)propan-2-yl)phenoxy)-2-hydroxypropyl)methanesulfonamide. The sticky oil (271 mg, 0.71 mmol, 1.0 eq.) from step d was dissolved in MeCN (36 mL) and treated with 5% NaClO solution (2.3 g, 1.56 mmol, 2.2 eq.) at 0° C. for 2 hours. The solution was extracted with ethyl acetate (3×50 mL). The combined organic layers were washed with deionized water (2×100 mL), dried over anhydrous magnesium sulfate, filtered, and concentrated under reduced pressure. The resulting residue was purified by gradient flash silica gel column chromatography (elution: methanol in DCM) to provide (R)—N-(3-(4-(2-(3,5-dichloro-4-hydroxyphenyl)propan-2-yl)phenoxy)-2-hydroxypropyl)methanesulfonamide (e) (262 mg, 81.2%, 2 steps) as a white foam. LRMS (M+Na$^+$) m/z: calcd 470.07. found 470.2.

Step f: Synthesis of N—((R)-3-(4-(2-(3,5-dichloro-4-(((R)-oxiran-2-yl)methoxy)phenyl)propan-2-yl)phenoxy)-2-hydroxypropyl)methanesulfonamide. The aforementioned intermediate (1e) (50 mg, 0.11 mmol, 1.0 eq.) was dissolved in DMF (3 mL) and treated with 60% NaH in mineral oil (5.3 mg, 0.132 mmol, 1.2 eq.) at 0-5° C. for 15 min. Glycidyl tosylate (27.4 mg, 0.12 mmol, 1.1 eq) was added. The reaction was stirred at the room temperature for 17 hours. The reaction was quenched with water and extracted with EtOAc. The extract was washed with water, concentrated to dryness and dried under high vacuum to afford N—((R)-3-(4-(2-(3,5-dichloro-4-(((R)-oxiran-2-yl)methoxy)phenyl)propan-2-yl)phenoxy)-2-hydroxypropyl)methanesulfonamide (f) (45 mg, 81.1% yield) as a white foam. LRMS (M+Na$^+$) m/z: calcd 526.09. found 526.1.

Step g: Synthesis of (R)—N-(3-(4-(2-(3,5-dichloro-4-(oxiran-2-ylmethoxy)phenyl)propan-2-yl)phenoxy)-2-oxopropyl)methanesulfonamide. To a solution of N—((R)-3-(4-(2-(3,5-dichloro-4-(((R)-oxiran-2-yl)methoxy)phenyl)propan-2-yl)phenoxy)-2-hydroxypropyl)methanesulfonamide (1f) (31.0 mg, 0.062 mmol) in anhydrous dichloromethane (6 mL) was treated Dess-Martin periodinane (53 mg, 0.124 mmol, 2.0 eq.) at 0° C. for 10 minutes. Then it was warmed to the room temperature for 16 hours. The reaction was quenched by the addition of a saturated solution of ammonium chloride (2 ml) and the solution was extracted with ethyl acetate (2×30 ml). The combined organic layers were washed with deionized water (2×30 ml), dried over anhydrous magnesium sulfate, filtered, and concentrated under reduced pressure. The resulting residue was purified by gradient flash column chromatography on silica gel (methanol in DCM) to provide the (R)—N-(3-(4-(2-(3,5-dichloro-4-(oxiran-2-ylmethoxy)phenyl)propan-2-yl)phenoxy)-2-oxopropyl)methanesulfonamide (g) (30 mg, 96% yield) as a colorless oil. LRMS (M+Na$^+$) m/z: calcd 524.08. found 524.2.

Step h: Synthesis of (S)—N-(3-(4-(2-(3,5-dichloro-4-(3-chloro-2-hydroxypropoxy)phenyl) propan-2-yl)phenoxy)-2-oxopropyl)methanesulfonamide. To a solution of (R)—N-(3-(4-(2-(3,5-dichloro-4-(oxiran-2-ylmethoxy)phenyl)propan-2-yl)phenoxy)-2-oxopropyl)methanesulfonamide (1g) (30 mg, 0.06 mmol, 1.0 eq.) in MeCN (6 mL) was added CeCl$_3$·7H$_2$O (34 mg, 0.09 mmol, 1.5 eq.) and the solution was heated to reflux for 16 hours. The resulting white paste was collected by filtration and washed with ethyl acetate and the clear suspension was concentrated under reduced pressure. The resulting residue was purified by flash silica gel column chromatography (elution: ethyl acetate in hexane) to provide (S)—N-(3-(4-(2-(3,5-dichloro-4-(3-chloro-2-hydroxypropoxy)phenyl) propan-2-yl)phenoxy)-2-oxopropyl)methanesulfonamide (A51(S)): (13.7 mg, 42.4%) as a colorless oil. LRMS (M+Na$^+$) m/z: calcd 560.05. found 560.0. MS-ESI 537.05. found 559.5. $^1$HNMR (400 MHz, DMSO-d6): δ 7.44 (t, J=5.6 Hz, 1H), 7.23 (s, 2H), 7.15 (d, J=8.8 Hz, 2H), 6.84 (d, J=8.8 Hz, 2H), 5.55 (d, J=5.2 Hz, 1H), 4.91 (s, 2H), 4.01-4.10 (m, 3H), 3.96 (d, J=5.6 Hz, 2H), 3.82 (dd, J=4.0, 11.2 Hz, 2H), 3.70 (dd, J=4.0, 11.2 Hz, 2H), 2.93 (s, 3H), 1.60 (s, 6H).

Example 1-02: N-(3-(4-(2-(3,5-dichloro-4-(3-chloropropoxy)phenyl)propan-2-yl)phenoxy)-2-oxopropyl)methanesulfonamide (A31)

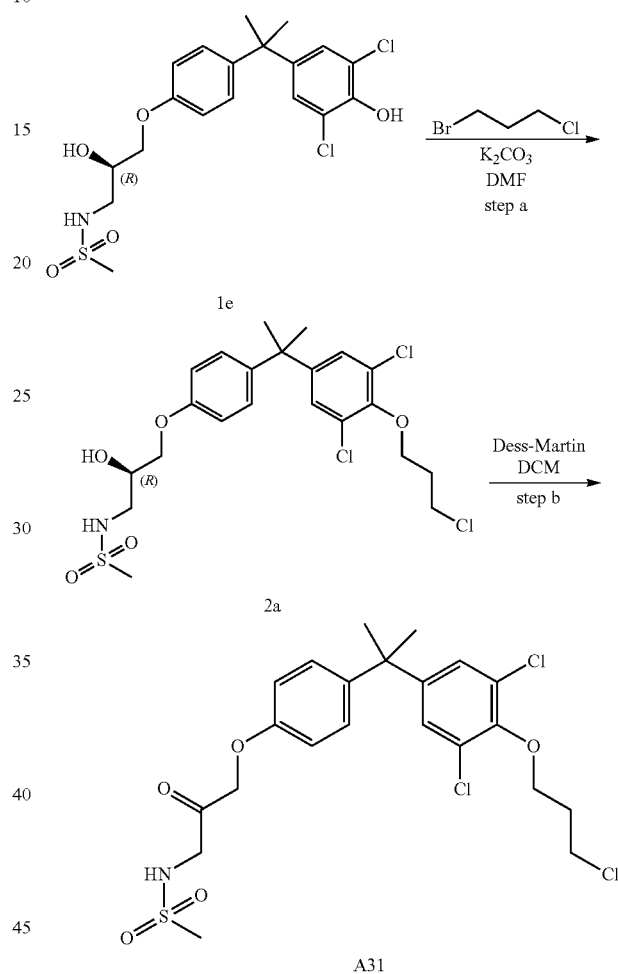

Step a: Synthesis of (S)-3-(4-(2-(3,5-dichloro-4-((S)-3-chloro-2-hydroxypropoxy)phenyl)propan-2-yl)phenoxy)-2-hydroxypropyl 4-methylbenzenesulfonate. A solution of 1-bromo-3-chloropropane (26 mg, 0.165 mmol, 1.5 eq.) in anhydrous DMF (1 mL) was added to a stirred solution of (R)—N-(3-(4-(2-(3,5-dichloro-4-hydroxyphenyl)propan-2-yl)phenoxy)-2-hydroxypropyl)methanesulfonamide (1e) (50 mg, 0.11 mmol, 1.0 eq.) and potassium carbonate (23 mg, 0.165 mmol, 1.5 eq.) in anhydrous DMF (3 mL) at room temperature. and the reaction were stirred under an atmosphere of argon for 16 hours. The reaction was quenched by the addition of a saturated solution of ammonium chloride (1 mL), and the solution was extracted with ethyl acetate (60 mL). The organic layer was washed with deionized water (2×30 mL), dried over anhydrous magnesium sulfate, filtered, and concentrated under reduced pressure. The resulting residue was purified by gradient flash silica gel column chromatography (elution: methanol in DCM) to provide (R)—N-(3-(4-(2-(3,5-dichloro-4-(3-chloropropoxy)phenyl)

propan-2-yl)phenoxy)-2-hydroxypropyl)methanesulfonamide (2a) (24.3 mg, 42% yield) as a colorless oil. LRMS (M+Na$^+$) m/z: calcd 546.08. found 546.

Step b: Synthesis of Compound A31. To a solution of (R)—N-(3-(4-(2-(3,5-dichloro-4-(3-CHloropropoxy)phenyl)propan-2-yl)phenoxy)-2-hydroxypropyl)methanesulfonamide (2a) (25.0 mg, 0.048 mmol, 1.0 eq.) in anhydrous dichloromethane (3 mL) was treated Dess-Martin periodinane (41 mg, 0.096 mmol, 2.0 eq.) at 0° C. for 10 minutes. Then it was warmed to the room temperature for 16 hours. The reaction was quenched by the addition of a saturated solution of ammonium chloride (2 ml) and the mixture was extracted with ethyl acetate (2×30 ml). The combined organic layers were washed with deionized water (2×30 ml), dried over anhydrous magnesium sulfate, filtered, and concentrated under reduced pressure. The resulting residue was purified by gradient flash silica gel column chromatography (elution: acetate in hexane) to provide N-(3-(4-(2-(3,5-dichloro-4-(3-chloropropoxy)phenyl)propan-2-yl)phenoxy)-2-oxopropyl)methanesulfonamide (A31) (30 mg, 88% yield) as a colorless oil. LRMS (M+Na$^+$) m/z: calcd 544.06. found 544.2. MS-ESI 521.06. found 521.5. $^1$HNMR (400 MHz, DMSO-d6): δ 7.44 (t, J=5.6 Hz, 1H), 7.24 (s, 2H), 7.15 (d, J=8.8 Hz, 2H), 6.85 (d, J=8.8 Hz, 2H), 4.91 (s, 2H), 4.01 (m, 4H), 3.86 (t, J=6.4 Hz, 2H), 2.93 (s, 3H), 2.19 (m, 2H), 1.60 (s, 6H).

Example 1-03: 1-(4-(2-(3,5-dichloro-4-(3-chloropropoxy)phenyl)propan-2-yl)phenoxy)-3-(methylsulfonyl)propan-2-one (A55)

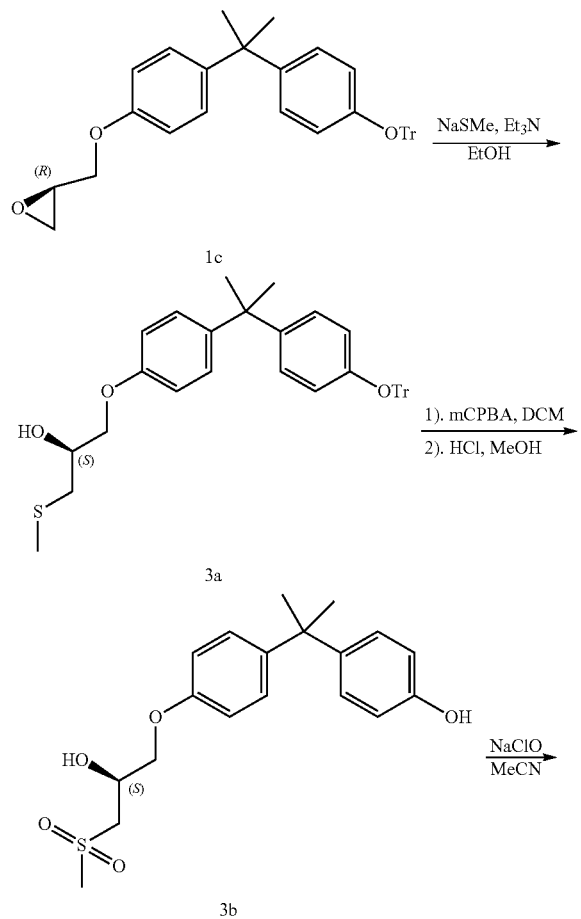

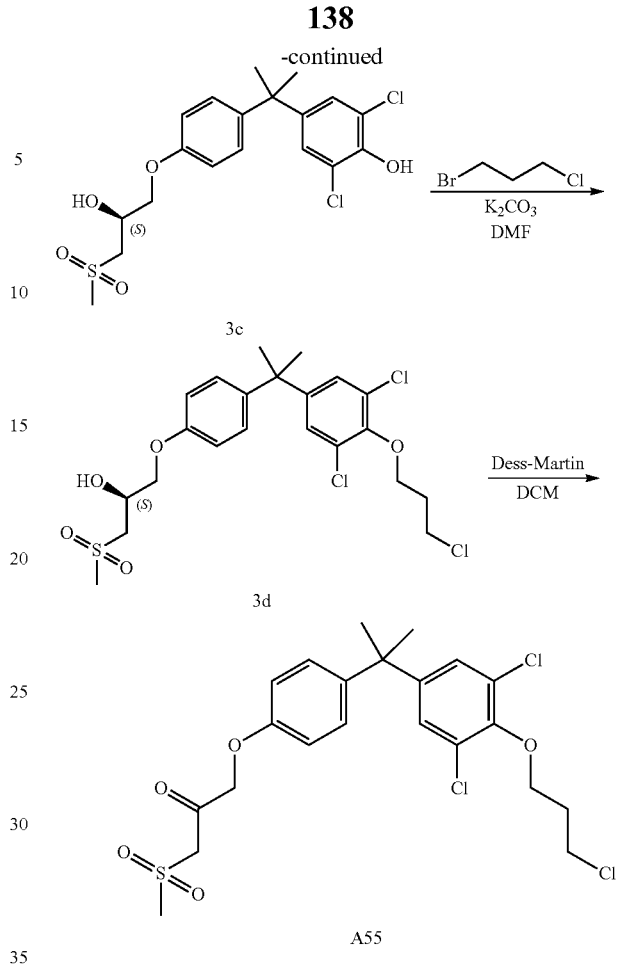

To a solution of (R)-2-((4-(2-(4-(trityloxy)phenyl)propan-2-yl)phenoxy)methyl)oxirane (1c) (300 mg, 0.57 mmol, 1.0 eq.) in ethanol (6 mL) was added sodium thiomethoxide (80 mg, 1.14 mmol, 2.0 eq.). The solution was warmed to 50° C. for 16 hours. The reaction was quenched by the H$_2$O (20 mL) and the solution was extracted with ethyl acetate (3×50 mL). The combined organic layers were washed with deionized water (2×100 mL), dried over anhydrous magnesium sulfate, filtered, and concentrated under reduced pressure. The resulting residue was purified by gradient flash silica gel column chromatography (elution: ethyl acetate in hexane) to provide (S)-1-(methylthio)-3-(4-(2-(4-(trityloxy)phenyl)propan-2-yl)phenoxy)propan-2-ol (3a) (324 mg, 98.9%) as a colorless oil. LRMS (M+Na$^+$) m/z: calcd 597.24. found 597.1.

To a solution of (S)-1-(methylthio)-3-(4-(2-(4-(trityloxy)phenyl)propan-2-yl)phenoxy)propan-2-ol (3a) (539 mg, 0.94 mmol, 1.0 eq.) in anhydrous dichloromethane (12 mL) was treated mCPBA (315 mg, 1.41 mmol, 1.5 eq.) at 0° C. for 2 hours. The reaction was quenched by the addition of a saturated solution of sodium bicarbonate (20 ml) and the solution was extracted with ethyl acetate (2×100 ml). The combined organic layers washed with deionized water (2×100 ml), dried over anhydrous magnesium sulfate, filtered, and concentrated under reduced pressure. The resulting residue was dissolved in MeOH (24 mL) and DCM (6 mL) and treated with 6M HCl (0.78 mL, 4.7 mmol, 5.0 equiv) at room temperature for 2 hours. The solvent was removed under reduced pressure and the residue was diluted with ethyl acetate (200 mL). The organic layer was washed with sodium bicarbonate solution (100 mL) and deionized water (2×100 mL), dried over anhydrous magnesium sulfate, filtered, and concentrated under reduced pressure. The resulting residue was purified by gradient flash silica gel column chromatography (elution: methanol in DCM) to provide (S)-4-(2-(4-(2-hydroxy-3-(methylsulfonyl) propoxy)phenyl)propan-2-yl)phenol (3b) (227 mg, 66.3% yield, 2 steps) as a colorless oil. LRMS (M+Na$^+$) m/z: calcd 387.12. found 387.2.

(S)-4-(2-(4-(2-hydroxy-3-(methylsulfonyl)propoxy)phenyl)propan-2-yl)phenol (3b) (227 mg, 0.62 mmol, 1.0 eq.) was dissolved in MeCN (16 mL) and treated with 10% NaClO solution (1.39 g, 1.86 mmol, 3.0 eq.) at 0° C. for 2 hours. The solution was extracted with ethyl acetate (3×50 mL). The organic layer was washed with deionized water (2×100 mL), dried over anhydrous magnesium sulfate, filtered, and concentrated under reduced pressure. The resulting residue was purified by gradient flash silica gel column chromatography (elution: ethyl acetate in hexane) to provide (S)-2,6-dichloro-4-(2-(4-(2-hydroxy-3-(methylsulfonyl) propoxy)phenyl)propan-2-yl)phenol (3c) (206 mg, 76.7%) as a sticky oil. LRMS (M+Na$^+$) m/z: calcd 455.05. found 455.1.

Compound (3d) was synthesized according to Compound (2a) by using (S)-2,6-dichloro-4-(2-(4-(2-hydroxy-3-(methylsulfonyl)propoxy)phenyl)propan-2-yl)phenol (3c) Yield (99.0%). LRMS (M+Na$^+$) m/z: calcd 531.05. found 531.1.

Compound (A55) was synthesized according to Compound (A31) by using (S)-2,6-dichloro-4-(2-(4-(2-hydroxy-3-(methylsulfonyl)propoxy)phenyl)propan-2-yl)phenol (3d) Yield (94.1%). LRMS (M+Na$^+$) m/z: calcd 529.06. found 529.3. MS-ESI 506.05. found 529.1. $^1$HNMR (400 MHz, DMSO-d6): δ 7.24 (s, 2H), 7.15 (d, J=9.2 Hz, 2H), 6.84 (d, J=8.8 Hz, 2H), 4.96 (s, 2H), 4.59 (s, 2H), 4.08 (t, J=6.0 Hz, 2H), 3.86 (t, J=6.0 Hz, 2H), 3.11 (s, 3H), 2.19 (m, 2H), 1.61 (s, 6H).

Example 1-04: N-(3-(4-(3-(3,5-dichloro-4-(3-chloropropoxy)phenyl)oxetan-3-yl)phenoxy)-2-oxopropyl)methanesulfonamide (A43)

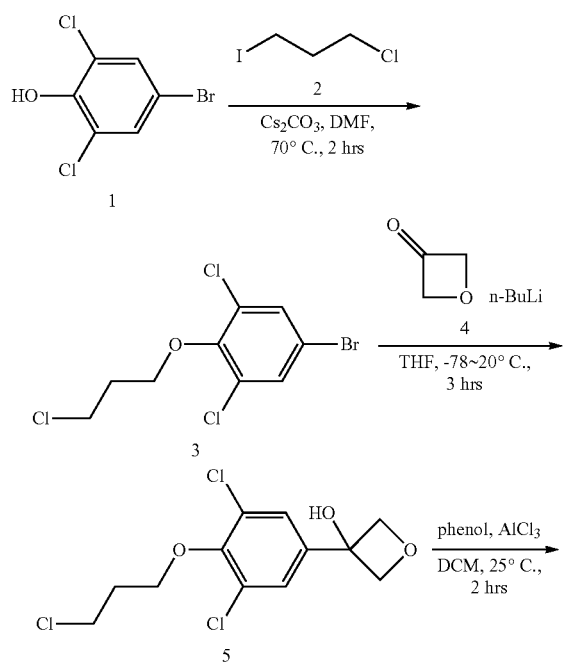

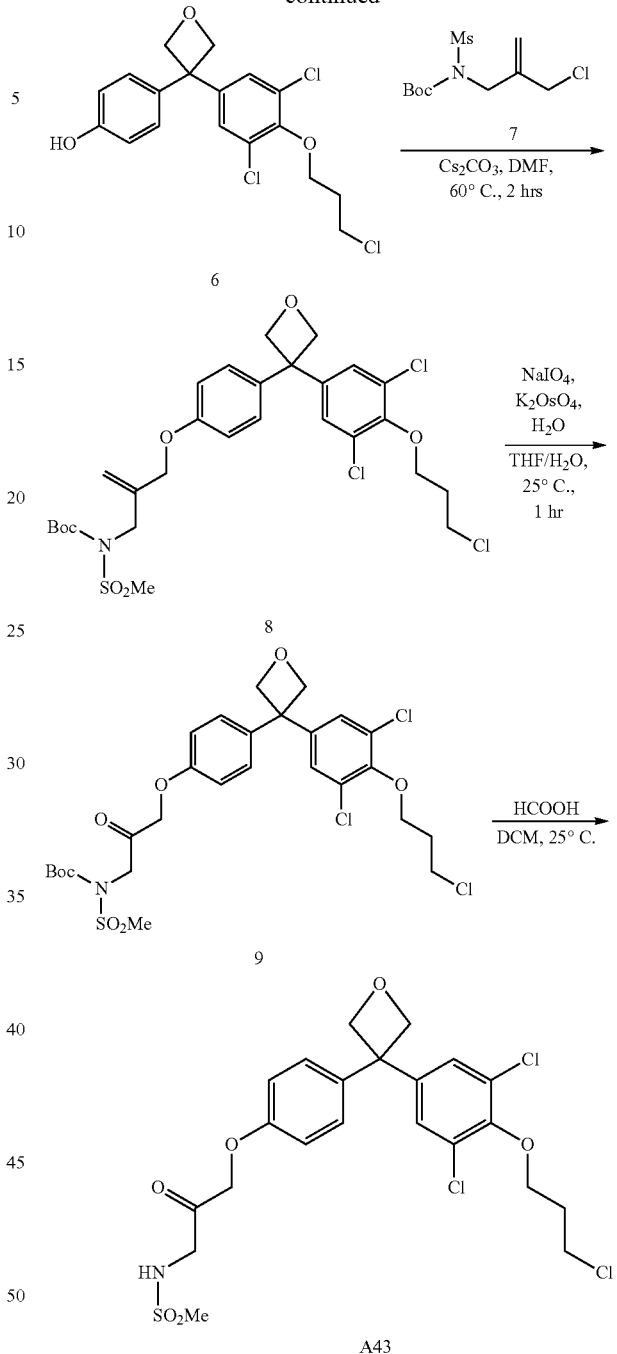

5-Bromo-1,3-dichloro-2-(3-chloropropoxy)benzene (3): To a solution of 4-bromo-2,6-dichlorophenol (10.0 g, 41.1 mmol) and 1-chloro-3-iodopropane (10.1 g, 49.0 mmol) in DMF (100 mL) was added Cs$_2$CO$_3$ (20.2 g, 61.4 mmol) at 20° C. The reaction was stirred at 70° C. for 2 hours. TLC showed the reaction was completed. The resulting solution was cooled down and quenched with water (100 mL), extracted with EtOAc (30 mL×3). The combined organic layers were washed with brine (100 mL), dried over Na$_2$SO$_4$, filtered and concentrated under reduced pressure. The residue was purified by silica-gel column chromatography to give 5-bromo-1,3-dichloro-2-(3-chloropropoxy) benzene (10.0 g, yield: 76.1%) as yellow oil. $^1$H NMR (400

MHz, CHCl$_3$-d) δ 7.46 (s, 2H), 4.16 (t, J=5.75 Hz, 2H), 3.85 (t, J=6.42 Hz, 2H), 2.29 (t, J=5.93 Hz, 2H).

3-(3,5-Dichloro-4-(3-chloropropoxy)phenyl)oxetan-3-ol (5): To a solution of 5-bromo-1,3-dichloro-2-(3-chloropropoxy)benzene (4.0 g, 13.0 mmol) in THF (40 mL) was added n-BuLi (2.5 M, 10 mL) at −78° C. and stirred for 0.5 hour under N$_2$ atmosphere. Oxetan-3-one (4.5 g, 63.2 mmol) was then added to the solution at −78° C. and stirred at 20° C. for 2.5 hours. TLC showed the reaction was completed. The resulting reaction was quenched with saturated aqueous NH$_4$Cl (50 mL), extracted with EtOAc (10 mL×3), and the combined organic layers were washed with brine (20 mL), dried over Na$_2$SO$_4$, filtered and concentrated under reduced pressure. The residue was purified by silica-gel column chromatography to give 3-(3,5-dichloro-4-(3-chloropropoxy)phenyl)oxetan-3-ol (1.2 g, yield: 31.2%) as colorless oil. $^1$H NMR (400 MHz, CHCl$_3$-d) δ 7.59 (s, 2H), 4.9-4.88 (m, 2H), 4.86-4.81 (m, 2H), 4.19 (t, J=5.7 Hz, 2H), 3.87 (t, J=6.4 Hz, 2H), 2.30 (quin, J=6.1 Hz, 2H).

4-(3-(3,5-Dichloro-4-(3-chloropropoxy)phenyl)oxetan-3-yl)phenol (6): To a solution of 3-[3,5-dichloro-4-(3-chloropropoxy)phenyl]oxetan-3-ol (500 mg, 1.60 mmol), phenol (151 mg, 1.60 mmol) in DCM (5 mL) was added AlCl$_3$ (2.2 g, 16.0 mmol) and the solution was stirred at 25° C. for 2 hours. TLC showed the reaction was completed. The resulting solution was quenched with water (10 mL), extracted with DCM (4 mL×3). The combined organic layers were washed with brine (10 mL), dried over Na$_2$SO$_4$, filtered and concentrated under reduced pressure. The residue was purified by silica-gel column chromatography to give 4-(3-(3,5-dichloro-4-(3-chloropropoxy)phenyl)oxetan-3-yl)phenol (150 mg, yield: 24.1%) as colorless oil. $^1$H NMR (400 MHz, CHCl$_3$-d) δ 7.18 (s, 2H), 7.02 (d, J=8.6 Hz, 2H), 6.88-6.83 (m, 2H), 5.22 (d, J=6.0 Hz, 2H), 5.10 (d, J=5.7 Hz, 2H), 4.17 (t, J=5.7 Hz, 2H), 3.87 (t, J=6.5 Hz, 2H), 2.29 (quin, J=6.1 Hz, 2H).

tert-Butyl (2-((4-(3-(3,5-dichloro-4-(3-chloropropoxy)phenyl)oxetan-3-yl)phenoxy)methyl) allyl)(methylsulfonyl)carbamate (8): To a solution of 4-[3-[3,5-dichloro-4-(3-chloro propoxy)phenyl]oxetan-3-yl]phenol (80 mg, 0.2 mmol) and Cs$_2$CO$_3$ (202 mg, 0.6 mmol) in DMF (4 mL) was added tert-butyl (2-(chloromethyl)allyl)(methylsulfonyl)carbamate (59 mg, 0.2 mmol) and the solution was stirred at 60° C. for 2 hours. TLC showed the reaction was completed. The resulting solution was cooled down, poured into H$_2$O (10 mL), extracted with EtOAc (5 mL×2), and the combined organic layers were washed with brine (5 mL), dried over Na$_2$SO$_4$, filtered and concentrated under reduced pressure. The residue was purified by silica-gel column chromatography to give tert-butyl (2-((4-(3-(3,5-dichloro-4-(3-chloropropoxy)phenyl) oxetan-3-yl)phenoxy)methyl)allyl)(methylsulfonyl)carbamate (110 mg, yield: 44.8%) as yellow oil. LCMS purity (220 nm): 71.4%. %). LRMS (M+Na$^+$) m/z: calcd 656.1. found 656.1.

tert-Butyl (3-(4-(3-(3,5-dichloro-4-(3-chloropropoxy) phenyl)oxetan-3-yl)phenoxy)-2-oxopropyl)(methylsulfonyl)carbamate (9): A solution of tert-butyl (2-((4-(3-(3,5-dichloro-4-(3-chloropropoxy)phenyl)oxetan-3-yl)phenoxy) methyl)allyl)(methylsulfonyl)carbamate (110 mg, 0.2 mmol), NaIO$_4$ (162 mg, 0.8 mmol), K$_2$OsO$_4$.H$_2$O (20 mg, 0.01 mmol) in THF (2 mL) and H$_2$O (2 mL) was stirred at 25° C. for 1 hour. LCMS showed the reaction was completed. The reaction was poured into H$_2$O (10 mL), extracted with EtOAc (5 mL×2), and the combined organic layers were washed with brine (5 mL), dried over Na$_2$SO$_4$, filtered and concentrated under reduced pressure to give tert-butyl (3-(4-(3-(3,5-dichloro-4-(3-chloropropoxy) phenyl)oxetan-3-yl) phenoxy)-2-oxopropyl)(methylsulfonyl)carbamate (90 mg, yield: 81.8%) as yellow oil. LRMS (M+Na$^+$) m/z: calcd 658.1. found 658.0.

N-(3-(4-(3-(3,5-Dichloro-4-(3-chloropropoxy)phenyl) oxetan-3-yl)phenoxy)-2-oxopropyl) methanesulfonamide (A43): To a solution of tert-butyl N-(3-(4-(3-(3,5-dichloro-4-(3-chloropropoxy)phenyl)oxetan-3-yl)phenoxy)-2-oxopropyl)-N-methylsulfonyl-carbamate (60 mg, 0.1 mmol) in DCM (2 mL) was added formic acid (1 mL) and the solution was stirred at 25° C. for 15 min. TLC showed the reaction was completed. The reaction was concentrated under reduced pressure. The residue was purified by prep-HPLC (HCO2H) to give N-(3-(4-(3-(3,5-dichloro-4-(3-chloropropoxy)phenyl)oxetan-3-yl)phenoxy)-2-oxopropyl)methanesulfonamide (6.7 mg, yield: 13.2%) as colorless oil. LCMS purity (220 nm): 94.5%. $^1$H NMR (400 MHz, CHCl$_3$-d) δ 7.18-7.10 (m, 4H), 6.93 (br d, J=7.7 Hz, 2H), 5.20 (br d, J=5.1 Hz, 2H), 5.12 (br d, J=5.3 Hz, 2H), 5.05 (br s, 1H), 4.69 (s, 2H), 4.41 (br d, J=4.2 Hz, 2H), 4.21-4.14 (m, 2H), 3.87 (br t, J=5.8 Hz, 2H), 3.01 (s, 3H), 2.30 (br t, J=5.8 Hz, 2H). %). LRMS (M+H$^+$) m/z: calcd 535.0. found 535.

Example 1-05: Synthesis of N-(4-(2-(3,5-dichloro-4-(3-chloropropoxy)phenyl)propan-2-yl)benzyl)-2-(methylsulfonamido)acetamide (A46)

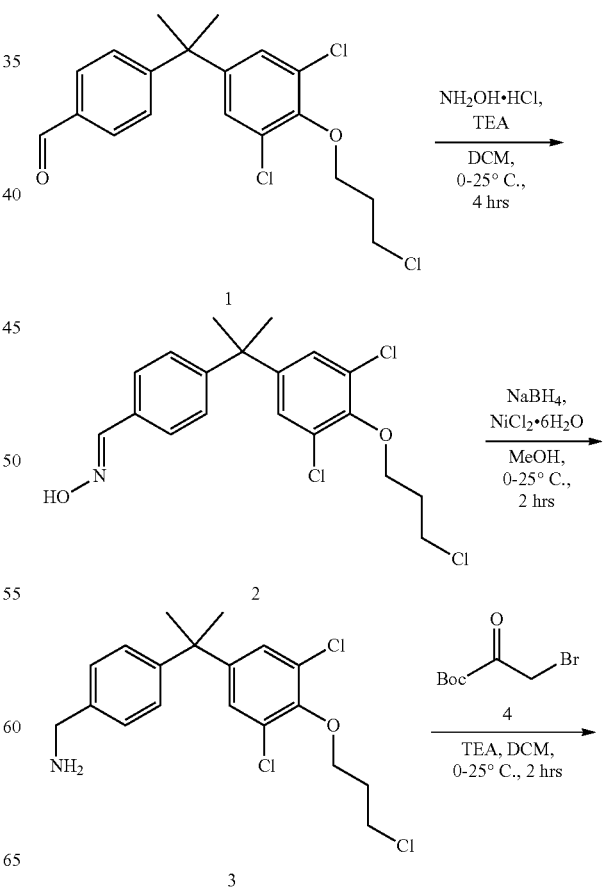

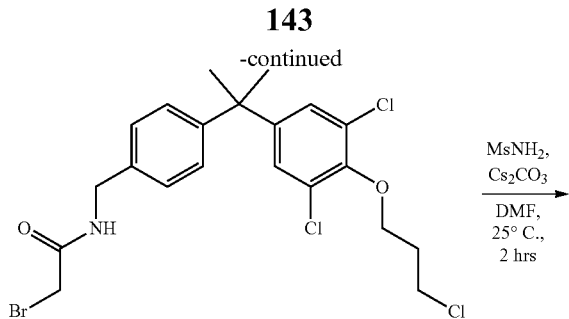

(E)-4-(2-(3,5-Dichloro-4-(3-chloropropoxy)phenyl)propan-2-yl)benzaldehyde oxime (2): To a solution of 4-[1-[3,5-dichloro-4-(3-chloropropoxy)phenyl]-1-methyl-ethyl]benzaldehyde (1) (1.0 g, 2.59 mmol) and TEA (1.81 mL, 13 mmol) in DCM (10 mL) was added hydroxylamine chloride (360 mg, 5.19 mmol) at 0° C., and the resulting solution was stirred at 25° C. for 4 hours. TLC showed the reaction was completed. The reaction solution was washed with water (5 mL×2), dried over $Na_2SO_4$, filtered and concentrated under reduced pressure to give the 4-[1-[3,5-dichloro-4-(3-chloropropoxy)phenyl]-1-methyl-ethyl]benzaldehyde oxime (1.0 g, yield: 96.3%) as brown oil.

[4-[1-[3,5-Dichloro-4-(3-chloropropoxy)phenyl]-1-methyl-ethyl]phenyl]methanamine (3): To a solution of (E)-4-[1-[3,5-dichloro-4-(3-chloropropoxy)phenyl]-1-methyl-ethyl]benzaldehyde oxime (2) (0.90 g, 2.25 mmol) and $NiCl_2 \cdot 6H_2O$ (1.19 g, 4.99 mmol) in MeOH (50 mL) was added $NaBH_4$ (378 mg, 10 mmol) at 0° C. Then the resulting solution was stirred at 25° C. for 2 hours. LCMS showed reaction was completed. The reaction mixture was filtered and the filtrate was concentrated under reduced pressure. The residue was partitioned between DCM (10 mL×3) and water (10 mL). The combined organic layers were dried over $Na_2SO_4$, filtered and concentrated under reduced pressure to give the [4-[1-[3,5-dichloro-4-(3-chloropropoxy)phenyl]-1-methyl-ethyl]phenyl]methanamine (780 mg crude, purity: 70%) as blue gum. LCMS (M+H$^+$) m/z: clcd 385.1. found 386.1.

2-bromo-N-[[4-[1-[3,5-dichloro-4-(3-chloropropoxy)phenyl]-1-methyl-ethyl]phenyl]-methyl]-acetamide (5): To a solution of [4-[1-[3,5-dichloro-4-(3-chloropropoxy)phenyl]-1-methyl-ethyl]phenyl]methanamine (3) (780 mg, crude) and TEA (1.1 mL, 7.99 mmol) in DCM (20 mL) was added 2-bromoacetyl bromide (814 mg, 4.03 mmol) at 0° C. Then the resulting solution was stirred at 25° C. for 2 hours. LCMS showed the reaction was completed. The resulting solution was poured into water (5 mL) and the organic layer was separated. The aqueous solution was extracted with DCM (3 mL×2). The combined organic layer was dried over $Na_2SO_4$, filtered and concentrated under reduced pressure. The residue was purified by MPLC to give the 2-bromo-N-[[4-[1-[3,5-dichloro-4-(3-chloropropoxy)phenyl]-1-methyl-ethyl]phenyl]methyl]acetamide (200 mg, yield: 19.5%) as a brown gum. $^1$H NMR (400 MHz, CHCl3-d) δ 7.24-7.16 (m, 4H), 7.12 (s, 2H), 4.46 (d, J=5.7 Hz, 2H), 4.17-4.14 (m, 2H), 3.94 (s, 2H), 3.86 (t, J=6.5 Hz, 2H), 2.28 (quin, J=6.1 Hz, 2H), 1.57 (s, 6H). LCMS (M+Na$^+$) m/z: clcd 530.0. found 530.0.

N-[[4-[1-[3,5-Dichloro-4-(3-chloropropoxy)phenyl]-1-methyl-ethyl]phenyl]methyl]-2-(methanesulfonamido)acetamide (A46): To a solution of 2-bromo-N-[[4-[1-[3,5-dichloro-4-(3-chloropropoxy)phenyl]-1-methyl-ethyl]phenyl]methyl]acetamide (5) (100 mg, 0.20 mol) and $Cs_2CO_3$ (321 mg, 0.98 mmol) in DMF (5 mL) was added methanesulfonamide (37.5 mg, 0.39 mmol). Then the resulting solution was stirred at 25° C. for 2 hours. LCMS showed the reaction was completed. The solution was poured into water (5 mL) and the organic layer was separated. The aqueous phase was extracted with EtOAc (3 mL×4). The combined organic layers were washed with brine (4 mL×3), dried over $Na_2SO_4$, filtered and concentrated. The crude product was purified by prep-HPLC (TFA) to give the N-[[4-[1-[3,5-dichloro-4-(3-chloropropoxy)phenyl]-1-methyl-ethyl]phenyl]methyl]-2-(methanesulfonamido)acetamide (24.1 mg, yield: 23.4%) as a yellow gum. HPLC purity (220 nm): 98.3%. $^1$H NMR (400 MHz, CHCl3-d) δ 7.26-7.18 (m, 4H), 7.14 (s, 2H), 6.34 (br s, 1H), 5.02 (br s, 1H), 4.49 (d, J=5.7 Hz, 2H), 4.18 (t, J=5.8 Hz, 2H), 3.92-3.85 (m, 4H), 3.03 (s, 3H), 2.31 (quin, J=6.1 Hz, 2H), 1.66 (s, 6H). LCMS (M+H$^+$) m/z: clcd 522.1. found 523.0.

Example 1-06: Synthesis of N-(3,5-dichloro-4-(3-chloropropoxy)phenyl)-N-(4-(3-(methylsulfonamido)-2-oxopropoxy)phenyl)acetamide (A71)

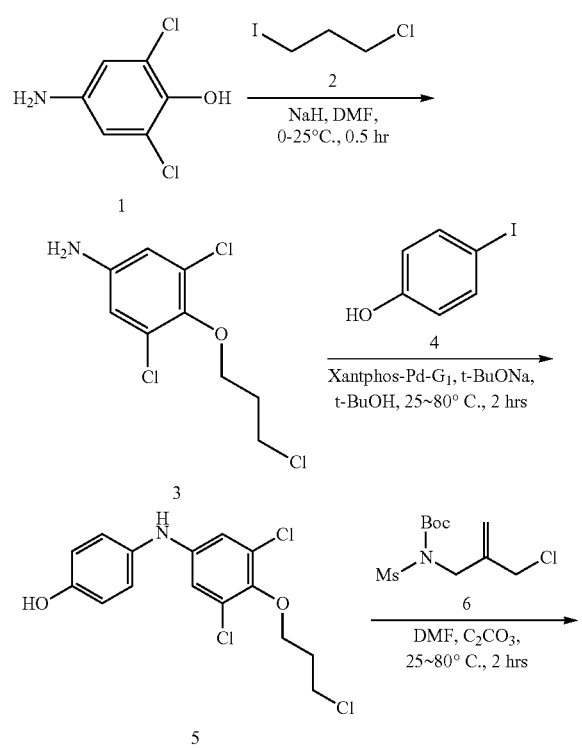

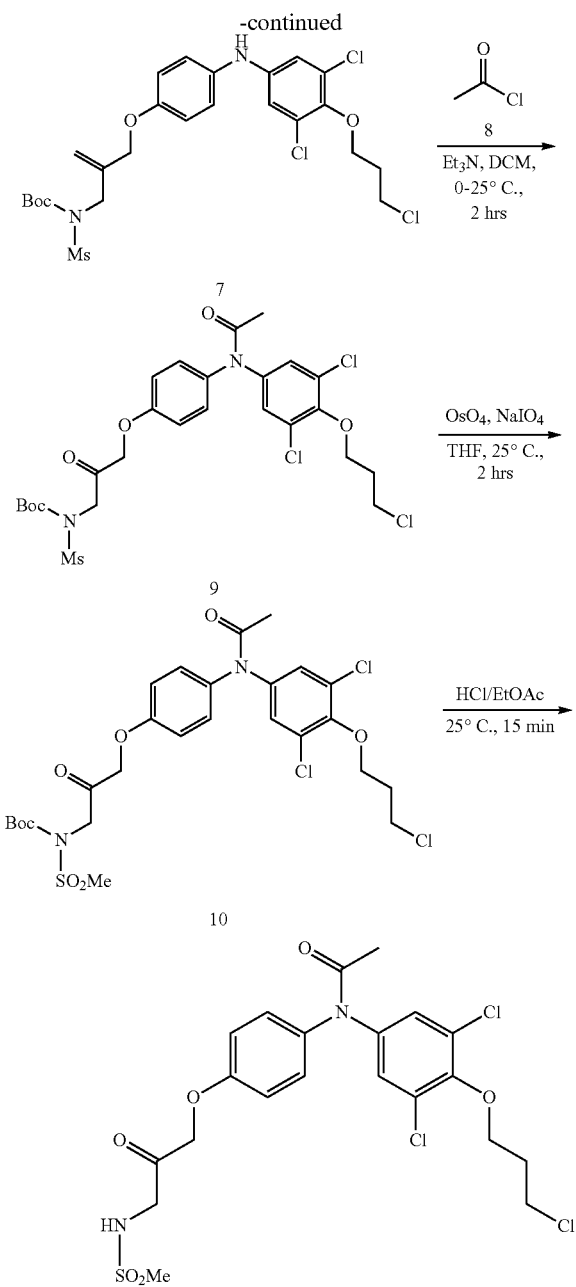

3,5-Dichloro-4-(3-chloropropoxy)aniline (3): To a solution of 4-amino-2,6-dichlorophenol (20.0 g, 112.0 mmol) and 1-chloro-3-iodopropane (23.0 g, 112.0 mmol) in DMF (200 mL) was added NaH (60%, 6.5 g, 169.0 mmol) at 0° C. and the solution was stirred at 25° C. for 0.5 hr. LCMS showed the reaction was completed. The reaction was quenched with saturated aqueous NH$_4$Cl (300 mL), extracted with EtOAc (100 mL×3). The combine organic layers were washed with brine (100 ml×2), dried over Na$_2$SO$_4$, filtered and concentrated under reduced pressure to give 3,5-dichloro-4-(3-chloropropoxy)aniline (15.0 g, 52.0%) as yellow solid. LCMS purity (220 nm): 90.3%. LCMS (M+H$^+$) m/z: clcd 253.0; found 254.0.

4-((3,5-Dichloro-4-(3-chloropropoxy)phenyl)amino)phenol (5): To a solution of 3,5-dichloro-4-(3-chloropropoxy)aniline (5.0 g, 20.0 mmol), 4-iodophenol (4.3 g, 20.0 mmol) and t-BuONa (2.8 g, 29.0 mmol) in t-BuOH (100 mL) was added Xantphos-Pd-Gi (2.3 g, 3.9 mmol) under N$_2$ atmosphere at 25° C., and the solution was stirred at 80° C. for 2 hours. TLC showed the reaction was completed. The reaction was quenched with H$_2$O (200 mL), extracted with EtOAc (50 mL×3). The combine organic layers were washed with brine (40 mL×2), dried over Na$_2$SO$_4$, filtered and concentrated under reduced pressure. The residue was purified by silica-gel column chromatography to give 4-((3,5-dichloro-4-(3-chloropropoxy)phenyl)amino)phenol (3.5 g, yield: 51.0%) as colorless oil. $^1$H NMR (400 MHz, CHCl$_3$-d) δ 7.02-6.98 (m, 2H), 6.85-6.80 (m, 2H), 6.76 (s, 2H), 5.39 (s, 1H), 4.83 (s, 1H), 4.09 (t, J=5.7 Hz, 2H), 3.86 (t, J=6.5 Hz, 2H), 2.27 (quin, J=6.1 Hz, 2H).

tert-Butyl (2-((4-((3,5-dichloro-4-(3-chloropropoxy)phenyl)amino)phenoxy)methyl)allyl) (methylsulfonyl)carbamate (7): To a solution of 4-((3,5-dichloro-4-(3-chloropropoxy)phenyl) amino)phenol (2.4 g, 6.8 mmol) and Cs$_2$CO$_3$ (4.4 g, 14.0 mmol) in DMF (20 mL) was added tert-butyl (2-(chloromethyl)allyl)(methylsulfonyl)carbamate tert-butyl (3.0 g, 11.0 mmol) at 25° C. and the solution was stirred at 80° C. for 2 hours. TLC showed the reaction was completed. The reaction was quenched with H$_2$O (100 mL), extracted with EtOAc (25 mL×3). The combine organic layers were washed with brine (30 mL×2), dried over Na$_2$SO$_4$, filtered and concentrated under reduced pressure to give tert-butyl (2-((4-((3,5-dichloro-4-(3-chloropropoxy)phenyl)amino) phenoxy)methyl)allyl)(methylsulfonyl)carbamate (2.0 g, yield: 32.0%) as brown oil. $^1$H NMR (400 MHz, CHCl$_3$-d) δ=7.08-6.99 (m, 2H), 6.94-6.85 (m, 2H), 6.77 (s, 2H), 5.42 (s, 1H), 5.37 (s, 1H), 5.27 (s, 1H), 4.52 (s, 2H), 4.45 (s, 2H), 4.14-4.03 (m, 2H), 3.86 (t, J=6.5 Hz, 2H), 3.33 (s, 3H), 2.27 (quin, J=6.1 Hz, 2H), 1.55-1.48 (m, 9H).

tert-Butyl (2-((4-(N-(3,5-dichloro-4-(3-chloropropoxy) phenyl)acetamido)phenoxy)methyl)allyl)(methylsulfonyl) carbamate (9): To a solution of tert-butyl (2-((4-((3,5-dichloro-4-(3-chloropropoxy)phenyl)amino)phenoxy)methyl) allyl)(methylsulfonyl)carbamate (600 mg, 1.0 mmol) and Et$_3$N (0.2 mL, 1.0 mmol) in DCM (10 mL) was added acetyl chloride (340 mg, 4.4 mmol) at 0° C. and the solution was stirred at 25° C. for 2 hours. TLC showed the reaction was completed. The reaction was quenched with H$_2$O (50 mL), extracted with DCM (20 mL×2). The combine organic layers were washed with brine (20 mL), dried over Na$_2$SO$_4$, filtered and concentrated under reduced pressure. The residue was purified by silica-gel column chromatography to give tert-butyl (2-((4-(N-(3,5-dichloro-4-(3-chloropropoxy) phenyl)acetamido) phenoxy)methyl)allyl) (methylsulfonyl) carbamate (320 mg, yield: 50.0%) as brown oil. $^1$H NMR (400 MHz, CHCl$_3$-d) δ 7.22 (s, 2H), 7.16 (d, J=8.8 Hz, 2H), 6.96 (br d, J=8.3 Hz, 2H), 5.38 (s, 1H), 5.29 (br s, 1H), 4.55 (s, 2H), 4.43 (s, 2H), 4.23-4.07 (m, 2H), 3.84 (t, J=6.4 Hz, 2H), 3.32 (s, 3H), 2.3-2.18 (m, 2H), 2.06-1.96 (m, 3H), 1.50 (s, 9H).

tert-Butyl (3-(4-(N-(3,5-dichloro-4-(3-chloropropoxy) phenyl)acetamido)phenoxy)-2-oxopropyl)(methylsulfonyl) carbamate (10): To a solution of tert-butyl (2-((4-(N-(3,5-dichloro-4-(3-chloropropoxy)phenyl)acetamido)phenoxy) methyl)allyl)(methylsulfonyl)carbamate (200 mg, 0.3 mmol) and NaIO$_4$ (700 mg, 3.1 mmol) in THF (2 mL) and H$_2$O (2 mL) was added OsO$_4$ (16 mg, 0.1 mmol) and the solution was stirred at 25° C. for 2 hours. TLC showed the reaction was completed. The reaction was quenched with H$_2$O (8 mL), extracted with EtOAc (2 mL×3). The combine organic layers were washed with brine (3 mL), dried over Na$_2$SO$_4$, filtered and concentrated under reduced pressure to give tert-butyl (3-(4-(N-(3,5-dichloro-4-(3-chloropropoxy)phenyl)acetamido)phenoxy)-2-oxopropyl)(methylsulfonyl)carbamate (200 mg, yield: 75.0%) as yellow oil.

N-(3,5-Dichloro-4-(3-chloropropoxy)phenyl)-N-(4-(3-(methylsulfonamido)-2-oxopropoxy)phenyl)acetamide (A71): A solution of tert-butyl (3-(4-(N-(3,5-dichloro-4-(3-chloropropoxy)phenyl)acetamido)phenoxy)-2-oxopropyl)(methylsulfonyl)carbamate (200 mg, 0.2 mmol) in HCl/EtOAc (4 M, 4 mL) was stirred at 25° C. for 15 min. TLC showed the reaction was completed. The reaction was concentrated under reduced pressure. The residue was purified by prep-HPLC (HCl) to give N-(3,5-dichloro-4-(3-chloropropoxy)phenyl)-N-(4-(3-(methylsulfonamido)-2-oxopropoxy)phenyl)acetamide (69 mg, yield: 59.0%) as yellow oil. HPLC purity (220 nm): 93.5%. $^1$H NMR (400 MHz, CHCl$_3$-d) δ=7.26-7.21 (m, 4H), 7.01-6.92 (m, 2H), 5.05 (br s, 1H), 4.70 (s, 2H), 4.40 (d, J=5.1 Hz, 2H), 4.15 (br s, 2H), 3.85 (t, J=6.4 Hz, 2H), 3.02 (s, 3H), 2.28 (quin, J=6.0 Hz, 2H), 2.10-2.01 (m, 3H). LCMS (M+H$^+$) m/z: clcd: 538.0; found: 539.0.

Example 1-07: Synthesis of N-(3-((3',5'-dichloro-4'-(3-chloropropoxy)-[1,1'-biphenyl]-4-yl)oxy)-2-oxopropyl)methanesulfonamide (A73)

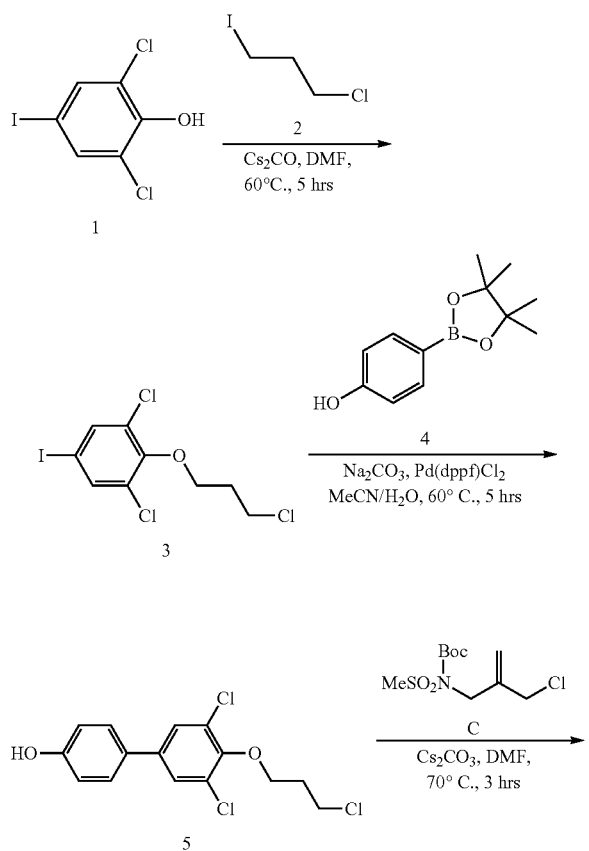

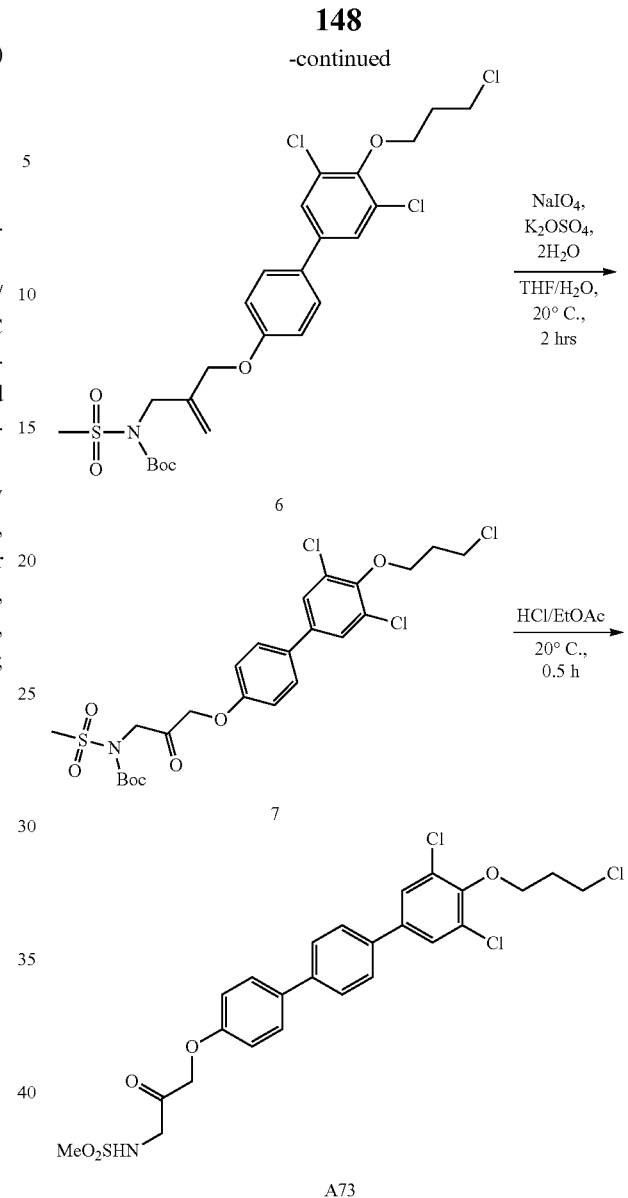

1,3-Dichloro-2-(3-chloropropoxy)-5-iodobenzene (3): To a solution of 2,6-dichloro-4-iodo-phenol (1) (1.0 g, 3.46 mmol) in DMF (20 mL) was added 1-chloro-3-iodo-propane (2) (708 mg, 3.46 mmol) and Cs$_2$CO$_3$ (2.26 g, 6.92 mmol) under N$_2$ atmosphere at 20° C. The reaction was stirred at 60° C. for 5 hours. TLC showed the reaction was completed. The solution was poured into H$_2$O (20 mL), extracted with EtOAc (50 mL×3). The combined organic layers were washed with brine (50 mL×3), dried over Na$_2$SO$_4$, filtered and concentrated under reduced pressure. The residue was purified by silica-gel column chromatography to give 1,3-dichloro-2-(3-chloropropoxy)-5-iodobenzene (80.0%, 1.27 g, yield: 80.3%) as brown oil. $^1$H NMR (400 MHz, CHCl$_3$-d) δ 7.63 (s, 2H), 4.15 (t, J=5.7 Hz, 2H), 3.85 (t, J=6.4 Hz, 2H), 2.28 (t, J=6.1 Hz, 2H).

3',5'-Dichloro-4'-(3-chloropropoxy)-[1,1'-biphenyl]-4-ol (5): To a solution of 1,3-dichloro-2-(3-chloropropoxy)-5-iodobenzene (3) (1.10 g, 3.01 mmol) in dioxane (12 mL), MeCN (4 mL) and H$_2$O (4 mL) was added 4-(4,4,5,5-tetramethyl-1,3,2-dioxaborolan-2-yl)phenol (4) (729 mg, 3.31 mmol), Na$_2$CO$_3$ (638 mg, 6.02 mmol) and Pd(dppf)C$_{12}$ (22 mg, 0.03 mmol) under N₂ atmosphere at 20° C. Then the reaction was stirred at 60° C. for 5 hours. LCMS showed the reaction was completed. The solution was poured into H₂O (10 mL), extracted with EtOAc (20 mL×3). The combined organic layers were washed with brine (20 mL), dried over Na₂SO₄, filtered and concentrated under reduced pressure. The residue was purified by MPLC to give 3',5'-dichloro-4'-(3-chloropropoxy)-[1,1'-biphenyl]-4-ol (80.000, 0.91 g, yield: 72.9%) as brown oil. $^1$H NMR (400 MHz, CHCl₃-d) δ 7.46 (s, 2H), 7.43-7.37 (d, J=5.7 Hz, 2H), 6.91 (d, J=8.6 Hz, 2H), 5.03 (s, 1H), 4.25-4.17 (t, J=5.7 Hz, 2H), 3.89 (t, J=6.4 Hz, 2H), 2.36-2.26 (m, 2H). LCMS (M+H⁺) m/z: clcd: 330.0. found 328.9.

tert-Butyl (2-(((3',5'-dichloro-4'-(3-chloropropoxy)-[1,1'-biphenyl]-4-yl)oxy) methyl)allyl) (methylsulfonyl)carbamate (6): To a solution of 3',5'-dichloro-4'-(3-chloropropoxy)-[1,1'-biphenyl]-4-ol (5) (0.4 g, 1.21 mmol) in DMF (10 mL) was added tert-butyl (2-(chloromethyl) allyl)((methylthio)peroxy)carbamate (C) (0.41 g, 1.45 mmol) and Cs₂CO₃ (0.786 g, 2.41 mmol) under N₂ atmosphere at 20° C. The reaction was stirred at 70° C. for 3 hours. TLC showed the reaction was completed. The solution was poured into H₂O (10 mL) and extracted with EtOAc (10 mL×3). The combined organic layers were washed with brine (10 mL×3), dried over Na₂SO₄, filtered and concentrated under reduced pressure. The residue was purified by MPLC to give tert-butyl (2-(((3',5'-dichloro-4'-(3-chloropropoxy)-[1,1'-biphenyl]-4-yl)oxy)methyl)allyl) (methylsulfonyl)carbamate (0.54 g, yield: 77.3%) as brown oil. $^1$H NMR (400 MHz, CHCl₃-d) δ 7.46 (s, 2H), 7.45-7.39 (d, J=5.7 Hz, 2H), 7.00-6.95 (d, J=8.6 Hz, 2H), 5.31 (s, 2H), 4.62-4.51 (m, 2H), 4.47-4.41 (m, 2H), 4.24-4.17 (t, J=5.7 Hz, 2H), 3.94-3.85 (t, J=6.4 Hz, 2H), 3.33 (s, 3H), 2.36-2.27 (m, 2H), 1.53-1.51 (s, 9H).

tert-Butyl (3-((3',5'-dichloro-4'-(3-chloropropoxy)-[1,1'-biphenyl]-4-yl)oxy)-2-oxopropyl) (methylsulfonyl)carbamate (7): To a solution of tert-butyl (2-(((3',5'-dichloro-4'-(3-chloropropoxy)-[1,1'-biphenyl]-4-yl)oxy)methyl)allyl) (methylsulfonyl)carbamate (6) (150 mg, 0.26 mmol) in THF (2 mL) and H₂O (2 mL) was added NaIO₄ (0.277 g, 1.30 mmol) and K₂OsO₄·2H₂O (9 mg, 0.26 mmol) under N₂ atmosphere at 0° C. The reaction was stirred at 20° C. for 2 hours. LCMS showed the reaction was completed. The solution was poured into H₂O (2 mL), extracted with EtOAc (5 mL×3). The combined organic layers were washed with brine (10 mL), dried over Na₂SO₄, filtered, and concentrated under reduced pressure to give the crude tert-butyl (3-((3', 5'-dichloro-4'-(3-chloropropoxy)-[1,1'-biphenyl]-4-yl)oxy)-2-oxopropyl) (methylsulfonyl)carbamate (70.0%, 0.13 g, yield: 60.5%) as brown oil. $^1$H NMR (400 MHz, CHCl₃-d) δ 7.51-7.43 (m, 4H), 7.00-6.94 (d, J=8.6 Hz, 2H), 4.89 (s, 2H), 4.75-4.66 (m, 2H), 4.24-4.18 (t, J=5.7 Hz, 2H), 3.93-3.86 (t, J=6.4 Hz, 2H), 3.44 (s, 3H), 2.32 (m, 2H), 1.54 (s, 9H), 1.34 (s, 3H). LCMS (M+H⁺) m/z: clcd: 579.1. found 597.2.

N-(3-((3',5'-Dichloro-4'-(3-chloropropoxy)-[1,1'-biphenyl]-4-yl)oxy)-2-oxopropyl) methanesulfonamide (A73): A solution of tert-butyl (3-((3',5'-dichloro-4'-(3-chloropropoxy)-[1,1'-biphenyl]-4-yl)oxy)-2-oxopropyl)(methylsulfonyl)carbamate (7) (70.0%, 0.13 g, 0.15 mol) in HCl/EtOAc (2 mL) was stirred at 20° C. for 0.5 hour. LCMS showed the reaction was completed. The solution was concentrated under reduced pressure. The crude product was purified by prep-HPLC (HCl) to give N-(3-((3',5'-dichloro-4'-(3-chloropropoxy)-[1,1'-biphenyl]-4-yl)oxy)-2-oxopropyl)methanesulfonamide (29 mg, yield: 27.0%) as brown oil. HPLC purity (220 nm): 90.5%. $^1$H NMR (400 MHz, CHCl₃-d) δ=7.51-7.48 (d, J=8.8 Hz, 2H), 7.47 (s, 2H), 7.00-6.96 (d, J=8.6 Hz, 2H), 5.12-4.99 (m, 1H), 4.72 (s, 2H), 4.46-4.37 (d, J=5.2 Hz, 2H), 4.25-4.17 (t, J=5.7 Hz, 2H), 3.96-3.83 (t, J=6.4 Hz, 2H), 3.02 (s, 3H), 2.38-2.25 (m, 2H). LCMS (M+H⁺) m/z: clcd: 480.0. found 480.0.

Example 1-08: Synthesis of N-(3-(4-(3,5-dichloro-4-(3-chloro-2-hydroxypropoxy)phenethyl)phenoxy)-2-oxopropyl)methanesulfonamide (A75)

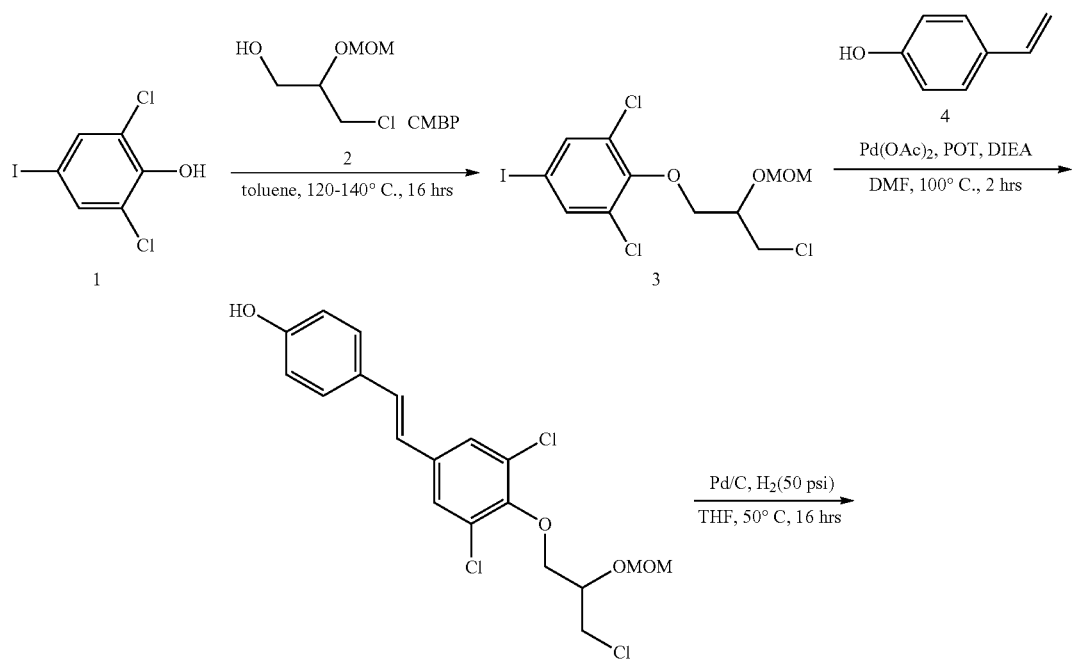

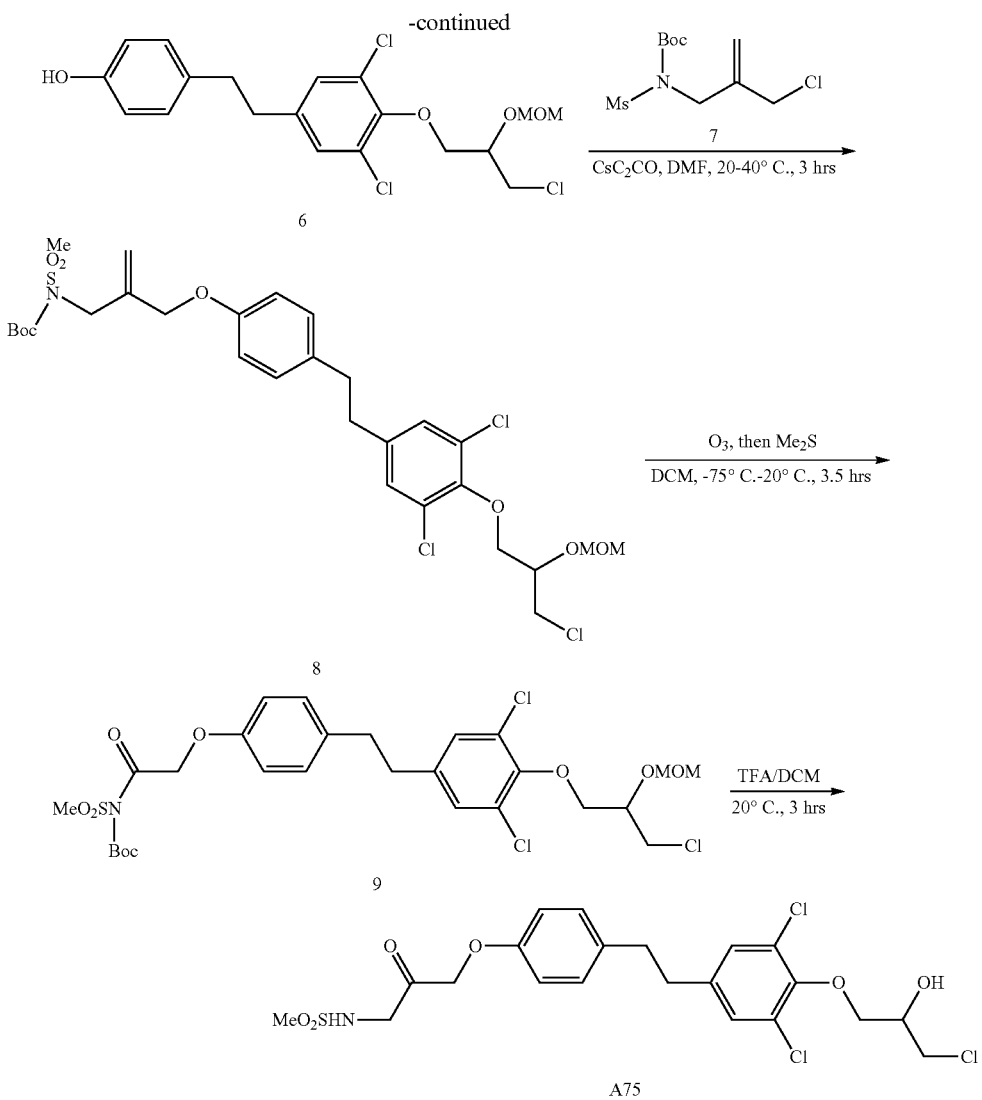

1,3-Dichloro-2-(3-chloro-2-(methoxymethoxy)propoxy)-5-iodobenzene (3): To a solution of 2,6-dichloro-4-iodophenol (2.28 g, 9.4 mmol) and 3-chloro-2-(methoxymethoxy) propan-1-ol (1) (1.75 g, 11.2 mmol) in toluene (30 mL) was added CMBP (5.56 g, 23.0 mmol) under $N_2$ atmosphere and the resulting solution was stirred at 120° C. for 4 hours, and at 140° C. for another 12 hours. TLC showed of the reaction was completed. Toluene was removed from the solution under reduced pressure. The residue was purified by MPLC to give 1,3-dichloro-2-(3-chloro-2-(methoxymethoxy)propoxy)-5-iodobenzene (3.3 g, yield: 80%) as white solid. $^1$HNMR (400 MHz, CHCl$_3$-d) δ ppm 7.63 (s, 2H), 4.86-4.80 (m, 1H), 4.78 (s, 1H), 4.20-4.15 (m, 3H), 3.91 (d, J=4.4 Hz 3H), 3.84-3.80 (m, 1H), 3.45 (s, 3H).

(E)-4-(3,5-Dichloro-4-(3-chloro-2-(methoxymethoxy) propoxy)styryl)phenol (5): To a solution of 1,3-dichloro-2-(3-chloro-2-(methoxymethoxy)propoxy)-5-iodobenzene (3) (1.6 g, 3.7 mmol), 4-vinylphenol (451 mg, 3.7 mmol), TEA (761 mg, 7.5 mmol) in DMF (20 mL) was added Pd(OAc)$_2$ (84.42 mg, 0.218 mmol) and POT (57.2 mg, 0.18 mmol) at 20° C. Under $N_2$ atmosphere. The resulting solution was stirred at 100° C. for 2 hours. LCMS showed the reaction was completed. The resulting solution was quenched with water (30 mL) and extracted with EtOAc (10 mL×3). The combined organic layers were washed with brine (20 mL), dried over Na$_2$SO$_4$, filtered and concentrated under reduced pressure. The residue was purified by silica gel chromatography eluted to give (E)-4-(3,5-dichloro-4-(3-chloro-2-(methoxymethoxy) propoxy)styryl)phenol (1.0 g, yield: 50%) as brown solid. $^1$H NMR (400 MHz, CHCl$_3$-d) 6 ppm 7.45 (s, 1H), 7.39 (d, J=9.2 Hz, 1H), 6.99 (s, 1H), 6.95 (s, 1H), 6.85-6.76 (m, 1H), 4.81 (d, J=4.4 Hz, 2H), 4.22-4.16 (m, 3H), 3.95-3.86 (m, 3H), 3.44 (d, J=18.8 Hz, 3H).

4-(3,5-Dichloro-4-(3-chloro-2-(methoxymethoxy) propoxy)phenethyl)phenol (6): To a solution of (E)-4-(3,5-dichloro-4-(3-chloro-2-(methoxymethoxy)propoxy)styryl) phenol (5) (200 mg, 0.47 mmol) in MeOH (5 mL) was added R$_h$(PPh$_3$)$_3$C$_1$ at 20° C. under H$_2$. Then the solution was stirred at 50° C. under H$_2$ (50 psi) for 16 hours. LCMS showed the reaction was completed. The resulting solution was cooled down and filtered. The filtrate was poured into water (10 mL) and extracted with EtOAc (10 mL×3). The combined organic layers were washed with brine (10 mL), dried over Na$_2$SO$_4$, filtered and concentrated to give 4-(3, 5-dichloro-4-(3-chloro-2-(methoxymethoxy)propoxy)phenethyl)phenol (200 mg crude).

tert-Butyl (2-((4-(3,5-dichloro-4-(3-chloro-2-(methoxymethoxy) propoxy) phenethyl) phenoxy)methyl) allyl)(methylsulfonyl)carbamate (8): To a solution of 4-(-(3, 5-dichloro-4-(3-chloro-2-(methoxymethoxy)propoxy)phenyl)ethyl)phenol (6) (200 mg, 0.467 mmol) and Cs₂CO₃ (228 mg, 0.7 mmol) in DMF (5 mL) was added tert-butyl N-(2-(chloromethyl)allyl)-N-methylsulfonyl-carbamate (159 mg, 0.56 mmol) at 20° C. under N₂ atmosphere, and the resulting solution was stirred at 40° C. for 3 hours. TLC showed the reaction was completed. The resulting solution was cooled down, quenched with water (10 mL) and extracted with EtOAc (5 mL×5). The combined organic layers were washed with brine (5 mL×2), dried over Na₂SO₄, filtered and concentrated under reduced pressure to give tert-butyl N-(2-((4-(2-(3,5-dichloro-4-(3-chloro-2-(methoxymethoxy)propoxy)phenyl)ethyl)phenoxy)methyl) allyl)-N-methylsulfonyl-carbamate (170 mg, yield: 51.8%) as yellow oil. ¹H NMR (400 MHz, CHCl₃-d) δ ppm 7.01-7.11 (m, 4H), 6.83 (d, J=8.68 Hz, 2H), 5.35 (s, 1H), 5.26 (s, 1H) 4.78-4.89 (m, 2H), 4.50 (s, 2H), 4.44 (s, 2H), 4.13-4.24 (m, 3H), 3.81-3.99 (m, 2H), 3.46 (s, 3H), 3.31 (s, 3H), 2.74-2.87 (m, 4H), 1.51 (s, 9H).

tert-Butyl (3-(4-(3,5-dichloro-4-(3-chloro-2-(methoxymethoxy)propoxy)phenethyl) phenoxy)-2-oxopropyl)(methylsulfonyl)carbamate (9): To a solution of tert-butyl N-(2-((4-(2-(3,5-dichloro-4-(3-chloro-2-(methoxymethoxy)propoxy)phenyl)ethyl)phenoxy)methyl) allyl)-N-methylsulfonyl-carbamate (8) (150 mg, 0.23 mmol) in CH₂Cl₂ (30 mL) was bubbled 03 at −75° C. for 0.5 hours. Then to the solution was added Me₂S (140 mg, 2.25 mmol) and the solution stirred at 20° C. for 3 hours. TLC showed the reaction was completed. The resulting solution was poured into water (50 mL) and extracted with CH₂Cl₂ (50 mL×5). The combined organic layers were washed with brine (20 mL×2), dried over Na₂SO₄, filtered and concentrated under reduced pressure to give tert-butyl N-(3-(4-(2-(3,5-dichloro-4-(3-chloro-2-(methoxymethoxy) propoxy) phenyl) ethyl) phenoxy)-2-oxo-propyl)-N-methylsulfonyl-carbamate (180 mg, purity: 80%, yield: 95.7%) as yellow oil. ¹H NMR (400 MHz, CHCl₃-d) δ ppm 7.06-7.12 (m, 4H), 6.83 (d, J=8.60 Hz, 2H), 4.88 (s, 2H) 4.87 (s, 1H), 4.79-4.82 (m, 1H), 4.64 (s, 2H), 4.13-4.24 (m, 3H), 3.80-4.00 (m, 2H), 3.46 (s, 3H), 3.43 (s, 3H), 2.78-2.88 (m, 4H), 1.53 (s, 9H).

N-(3-(4-(3,5-Dichloro-4-(3-chloro-2-hydroxypropoxy) phenethyl)phenoxy)-2-oxopropyl) methanesulfonamide (A75): A solution of tert-butyl N-(3-(4-(2-(3,5-dichloro-4-(3-chloro-2-(methoxymethoxy)propoxy)phenyl)ethyl)phenoxy)-2-oxo-propyl)-N-methylsulfonyl-carbamate (9) (180 mg, 0.27 mmol) in TFA (2 mL) and DCM (10 mL) was stirred at 20° C. for 3 hours. LCMS showed the reaction was completed. The resulting solution was concentrated under reduced pressure. The residue was purified by prep-HPLC (HCl) to give N-(3-(4-(2-(3, 5-dichloro-4-(3-chloro-2-hydroxy-propoxy)phenyl)ethyl)phenoxy)-2-oxo-propyl)methanesulfonamide (13.9 mg, yield: 9.84%) as white solid. HPLC purity (220 nm): 92%. ¹H NMR (400 MHz, CHCl3-d) δ ppm 7.06-7.11 (m, 4H), 6.80-6.86 (m, 2H), 5.02 (br s, 1H), 4.63-4.69 (m, 2H), 4.40 (d, J=5.14 Hz, 2H), 4.23 (br s, 1H), 4.12-4.20 (m, 2H), 3.74-3.90 (m, 2H), 3.00 (s, 3H), 2.83-2.86 (m, 2H), 2.79-2.83 (m, 2H).

Example 1-09: Synthesis of N-(3-((4-(2-(3,5-dichloro-4-(2-chloroethoxy)phenyl)propan-2-yl)phenyl) (methyl)amino)-2-oxopropyl)methanesulfonamide hydrochloride (A81)

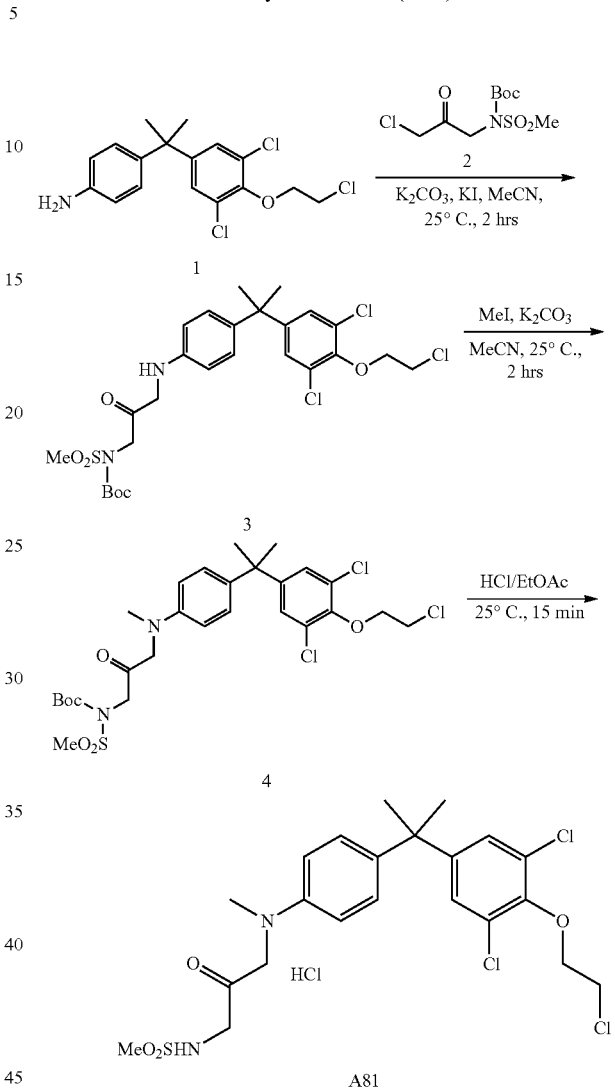

tert-Butyl (3-((4-(2-(3,5-dichloro-4-(2-chloroethoxy)phenyl)propan-2-yl)phenyl)amino)-2-oxopropyl)(methylsulfonyl)carbamate (3): To a solution of 4-(2-(3,5-dichloro-4-(2-chloroethoxy)phenyl)propan-2-yl)aniline (100 mg, 0.3 mmol), K₂CO₃ (116 mg, 0.8 mmol), KI (463 mg, 0.3 mmol) in MeCN (5 mL) was added tert-butyl (3-chloro-2-oxopropyl) (methylsulfonyl)carbamate (791 mg, 0.3 mmol), and the solution was stirred at 25° C. for 2 hours. TLC showed the reaction was completed. The solution was poured into H₂O (5 mL), extracted with EtOAc (5 mL×2). The combined organic layers were washed with brine (10 mL), dried over Na₂SO₄, filtered and concentrated under reduced pressure. The residue was purified by silica-gel column chromatography to give tert-butyl (3-((4-(2-(3,5-dichloro-4-(2-chloroethoxy)phenyl) propan-2-yl)phenyl)amino)-2-oxopropyl) (methylsulfonyl)carbamate (120 mg, yield: 70.8%) as yellow oil. LCMS (220 nm): 79.0%. LCMS (M+H⁺) m/z: clcd: 606.1. found 607.1.

tert-Butyl (3-((4-(2-(3,5-dichloro-4-(2-chloroethoxy)phenyl)propan-2-yl)phenyl)(methyl) amino)-2-oxopropyl)

(methylsulfonyl)carbamate (4): To a solution of tert-butyl (3-((4-(2-(3,5-dichloro-4-(2-chloroethoxy)phenyl)propan-2-yl)phenyl)amino)-2-oxopropyl)(methylsulfonyl) carbamate (100 mg, 0.3 mol), $K_2CO_3$ (116 mg, 0.8 mol) and KI (46 mg, 0.3 mmol) in MeCN (5 mL) was added iodomethane (467 mg, 0.3 mmol) and the solution was stirred at 25° C. for 2 hours. TLC showed the reaction was completed. The solution was poured into $H_2O$ (5 mL), extracted with EtOAc (5 mL×2). The combined organic layers were washed with brine (10 mL), dried over $Na_2SO_4$, filtered and concentrated under reduced pressure. The residue was purified by silica-gel column chromatography to give tert-butyl (3-((4-(2-(3,5-dichloro-4-(2-chloroethoxy)phenyl)propan-2-yl)phenyl)(methyl)amino)-2-oxopropyl)(methylsulfonyl)carbamate (100 mg, yield: 97.7%) as yellow oil. LCMS (220 nm): 71.1%. LCMS (M+H$^+$) m/z: clcd: 620.1. found 621.1.

N-(3-((4-(2-(3,5-Dichloro-4-(2-chloroethoxy)phenyl)propan-2-yl)phenyl)(methyl)amino)-2-oxopropyl)methanesulfonamide hydrochloride (A81): A solution of tert-butyl (3-((4-(2-(3,5-dichloro-4-(2-chloroethoxy)phenyl)propan-2-yl)phenyl)(methyl)amino)-2-oxopropyl) (methylsulfonyl) carbamate (100 mg, 0.2 mmol) in HCl/EtOAc (2 mL) was stirred at 25° C. for 15 min. TLC showed the reaction was completed. The reaction was concentrated under reduced pressure. The residue was purified by prep-HPLC (HCl) to give N-(3-((4-(2-(3,5-dichloro-4-(2-chloroethoxy)phenyl)propan-2-yl)phenyl)(methyl)amino)-2-oxopropyl)methanesulfonamide hydrochloride (7.6 mg, yield: 9.1%) as yellow oil. $^1$H NMR (400 MHz, CHCl$_3$-d) δ 7.16 (br s, 2H), 7.12 (s, 2H), 6.95 (br s, 2H), 5.70 (br s, 1H), 4.49-4.22 (m, 4H), 4.15-3.81 (m, 4H), 3.18 (br s, 3H), 2.94 (br s, 3H), 1.62 (s, 6H). LCMS (M+H$^+$) m/z: clcd: 520.1. found 521.0.

Example 1-10: Synthesis of N-(3-(4-(2-(3,5-dichloro-4-(3-chloro-2-hydroxy-2-methyl propoxy)phenyl)propan-2-yl)phenoxy)-2-oxopropyl)methanesulfonamide (A52)

Compound A52 was synthesized according to Example 1-01 by using (2-methyloxiran-2-yl)methyl 4-methylbenzenesulfonate instead of (R)-oxiran-2-ylmethyl 4-methylbenzenesulfonate in step f. $^1$H NMR (400 MHz, DMSO-d6) δ (ppm)=7.42-7.45 (t, 1H), 7.23 (s, 2H), 7.14-7.16 (d, 2H), 6.84-6.86 (d, 2H), 5.19 (s, 1H), 4.91 (s, 2H), 4.09-4.10 (d, 2H), 3.78-3.92 (m, 2H), 3.73 (s, 2H), 2.93 (s, 3H), 1.60 (s, 6H) 1.34 (s, 3H).

Example 1-11: Synthesis of N-(3-(4-(2-(3,5-dichloro-4-(2-chloroethoxy)phenyl)propan-2-yl)phenoxy)-2-oxopropyl)methanesulfonamide (A33)

Compound A33 was synthesized according to Example 1-02 by using 1-bromo-2-chloroethane in step a instead of 1-bromo-3-chloropropanel. $^1$H NMR (400 MHz, DMSO-d$_6$) δ (ppm)=7.42-7.45 (t, 1H), 7.24 (s, 2H), 7.14-7.17 (d, 2H), 6.84-6.86 (d, 2H), 4.91 (s, 2H), 4.20-4.23 (t, 2H), 4.08-4.10 (d, 2H), 3.92-3.95 (t, 2H), 2.93 (s, 3H), 1.60 (s, 6H). MS-ESI 507.04. found 530.3.

Example 1-12: Synthesis of 1-(4-(2-(3,5-dichloro-4-(3-chloro-2-hydroxy-2-methy propoxy)phenyl)propan-2-yl)phenoxy)-3-(methylsulfonyl)propan-2-one (A53)

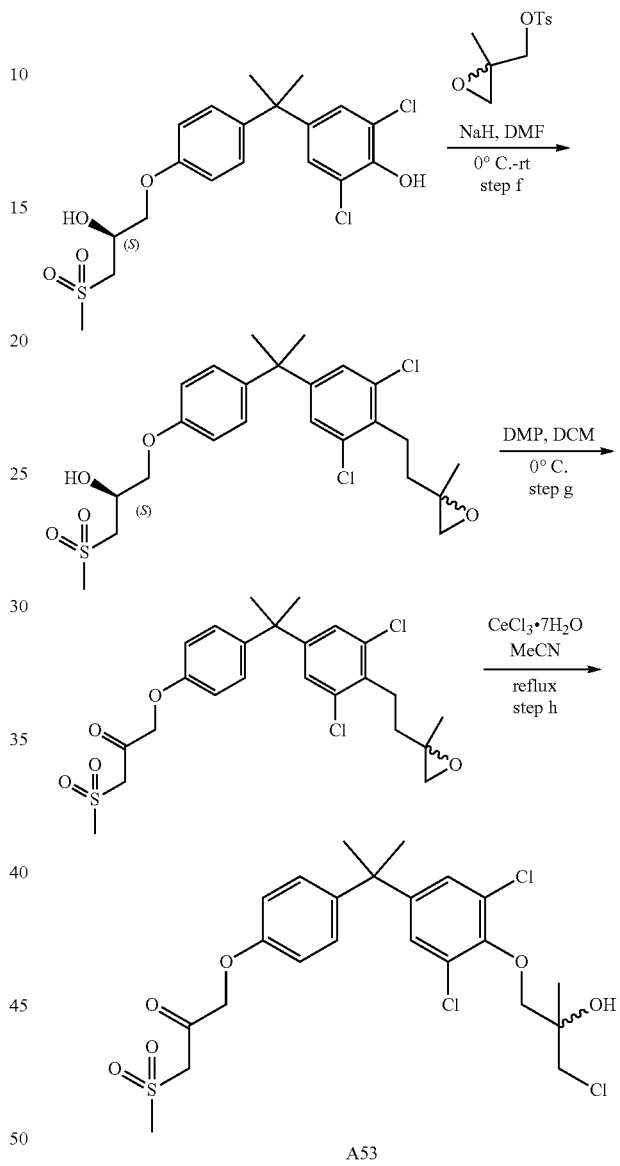

Step f: Synthesis of N—((R)-3-(4-(2-(3,5-dichloro-4-(((R)-oxiran-2-yl)methoxy)phenyl)propan-2-yl)phenoxy)-2-hydroxypropyl)methanesulfonamide. The titled compound was synthesized according to the procedures of Example 1-01, step f by using (2-methyloxiran-2-yl)methyl 4-methylbenzenesulfonate instead of 2(R)-glycidyl tosylate.

Step g: Synthesis of (2S)-1-(4-(2-(3,5-dichloro-4-((2-methyloxiran-2-yl)methoxy)phenyl)propan-2-yl)phenoxy)-3-(methylsulfonyl)propan-2-ol. The titled compound was synthesized according to the procedures of Example 1-01, step g.

Step h: Synthesis of 1-(4-(2-(3,5-dichloro-4-((2-methyloxiran-2-yl)methoxy)phenyl)propan-2-yl)phenoxy)-3-(methylsulfonyl)propan-2-one. Compound A53 was synthesized according to the procedures of Example 1-01, step h.

$^1$H NMR (400 MHz, DMSO-d$_6$) δ (ppm)=7.23 (s, 2H), 7.14-7.17 (d, 2H), 6.83-6.86 (d, 2H), 5.21 (s, 1H), 4.96 (s, 2H), 4.59 (s, 2H), 3.79-3.93 (m, 2H), 3.74 (s, 2H), 3.12 (s, 3H), 1.61 (s, 6H), 1.34 (s, 3H). MS-ESI 536.06. found 537.2.

Example 1-13: Synthesis of (S)-1-(4-(2-(3,5-dichloro-4-(3-chloro-2-hydroxypropoxy)phenyl)propan-2-yl)phenoxy)-3-(methylsulfonyl)propan-2-one (A54(S))

Compound A54(S) was synthesized according to Example 1-12 by using (2R)-glycidyl tosylate in step f instead of (2-methyloxiran-2-yl)methyl 4-methylbenzenesulfonate. $^1$H NMR (300 MHz, DMSO-d6) δ (ppm)=7.25 (s, 2H), 7.15-7.18 (d, 2H), 6.83-6.86 (d, 2H), 5.55-5.57 (d, 1H), 4.97 (s, 2H), 4.60 (s, 2H), 4.04-4.09 (m, 1H), 3.96-3.98 (d, 2H), 3.81-3.86 (m, 1H), 3.69-3.75 (m, 1H), 3.12 (s, 3H), 1.61 (s, 6H). MS-ESI 522.04. found 522.6.

Example 1-14: Synthesis of (S)-1-(4-(2-(3,5-dichloro-4-(3-chloro-2-hydroxypropoxy)phenyl)propan-2-yl)phenoxy)-3-methoxypropan-2-one (A56(S))

Compound A56(S) was synthesized according to Example 1-01 by using methanol and Bi(OTf)$_3$ instead of methanesulfonamide, Cs$_2$CO$_3$ and DMF in step c. $^1$H NMR (400 MHz, DMSO-d6) δ (ppm)=7.19 (s, 2H), 7.10-7.13 (d, 2H), 6.79-6.82 (d, 2H), 5.50-5.52 (d, 1H), 4.82 (s, 2H), 4.22 (s, 2H), 4.00-4.04 (m, 1H), 3.92-3.94 (d, 2H), 3.77-3.81 (m, 1H), 3.65-3.70 (m, 1H), 1.57 (s, 6H). MS-ESI 474.08. found 498.9.

Example 1-15: Synthesis of 1-(4-(2-(3,5-dichloro-4-(3-chloropropoxy)phenyl)propan-2-yl)phenoxy)propan-2-one (A74)

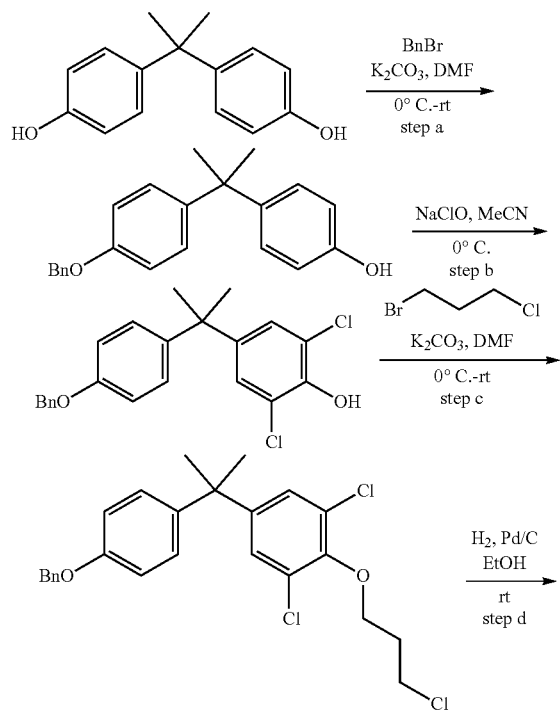

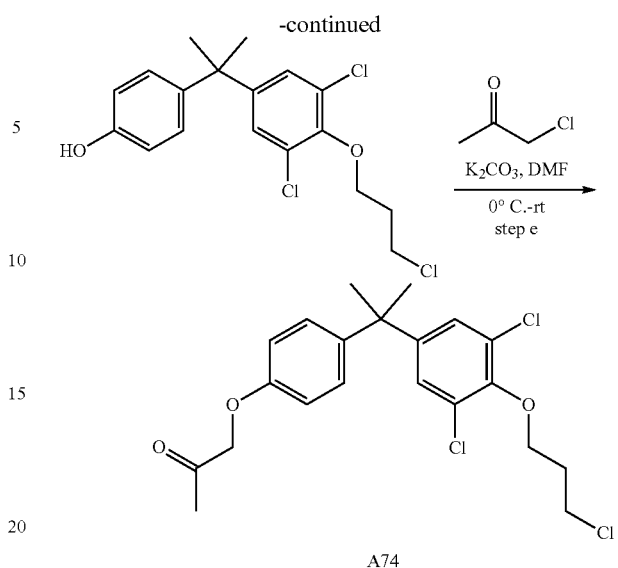

A74

Step a: Synthesis of 4-(2-(4-(benzyloxy)phenyl)propan-2-yl)phenol. Benzyl bromide (1.0 equiv) was added to a stirred solution of biphenol A (2.0 equiv) and K$_2$CO$_3$ (1.0 equiv) in anhydrous DMF at 0° C. and the mixture was allowed to react at room temperature for 16 h. The reaction was quenched by the addition of a saturated solution of ammonium chloride, and the mixture was extracted with ethyl acetate. The organic layer was washed with water, dried over anhydrous magnesium sulfate, filtered, and concentrated under reduced pressure. The resulting residue was purified by flash column chromatography on silica gel to provide the titled compound.

Step b: Synthesis of 4-(2-(4-(benzyloxy)phenyl)propan-2-yl)-2,6-dichlorophenol. The titled compound was synthesized according to the procedures of Example 1-01, step e.

Step c: Synthesis of 5-(2-(4-(benzyloxy)phenyl)propan-2-yl)-1,3-dichloro-2-(3-chloropropoxy)benzene. The titled compound was synthesized according to the procedures of Example 1-02, step to make Compound 3d.

Step d: Synthesis of 4-(2-(3,5-dichloro-4-(3-chloropropoxy)phenyl)propan-2-yl)phenol, 5-(2-(4-(benzyloxy)phenyl)propan-2-yl)-1,3-dichloro-2-(3-chloropropoxy)benzene (1.0 equiv) was added to a stirred solution of Pd/C (0.1 equiv) in ethanol at room temperature and the mixture was allowed to react at the environment of H$_2$ for 3 h. The palladium carbon was filtered off, the solution concentrated, and the resulting residue was purified by flash column chromatography on silica gel to provide the titled compound.

Step e: Synthesis of 1-(4-(2-(3,5-dichloro-4-(3-chloropropoxy)phenyl)propan-2-yl)phenoxy)propan-2-one. Compound A74 was synthesized according to the procedures of Example 1-01 in step f. $^1$H NMR (400 MHz, DMSO-d6) δ (ppm)=7.23 (s, 2H), 7.13-7.16 (d, 2H), 6.81-6.83 (d, 2H), 4.77 (s, 2H), 4.06-4.09 (t, 2H), 3.84-3.87 (t, 2H), 2.16-2.22 (m, 2H), 2.15 (s, 3H), 1.60 (s, 6H). MS-ESI 428.07. found 452.8.

Example 1-16: Synthesis of 1-(4-(2-(3,5-dichloro-4-(3-chloropropoxy)phenyl)propan-2-yl)phenoxy)propan-2-one (A86)

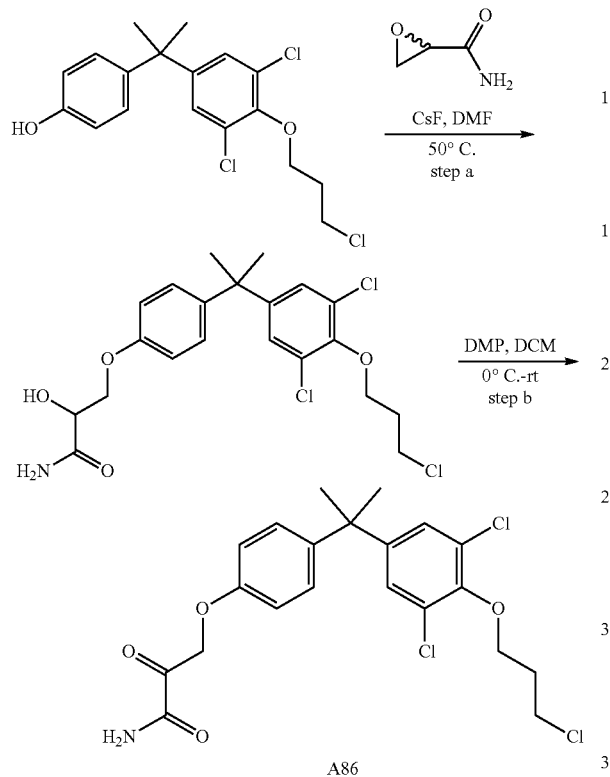

Step a. Glycidamide (1.2 equiv) was added to a stirred solution of 4-(2-(3,5-dichloro-4-(3-chloropropoxy)phenyl)propan-2-yl)phenol (1.0 equiv) and CsF (1.2 equiv) in anhydrous DMF at room temperature and the mixture was allowed to react at 50° C. for 16 h. The reaction was quenched by the addition of a saturated solution of ammonium chloride, and the mixture was extracted with ethyl acetate. The organic layer was washed with water, dried over anhydrous magnesium sulfate, filtered, and concentrated under reduced pressure. The resulting residue was purified by flash column chromatography on silica gel to provide the titled compound.

Step b. Compound A86 was synthesized according to the procedures of Example 1-01, step g. $^1$H NMR (600 MHz, CDCl$_3$) δ (ppm)=7.32 (s, 2H), 7.16-7.17 (d, 2H), 6.90-6.91 (d, 2H), 5.39 (s, 2H), 4.18-4.20 (t, 2H), 3.90-3.92 (t, 2H), 2.31-2.35 (m, 2H), 1.67 (s, 6H).

Example 1-17: Synthesis of 3-(4-(2-(3,5-dichloro-4-(3-chloropropoxy)phenyl)propan-2-yl)phenoxy)-1,1,1-trifluoropropan-2-one (A91)

Compound A91 was synthesized according to Example 1-16 by using 3,3,3-trifluoro-1,2-epoxypropane instead of glycidamide in step a. $^1$H NMR (600 MHz, DMSO-d6) δ (ppm)=7.30 (s, 2H), 7.24 (s, 2H), 7.16-7.18 (d, 2H), 6.89-6.94 (d, 2H), 4.06-4.09 (t, 2H), 4.02 (s, 2H), 3.85-3.87 (t, 2H), 2.17-2.21 (m, 2H), 1.61 (s, 6H). MS-ESI 482.04. found 506.4.

Example 1-18: Synthesis of N-(4-(4-(2-(3,5-dichloro-4-(3-chloropropoxy)phenyl) propan-2-yl) phenoxy)-4,4-difluoro-3-oxobutyl)methanesulfonamide (A94)

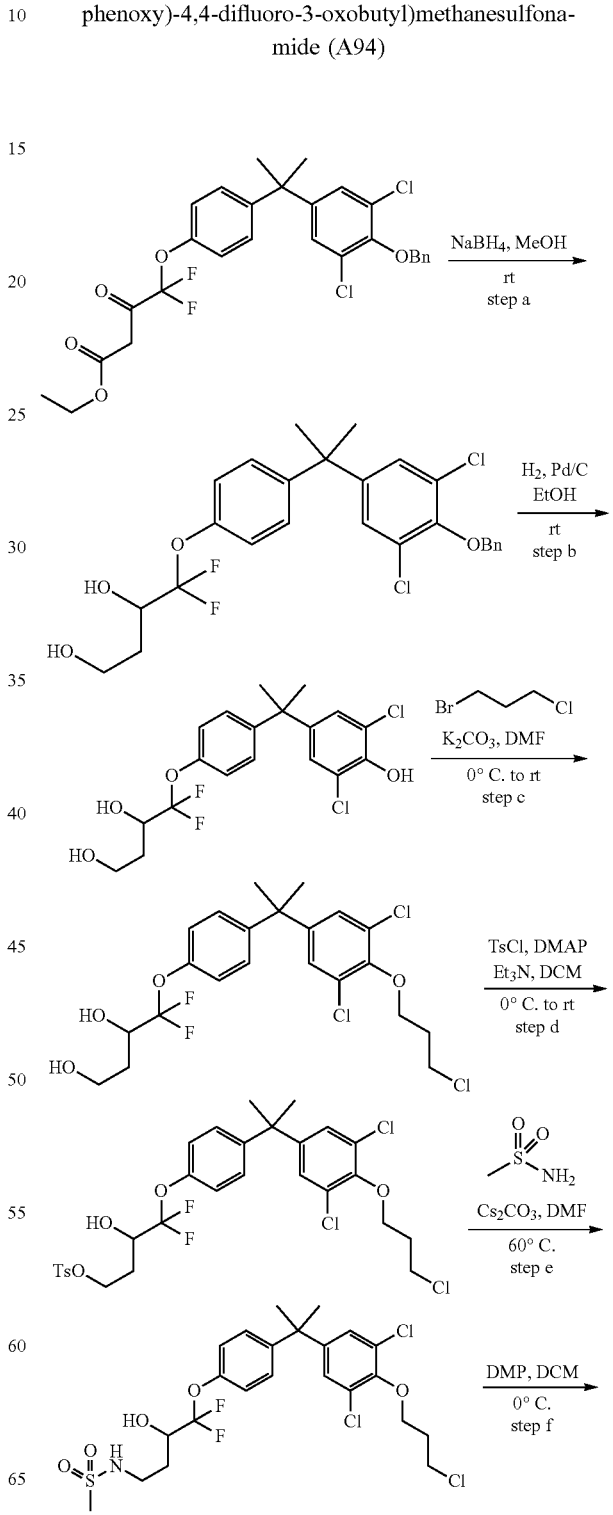

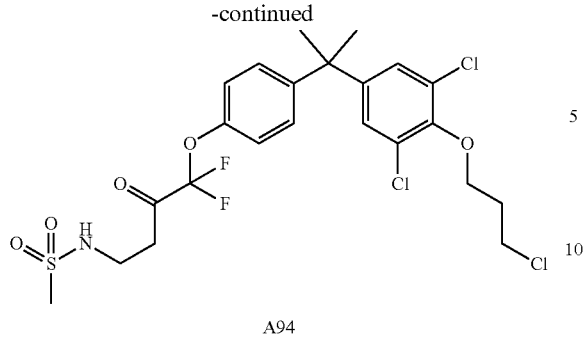

A94

Steps a: Synthesis of 4-(4-(2-(4-(benzyloxy)-3,5-dichlorophenyl)propan-2-yl)phenoxy)-4,4-difluorobutane-1,3-diol. To a solution of ethyl 4-(4-(2-(4-(benzyloxy)-3,5-dichlorophenyl)propan-2-yl)phenoxy)-4,4-difluoro-3-oxobutanoate (1.0 equiv) in MeOH was added NaBH$_4$ (3.0 equiv). The solution was allowed to react at room temperature for 6 hours. The reaction was quenched by H$_2$O and the mixture was extracted with ethyl acetate. The organic layer was washed with water, dried over anhydrous magnesium sulfate, filtered, and concentrated under reduced pressure. The resulting residue was purified by flash column chromatography on silica gel to provide the titled compound.

Steps b: Synthesis of 4-(4-(2-(3,5-dichloro-4-hydroxyphenyl)propan-2-yl)phenoxy)-4,4-difluorobutane-1,3-diol. The titled compound was synthesized according to the procedures of Example 1-15, step d.

Steps c: Synthesis of 4-(4-(2-(3,5-dichloro-4-(3-chloropropoxy)phenyl)propan-2-yl)phenoxy)-4,4-difluorobutane-1,3-diol. The titled compound was synthesized according to the procedures of Example 1-02, step a.

Steps d: Synthesis of 4-(4-(2-(3,5-dichloro-4-(3-chloropropoxy)phenyl)propan-2-yl)phenoxy)-4,4-difluoro-3-hydroxybutyl 4-methylbenzenesulfonate. The titled compound was synthesized according to the procedures of Example 1-01, step a.

Steps e: Synthesis of N-(4-(4-(2-(3,5-dichloro-4-(3-chloropropoxy)phenyl)propan-2-yl)phenoxy)-4,4-difluoro-3-hydroxybutyl)methanesulfonamide. The titled compound was synthesized according to the procedures of Example 1-01, step c.

Steps f: Synthesis of N-(4-(4-(2-(3,5-dichloro-4-(3-chloropropoxy)phenyl)propan-2-yl)phenoxy)-4,4-difluoro-3-hydroxybutyl)methanesulfonamide. Compound A94 was synthesized according to the procedures of Example 1-01, step g. $^1$H NMR (400 MHz, CDCl$_3$) δ (ppm)=7.23 (s, 2H), 7.16-7.19 (d, 2H), 7.09-7.11 (d, 2H), 4.71-4.75 (t, 1H), 4.11-4.14 (t, 2H), 3.81-3.84 (t, 2H), 3.46-3.51 (m, 2H), 3.12-3.15 (t, 2H), 2.97 (s, 3H), 2.22-2.28 (m, 2H), 1.61 (s, 6H). MS-ESI 571.06. found 573.4.

Example 1-19: Synthesis of N-(3-(4-(2-(3,5-dichloro-4-(3-chloropropoxy)phenyl) propan-2-yl) phenoxy)-3,3-difluoro-2-oxopropyl)methanesulfonamide (A99)

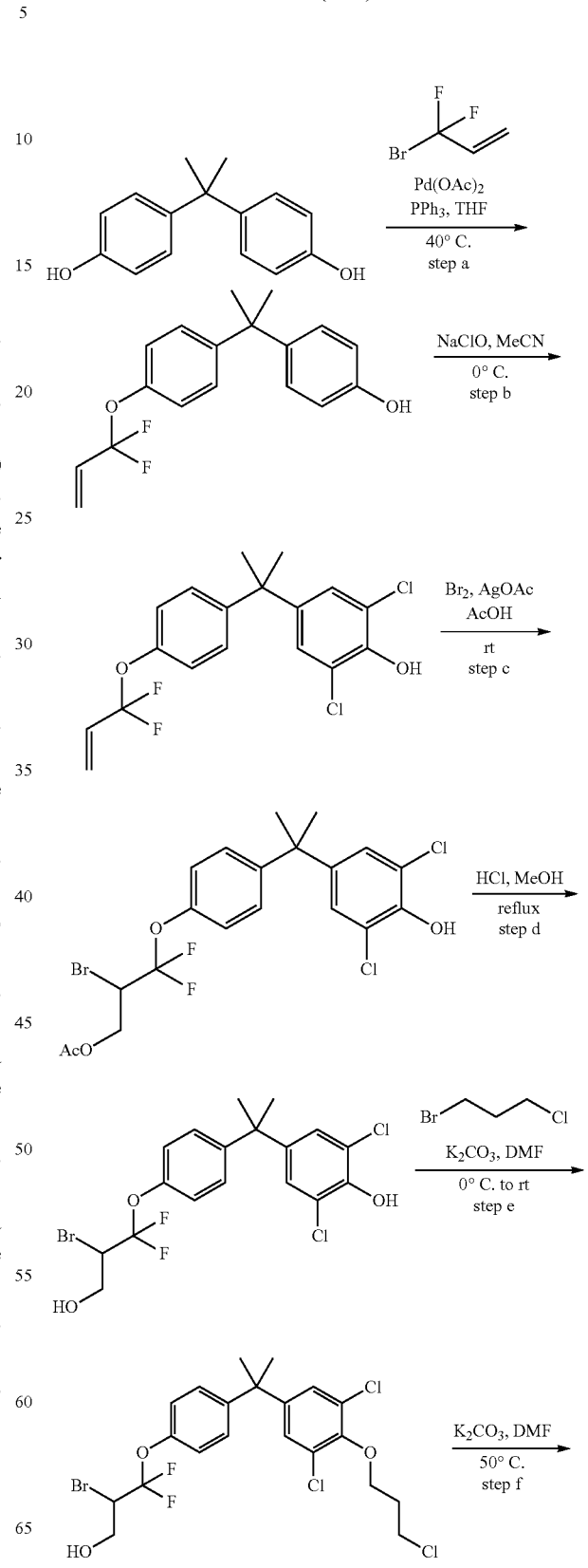

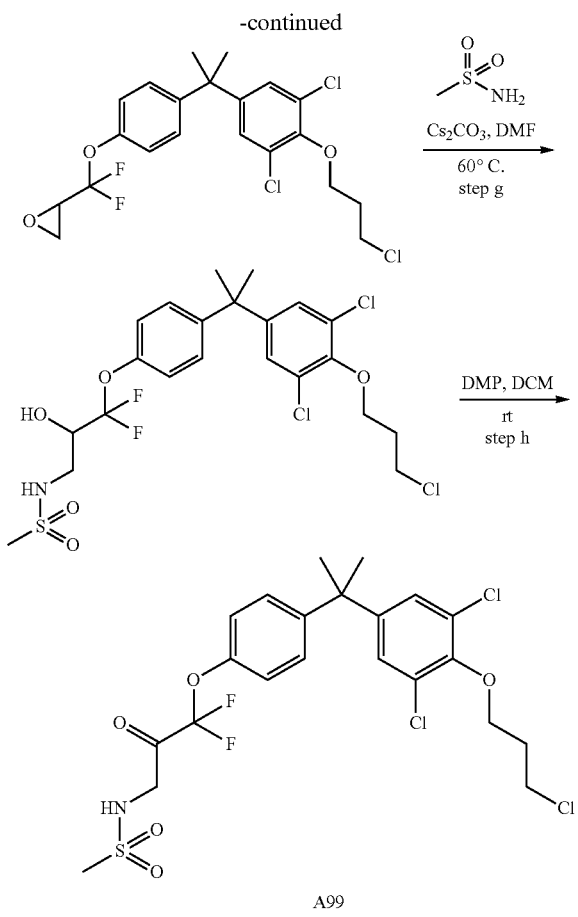

Steps a: Synthesis of 4-(2-(4-(((1,1-difluoroallyl)oxy)phenyl)propan-2-yl)phenol. To a solution of bisphenol A (2.0 equiv), Pd(OAc)₂ (0.01 equiv) and PPh₃ (0.04 equiv) in anhydrous THF was added 3-Bromo-3,3-difluoropropene (1.0 equiv). The solution was allowed to react at 40° C. for 16 hours. The reaction was quenched by H₂O and the mixture was extracted with ethyl acetate. The organic layer was washed with water, dried over anhydrous magnesium sulfate, filtered, and concentrated under reduced pressure. The resulting residue was purified by flash column chromatography on silica gel to provide the titled compound.

Steps b: Synthesis of 2,6-dichloro-4-(2-(4-((1,1-difluoroallyl)oxy)phenyl)propan-2-yl)phenol. The titled compound was synthesized according to the procedures of Example 1-01, step e.

Steps c: Synthesis of 2-bromo-3-(4-(2-(3,5-dichloro-4-hydroxyphenyl)propan-2-yl)phenoxy)-3,3-difluoropropyl acetate. To a solution of 2,6-dichloro-4-(2-(4-((1,1-difluoroallyl)oxy)phenyl)propan-2-yl)phenol (1.0 equiv) and AgOAc (2 equiv) in AcOH was added bromine (1.0 equiv). The solution was allowed to react at room temperature for 1 hour. The reaction was quenched by NaHSO₃ solution and the mixture was extracted with ethyl acetate. The organic layer was washed with sodium bicarbonate, water, dried over anhydrous magnesium sulfate, filtered, and concentrated under reduced pressure. The resulting residue was purified by flash column chromatography on silica gel to provide the titled compound.

Steps d: Synthesis of 4-(2-(4-(2-bromo-1,1-difluoro-3-hydroxypropoxy)phenyl)propan-2-yl)-2,6-dichlorophenol. The titled compound was synthesized according to the procedures of Example 1-01 by using reflux condition instead of room temperature in step d.

Steps e: Synthesis of 2-bromo-3-(4-(2-(3,5-dichloro-4-(3-chloropropoxy)phenyl)propan-2-yl)phenoxy)-3,3-difluoropropan-1-ol. The titled compound was synthesized according to the procedures of Example 1-02, step a.

Steps f: Synthesis of 2-((4-(2-(3,5-dichloro-4-(3-chloropropoxy)phenyl)propan-2-yl)phenoxy)difluoromethyl)oxirane. To a solution of 2-bromo-3-(4-(2-(3,5-dichloro-4-(3-chloropropoxy)phenyl)propan-2-yl)phenoxy)-3,3-difluoropropan-1-ol (1.0 equiv) in anhydrous DMF was added K₂CO₃ (1.5 equiv). The solution was heated to 50° C. for 16 hours. The reaction was quenched by H₂O and the mixture was extracted with ethyl acetate. The organic layer was washed with water, dried over anhydrous magnesium sulfate, filtered, and concentrated under reduced pressure. The resulting residue was purified by flash column chromatography on silica gel to provide the titled compound.

Steps g: Synthesis of N-(3-(4-(2-(3,5-dichloro-4-(3-chloropropoxy)phenyl)propan-2-yl)phenoxy)-3,3-difluoro-2-hydroxypropyl)methanesulfonamide. The titled compound was synthesized according to the procedures of Example 1-01, step c.

Steps h: Synthesis of N-(3-(4-(2-(3,5-dichloro-4-(3-chloropropoxy)phenyl)propan-2-yl)phenoxy)-3,3-difluoro-2-oxopropyl)methanesulfonamide. Compound A99 was synthesized according to the procedures of Example 1-01, step g. ¹H NMR (600 MHz, DMSO-d6) δ (ppm)=7.64-7.66 (t, 1H), 7.32-7.36 (d, 2H), 7.22-7.28 (m, 4H), 4.48-4.49 (d, 2H), 4.08-4.10 (t, 2H), 3.84-3.86 (t, 2H), 2.98 (s, 3H), 2.18-2.22 (m, 2H), 1.61 (s, 6H).

Example 1-20: Synthesis of 1-(4-(2-(3,5-dichloro-4-(3-chloropropoxy)phenyl)propan-2-yl)phenoxy)-1,1-difluoro-3-methoxypropan-2-one (A100)

Compound A100 was synthesized according to Example 1-19 by using methanol and Bi(OTf)₃ instead of methanesulfonamide, Cs₂CO₃ and DMF in step g. ¹H NMR (400 MHz, CDCl₃) δ (ppm)=7.21-7.23 (d, 2H), 7.11-7.14 (m, 4H), 4.75 (s, 2H), 4.10-4.17 (t, 2H), 3.84-3.88 (t, 2H), 3.50 (s, 3H), 2.25-2.32 (m, 2H), 1.64 (s, 6H). MS-ESI 494.06; found [M+CH₃OH+Na]⁺ 549.19.

Example 1-21: Characterization of Compounds

| Compound ID | ¹H NMR and LCMS |
|---|---|
| A1 | ¹H NMR (400 MHz, CDCl₃) δ = 7.20 (d, J = 7.2 Hz, 2H), 7.00 (dd, J = 2.4, 8.4 Hz, 1H), 6.97 (s, 1H), 6.80 (d, J = 8.8 Hz, 2H), 6.74 (d, J = 8.4 Hz, 1H), 5.00 (br s, 1H), 4.65 (s, 2H), 4.39 (d, J = 4.8 Hz, 2H), 4.10 (t, J = 5.6 Hz, 2H), 3.77 (t, J = 6.4 Hz, 2H), 2.98 (s, 3H), 2.25 (quin, J = 6.0 Hz, 2H), 2.17 (s, 3H), 1.64 (s, 6H). LCMS (220 nm): 94.4%, Exact Mass: 465.2; found 466.1/468.1 |

-continued

| Compound ID | ¹H NMR and LCMS |
|---|---|
| A2 | ¹H NMR (400 MHz, CDCl₃) δ = 7.48 (d, J = 8.8 Hz, 1H), 7.13 (d, J = 8.8 Hz, 2H), 6.82-6.75 (m, 3H), 6.65 (d, J = 2.8 Hz, 1H), 5.03 (br s, 1H), 4.65 (s, 2H), 4.41 (d, J = 5.0 Hz, 2H), 4.13 (t, J = 5.8 Hz, 2H), 3.77 (t, J = 6.4 Hz, 2H), 3.00 (s, 3H), 2.25 (quin, J = 6.0 Hz, 2H), 1.78 (s, 3H), 1.65 (s, 6H). LCMS (220 nm): 97.5%, Exact Mass: 467.2; found 490.1/492.1 |
| A4 | ¹H NMR (400 MHz, CDCl₃) δ = 7.32 (d, J = 8.4 Hz, 1H), 7.15-7.09 (m, 2H), 6.77-6.72 (m, 2H), 6.50 (dd, J = 2.6, 8.6 Hz, 1H), 6.39 (d, J = 2.4 Hz, 1H), 5.03 (br s, 1H), 4.63 (s, 2H), 4.39 (d, J = 5.0 Hz, 2H), 4.12 (t, J = 5.8 Hz, 2H), 3.76 (t, J = 6.2 Hz, 2H), 3.39 (s, 3H), 2.97 (s, 3H), 2.24 (quin, J = 6.2 Hz, 2H), 1.63 (s, 6H). LCMS (220 nm): 86.1%. Exact Mass: 483.1; found 506.1/508.1 |
| A5 | ¹H NMR (400 MHz, CDCl₃) δ = 7.23-7.18 (m, 3H), 7.04 (d, J = 8.6 Hz, 1 H), 6.87-6.81 (m, 3H), 5.02 (br t, J = 4.8 Hz, 1H), 4.67 (s, 2H), 4.41 (d, J = 5.2 Hz, 2H), 4.17 (t, J = 5.6 Hz, 2H), 3.82 (t, J = 6.4 Hz, 2H), 3.00 (s, 3H), 2.29 (quin, J = 6.0 Hz, 2H), 1.65 (s, 6H) LCMS (220 nm): 91.0%. Exact Mass: 487.1; found 510.1/512.1 |
| A6 | ¹H NMR (400 MHz, CDCl₃) δ = 7.52 (d, J = 8.8 Hz, 1H), 7.09 (d, J = 8.8 Hz, 2H), 6.86-6.83 (m, 2H), 6.78 (d, J = 9.2 Hz, 2H) 5.02 (br s, 1H), 4.64 (s, 2H), 4.39 (d, J = 4.8 Hz, 2H), 4.11 (t, J = 6.0 Hz, 2H), 3.75 (t, J = 6.0 Hz, 2H), 2.98 (s, 3H), 2.22 (quin, J = 6.0 Hz, 2 H), 1.71 (s, 6H) LCMS (220 nm): 90.5%. Exact Mass: 487.1; found 505.1, 507.1/ 510.0, 512.0 |
| A7 | ¹H NMR (400 MHz, CDCl₃) δ = 7.42 (d, J = 2.4 Hz, 1H), 7.37 (dd, J = 2.4, 8.8 Hz, 1H), 7.16 (d, J = 8.8 Hz, 2H), 6.91 (d, J = 8.8 Hz, 1H), 6.84 (d, J = 8.8 Hz, 2H), 5.06 (br t, J = 4.6 Hz, 1H), 4.67 (s, 2H), 4.41 (d, J = 5.0 Hz, 2H), 4.23 (t, J = 5.6 Hz, 2H), 3.83 (t, J = 6.0 Hz, 2H), 3.01 (s, 3H), 2.31 (quin, J = 6.0 Hz, 2H), 1.66 (s, 6H). LCMS (220 nm): 95.1%. Exact Mass: 478.1; found: 479.1/481.1 |
| A9 | ¹H NMR (400 MHz, CDCl₃): δ = 7.13 (d, J = 8.4 Hz, 2H), 7.06-7.00 (m, 2H), 6.81 (d, J = 8.8 Hz, 2H), 6.59 (d, J = 8.4 Hz, 1H), 5.02 (br s, 1H), 4.65 (s, 2H), 4.42 (d, J = 5.6 Hz, 2H), 4.10 (t, J = 5.6 Hz, 2H), 3.75 (t, J = 6.4 Hz, 2H), 2.99 (s, 3H), 2.26 (s, 3H), 2.23 (t, J = 6.4 Hz, 2H), 1.64 (s, 6H) LCMS (220 nm): 96.1%. Exact Mass: 487.1; found 510.0/512.0 |
| A11 | ¹H NMR (400 MHz, CDCl3) δ = 7.15-7.12 (m, 2 H), 6.83-6.75 (m, 5H), 5.17 (br s, 1H), 4.66 (s, 2H), 4.66-4.37 (d, J = 9.2 Hz, 2H), 4.12-4.10 (m, 2H), 3.77-3.73 (m, 5H), 2.97 (s, 3H), 2.23 (t, J = 6.0 Hz, 2H), 1.65 (s, 6H). LCMS (220 nm): 86.2%. Exact Mass: 483.1; found 506.0/508.0 |
| A12 | ¹H NMR (400 MHz, CDCl₃) δ = 7.35 (d, J = 8.4 Hz, 1H), 7.07 (d, J = 8.8 Hz, 2H), 6.78 (d, J = 8.8 Hz, 2H), 6.47-6.39 (m, 2H), 5.09 (br t, J = 4.6 Hz, 1H), 4.68 (s, 2H), 4.42 (d, J = 5.2 Hz, 2H), 4.10 (t, J = 6.0 Hz, 2H), 3.76 (t, J = 6.4 Hz, 2H), 3.51-3.38 (m, 3H), 3.01 (s, 3H), 2.24 (quin, J = 6.0 Hz, 2H), 1.65 (s, 6H). LCMS (220 nm): 96.7%. Exact Mass: 483.1; found: 506.1/508.1 |
| A13 | ¹H NMR (400 MHz, CDCl₃): δ = 7.28 (s, 1H), 7.10 (d, J = 6.8 Hz, 2H), 7.05 (d, J = 2.4 Hz, 1H), 6.81 (d, J = 8.8 Hz, 2H), 6.73 (d, J = 8.8 Hz, 1H), 5.02 (br t, J = 4.8 Hz, 1H), 4.66 (s, 2H), 4.47 (d, J = 5.6 Hz, 2H), 4.09 (t, J = 6.0 Hz, 2H), 3.74 (t, J = 6.4 Hz, 2H), 3.00 (s, 3H), 2.23 (quin, J = 6.0 Hz, 2H), 1.65 (s, 6H). LCMS (220 nm): 96.9%. Exact Mass: 487.1; found: 510.0/512.0 |
| A14 | ¹H NMR (400 MHz, CDCl₃) δ = 7.57 (d, J = 8.8 Hz, 2H), 7.02 (d, J = 8.8 Hz, 2H), 6.87-6.78 (m, 4H), 5.03 (br t, J = 5.2 Hz, 1H), 4.66 (s, 2H), 4.39 (d, J = 5.2 Hz, 2H), 4.09 (t, J = 6.0 Hz, 2H), 3.75 (t, J = 6.0 Hz, 2H), 3.01 (s, 3H), 2.23 (quin, J = 6.0 Hz, 2H), 1.71 (s, 6H) LCMS (220 nm): 93.8%. Exact Mass: 478.1; found: 501.1/503.1 |
| A15 | ¹H NMR (400 MHz, CDCl₃) δ = 7.49 (d, J = 2.4 Hz, 1H), 7.40 (dd, J = 2.4, 8.8 Hz, 1H), 7.12-7.06 (m, 2H), 6.87-6.81 (m, 2H), 6.78 (d, J = 8.8 Hz, 1H), 5.03 (br t, J = 5.1 Hz, 1H), 4.75 (s, 2H), 4.44 (d, J = 5.4 Hz, 2H), 4.11 (t, J = 5.8 Hz, 2H), 3.75 (t, J = 6.4 Hz, 2H), 3.03 (s, 3H), 2.24 (quin, J = 6.0 Hz, 2H), 1.65 (s, 6H). LCMS (220 nm): 93.8%. Exact Mass: 478.1; found: 501.1 |
| A21 | ¹H NMR (400 MHz, CDCl₃) δ = 7.12 (d, J = 8.6 Hz, 2H), 7.07 (s, 2H), 6.85 (d, J = 8.6 Hz, 2H), 5.00 (br s, 1H), 4.65 (s, 2H), 4.39 (d, J = 5.0 Hz, 2H), 4.13 (t, J = 5.6 Hz, 2H), 3.88-3.77 (m, 4H), 2.99 (s, 3H), 2.27 (quin, J = 6.0 Hz, 2H). LCMS (220 nm): 89.9%. Exact Mass: 493.0; found: 516.0 |
| A23 | ¹H NMR (400 MHz, CDCl₃): δ = 7.11 (d, J = 4.4 Hz, 2H), 6.92 (d, J = 7.6 Hz, 2H), 6.65 (s, 2H), 5.03 (br s, 1H), 4.69 (s, 2H), 4.42 (d, J = 5.2 Hz, 2H), 4.09 (t, J = 6.0 Hz, 2H), 3.86 (t, J = 6.8 Hz, 2H), 3.22 (s, 3H), 3.02 (s, 3H), 2.26 (quin, J = 6.4 Hz, 2H). LCMS (220 nm): 92.7%. Exact Mass: 508.0; found: 509.0, 511.0, /531.0, 533.0 |
| A24 | ¹H NMR (400 MHz,CDCl₃): δ = 7.26-7.24 (m, 2H), 6.90-6.86 (m, 2H), 6.75 (d, J = 8.0 Hz, 1H), 6.71 (s, 1H), 5.01 (br s, 1H), 4.64 (s, 2H), 4.37 (d, J = 5.2 Hz, 2H), 4.17 (t, J = 5.6 Hz, 2H), 4.07 (s, 2H), 3.88 (t, J = 6.4 Hz, 2H), 2.99 (s, 3H), 2.31 (quin, J = 6.0 Hz, 2H). LCMS (220 nm): 98.8%. Exact Mass: 493.0; found: 494.0/496.0 |
| A25 | ¹H NMR (400 MHz, CDCN): δ = 7.64 (s, 2 H), 7.58 (d, J = 6.8 Hz, 2H), 7.01 (d, J = 6.8 Hz, 2H), 5.63 (br s, 1H), 4.87 (s, 2H), 4.20-4.17 (m, 3H), 4.13-4.12 (m, 2H), 3.89-3.86 (m, 1H), 3.78-3.65 (m, 1H), 2.94 (s, 3H), 3.02 (s, 3H), 2.26 (quin, J = 6.4 Hz, 2H). LCMS (220 nm): 92.7%. Exact Mass: 495.0; found: 513.0/515.0 |

| Compound ID | ¹H NMR and LCMS |
|---|---|
| A27 | ¹H NMR (400 MHz, CDCl$_3$) δ = 7.15-7.06(m, 6H), 6.03 (br s, 1H), 4.35 (s, 2H), 4.22 (s, 2H), 4.14 (m, 2H), 3.86 (t, J = 6.0 Hz, 2H), 4.09 (s, 2H), 2.98 (s, 3H), 2.30-2.25 (m, 2H), 1.60 (s, 6H). LCMS (220 nm): 84.6%. Exact Mass: 520.1; found: 521.0/523.0 |
| A28 | ¹H NMR (400 MHz, CDCl$_3$) δ = 7.21-7.13 (m, 4H), 7.11 (s, 2H), 6.11 (br s, 1H), 4.59 (br s, 1H), 4.17-4.09 (m, 4H), 3.86 (t, J = 6.4 Hz, 2H), 3.19 (s, 3H), 2.96 (s, 3H), 2.28 (t, J = 6.0 Hz, 2H), 1.62 (s, 6H) LCMS (220 nm): 96.6%. Exact Mass: 534.1; found 535.0/537.0 |
| A30 | ¹H NMR (400 MHz, DMSO-d$_6$) δ 7.83 (br d, J = 7.9 Hz, 1H), 7.22 (s, 2H), 7.17 (d, J = 8.8 Hz, 2H), 6.88 (d, J = 8.8 Hz, 2H), 4.40 (s, 2H), 4.07 (t, J = 6.0 Hz, 2H), 3.94 (qd, J = 6.7, 14.0 Hz, 1H), 3.85 (t, J = 6.4 Hz, 2H), 2.19 (quin, J = 6.2 Hz, 2H), 1.60 (s, 6H), 1.08 (d, J = 6.6 Hz, 6H) LCMS (220 nm): 99.2%. Exact Mass: 471.1; found 472.1/473.1 |
| A32 | ¹H NMR (400 MHz, CDCl$_3$) δ = 7.16 (d, J = 6.8 Hz, 2H), 7.10 (s, 2H), 6.84 (d, J = 6.4 Hz, 2H), 5.04 (br s, 1H), 4.66 (s, 2H), 4.40 (d, J = 5.2 Hz, 2H), 3.96 (d, J = 5.2 Hz, 2H), 3.87-3.70 (m, 2H), 3.00 (s, 3H), 2.46-2.35 (m, 1H), 1.63 (s, 6H), 1.19 (d, J = 6.8 Hz, 3H) LCMS (220 nm): 97.8%. Exact Mass: 535.08; found 553.0, 555.0/558.0, 560.0. |
| A34 | ¹H NMR (400 MHz, DMSO-d$_6$) δ = 7.44 (t, J = 6.0 Hz, 1H), 7.19 (s, 2H), 7.14 (d, J = 8.4 Hz, 2H), 6.84 (d, J = 8.8 Hz, 2H), 4.90 (s, 2H), 4.09 (d, J = 6.0 Hz, 2H), 3.67 (t, J = 6.4 Hz, 2H), 2.93 (s, 3H), 2.82 (t, J = 8.4 Hz, 2H), 1.83-1.75 (m, 2H), 1.66- 1.56(m, 8H). LCMS (220 nm): 94.2%. Exact Mass: 519.1; found 542.0/544.0 |
| A35 | ¹H NMR (400 MHz, CDCl$_3$) δ = 7.17 (d, J = 7.2 Hz, 2H), 7.10 (s, 2H), 6.83 (d, J = 7.2 Hz, 2H), 5.06 (br s, 1H), 4.67 (s, 2H), 4.40 (s, 2H), 3.68 (br s, 2H), 3.53 (s, 2 H), 3.00 (s, 3H), 2.14 (s, 2H), 1.62 (s, 6H). LCMS: (220 nm): 97.0%. Exact Mass: 520.1; found 521.0/523.0. |
| A36 | ¹H NMR (400 MHz, CDCl$_3$) δ = 7.18 (d, J = 8.4 Hz, 2H), 7.10 (s, 2H), 6.84 (d, J = 8.8 Hz, 2H), 5.01 (brs, 1H), 4.67 (s, 2H), 4.40 (d, J = 5.2 Hz, 2H), 3.71 (t, J = 6.0 Hz, 2H), 3.30 (s, 2 H), 2.99 (s, 3H), 2.82 (s, 3H), 1.94 (brs, 2H), 1.63 (s, 6H). LCMS: (220 nm): 94.1%. Exact Mass: 534.1; found 535.0/537.0. |
| A37 | ¹H NMR (400 MHz, CDCl$_3$) δ = 7.56 (s, 1H), 7.44-7.41 (m, 1H), 7.34-7.33 (m, 2H), 7.19-7.16 (m, 2H), 7.15 (s, 2H), 6.85 (d, J = 6.8 Hz, 2H), 5.01 (br s, 1H), 5.00 (s, 2H), 4.67 (s, 2H), 4.40 (d, J = 4.8 Hz, 2H), 3.00 (s, 3H), 1.65 (s, 6H) LCMS: (220 nm): 95.6% Exact Mass: 569.1; found 587.0, 589.0/592.0, 594.0. |
| A38 | ¹H NMR (400 MHz, CDCl$_3$) δ = 7.49 (d, J = 8.4 Hz, 2H), 7.38 (d, J = 8.0 Hz, 2H), 7.19-7.14 (m, 4H), 6.84 (d, J = 8.8 Hz, 2H), 5.03 (m, 1H), 4.99 (s, 2H), 4.67 (s, 2H), 4.40 (d, J = 4.8 Hz, 2H), 3.30 (s, 3H), 1.64 (s, 6H). LCMS: (220 nm): 98.0%. Exact Mass: 569.1; found 587.0, 589.0/592.0, 594.0 |
| A42 | ¹H NMR (400 MHz, CDCl$_3$) δ = 7.16 (d, J = 8.8 Hz, 2H), 7.12 (s, 2H), 6.86 (d, J = 8.8 Hz, 2H), 4.50 (s, 2H), 4.15 (t, J = 6.0 Hz, 2H), 3.86 (t, J = 6.6 Hz, 2H), 2.29 (quin, J = 6.0 Hz), 1.63 (s, 6H). LCMS (220 nm): 98.2%. Exact Mass: 429.1; found: 430.0, 432.0, 452.0, 454.0 |
| A44 | ¹H NMR (400 MHz, CDCl$_3$) δ = 7.14 (d, J = 8.8 Hz, 2H), 7.11 (s, 2H), 6.87 (d, J = 8.8 Hz, 2H), 4.70 (s, 2H), 4.15 (t, J = 6.0 Hz, 2H), 3.86 (t, J = 6.4 Hz, 2H), 3.75 (br s, 4H), 3.23 (br s, 4H), 2.77 (s, 3H), 2.31-2.25 (m, 2H), 1.60 (s, 6H). LCMS (220 nm): 99.3%. Exact Mass: 576.1; found: 577.0,/579.0. |
| A45 | ¹H NMR (400 MHz, CDCl$_3$) δ = 7.41 (d, J = 8.8 Hz, 2H), 7.35 (s, 1H), 7.16 (d, J = 8.4 Hz, 2H), 7.10 (s, 2H), 5.16 (br s, J = 6.2 Hz, 1H), 4.14 (t, J = 5.6 Hz, 2H), 3.85 (t, J = 6.4 Hz, 2H), 3.50-3.46 (m, 2H), 2.98 (s, 3H), 2.69 (t, J = 5.2 Hz, 2H), 2.27 (quin, J = 6.4 Hz, 2H), 1.62 (s, 6H). LCMS (M + H) m/z: calcd 520.08; found 521.0/523.0. |
| A47 | ¹H NMR (400 MHz, CDCl$_3$) δ = 7.26-7.22 (m, 2H), 7.16-7.14 (m, 2H), 7.12 (s, 2H), 4.41 (s, 2H), 4.14 (t, J = 5.6 Hz, 2H), 3.85 (t, J = 6.4 Hz, 2H), 2.93 (s, 6H), 2.27 (quin, J = 6.0 Hz, 2H), 1.62 (s, 6H). LCMS (220 nm): 98.3%. Exact Mass: 456.11; found 455.0/457.0. |
| A48 | ¹H NMR (400 MHz, CDCl$_3$) δ = 7.10 (s, 2H), 7.00-6.80 (m, 3H), 5.05 (s, 1H), 4.72 (s, 2H), 4.43 (d, J = 5.2 Hz, 2H), 4.16 (t, J = 5.6 Hz, 2H), 3.86 (t, J = 5.6 Hz, 2H), 3.01 (s, 3H), 2.29-2.25 (m, 2H), 1.62 (s, 6H). LCMS (220 nm): 97.9% Exact Mass 539.05; found 562.0/564.0 |
| A49 | ¹H NMR (400 MHz, CDCl$_3$) δ = 7.30-7.27 (m, 1H), 7.19 (d, J = 7.6 Hz, 1H), 7.12 (s, 2H), 7.05 (t, J = 7.2 Hz, 1H), 7.76 (d, J = 8.0 Hz, 1H), 4.94 (br s, 1H), 4.66 (s, 2H), 4.16 -4.13 (m, 4H), 3.96 (s, 2H), 3.85 (t, J = 6.4 Hz, 2H), 2.94 (s, 3H), 2.31-2.25 (m, 2H). LCMS (220 nm): 96.6%. Exact Mass: 493.0; found: 494.0/496.0 |
| A62 | ¹H NMR (400 MHz, CDCl$_3$) δ = 7.15 (d, J = 8.8 Hz, 2H), 7.10 (s, 2H), 7.03 (br s, 1H), 6.86 (d, J = 8.8 Hz, 2H), 4.75 (br s, 1H), 4.50 (s, 2H), 4.14 (t, J = 5.6 Hz, 2H), 3.85 (t, J = 6.4 Hz, 2H), 3.55 (q, J = 6.0 Hz, 2H), 3.33 (q, J = 5.6 Hz, 2H), 2.96 (s, 3H), 2.27 (quin, J = 6.0 Hz, 2H), 1.62 (s, 6H). LCMS (220 nm): 100%, Exact Mass: 550.09, found 551.0/553.0. |

-continued

| Compound ID | ¹H NMR and LCMS |
|---|---|
| A63 | ¹H NMR (400 MHz, CDCl$_3$) δ = 7.12 -7.10 (m, 4H), 6.77 (d, J = 6.8 Hz, 2H), 5.05 (brs, 1 H), 4.45 (d, J = 5.2 Hz, 2H), 4.16 (t, J = 6.0 Hz, 2H), 3.86 (t, J = 6.4 Hz, 2H), 2.96 (s, 3H), 2.29 (quin, J = 6.4 Hz, 2H), 1.62 (s, 6H), 1.51 (s, 6H). LCMS (220 nm): 95.8%, Exact Mass 549.1; found 532.0, 534.0/567.0, 569.0 |
| A64 | ¹H NMR (400 MHz, CDCl$_3$) δ = 7.13-7.11 (m, 4H), 6.86 (d, J = 8.8 Hz, 2H), 5.10 (s, 1H), 5.03 (s, 2H), 4.15 (t, J = 6.0 Hz, 2H), 3.86 (t, J = 6.4 Hz, 2H), 3.08 (s, 3H), 2.28 (quin, J = 6.0 Hz, 2H), 1.62 (s, 12H). LCMS (220 nm): 90.5%. Exact Mass: 549.09, found: 567.0, 569.0, /572.0, 574.0. |
| A65 | ¹H NMR (400 MHz, CDCl$_3$) δ = 7.15 (d, J = 9.2 Hz, 2H), 7.11 (s, 2H), 6.83 (d, J = 9.2 Hz, 2H), 6.22 (s, 1H), 4.65 (s, 2H), 4.47 (d, J = 4.4 Hz, 2H), 4.15 (t, J = 5.6 Hz, 2H), 3.86 (t, J = 6.4 Hz, 2H), 2.29-2.08 (m, 2H), 2.09 (s, 3H), 1.62 (s, 6 H). LCMS (220 nm): 91.2% Exact Mass 485.1, found 486.0/488.0. |
| A69 | ¹H NMR (400 MHz, CDCl$_3$) δ = 7.16 (d, J = 8.8 Hz, 2H) 7.11 (s, 2H) 6.83 (d, J = 8.8 Hz, 2H) 4.63 (s, 2H) 4.48 (s, 2H) 4.15 (t, J = 6.0 Hz, 2H) 3.86 (t, J = 6.8 Hz, 2H) 3.00 (s, 3H) 2.97 (s, 3H) 2.31-2.25 (m, 2H) 1.63 (s, 6H). LCMS (220 nm): 99.1% Exact Mass: 535.08; found 558.0/560.0. |
| A70 | ¹H NMR (400 MHz, CDCl$_3$) δ = 7.04 (d, J = 8.8 Hz, 2H), 6.96 (d, J = 8.8 Hz, 2H), 6.44 (s, 2H), 5.10 (s, 1H), 4.71 (s, 2H), 4.43 (d, J = 5.2 Hz, 2H), 4.16 (m, 1H), 4.06 (t, J = 5.6 Hz, 2H), 3.84 (t, J = 6.8 Hz, 2H), 3.02 (s, 3H), 2.27-2.21 (m, 2H), 1.13 (t, J = 6.4 Hz, 6H). LCMS (220 nm): 92.6%. Exact Mass: 536.1; found: 537.0/539.0. |
| A76 | ¹H NMR (400 MHz, CDCl$_3$) δ = 7.46-7.43 (m, 4H), 6.95 (d, J = 8.8 Hz, 2H), 5.07 (br s, 1H), 4.33 (t, J = 5.6 Hz, 2H), 4.22-4.19 (m, 4H), 3.89 (t, J = 6.4 Hz, 2H), 2.98 (s, 3H), 2.95 (t, J = 6.0 Hz, 2H), 2.33-2.29 (m, 2H) LCMS (220 nm): 96.0%. Exact Mass: 493.0; found 511.0/513.0 |
| A77 | ¹H NMR (400 MHz, CDCl$_3$) δ = 7.12 (d, J = 2.4 Hz, 2H), 7.11 (s, 2H), 6.80 (d, J = 6.8 Hz, 2H), 5.09 (br s, 1H), 4.27 (t, J = 6.0 Hz, 2H), 4.19 (d, J = 4.8 Hz, 2H), 4.14 (t, J = 5.6 Hz 2H), 3.86 (t, J = 6.4 Hz, 2H), 2.98 (s, 3H), 2.91 (t, J = 6.0 Hz, 2H), 2.29-2.26 (m, 2H), 1.62 (s, 6H) LCMS (220 nm): 97.7%. Exact Mass: 535.1; found 553.0/555.0 |
| A79 | ¹H NMR (400 MHz, CDCl$_3$) δ = 7.80 (d, J = 7.2 Hz, 1H), 7.41-7.34 (m, 3H), 7.30 (d, J = 7.6 Hz, 2H), 7.15 (s, 2H), 6.85 (d, J = 8.8 Hz, 2H), 5.16 (s, 2H), 5.02 (br, s, 1H), 4.67 (s, 2H), 4.40 (d, J = 5.2 Hz 2H), 2.99 (s, 3H), 1.65 (s, 6H). LCMS:(220 nm): 92.6%. Exact Mass: 569.1; found 587.0/589.0 |
| A80 | ¹H NMR (400 MHz, CDCl$_3$) δ = 8.45 (d, J = 4.8 Hz, 1H), 7.11 (d, J = 2.4 Hz, 2H), 7.03 (s, 2H), 6.79 (d, J = 2.4 Hz, 2H), 6.75 (d, J = 5.6 Hz, 1H), 4.59 (s, 2H), 4.08 (t, J = 6.0 Hz, 2H), 3.79 (t, J = 6.4 Hz, 2H), 2.97 (s, 3H), 2.23-2.19 (m, 2H), 1.56 (s, 6H) LCMS:(220 nm): 98.7%. Exact Mass: 522.1; found 523.0/525.0 |
| A84 | ¹H NMR (400 MHz, CDCl$_3$) δ = 7.90 (d, J = 8.6 Hz, 2H), 7.31 (d, J = 8.6 Hz, 2H), 7.11 (s, 2H), 4.42 (br s, 1H), 4.16 (t, J = 5.7 Hz, 2H), 3.86 (t, J = 6.6 Hz, 2H), 3.26 (q, J = 6.6 Hz, 2H), 3.11 (t, J = 6.6 Hz, 2H), 2.97(s, 3H), 2.29 (quin, J = 6.2 Hz, 2H), 2.08-2.00 (m, 2H), 1.67 (s, 6H). LCMS (220 nm): 99.2%. Exact Mass: 519.1; found: 522.0/520.1 |
| A93 | ¹H NMR (DMSO-d$_6$): δ 1.62 (s, 6H), δ 2.20 (m, 2H), δ 3.86 (t, 2H, J = 6 Hz), δ 4.08 (t, 2H, J = 6 Hz), δ 7.24 (m, 4H), δ 7.65 (s, 1H), δ 7.67 (s, 1H), δ 8.04 (s, 2H), δ 9.98 (s, 1H); ESI-MS: 100%. Exact mass: 495.1, found: 495.9 (M−). |
| A95 | ¹H NMR (DMSO-d$_6$): δ 1.34 (s, 3H), δ 1.62 (s, 6H), δ 3.73 (s, 2H), δ 3.80 (d, 1H, J = 8 Hz), δ 3.92 (d, 1H, J = 8 Hz), δ 5.19 (s, 1H), δ 7.23 (m, 4H), 7.64 (d, 1H, J = 2 Hz), 7.67 (d, 1H, J = 2 Hz), δ 8.05 (s, 1H), δ 8.41 (s, 1H), δ 9.99 (s, 1H); ESI-MS: 100%. |
| A96 | ¹H NMR (DMSO-d$_6$): δ 1.34 (s, 3H), δ 1.62 (s, 6H), δ 2.43 (s, 3H), δ 3.73 (s, 2H), δ 3.80 (d, 1H, J = 8 Hz), δ 3.91 (d, 1H, J = 12 Hz), 5.19 (s, 1H), δ 7.23 (m, 4H), 7.71 (s, 1H), δ 7.72 (s, 1H), δ 10.41 (s, 1H); ESI-MS: 100%. Exact mass 471.1, found: 472.0 (M−). |

Example 2: Activity of Exemplary Compounds of the Disclosure

Lysates were thawed on ice then collected into V-bottom 96-well tissue culture plates. Lysates were centrifuged at 4° C. for 5 minutes at 4000 rpm. To measure luminescence of LNCaP cell lysates the Firefly Luciferase Assay System (Promega) was employed, according to manufacturer's protocol. Relative luminescence units (RLU) in cell lysates were detected for 10 seconds using Promega GoMax-Multi Detection Luminometer (Promega).

Statistical analyses were performed using GraphPad Prism (Version 6.01 for Windows; La Jolla, Calif., USA). Comparisons between treatment and control groups were compared using Two-Way ANOVA with post-hoc Dunnett's and Tukey's tests. Differences were considered statistically significant at P values less than 0.05. Densitometric quantification of relative AR levels was determined by Image.

TABLE 1

IC$_{50}$ Ranges of Various Compound in Luciferase Assay

| Compound ID | LNCaP ARE-Luc % inhibition IC$_{50}$ Ranges |
|---|---|
| A1 | *** |
| A2 | ** |
| A3 | N/A |

TABLE 1-continued

IC$_{50}$ Ranges of Various Compound in Luciferase Assay

| Compound ID | LNCaP ARE-Luc % inhibition IC$_{50}$ Ranges |
|---|---|
| A4 | * |
| A5 | *** |
| A6 | * |
| A7 | *** |
| A8 | N/A |
| A9 | * |
| A10 | N/A |
| A11 | * |
| A12 | * |
| A13 | * |
| A14 | * |
| A15 | * |
| A16 | N/A |
| A17 | N/A |
| A18 | N/A |
| A19 | N/A |
| A20 | N/A |
| A21 | * |
| A22 | N/A |
| A23 | * |
| A24 | * |
| A25 | * |
| A26 | N/A |
| A27 | * |
| A28 | * |
| A29 | N/A |
| A30 | * |
| A31 | *** |
| A32 | *** |
| A33 | *** |
| A34 | * |
| A35 | ** |
| A36 | ** |
| A37 | * |
| A38 | * |
| A39 | N/A |
| A40 | N/A |
| A41 | N/A |
| A42 | * |
| A43 | *** |
| A44 | * |
| A45 | * |
| A46 | * |
| A47 | * |
| A48 | ** |
| A49 | * |
| A50 | N/A |
| A51(S) | *** |
| A52 | *** |
| A53 | * |
| A54(S) | * |
| A55 | * |
| A56(S) | * |
| A57 | N/A |
| A58 | N/A |
| A59 | N/A |
| A60 | N/A |
| A61 | ** |
| A62 | * |
| A63 | *** |
| A64 | * |
| A65 | * |
| A66 | N/A |
| A67 | N/A |
| A68 | N/A |
| A69 | * |
| A70 | * |
| A71 | * |
| A72 | N/A |
| A73 | * |
| A74 | * |
| A75 | ** |
| A76 | * |
| A77 | *** |
| A78 | N/A |
| A79 | * |
| A80 | * |
| A81 | * |
| A82 | N/A |
| A83 | N/A |
| A84 | * |
| A85 | * |
| A86 | * |
| A87 | N/A |
| A88 | N/A |
| A89 | N/A |
| A90 | N/A |
| A91 | * |
| A92 | * |
| A93 | * |
| A94 | * |
| A95 | * |
| A96 | * |
| A97 | ** |
| A98 | N/A |
| A99 | ** |
| A100 | * |
| A101 | * |
| A102 | * |
| A103 | *** |
| A104 | * |

[1]Note:
*** represent IC$_{50}$ <100 nM,
** represents IC$_{50}$ in the range of 100-250 nM,
* represents IC$_{50}$ in the range of ≥250 nM.

Example 3. Stability Assays

Microsomal Stability Assay: Microsomal stability assay is a widely used in vitro model to characterize the metabolic conversion by phase I enzymes, such as cytochrome P450 (CYP) enzymes. Since metabolism is known to be highly variable in different species, microsomal stability assay is commonly run in multiple species. Metabolic stability of testing compound can be evaluated using human, rat, mouse, or other animal liver or intestine microsomes to predict intrinsic clearance.

The assay was carried out in 96-well microtiter plates at 37° C. Reaction mixtures (25 µL) contained a final concentration of 1 µM test compound, 0.5 mg/mL liver microsomes protein, and 1 mM NADPH and/or 1 mM UDPGA (with alamethicin) in 100 mM potassium phosphate, pH 7.4 buffer with 3 mM MgCl$_2$. The incubation was done with N=1, but duplicate incubation at each time point can be prepared if necessary. At each of the time points (for example, 0, 15, 30, and 60 minutes), 150 µL of quench solution (100% acetonitrile with 0.1% formic acid) with internal standard was transferred to each well. Besides the zero minute controls, mixtures containing the same components except the NADPH can also be prepared as the negative control. Verapamil was included as a positive control to verify assay performance. Plates were sealed, vortexed, and centrifuged at 4° C. for 15 minutes at 4000 rpm. The supernatant is transferred to fresh plates for LC/MS/MS analysis.

Summarized conditions: [Compound]=1 µM, [LM]=0.5 mg/mL, [NADPH]=1 mM and/or [UDPGA]=1 mM, Buffer=100 mM Potassium Phosphate, pH 7.4 with 3 mM MgCl$_2$, Time=0, 15, 30, and 60 min, and Temperature=37° C.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism is calculated as the disappearance of the test compound, compared to the 0-min time incubation. Initial rates are calculated for the compound concentration and used to determine half-life (t½) values and subsequently, the intrinsic clearance ($Cl_{int}$).

$Cl_{int}$=(0.693)(1/t½ (min))(g of liver/kg of body weight)(mL incubation/mg of microsomal protein)(45 mg of microsomal protein/g of liver weight)

Hepatocyte Stability Assay: The termination of in vitro intrinsic clearance ($Cl_{int}$) for drug candidates in the early discovery stage is common practice in the pharmaceutical industry. The $Cl_{int}$ values of drug candidates can help to confirm whether metabolism is the main clearance pathway when it is compared with the total body clearance in vivo. Hepatocytes are among the routinely used in vitro systems for measuring clearance. Hepatocytes have been reported to retain most of the phase I and phase II metabolic activities, and therefore, it is a useful tool to estimate the intrinsic clearance for potential drug candidates.

Metabolic stability of testing compound were be evaluated using human and mouse hepatocytes and can also be use rat, mouse, or other animal hepatocytes to predict intrinsic clearance. Cryopreserved hepatocytes were removed from the liquid nitrogen tank and thawed in a 37° C. water bath. As soon as the cells pulled away from the vial wall, they were decanted into 48 ml of warm HT medium. Cells were centrifuged for four minutes at 420 rpm (50 g). After removing the supernatant, pellet was re-suspended in warm DMEM medium. Cell density was counted by a hemacytometer.

The assay was carried out in 96-well microtiter plates. Compounds were incubated for 0, 60, 120, and 180 minutes at 37° C. with hepatocytes. Reaction mixtures (50 µL) contained a final concentration of 1 µM test compound, 0.5 million cells/mL hepatocytes in the DMEM medium. At each of the time points (for example, 0, 1, 2, and 3 hours), 200 µL of quench solution (100% acetonitrile with 0.1% formic acid) with internal standard was transferred to each well. Midazolam was included as a positive control to verify assay performance. Plates were sealed and centrifuged at 4° C. for 15 minutes at 4000 rpm. The supernatant is transferred to fresh plates for LC/MS/MS analysis.

Summarized conditions (customizable): [Compound]=1 M, Positive control: midazolam and/or naloxone, [Hepatocyte]=0.5 million cells/Ml, time=0, 60, 120, and 180 m t=37° C.

All samples were analyzed on LC/MS/MS using an ABSciex API 4000 instrument, coupled to a Shimadzu LC-20AD LC Pump system. Analytical samples were separated using a Waters Atlantis T3 dC18 reverse phase HPLC column (20 mm×2.1 mm) at a flow rate of 0.5 mL/min. The mobile phase consisted of 0.1% formic acid in water (solvent A) and 0.1% formic acid in 100% acetonitrile (solvent B).

The extent of metabolism was calculated as the disappearance of the test compound, compared to the 0-min control reaction incubations. Initial rates were calculated for the compound concentration and used to determine t½ values and subsequently, the intrinsic clearance, $Cl_{int}$.

$Cl_{int}$=(0.693)(1/t½ (min))(mL incubation/million cells)

Metabolic stability assay results of representative compounds from Tables A1, A2, and A3 are listed in Table 2 below.

TABLE 2

Stability Results of Representative Compounds from Tables A1, A2, and A3

| Compound ID | MLM +/− NADPH: $Cl_{int}$ (µL/min/ mg protein)[1] | HLM +/− NADPH: $Cl_{int}$ (µL/min/ mg protein)[1] | MH +/− NADPH: $Cl_{int}$ (µL/min/ million cells)[2] |
|---|---|---|---|
| A1 | * | * | N/A |
| A2 | * | * | N/A |
| A3 | N/A | N/A | N/A |
| A4 | N/A | * | N/A |
| A5 | * | * | N/A |
| A6 | N/A | * | N/A |
| A7 | N/A | * | N/A |
| A8 | N/A | N/A | N/A |
| A9 | * | * | N/A |
| A10 | N/A | N/A | N/A |
| A11 | N/A | * | N/A |
| A12 | N/A | * | N/A |
| A13 | * | * | N/A |
| A14 | N/A | * | N/A |
| A15 | N/A | * | N/A |
| A16 | N/A | N/A | N/A |
| A17 | N/A | N/A | N/A |
| A18 | N/A | N/A | N/A |
| A19 | N/A | N/A | N/A |
| A20 | N/A | N/A | N/A |
| A21 | * | * | N/A |
| A22 | N/A | N/A | N/A |
| A23 | * | * | N/A |
| A24 | NA | * | N/A |
| A25 | * | * | N/A |
| A26 | N/A | N/A | N/A |
| A27 | ** | * | N/A |
| A28 | ** | ** | N/A |
| A29 | N/A | N/A | N/A |
| A30 | *** | ** | N/A |
| A31 | N/A | * | * |
| A32 | N/A | * | N/A |
| A33 | N/A | * | N/A |
| A34 | * | * | N/A |
| A35 | N/A | * | N/A |
| A36 | N/A | * | N/A |
| A37 | * | * | N/A |
| A38 | N/A | * | N/A |
| A39 | N/A | N/A | N/A |
| A40 | N/A | N/A | N/A |
| A41 | N/A | N/A | N/A |
| A42 | *** | ** | N/A |
| A43 | N/A | * | N/A |
| A44 | N/A | ** | N/A |
| A45 | N/A | *** | N/A |
| A46 | N/A | ** | N/A |
| A47 | N/A | * | N/A |
| A48 | N/A | * | N/A |
| A49 | * | * | N/A |
| A50 | N/A | N/A | N/A |
| A51(S) | N/A | * | * |
| A52 | N/A | * | N/A |
| A53 | N/A | N/A | N/A |
| A54 | * | * | * |
| A55 | * | * | * |
| A56(S) | * | * | * |
| A57 | * | * | * |
| A58 | * | * | * |
| A59 | * | * | * |
| A60 | * | * | * |
| A61 | * | * | * |

TABLE 2-continued

Stability Results of Representative Compounds from Tables A1, A2, and A3

| Compound ID | MLM +/− NADPH: $Cl_{int}$ (μL/min/ mg protein)[1] | HLM +/− NADPH: $Cl_{int}$ (μL/min/ mg protein)[1] | MH +/− NADPH: $Cl_{int}$ (μL/min/ million cells)[2] |
|---|---|---|---|
| A62 | N/A | ** | N/A |
| A63 | N/A | * | N/A |
| A64 | N/A | *** | N/A |
| A65 | N/A | * | N/A |
| A66 | N/A | N/A | N/A |
| A67 | N/A | N/A | N/A |
| A68 | N/A | N/A | N/A |
| A69 | N/A | * | N/A |
| A70 | N/A | * | N/A |
| A71 | N/A | * | N/A |
| A72 | N/A | N/A | N/A |
| A73 | N/A | ** | N/A |
| A74 | N/A | N/A | N/A |
| A75 | N/A | * | N/A |
| A76 | N/A | ** | N/A |
| A77 | ** | *** | N/A |
| A78 | N/A | N/A | N/A |
| A79 | N/A | * | N/A |
| A80 | N/A | ** | N/A |
| A81 | ** | ** | N/A |
| A82 | N/A | N/A | N/A |
| A83 | N/A | N/A | N/A |
| A84 | N/A | ** | N/A |
| A85 | N/A | * | N/A |
| A86 | N/A | N/A | N/A |
| A87 | N/A | N/A | N/A |
| A88 | N/A | N/A | N/A |
| A89 | N/A | N/A | N/A |
| A90 | N/A | N/A | N/A |
| A91 | N/A | *** | N/A |
| A92 | N/A | N/A | N/A |
| A93 | N/A | *** | N/A |
| A94 | N/A | * | N/A |
| A95 | N/A | *** | N/A |
| A96 | N/A | N/A | N/A |
| A97 | N/A | N/A | N/A |
| A98 | N/A | N/A | N/A |

[1]For MLM and HLM: * represent Cl <12 μL/min/mg protein,  represents Cl in the range of 12-48 μL/min/mg protein, * represents Cl in the range of ≥48 μL/min/mg protein.
[2]For MH: * represent Cl <4 μL/min/million cells,  represents Cl in the range of 4-18 μL/min/million cells, * represents Cl in the range of ≥18 μL/min/million cells.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

While specific embodiments have been discussed, the above specification is illustrative and not restrictive. Many variations will become apparent to those skilled in the art upon review of this specification and the claims below. The full scope of the disclosure should be determined by reference to the claims, along with their full scope of equivalents, and the specification, along with such variations.

What is claimed is:

1. A compound having the structure (I-A):

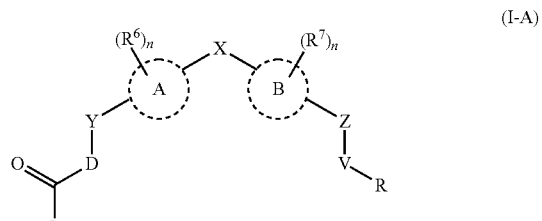

or a pharmaceutically acceptable salt, tautomer, stereoisomer or prodrug thereof, wherein:

A and B are each independently aryl or heteroaryl;

X is a bond, $-(CR^8R^9)_t-$, $-O-$, $-C(=O)-$, $-S(O)_p-$, $-NR^{10}-$, $-CONR^{10}-$, $-SO_2NR^{10}-$, or $-NR^{10}SO_2-$;

Y and Z are each independently a bond, $-(CR^8R^9)_t-$, $-O-$, $-S(O)_p-$, $-NR^{10}-$, $-CONR^{10}-$, $-NR^{10}CO-$, $-SO_2NR^{10}-$, or $-NR^{10}SO_2-$;

V is a bond, optionally substituted $-(CR^{11}R^{12})_m-$, $-C(=O)-$, $-N(R^{10})CO-$, $-CONR^{10}-$, or $-NSO_2R^{10}-$;

R is $-(CR^{4a}R^{4b})-(CR^{5a}R^{5b})-W$ or W;

W is hydrogen, halogen, $-CF_3$, $-CF_2R^{10}$, $-CN$, $-OR^{13}$, $-NR^{13}R^{14}$, optionally substituted $-CONR^{13}R^{14}$, optionally substituted carbocyclyl, optionally substituted heterocyclyl, optionally substituted aryl, or optionally substituted heteroaryl;

D is $-(CR^{1a}R^{1b})_q-$, $-O-$, or $-NR^{10}-$;

L is $-(CR^{2a}R^{2b})-R^3$ or -E-$R^3$;

E is $-(CR^{2a}R^{2b})_g-$, $-O-$, $-NR^{10}-$, or $-NR^{10}-(CR^{2a}R^{2b})_g-$;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl-$CONR^{14}R^{15}$, optionally substituted carbocyclyl, optionally substituted heterocyclyl, optionally substituted aryl, or optionally substituted heteroaryl;

or alternatively, $R^{1a}$ and $R^{1b}$ taken together form an optionally substituted carbocyclyl, optionally substituted heterocyclyl, optionally substituted aryl, or optionally substituted heteroaryl;

or alternatively, $R^{2a}$ and $R^{2b}$ taken together form a CO, optionally substituted carbocyclyl, optionally substituted heterocyclyl, optionally substituted aryl, or optionally substituted heteroaryl;

or alternatively, $R^{1a}$, $R^{1b}$, $R^{2a}$ and $R^{2b}$ taken together form an optionally substituted carbocyclyl, optionally substituted heterocyclyl, optionally substituted aryl, or optionally substituted heteroaryl;

$R^{4a}$, $R^{4b}$, $R^{5a}$, and $R^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-NR$^{13}$R$^{14}$, NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl-CONR$^{14}$R$^{15}$, optionally substituted carbocyclyl, optionally substituted heterocyclyl, optionally substituted aryl, or optionally substituted heteroaryl;

or alternatively, R$^{4a}$ and R$^{4b}$ taken together form a CO, optionally substituted carbocyclyl, optionally substituted heterocyclyl, optionally substituted aryl, or optionally substituted heteroaryl;

or alternatively, R$^{4a}$, R$^{4b}$, R$^{5a}$ and R$^{5b}$ taken together form an optionally substituted carbocyclyl, optionally substituted heterocyclyl, optionally substituted aryl, or optionally substituted heteroaryl;

R$^3$ is absent, hydrogen, —CN, —CF$_3$, —OH, optionally substituted C$_1$-C$_6$ alkyl, optionally substituted C$_2$-C$_6$ alkenyl, optionally substituted C$_2$-C$_6$ alkynyl, optionally substituted —OR$^{15}$, optionally substituted C$_1$-C$_6$ alkoxy, —NH$_2$, —NR$^{16}$R$^{17}$, —NR$^{16}$COR$^{18}$, NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted carbocyclyl, optionally substituted heterocyclyl, optionally substituted aryl, or optionally substituted heteroaryl;

or alternatively, R$^{2a}$, R$^{2b}$ and R$^3$ taken together form an optionally substituted carbocyclyl, optionally substituted heterocyclyl, optionally substituted aryl, or optionally substituted heteroaryl;

or alternatively, R$^{2a}$ and R$^{10}$ taken together form an optionally substituted heterocyclyl;

R$^6$ and R$^7$ are each independently H, methyl, methoxy, —CN, F, Cl, Br, I, $^{123}$I, —CF$_3$, —OH, optionally substituted C$_1$-C$_6$ alkyl, optionally substituted C$_1$-C$_6$ alkoxy, optionally substituted —(C$_1$-C$_6$ alkyl)-(C$_1$-C$_6$ alkoxy), optionally substituted —(C$_1$-C$_6$ alkyl)-OH, —NR$^{13}$R$^{14}$, optionally substituted —(C$_1$-C$_6$ alkyl-NR$^{13}$R$^{14}$, —NR$^{14}$SO$_2$R$^{16}$, optionally substituted —(C$_1$-C$_6$ alkyl)NR$^{14}$SO$_2$R$^{16}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, —SO$_2$NR$^{14}$R$^{15}$, optionally substituted —(C$_1$-C$_6$ alkyl)-SO$_2$NR$^{14}$R$^{15}$, optionally substituted —SO$_2$R$^{16}$, or optionally substituted —(C$_1$-C$_6$ alkyl)-SO$_2$R$^{16}$, optionally substituted carbocyclyl, optionally substituted heterocyclyl, optionally substituted aryl, or optionally substituted heteroaryl;

R$^8$, R$^9$, R$^{11}$ and R$^{12}$ are each independently hydrogen, —OH, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, optionally substituted C$_1$-C$_6$ alkylamino, optionally substituted —OCO(C$_1$-C$_6$ alkyl), —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl-CONR$^{14}$R$^{15}$, optionally substituted carbocyclyl, optionally substituted heterocyclyl, optionally substituted aryl, or optionally substituted heteroaryl;

or alternatively, R$^8$ and R$^9$ taken together form an optionally substituted carbocyclyl or optionally substituted heterocyclyl;

or alternatively, R$^{11}$ and R$^{12}$, on a same carbon atom or a different carbon atom, taken together form an optionally substituted carbocyclyl, optionally substituted heterocyclyl, optionally substituted aryl, or optionally substituted heteroaryl;

R$^{10}$ is hydrogen, halogen, optionally substituted C$_1$-C$_6$ alkyl, optionally substituted C$_1$-C$_6$ alkoxy, —CO (C$_1$-C$_6$ alkyl), optionally substituted C$_1$-C$_6$ alkylamino, optionally substituted carbocyclyl, optionally substituted heterocyclyl, optionally substituted aryl, or optionally substituted heteroaryl;

R$^{13}$, R$^{14}$, R$^{15}$, R$^{16}$, R$^{17}$ and R$^{18}$ are each independently hydrogen, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl;

or alternatively, R$^{14}$ and R$^{15}$ are taken together to form an optionally substituted heterocyclyl, or optionally substituted heteroaryl;

or alternatively, R$^{16}$ and R$^{17}$ are taken together to form an optionally substituted heterocyclyl, or optionally substituted heteroaryl;

m is 0, 1, 2, 3, or 4;

each n is independently 0, 1 or 2;

each p is independently 0, 1 or 2;

q is 0, 1 or 2;

each g is independently 0, 1, 2, 3, or 4; and each t is independently 1 or 2.

2. The compound of claim 1, wherein R is W.

3. The compound of claim 1, wherein W is hydrogen, halogen, —CF$_3$, or —NR$^{13}$R$^{14}$.

4. The compound of claim 1, wherein L is -E-R$^3$.

5. The compound of claim 1, wherein R$^3$ is selected from hydrogen, optionally substituted C$_1$-C$_6$ alkyl, optionally substituted —OR$^{15}$, optionally substituted —SR$^{18}$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, or optionally substituted —SO$_2$R$^{18}$.

6. The compound of claim 1, wherein R$^3$ is selected from hydrogen, —C$_1$-C$_3$ alkyl, —NR$^{16}$SO(C$_1$-C$_3$ alkyl), —NR$^{16}$SO$_2$(C$_1$-C$_3$ alkyl), —SONR$^{14}$R$^{15}$, —SO$_2$NR$^{14}$R$^{15}$, —SOR$^{18}$, or —SO$_2$R$^{18}$.

7. The compound of claim 1, having the structure of formula (Ic):

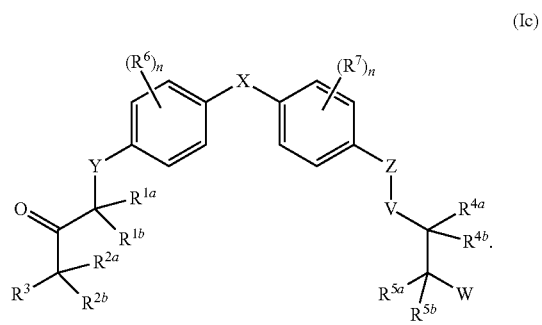

(Ic)

or a pharmaceutically acceptable salt, tautomer, stereoisomer or prodrug thereof, wherein:

X, Y, Z are each independently a bond, —(CR$^8$R$^9$)$_t$—, O, S(O)$_p$, NR$^{10}$, CONR$^{10}$, NR$^{10}$CO, SO$_2$NR$^{10}$, or NR$^{10}$SO$_2$;

V is a bond or optionally substituted —(CR$^{11}$R$^{12}$)$_m$—;

W is hydrogen, halogen, —CF$_3$, CN, OR$^{13}$ or optionally substituted CON(R$^{13}$R$^{14}$);

$R^{1a}$, $R^{1b}$, $R^{2a}$, $R^{2b}$, $R^{4a}$, $R^{4b}$, $R^{5a}$, and $R^{5b}$ are each independently hydrogen, halogen, hydroxy, optionally substituted $C_{1-6}$ alkyl, or optionally substituted $C_{1-6}$ alkoxy; or $R^{1a}$ and $R^{1b}$ taken together are optionally substituted carbocyclyl, optionally substituted heterocyclyl, optionally substituted aryl, or optionally substituted heteroaryl; or $R^{2a}$ and $R^{2b}$ taken together are CO, optionally substituted carbocyclyl, optionally substituted heterocyclyl, optionally substituted aryl, or optionally substituted heteroaryl; or $R^{1a}$, $R^{1b}$, $R^{2a}$ and $R^{2b}$ taken together are optionally substituted carbocyclyl, optionally substituted heterocyclyl, optionally substituted aryl, or optionally substituted heteroaryl; or $R^{4a}$ and $R^{4b}$ taken together are CO, optionally substituted carbocyclyl, optionally substituted heterocyclyl, optionally substituted aryl, or optionally substituted heteroaryl; or $R^{4a}$, $R^{4b}$, $R^{5a}$ and $R^{5b}$ taken together are optionally substituted carbocyclyl, optionally substituted heterocyclyl, optionally substituted aryl, or optionally substituted heteroaryl;

$R^3$ is absent, hydrogen, OH, $OR^{15}$, $NH_2$, $NR^{16}R^{17}$, $NR^{16}COR^{18}$, $NR^{16}S(O)_pR^{18}$, $S(O)_pR^{18}$, $N_3$, optionally substituted carbocyclyl, optionally substituted heterocyclyl, optionally substituted aryl, or optionally substituted heteroaryl; or $R^{2a}$, $R^{2b}$ and $R^3$ taken together are optionally substituted carbocyclyl, optionally substituted heterocyclyl, optionally substituted aryl, or optionally substituted heteroaryl;

each $R^6$ and $R^7$ is independently H, methyl, methoxy, —CN, F, Cl, Br, I, $^{123}$I or —$CF_3$;

$R^8$, $R^9$, $R^{10}$, $R^{11}$ and $R^{12}$ are each independently hydrogen, halogen, optionally substituted $C_1$-$C_6$ alkyl, optionally substituted $C_1$-$C_6$ alkoxy, or optionally substituted $C_1$-$C_6$ alkylamino; or $R^8$ and $R^9$ are optionally substituted carbocyclyl or optionally substituted heterocyclyl; or $R^{11}$ and $R^{12}$ taken together form an optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted carbocyclyl, optionally substituted heterocyclyl, optionally substituted aryl, or optionally substituted heteroaryl; or $R^{16}$ and $R^{17}$ are taken together to form an optionally substituted heterocyclyl, or optionally substituted heteroaryl;

m is independently 0, 1 or 2;

each n is independently 0, 1 or 2;

each p is independently 0, 1 or 2; and each t is independently 1 or 2.

8. The compound of claim 1, wherein X is bond, —$(CR^8R^9)_t$— or —$NR^{10}$—.

9. The compound of claim 1, wherein each $R^8$ and $R^9$ are hydrogen or methyl.

10. The compound claim 1, wherein Y is —$(CR^8R^9)_t$—, —O—, or —$NR^{10}$—.

11. The compound of claim 1, wherein Z is —$(CR^8R^9)_t$—, O, or $NR^{10}$.

12. The compound of claim 1, wherein V is a bond or an optionally substituted —$C(R^{11}R^{12})_m$—.

13. The compound of claim 1, having the structure of formula (Id) or (Ie):

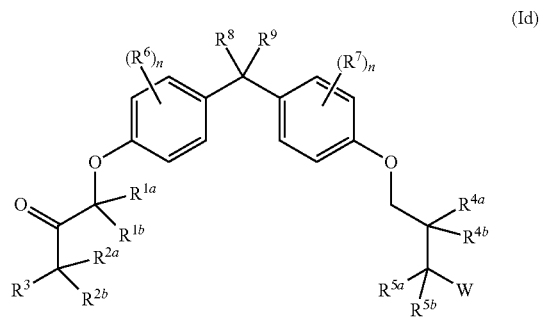

(Id)

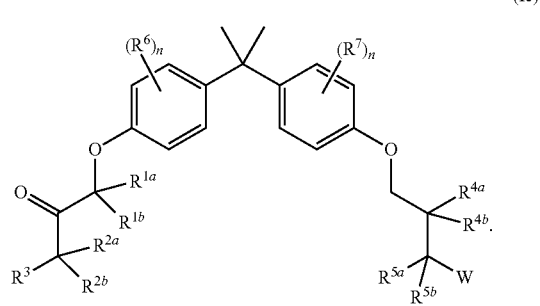

(Ie)

14. The compound of claim 1, wherein $R^{1a}$ and $R^{1b}$ are each hydrogen or optionally substituted $C_{1-6}$ alkyl.

15. The compound of claim 1, wherein $R^{2a}$ and $R^{2b}$ are each hydrogen or optionally substituted $C_{1-6}$ alkyl.

16. The compound of claim 1, wherein $R^3$ is —$NR^{16}R^{17}$, —$NR^{16}COR^{18}$, —$NR^{16}S(O)_pR^{18}$, —$S(O)_pR^{18}$, optionally substituted carbocyclyl, optionally substituted heterocyclyl, optionally substituted aryl, or optionally substituted heteroaryl.

17. The compound of claim 1, wherein $R^3$ is —$NR^{16}S(O)_pR^{18}$ or —$S(O)_pR^{18}$.

18. The compound of claim 17, wherein $R^{16}$ is hydrogen; $R^{18}$ is $C_1$-$C_6$ alkyl; and p is 2.

19. The compound of claim 1, wherein $R^{4a}$, $R^{4b}$, $R^{5a}$, and $R^{5b}$ are each independently hydrogen, halogen, optionally substituted $C_{1-6}$ alkyl, or optionally substituted $C_{1-6}$ alkoxy.

20. The compound claim 1, wherein W is Cl.

21. The compound of claim 1, wherein each occurrence of $R^6$ and $R^7$ is independently H, methyl, methoxy, CN, F, Cl, Br, or I.

22. The compound of claim 1, wherein D is —$(CH_2)_2$—.

23. The compound of claim 1, wherein the compound has the structure of formula (D):

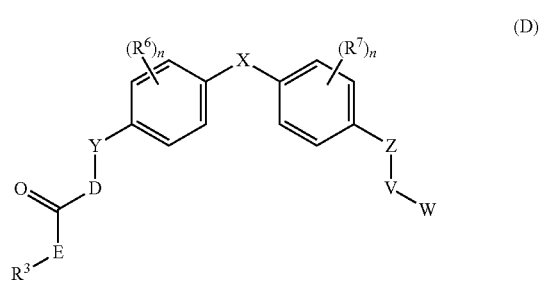

(D)

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is halogen, —NH$_2$, or —CF$_3$;

D is —NR$^{10}$— and E is —(CR$^{2a}$R$^{2b}$)$_g$—, —NR$^{10}$—, or —NR$^{10}$—(CR$^{2a}$R$^{2b}$)$_g$—;

or alternatively, E is —NR$^{10}$— or —NR$^{10}$—(CR$^{2a}$R$^{2b}$)$_g$—, and D is —(CR$^{1a}$R$^{1b}$)$_q$— or —NR$^{10}$—;

R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —C$_1$-C$_6$ alkyl, —OR$^{15}$, —SR$^{18}$, —C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, SOR$^{18}$, or —SO$_2$R$^{18}$;

R$^6$ and R$^7$ are each independently H, halogen, —CN, —CF$_3$, —OH, or C$_1$-C$_3$ alkyl;

R$^{8a}$ and R$^{9a}$ are each independently hydrogen, halogen, —OH, or C$_1$-C$_3$ alkyl; or R$^{8a}$ and R$^{9a}$ taken together form an 3- to 6-membered carbocyclyl or heterocyclyl;

R$^{10}$ is each independently hydrogen, C$_1$-C$_3$ alkyl, C$_2$-C$_3$ alkenyl, C$_2$-C$_3$ alkynyl, or —CO(C$_1$-C$_3$ alkyl);

R$^{13}$, R$^{14}$, R$^{15}$, R$^{16}$, R$^{17}$ and R$^{18}$ a are each independently hydrogen, C$_1$-C$_3$ alkyl, C$_2$-C$_3$ alkenyl, or C$_2$-C$_3$ alkynyl; or R$^{14}$ and R$^{15}$ taken together form an optionally substituted 5- or 6-membered heterocyclyl;

m is 0, 1, 2, 3, or 4;

each n is independently 0, 1 or 2;

q is 0, 1 or 2;

each g is independently 0, 1, 2, 3, or 4; and each t is independently 1 or 2.

24. The compound of claim 1, wherein the compound has the structure of formula (E):

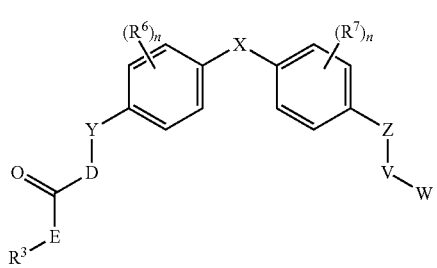

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is halogen, —NH$_2$ or —CF$_3$;

D is —O— or —NR$^{10}$— and E is —(CR$^{2a}$R$^{2b}$)$_{gg}$—;

or alternatively, E is —O—, —NR$^{10}$— or —NR$^{10}$—(CR$^{2a}$R$^{2b}$)$_g$—, and D is —(CR$^{1a}$R$^{1b}$)$_q$—;

R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —(C$_1$-C$_3$ alkyl-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —C$_1$-C$_6$ alkyl, —OR$^{15}$, —SR$^{18}$, —C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SO$_2$NR$^{14}$R$^{15}$, —SOR$^{18}$, or —SO$_2$R$^{18}$;

R$^6$ and R$^7$ are each independently H, halogen, —CN, —CF$_3$, —OH, or C$_1$-C$_3$ alkyl;

R$^{8a}$ and R$^{9a}$ are each independently hydrogen, halogen, —OH, or C$_1$-C$_3$ alkyl; or R$^{8a}$ and R$^{9a}$ taken together form an 3- to 6-membered carbocyclyl or heterocyclyl;

R$^{10}$ is each independently hydrogen, C$_1$-C$_3$ alkyl, C$_2$-C$_3$ alkenyl, C$_2$-C$_3$ alkynyl, or —CO(C$_1$-C$_3$ alkyl);

R$^{13}$, R$^{14}$, R$^{15}$, R$^{16}$, R$^{17}$ an R$^{18}$ are each independently hydrogen, C$_1$-C$_3$ alkyl, C$_2$-C$_3$ alkenyl, or C$_2$-C$_3$ alkynyl; or R$^{14}$ and R$^{15}$ taken together form an optionally substituted 5- or 6-membered heterocyclyl;

m is 0, 1, 2, 3, or 4;

each n is independently 0, 1 or 2;

q is 1 or 2;

g is 0, 1, 2, 3, or 4;

gg is 1, 2, 3, or 4; and t is 1 or 2.

25. The compound of claim 24, wherein R$^3$ is selected from —NHSO$_2$(C$_1$-C$_3$ alkyl), —NCH$_3$SO$_2$(C$_1$-C$_3$ alkyl), or —SO$_2$(C$_1$-C$_3$ alkyl).

26. A compound selected from

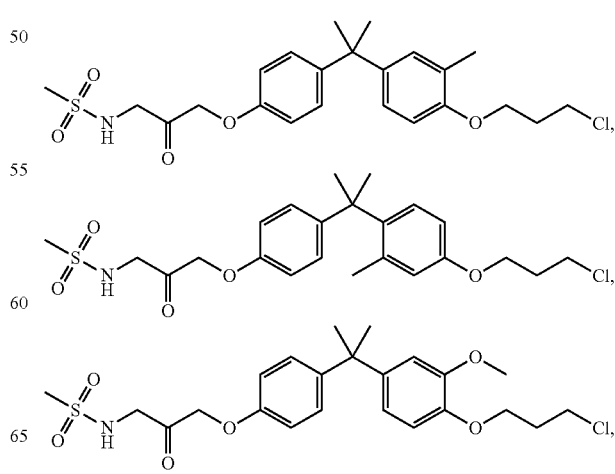

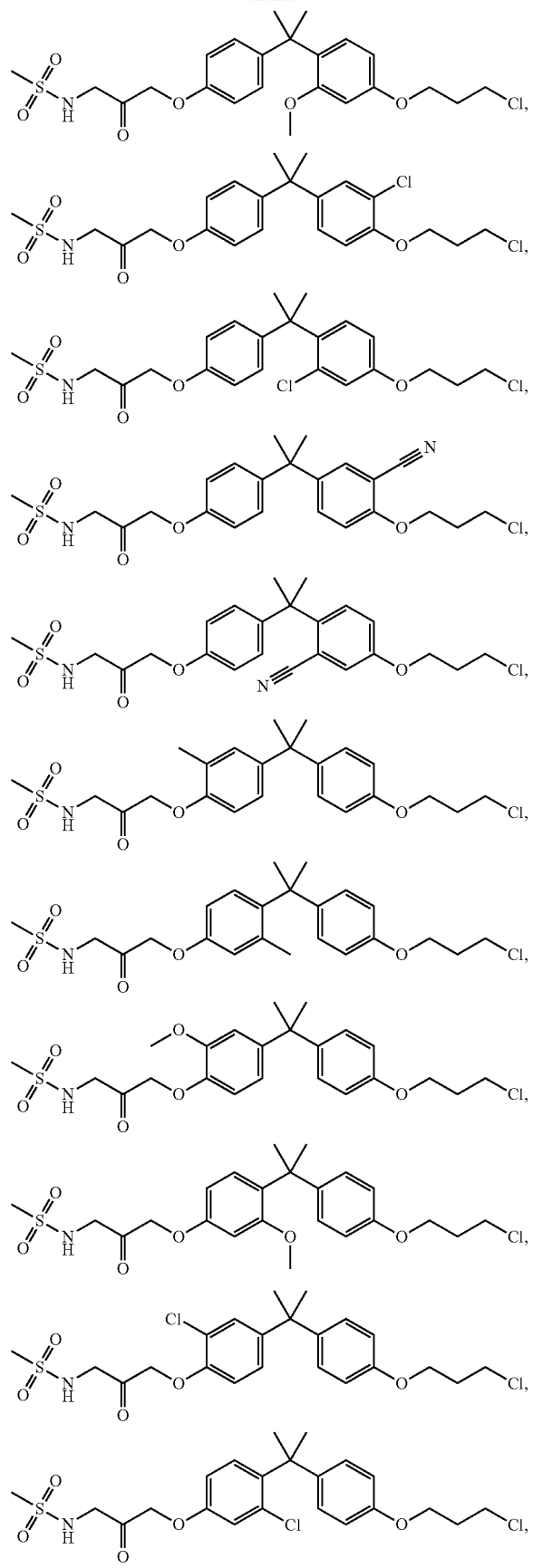
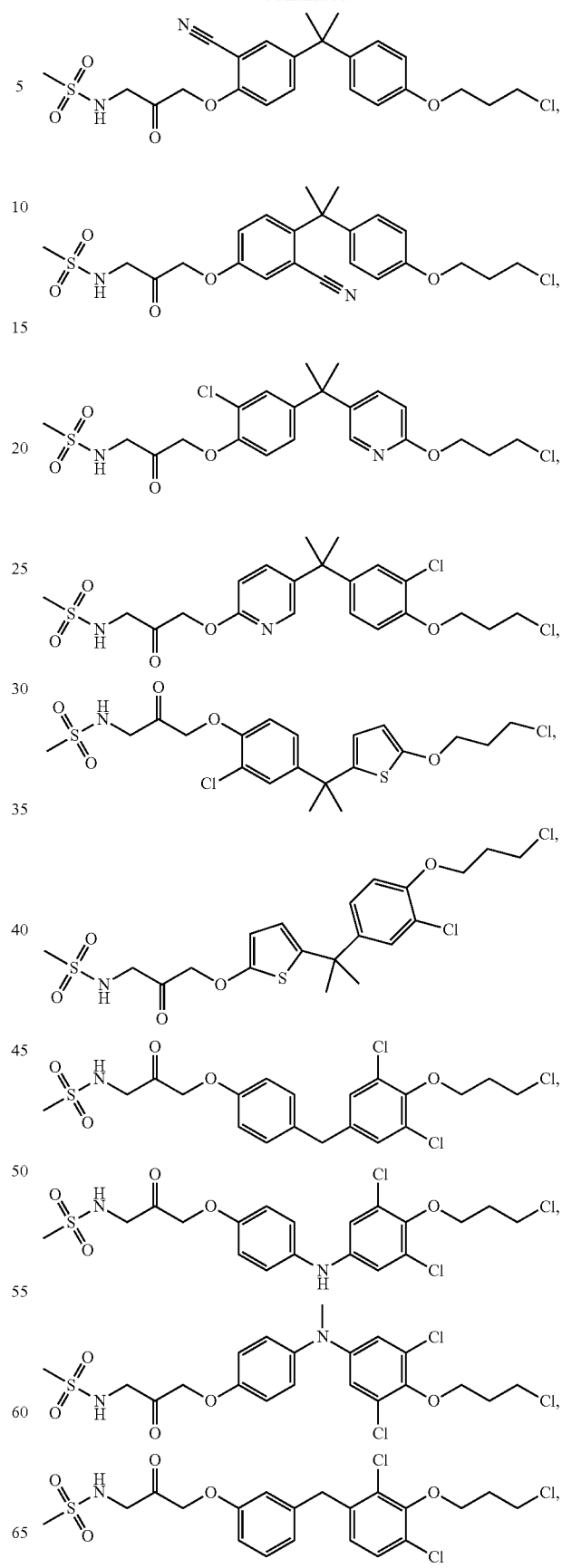

185
-continued

186
-continued

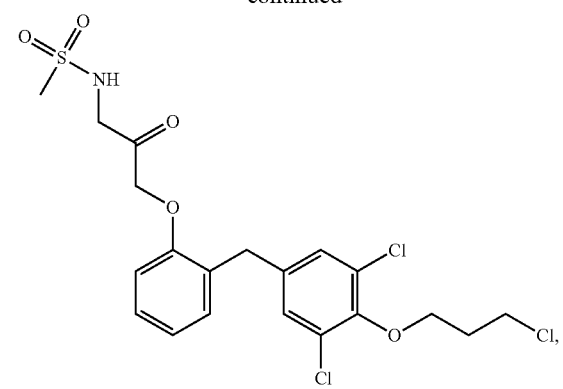
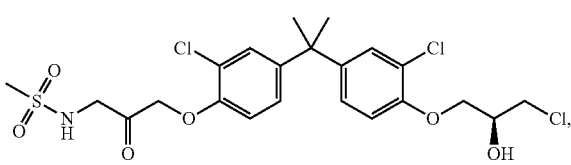
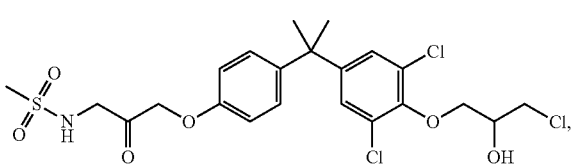
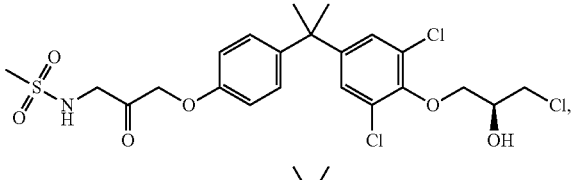
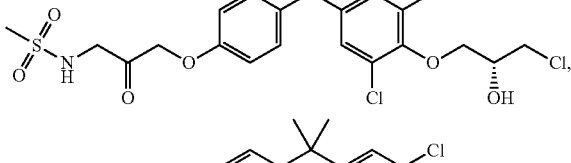
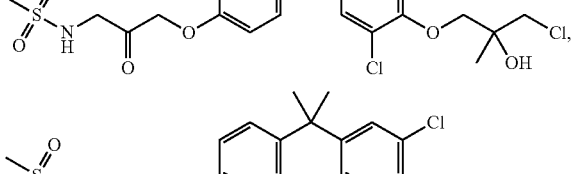
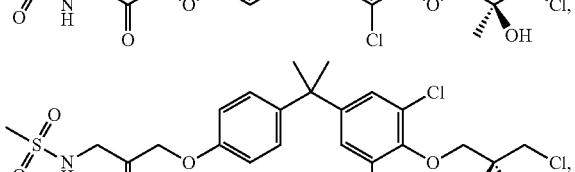
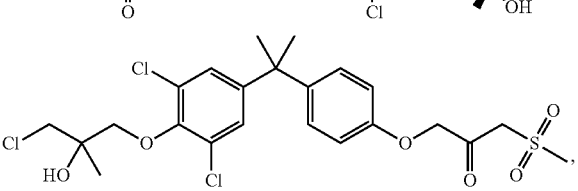
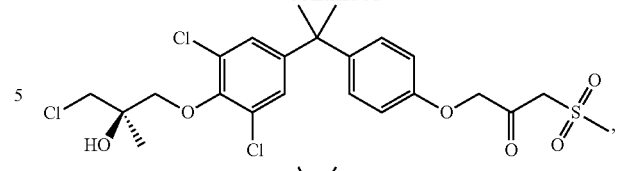
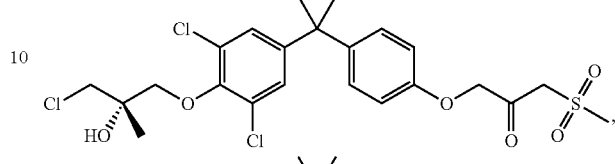
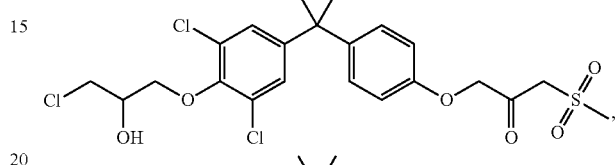
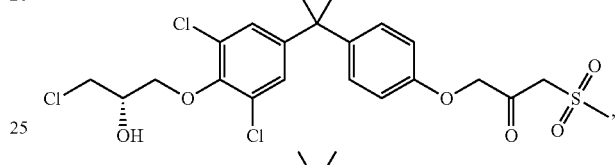
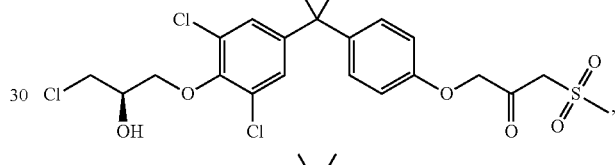
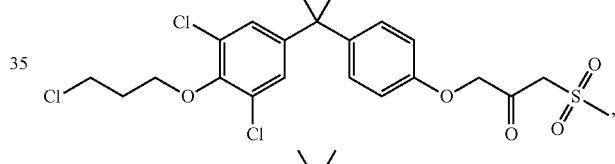
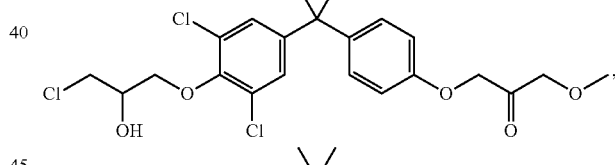
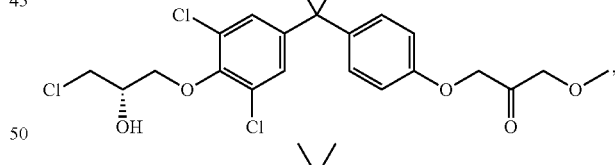
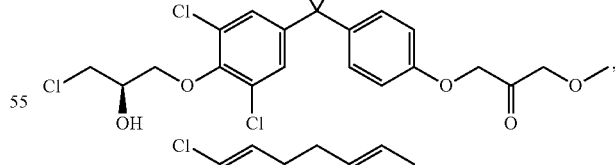
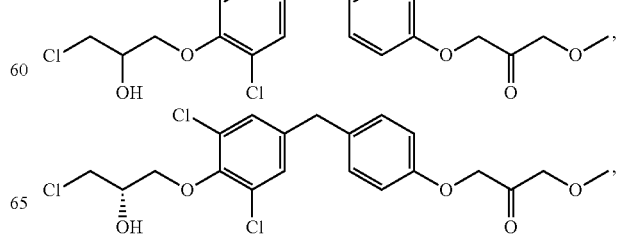

189
-continued
190
-continued
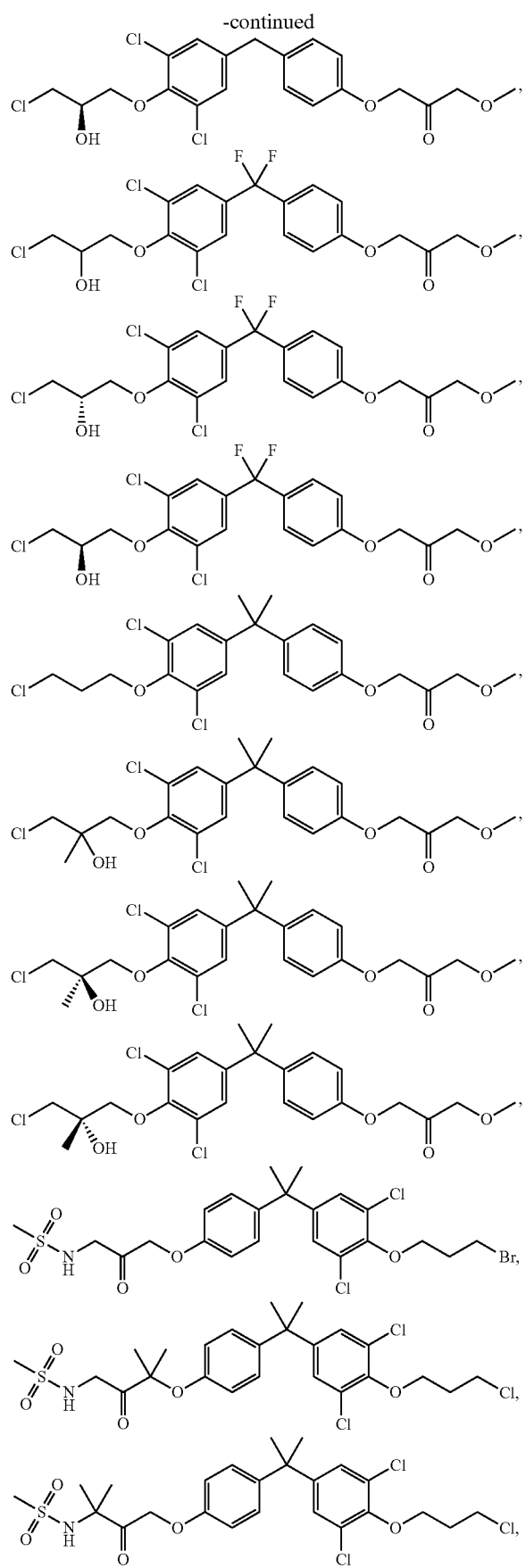
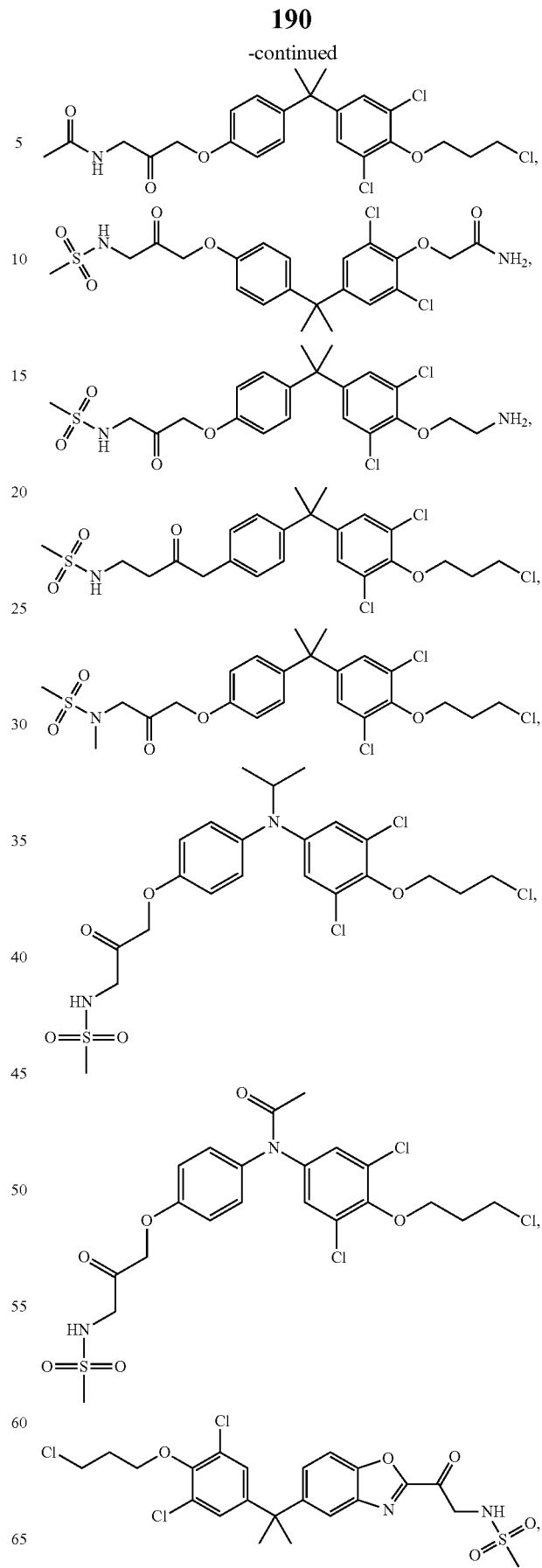

191
-continued
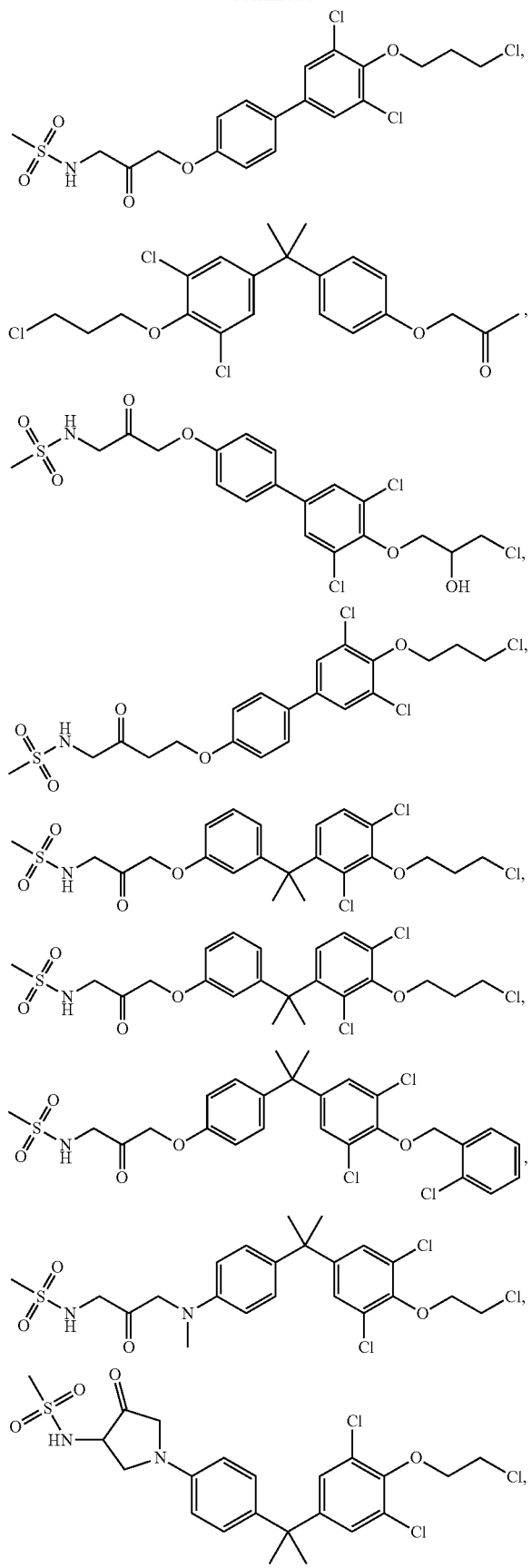
192
-continued
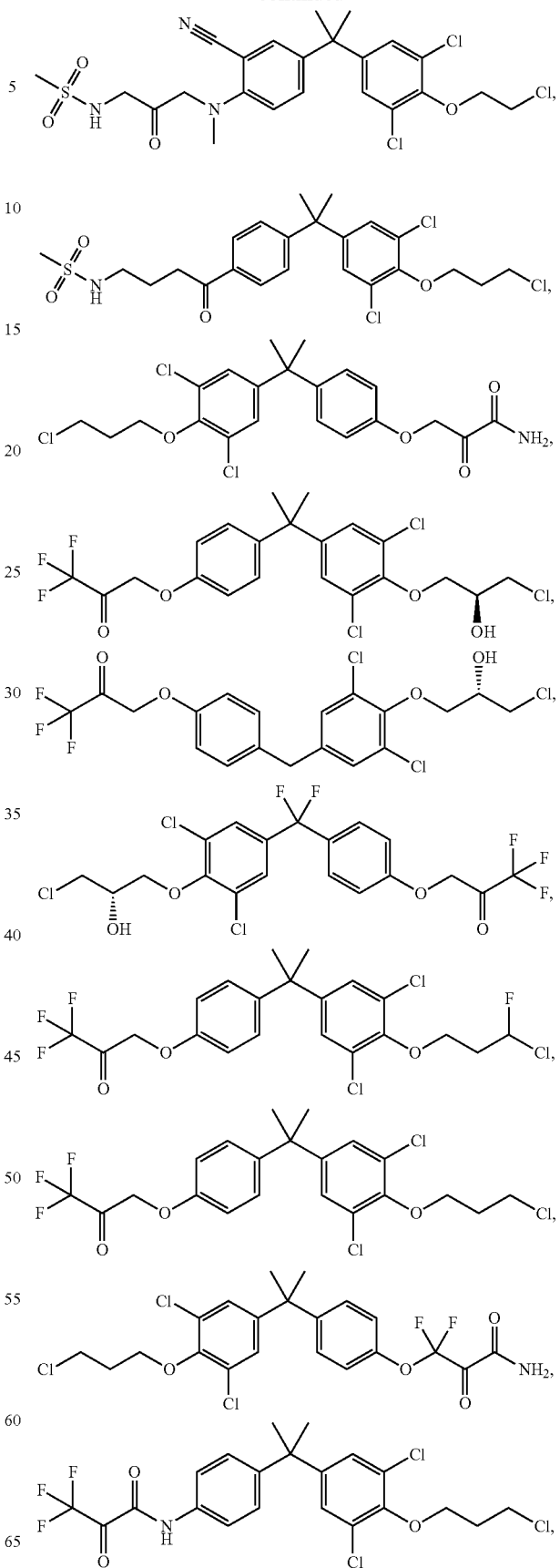

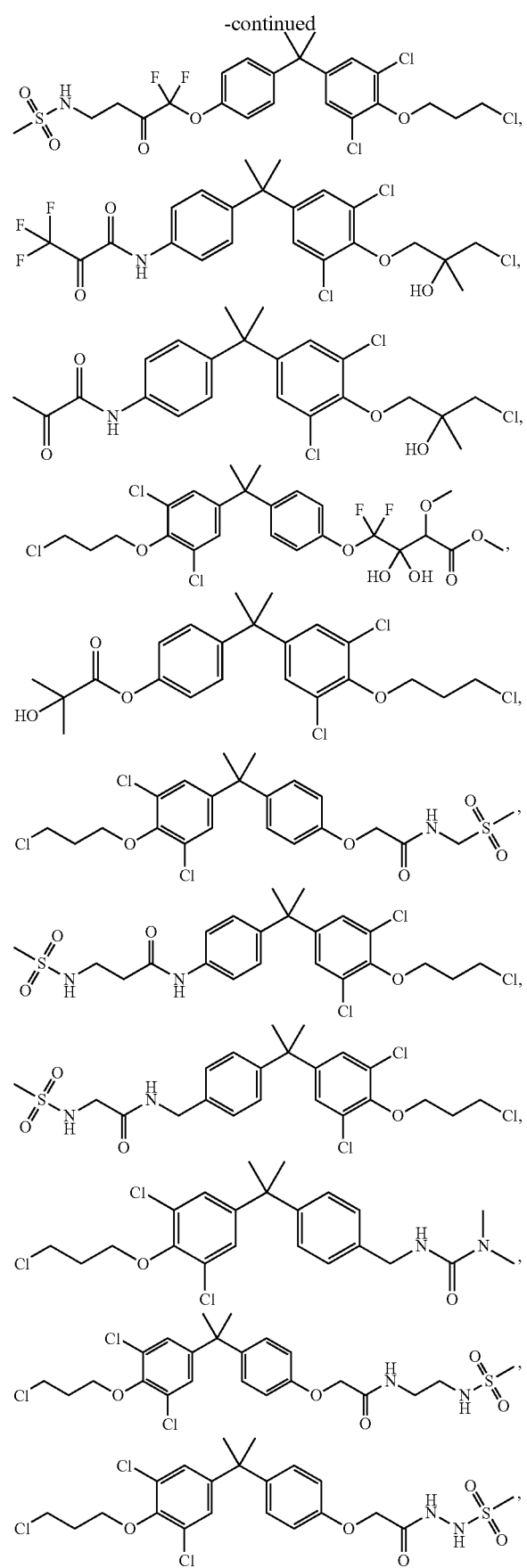
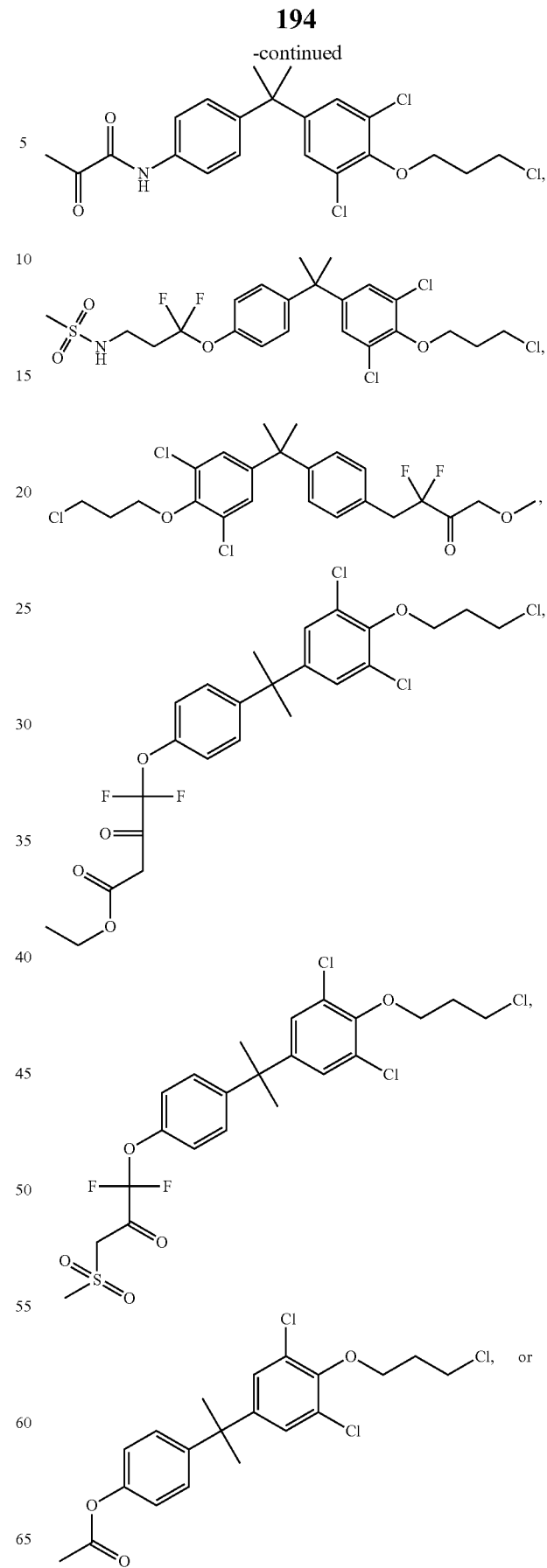

-continued
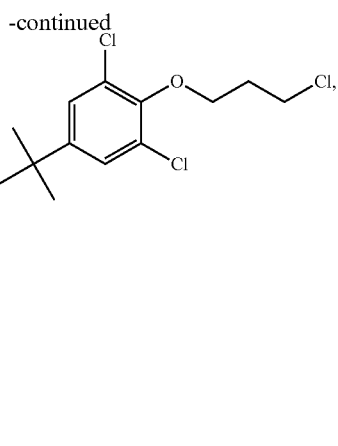
or a pharmaceutically acceptable salt, tautomer, stereoisomer or prodrug thereof.
27. A pharmaceutical composition comprising a compound of claim 1 and a pharmaceutically acceptable carrier.
28. The pharmaceutical composition of claim 27, further comprising one or more additional therapeutic agents.
* * * * *

UNITED STATES PATENT AND TRADEMARK OFFICE
CERTIFICATE OF CORRECTION

| | | |
|---|---|---|
| PATENT NO. | : 11,485,713 B2 | Page 1 of 1 |
| APPLICATION NO. | : 17/058481 | |
| DATED | : November 1, 2022 | |
| INVENTOR(S) | : Han-Jie Zhou et al. | |

It is certified that error appears in the above-identified patent and that said Letters Patent is hereby corrected as shown below:

In the Specification

At Column 1, Line 16, please insert:
-- STATEMENT REGARDING FEDERALLY SPONSORED RESEARCH OR DEVELOPMENT
This invention was made with government support under R01 CA105304 awarded by the National Institutes of Health. The government has certain rights in the invention. --

Signed and Sealed this
Second Day of January, 2024

Katherine Kelly Vidal
*Director of the United States Patent and Trademark Office*